(12) United States Patent
Geall et al.

(10) Patent No.: US 11,554,176 B2
(45) Date of Patent: *Jan. 17, 2023

(54) COMPOSITIONS AND METHODS OF TREATING MUSCLE ATROPHY AND MYOTONIC DYSTROPHY

(71) Applicant: Avidity Biosciences, Inc., La Jolla, CA (US)

(72) Inventors: Andrew John Geall, Carlsbad, CA (US); Venkata Ramana Doppalapudi, San Diego, CA (US); David Sai-Ho Chu, La Jolla, CA (US); Michael Caramian Cochran, La Jolla, CA (US); Michael Hood, San Diego, CA (US); Beatrice Diana Darimont, San Diego, CA (US); Rob Burke, Encinitas, CA (US); Yunyu Shi, San Diego, CA (US); Gulin Erdogan Marelius, San Diego, CA (US); Barbora Malecova, La Jolla, CA (US)

(73) Assignee: AVIDITY BIOSCIENCES, INC., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/464,607

(22) Filed: Sep. 1, 2021

(65) Prior Publication Data
US 2022/0008550 A1 Jan. 13, 2022

Related U.S. Application Data

(60) Division of application No. 17/024,624, filed on Sep. 17, 2020, which is a continuation of application No. 16/435,422, filed on Jun. 7, 2019, now Pat. No. 10,881,743, which is a continuation of application No. PCT/US2018/064359, filed on Dec. 6, 2018.

(60) Provisional application No. 62/725,883, filed on Aug. 31, 2018, provisional application No. 62/595,545, filed on Dec. 6, 2017.

(51) Int. Cl.
| | |
|---|---|
| *C07H 21/04* | (2006.01) |
| *A61K 47/68* | (2017.01) |
| *A61K 31/712* | (2006.01) |
| *A61K 31/713* | (2006.01) |
| *C07K 16/18* | (2006.01) |
| *C12N 15/113* | (2010.01) |
| *A61P 21/00* | (2006.01) |
| *A61K 39/395* | (2006.01) |
| *A61K 9/51* | (2006.01) |

(52) U.S. Cl.
CPC ........ *A61K 47/6807* (2017.08); *A61K 31/712* (2013.01); *A61K 31/713* (2013.01); *A61K 39/395* (2013.01); *A61K 47/6849* (2017.08); *A61P 21/00* (2018.01); *C07K 16/18* (2013.01); *C12N 15/113* (2013.01); *A61K 9/5107* (2013.01); *C12N 2310/14* (2013.01); *C12N 2310/315* (2013.01); *C12N 2310/317* (2013.01); *C12N 2310/3513* (2013.01); *C12N 2310/3515* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,694,778 A | 9/1987 | Learn et al. |
| 5,142,047 A | 8/1992 | Summerton et al. |
| 5,185,444 A | 2/1993 | Summerton et al. |
| 5,334,711 A | 8/1994 | Sproat et al. |
| 5,627,053 A | 5/1997 | Usman et al. |
| 5,716,824 A | 2/1998 | Beigelman et al. |
| 5,736,557 A | 4/1998 | Hofheinz et al. |
| 5,889,136 A | 3/1999 | Scaringe et al. |
| 5,898,031 A | 4/1999 | Crooke |
| 6,008,400 A | 12/1999 | Scaringe et al. |
| 6,107,094 A | 8/2000 | Crooke |
| 6,111,086 A | 8/2000 | Scaringe |
| 6,194,551 B1 | 2/2001 | Idusogie et al. |
| 6,528,624 B1 | 3/2003 | Idusogie et al. |
| 6,538,124 B1 | 3/2003 | Idusogie et al. |
| 6,821,783 B1 | 11/2004 | Comely et al. |
| 6,849,272 B1 | 2/2005 | Langer et al. |
| 6,884,869 B2 | 4/2005 | Senter et al. |
| 6,942,972 B2 | 9/2005 | Farooqui et al. |
| 7,056,704 B2 | 6/2006 | Tuschl et al. |
| 7,078,196 B2 | 7/2006 | Tuschl et al. |
| 7,132,519 B2 | 11/2006 | Monforte et al. |
| 7,250,496 B2 | 7/2007 | Bentwich |

(Continued)

FOREIGN PATENT DOCUMENTS

| | | |
|---|---|---|
| EP | 0336675 A1 | 10/1989 |
| EP | 0334656 B1 | 3/1994 |

(Continued)

OTHER PUBLICATIONS

Bodine, Sue C., et al. ("Identification of ubiquitin ligases required for skeletal muscle atrophy." Science 294.5547 (2001): 1704-1708).*
Vignaud et al. (Neuromuscular Disorders 20 (2010) 319-325).*
PCT/US2021/024303 International Search Report and Written Opinion dated Aug. 31, 2021.
UniProtKB Accession No. A0A2A5YEL5 "Uncharacterized protein", Dec. 20, 2017 [online]. 2-4, 68 [Retrieved on Jul. 29, 2021]. Retrieved from the internet: https://www.uniprot.org/uniprot/AOA2A5YEL5.

(Continued)

*Primary Examiner* — Kimberly Chong
(74) *Attorney, Agent, or Firm* — Wilson Sonsini Goodrich & Rosati

(57) ABSTRACT

Disclosed herein are polynucleic acid molecules, pharmaceutical compositions, and methods for treating muscle atrophy or myotonic dystrophy.

16 Claims, 74 Drawing Sheets

Specification includes a Sequence Listing.

(56) References Cited

U.S. PATENT DOCUMENTS

| | | |
|---|---|---|
| 7,351,855 B2 | 4/2008 | Coutts et al. |
| 7,364,731 B2 | 4/2008 | Idusogie et al. |
| 7,432,249 B2 | 10/2008 | Crooke |
| 7,432,250 B2 | 10/2008 | Crooke |
| 7,452,987 B2 | 11/2008 | Giese et al. |
| 7,459,547 B2 | 12/2008 | Zamore et al. |
| 7,498,298 B2 | 3/2009 | Doronina et al. |
| 7,521,232 B2 | 4/2009 | Moon |
| 7,595,387 B2 | 9/2009 | Leake et al. |
| 7,629,321 B2 | 12/2009 | Crooke |
| 7,691,997 B2 | 4/2010 | Khvorova et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 7,786,290 B2 | 8/2010 | Woppmann et al. |
| 7,829,693 B2 | 11/2010 | Kreutzer et al. |
| 7,833,992 B2 | 11/2010 | Vargeese et al. |
| 7,834,171 B2 | 11/2010 | Khvorova et al. |
| 7,850,975 B2 | 12/2010 | Mullis |
| 7,893,245 B2 | 2/2011 | Giese et al. |
| 7,923,547 B2 | 4/2011 | McSwiggen et al. |
| 7,928,217 B2 | 4/2011 | Vornlocher et al. |
| 7,943,762 B2 | 5/2011 | Weller et al. |
| 8,084,582 B2 | 12/2011 | Dahiyat et al. |
| 8,084,598 B1 | 12/2011 | Bentwich |
| 8,090,542 B2 | 1/2012 | Khvorova et al. |
| 8,137,695 B2 | 3/2012 | Rozema et al. |
| 8,202,979 B2 | 6/2012 | Mcswiggen et al. |
| 8,268,986 B2 | 9/2012 | Beigelman et al. |
| 8,273,866 B2 | 9/2012 | Mcswiggen et al. |
| 8,283,329 B2 | 10/2012 | Fire et al. |
| 8,288,352 B2 | 10/2012 | Doronina et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,324,370 B2 | 12/2012 | Giese et al. |
| 8,324,371 B2 | 12/2012 | Popplewell et al. |
| 8,329,892 B2 | 12/2012 | Zamore et al. |
| 8,334,373 B2 | 12/2012 | Vornlocher et al. |
| 8,361,979 B2 | 1/2013 | Aartsma-Rus et al. |
| 8,362,231 B2 | 1/2013 | Tuschl et al. |
| 8,372,968 B2 | 2/2013 | Tuschl et al. |
| 8,389,710 B2 | 3/2013 | Bruno et al. |
| 8,420,391 B2 | 4/2013 | Tuschl et al. |
| 8,445,237 B2 | 5/2013 | Tuschl et al. |
| 8,461,325 B2 | 6/2013 | Popplewell et al. |
| 8,481,698 B2 | 7/2013 | Lieberman et al. |
| 8,501,703 B2 | 8/2013 | Bennett et al. |
| 8,501,930 B2 | 8/2013 | Rozema et al. |
| 8,546,143 B2 | 10/2013 | Kreutzer et al. |
| 8,552,171 B2 | 10/2013 | Tuschl et al. |
| 8,557,292 B2 | 10/2013 | Davis et al. |
| 8,591,910 B2 | 11/2013 | Mullis |
| 8,604,184 B2 | 12/2013 | Mullis et al. |
| 8,609,105 B2 | 12/2013 | Senter et al. |
| 8,618,277 B2 | 12/2013 | Beigelman et al. |
| 8,632,997 B2 | 1/2014 | Tuschl et al. |
| 8,648,185 B2 | 2/2014 | Mcswigen et al. |
| 8,691,786 B2 | 4/2014 | Rossi et al. |
| 8,697,688 B2 | 4/2014 | Howard et al. |
| 8,746,999 B2 | 6/2014 | Davis et al. |
| 8,765,930 B2 | 7/2014 | Tuschl et al. |
| 8,772,469 B2 | 7/2014 | Uhlmann et al. |
| 8,778,902 B2 | 7/2014 | Tuschl et al. |
| 8,790,922 B2 | 7/2014 | Tuschl et al. |
| 8,796,016 B2 | 8/2014 | Tuschl et al. |
| 8,796,443 B2 | 8/2014 | Khvorova et al. |
| 8,835,402 B2 | 9/2014 | Kole et al. |
| 8,846,875 B2 | 9/2014 | Schwartz et al. |
| 8,846,894 B2 | 9/2014 | Mcswiggen et al. |
| 8,853,384 B2 | 10/2014 | Tuschl et al. |
| 8,895,718 B2 | 11/2014 | Tuschl et al. |
| 8,895,721 B2 | 11/2014 | Tuschl et al. |
| 8,895,722 B2 | 11/2014 | Iversen et al. |
| 8,906,847 B2 | 12/2014 | Cleemann et al. |
| 8,933,044 B2 | 1/2015 | Tuschl et al. |
| 8,933,215 B2 | 1/2015 | Giese et al. |
| 8,936,910 B2 | 1/2015 | Mitsch et al. |
| 8,969,526 B2 | 3/2015 | Baehner et al. |
| 8,993,745 B2 | 3/2015 | Tuschl et al. |
| 9,012,138 B2 | 4/2015 | Tuschl et al. |
| 9,012,621 B2 | 4/2015 | Tuschl et al. |
| 9,078,911 B2 | 7/2015 | Lu |
| 9,089,614 B2 | 7/2015 | Lin et al. |
| 9,096,636 B2 | 8/2015 | Baker et al. |
| 9,096,877 B2 | 8/2015 | Johnson et al. |
| 9,139,828 B2 | 9/2015 | Platenburg et al. |
| 9,175,286 B2 | 11/2015 | Wilton et al. |
| 9,175,289 B2 | 11/2015 | Khvorova et al. |
| 9,181,551 B2 | 11/2015 | Mcswiggen et al. |
| 9,193,753 B2 | 11/2015 | Tuschl et al. |
| 9,212,364 B2 | 12/2015 | Sah et al. |
| 9,222,092 B2 | 12/2015 | Giese et al. |
| 9,228,187 B2 | 1/2016 | Wilton et al. |
| 9,243,251 B2 | 1/2016 | Popplewell et al. |
| 9,243,252 B2 | 1/2016 | Popplewell et al. |
| 9,249,416 B2 | 2/2016 | Wilton et al. |
| 9,260,471 B2 | 2/2016 | Cancilla et al. |
| 9,284,551 B2 | 3/2016 | Puri et al. |
| 9,328,345 B2 | 5/2016 | Li et al. |
| 9,364,553 B2 | 6/2016 | Lee |
| 9,416,361 B2 | 8/2016 | Iversen et al. |
| 9,434,948 B2 | 9/2016 | Sazani et al. |
| 9,441,229 B2 | 9/2016 | Wilton et al. |
| 9,447,415 B2 | 9/2016 | Wilton et al. |
| 9,447,417 B2 | 9/2016 | Sazani et al. |
| 9,481,905 B2 | 11/2016 | Chen et al. |
| 9,499,818 B2 | 11/2016 | Van |
| 9,528,109 B2 | 12/2016 | De Kimpe et al. |
| 9,605,019 B2 | 3/2017 | Verdine et al. |
| 9,657,294 B2 | 5/2017 | Beigelman et al. |
| 9,695,211 B2 | 7/2017 | Wada et al. |
| 9,695,423 B2 | 7/2017 | Giese et al. |
| 9,732,344 B2 | 8/2017 | Beigelman et al. |
| 9,765,338 B2 | 9/2017 | Bennett et al. |
| 9,771,588 B2 | 9/2017 | Mcswiggen et al. |
| 9,796,974 B2 | 10/2017 | Rajeev et al. |
| 9,890,379 B2 | 2/2018 | De Kimpe et al. |
| 9,926,557 B2 | 3/2018 | De Kimpe et al. |
| 9,982,257 B2 | 5/2018 | Butler et al. |
| 10,000,754 B2 | 6/2018 | Beigelman et al. |
| 10,487,149 B2 | 11/2019 | Geall et al. |
| 10,550,188 B2 | 2/2020 | Geall et al. |
| 10,787,519 B2 | 9/2020 | Geall et al. |
| 10,881,743 B2 | 1/2021 | Geall et al. |
| 2002/0142980 A1 | 10/2002 | Thompson et al. |
| 2003/0073207 A1 | 4/2003 | Akhtar et al. |
| 2004/0224893 A1 | 11/2004 | Wang et al. |
| 2007/0004665 A1 | 1/2007 | McSwiggen et al. |
| 2008/0038257 A1 | 2/2008 | Han et al. |
| 2008/0097092 A1 | 4/2008 | Khvorova et al. |
| 2008/0160030 A1 | 7/2008 | Banchereau et al. |
| 2009/0092985 A1 | 4/2009 | Cardozo et al. |
| 2009/0149403 A1 | 6/2009 | MacLachlan et al. |
| 2009/0227655 A1 | 9/2009 | Khan |
| 2011/0039914 A1 | 2/2011 | Pavco et al. |
| 2011/0081362 A1 | 4/2011 | Elledge et al. |
| 2011/0263680 A1 | 10/2011 | Khvorova et al. |
| 2011/0263686 A1 | 10/2011 | Wilton et al. |
| 2011/0293512 A1 | 12/2011 | Violette et al. |
| 2011/0294753 A1 | 12/2011 | De Kimpe et al. |
| 2011/0301218 A1 | 12/2011 | Bozzoni et al. |
| 2012/0065169 A1 | 3/2012 | Hanson et al. |
| 2012/0094299 A1 | 4/2012 | Ranum et al. |
| 2012/0122800 A1 | 5/2012 | Kadushin et al. |
| 2012/0172415 A1 | 7/2012 | Voit et al. |
| 2012/0270925 A1 | 10/2012 | Wilton et al. |
| 2013/0028919 A1 | 1/2013 | Howard et al. |
| 2013/0045520 A1 | 2/2013 | Woolf et al. |
| 2013/0052731 A1 | 2/2013 | Ma et al. |
| 2013/0164366 A1 | 6/2013 | Kreutzer et al. |
| 2013/0172238 A1 | 7/2013 | Mitsch et al. |
| 2013/0177579 A1 | 7/2013 | Lin et al. |
| 2013/0177631 A1 | 7/2013 | Kreutzer et al. |

(56) References Cited

U.S. PATENT DOCUMENTS

| | | |
|---|---|---|
| 2013/0309256 A1 | 11/2013 | Lyon et al. |
| 2014/0127239 A1 | 5/2014 | Howard |
| 2014/0194610 A1 | 7/2014 | Verdine et al. |
| 2014/0286970 A1 | 9/2014 | Jeffrey et al. |
| 2014/0288158 A1 | 9/2014 | Rajeev et al. |
| 2014/0294851 A1 | 10/2014 | Nguyen |
| 2014/0296321 A1 | 10/2014 | Iversen |
| 2014/0315862 A1 | 10/2014 | Kaye |
| 2014/0357700 A1 | 12/2014 | Rossi et al. |
| 2015/0018540 A1 | 1/2015 | Prakash et al. |
| 2015/0037360 A1 | 2/2015 | Smith |
| 2015/0038554 A1 | 2/2015 | Brown |
| 2015/0038555 A1 | 2/2015 | Brown |
| 2015/0056220 A1 | 2/2015 | Chennamsetty et al. |
| 2015/0105539 A1 | 4/2015 | Miao et al. |
| 2015/0105540 A1 | 4/2015 | Miao et al. |
| 2015/0110791 A1 | 4/2015 | Zhang et al. |
| 2015/0111954 A1 | 4/2015 | Sliz et al. |
| 2015/0141492 A1 | 5/2015 | Tuschl et al. |
| 2015/0211006 A1 | 7/2015 | Butler et al. |
| 2015/0238516 A1 | 8/2015 | Dowdy et al. |
| 2015/0275212 A1 | 10/2015 | Albaek et al. |
| 2015/0366987 A1 | 12/2015 | Bodyak et al. |
| 2016/0002637 A1 | 1/2016 | Sazani et al. |
| 2016/0030332 A1 | 2/2016 | Lee et al. |
| 2016/0032288 A1 | 2/2016 | Tuschl et al. |
| 2016/0053262 A1 | 2/2016 | Platenburg et al. |
| 2016/0102135 A1 | 4/2016 | Escobar-Cabrera |
| 2016/0102148 A1 | 4/2016 | Park et al. |
| 2016/0193354 A1 | 7/2016 | Noe et al. |
| 2016/0298111 A1 | 10/2016 | Bestwick et al. |
| 2016/0304864 A1 | 10/2016 | De Kimpe et al. |
| 2016/0304874 A1 | 10/2016 | Krauss |
| 2016/0304877 A1 | 10/2016 | Swayze et al. |
| 2016/0367687 A1 | 12/2016 | Manoharan et al. |
| 2017/0081425 A1 | 3/2017 | Colletti et al. |
| 2017/0107512 A1 | 4/2017 | De Kimpe et al. |
| 2017/0204410 A1 | 7/2017 | Watanabe et al. |
| 2017/0204414 A1 | 7/2017 | Van Deutekom et al. |
| 2017/0281795 A1 | 10/2017 | Geall et al. |
| 2017/0342416 A1 | 11/2017 | Mcswiggen et al. |
| 2018/0016574 A1 | 1/2018 | Bestwick et al. |
| 2018/0044675 A1 | 2/2018 | Watanabe et al. |
| 2018/0112214 A1 | 4/2018 | De Kimpe et al. |
| 2018/0127758 A1 | 5/2018 | Bennett |
| 2018/0163209 A1 | 6/2018 | Bennett et al. |
| 2018/0305689 A1 | 10/2018 | Sætrom et al. |
| 2018/0344817 A1 | 12/2018 | Smith et al. |
| 2018/0369400 A1 | 12/2018 | Levin et al. |
| 2019/0000986 A1 | 1/2019 | Levin et al. |
| 2019/0062435 A1 | 2/2019 | Geall et al. |
| 2019/0062436 A1 | 2/2019 | Geall et al. |
| 2019/0083662 A1 | 3/2019 | Burak et al. |
| 2019/0192681 A1 | 6/2019 | Geall et al. |
| 2019/0240346 A1 | 8/2019 | Sugo et al. |
| 2020/0123261 A1 | 4/2020 | Geall et al. |
| 2020/0282074 A1 | 9/2020 | Levin et al. |
| 2020/0405877 A1 | 12/2020 | Geall et al. |
| 2021/0187116 A1 | 6/2021 | Geall et al. |
| 2022/0040323 A1 | 2/2022 | Geall et al. |
| 2022/0062434 A1 | 3/2022 | Geall et al. |
| 2022/0096647 A1 | 3/2022 | Geall et al. |

FOREIGN PATENT DOCUMENTS

| | | |
|---|---|---|
| EP | 1144623 B1 | 8/2002 |
| EP | 0928290 B1 | 3/2005 |
| EP | 1214945 B1 | 6/2005 |
| EP | 1579015 A2 | 9/2005 |
| EP | 1352061 B1 | 5/2006 |
| EP | 1742958 A2 | 1/2007 |
| EP | 1407044 B1 | 9/2007 |
| EP | 1068241 B1 | 10/2007 |
| EP | 1550719 B1 | 12/2008 |
| EP | 2119783 A1 | 11/2009 |
| EP | 1349927 B1 | 3/2010 |
| EP | 1409670 B1 | 10/2010 |
| EP | 1633890 B1 | 10/2010 |
| EP | 2336317 A1 | 6/2011 |
| EP | 2361923 A2 | 8/2011 |
| EP | 2049664 B1 | 9/2011 |
| EP | 1608733 B1 | 12/2011 |
| EP | 1873259 B1 | 1/2012 |
| EP | 2278004 B1 | 10/2012 |
| EP | 2514758 A1 | 10/2012 |
| EP | 2580326 A1 | 4/2013 |
| EP | 2351852 B1 | 10/2013 |
| EP | 2195428 B1 | 12/2013 |
| EP | 2028278 B1 | 3/2014 |
| EP | 2348133 B1 | 7/2014 |
| EP | 2344637 B1 | 12/2014 |
| EP | 1633770 B1 | 4/2015 |
| EP | 2340310 B1 | 6/2015 |
| EP | 1423406 B2 | 11/2015 |
| EP | 2949752 A2 | 12/2015 |
| EP | 2548962 B1 | 1/2016 |
| EP | 3031920 A1 | 6/2016 |
| EP | 2421971 B1 | 7/2016 |
| EP | 2287306 B2 | 10/2016 |
| EP | 3030658 A4 | 3/2017 |
| EP | 2813582 B1 | 4/2017 |
| EP | 2287305 B2 | 11/2017 |
| EP | 2486141 B1 | 1/2018 |
| EP | 2902406 B1 | 1/2018 |
| EP | 2595664 B1 | 10/2018 |
| JP | 2002095476 A | 4/2002 |
| WO | WO-9104753 A1 | 4/1991 |
| WO | WO-9207065 A1 | 4/1992 |
| WO | WO-9315187 A1 | 8/1993 |
| WO | WO-9726270 A2 | 7/1997 |
| WO | WO-9734631 A1 | 9/1997 |
| WO | WO-9813526 A1 | 4/1998 |
| WO | WO-0050008 A2 | 8/2000 |
| WO | WO-0149698 A1 | 7/2001 |
| WO | WO-2006000057 A1 | 1/2006 |
| WO | WO-2006006948 A2 | 1/2006 |
| WO | WO-2006128138 A2 | 11/2006 |
| WO | WO-2007021142 A1 | 2/2007 |
| WO | WO-2008036127 A2 | 3/2008 |
| WO | WO-2009099942 A2 | 8/2009 |
| WO | WO-2009099991 A2 | 8/2009 |
| WO | WO-2009108217 A2 | 9/2009 |
| WO | WO-2009126933 A2 | 10/2009 |
| WO | WO-2009129281 A2 | 10/2009 |
| WO | WO-2009144481 A2 | 12/2009 |
| WO | WO-2011003557 A1 | 1/2011 |
| WO | WO-2011009624 A1 | 1/2011 |
| WO | WO-2012012443 A2 | 1/2012 |
| WO | WO-2012092373 A2 | 7/2012 |
| WO | WO-2013138662 A1 | 9/2013 |
| WO | WO-2013166004 A2 | 11/2013 |
| WO | WO-2013166155 A1 | 11/2013 |
| WO | WO-2014080251 A1 | 5/2014 |
| WO | WO-2014140317 A2 | 9/2014 |
| WO | WO-2014145090 A1 | 9/2014 |
| WO | WO-2014154835 A2 | 10/2014 |
| WO | WO-2014177042 A1 | 11/2014 |
| WO | WO-2014197854 A1 | 12/2014 |
| WO | WO-2015021457 A2 | 2/2015 |
| WO | WO-2015038426 A1 | 3/2015 |
| WO | WO-2015057699 A2 | 4/2015 |
| WO | WO-2015069587 A2 | 5/2015 |
| WO | WO-2015084846 A1 | 6/2015 |
| WO | WO-2015107425 A2 | 7/2015 |
| WO | WO-2015113922 A1 | 8/2015 |
| WO | WO-2015200223 A1 | 12/2015 |
| WO | WO-2016028649 A2 | 2/2016 |
| WO | WO-2016187425 A1 | 11/2016 |
| WO | WO-2016207240 A1 | 12/2016 |
| WO | WO-2017148879 A1 | 9/2017 |
| WO | WO-2017173408 A1 | 10/2017 |
| WO | WO-2017192679 A1 | 11/2017 |
| WO | WO-2017221883 A1 | 12/2017 |
| WO | WO-2018002812 A1 | 1/2018 |

(56) References Cited

FOREIGN PATENT DOCUMENTS

| WO | WO-2018078131 A1 | 5/2018 |
|---|---|---|
| WO | WO-2018078134 A1 | 5/2018 |
| WO | WO-2018129384 A1 | 7/2018 |
| WO | WO-2019060775 A1 | 3/2019 |
| WO | WO-2019071028 A1 | 4/2019 |
| WO | WO-2019113393 A1 | 6/2019 |
| WO | WO-2021195469 A1 | 9/2021 |

OTHER PUBLICATIONS

U.S. Appl. No. 17/187,650 Office Action dated Aug. 31, 2021.
Aartsma-Rus et al. Guidelines for antisense oligonucleotide design and insight into splice-modulating mechanisms. Mol Ther 17(3):548-53 (2009).
Aartsma-Rus et al. Progress in therapeutic antisense applications for neuromuscular disorders. Eur J Hum Genet 18(2):146-153 (2010).
Aartsma-Rus et al. Targeted exon skipping as a potential gene correction therapy for Duchenne muscular dystrophy. Neuromuscul Disord. 12 Suppl 1:S71-7 (2002).
Abramova et al. Novel oligonucleotide analogues based on morpholino nucleoside subunits—antisense technologies: new chemical possibilities. Indian Journal of Chemistry 48B:1721-1726 (2009).
Agarwal et al. A Pictet-Spengler ligation for protein chemical modification. PNAS 110(1):46-51 (2013).
Albarran et al. Efficient intracellular delivery of a pro-apoptotic peptide with a pH-responsive carrier. React Funct Polym 71:261-265 (2011).
Arechavala-Gomeza et al. Comparative analysis of antisense oligonucleotide sequences for targeted skipping of exon 51 during dystrophin pre-mRNA splicing in human muscle. Hum Gene Ther. 18(9):798-810 (2007).
Axup et al. Synthesis of site-specific antibody-drug conjugates using unnatural amino acids. PNAS 109(40):16101-16106 (2012).
Baumer et al. Antibody-mediated delivery of anti-KRAS-siRNA in vivo overcomes therapy resistance in colon cancer. Clin Can Res 21(6):1383-1394 (2015).
Beduneau et al. Design of targeted lipid nanocapsules by conjugation of whole antibodies and antibody Fab' fragments. Biomaterials 28(33):4978-4990 (2007).
Beigelman et al. Chemical modification of hammerhead ribozymes. Catalytic activity and nuclease resistance. J Biol Chem 270:25702-25708 (1995).
Bell et al. Epidermal Growth Factor Receptor Mutations and Gene Amplification in Non-Small-Cell Lung Cancer: Molecular Analysis of the Ideal/Intact Gefitinib Trials. J Clin Oncol 23(31):8081-8092 (2005).
Bird et al. Single-chain antigen-binding proteins. Science 242:423-442 (1988).
Bjarne Udd et al., The myotonic dystrophies: molecular, clinical, and therapeutic challenges. Lancet Neurol. 11(10):891-905 (2012).
Blaney et al. Traceless solid-phase organic synthesis. Chem. Rev. 102:2607-2024 (2002.
Bulmus et al. A new pH-responsive and glutathione-reactive, endosomal membrane-disruptive polymeric carrier for intracellular delivery of biomolecular drugs. J Controlled Release 93:105-120 (2003).
Burke et al. siRNA-mediated knockdown of P450 oxidoreductase in rats: a tool to reduce metabolism by CYPs and increase exposure of high clearance compounds. Pharm. Res. 31(12):3445-3460 (2014).
Burlina et al. Chemical engineering of RNase resistant and catalytically active hammerhead ribozymes. Bioorg Med Chem 5:1999-2010 (1997).
Carter et al. Antibody-drug conjugates for cancer therapy. Cancer J 14(3):154-69 (2008).
Casi et al. Antibody-drug conjugates: basic concepts, examples and future perspectives. J Control Release 161:422-428 (201).
Casi et al. Site-specific traceless coupling of potent cytotoxic drugs to recombinant antibodies for pharmacodelivery. J Am Chem Soc 134(13):5887-5892 (2012).

Castaneda et al. Acid-cleavable thiomaleamic acid linker for homogeneous antibody-drug conjugation, Chem. Commun. 49:8187-8189 (2013).
JP2016-122187, filed on Jun. 20, 2016 (English counterpart US2019240346).
U.S. Appl. No. 62/316,919, filed Apr. 1, 2016.
Chen et al. Strand-specific 5'-O-methylation of siRNA duplexes controls guide strand selection and targeting specificity. RNA 14:263-274 (2008).
Clackson et al. Making antibody fragments using phage display libraries. Nature 352(6336):624-628 (1991).
Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Co-pending U.S. Appl. No. 17/214,525, inventors Doppalapudi; Venkata Ramana et al., filed on Mar. 26, 2021.
Co-pending U.S. Appl. No. 17/464,618, inventors Geall; Andrew John et al., filed on Sep. 1, 2021.
Crouse et al. Expression and amplification of engineered mouse dihydrofolate reductase minigenes. Mol Cell Biol 3(2):257-266 (1983).
Cuellar et al. Systematic evaluation of antibody-mediated siRNA delivery using an industrial platform of THIOMAB-siRNA conjugates. Nucleic Acids Res 43(2):1189-1203 (2015).
Dawson et al. Modulation of Reactivity in Native Chemical Ligation through the Use of Thiol Additives. J. Am. Chem. Soc. 119:4325-4329 (1997).
Dawson et al. Synthesis of proteins by native chemical ligation. Science 266(5186):776-779 (1994).
De Angelis et al. Chimeric snRNA molecules carrying antisense sequences against the splice junctions of exon 51 of the dystrophin pre-mRNA induce exon skipping and restoration of a dystrophin synthesis in Delta 48-50 DMD cells. PNAS USA 99:9456-9461 (2002).
Debinski et al. Monovalent immunotoxin containing truncated form of Pseudomonas exotoxin as potent antitumor agent. Cancer Research 52(19):5379-5385 (1992).
Deleavey et al. Designing chemically modified oligonucleotides for targeted gene silencing. Chem Biol. 19(8):937-954 (2012).
Dietel et al. A 2015 update on predictive molecular pathology and its role in targeted cancer therapy: a review focussing on clinical relevance. Cancer Gene Ther 22(9):417-430 (2015).
Dimasi et al. Development of a trispecific antibody designed to simultaneously and efficiently target three different antigens on tumor cells. Mol Pharm 12(9):3490-3501 (2015).
Domingo et al. Transferrin receptor as a target for antibody—drug conjugates. Methods in Enzymology 112:238-247 (1985).
Duncan et al. A polymer-Triton X-100 conjugate capable of pH-dependent red blood cell lysis: a model system illustrating the possibility of drug delivery within acidic intracellular compartments. J Drug Target 2:341-347 (1994).
Earnshaw et al. Modified oligoribonucleotides as site-specific probes of RNA structure and function. Biopolymers (Nucleic Acid Sciences) 48:39-55 (1998).
Echigoya et al. In Silico Screening Based on Predictive Algorithms as a Design Tool for Exon Skipping Oligonucleotides in Duchenne Muscular Dystrophy. PLoS One 10(3):e0120058 (2015).
El-Sayed et al. Rational design of composition and activity correlations for pH-responsive and glutathione-reactive polymer therapeutics. J Control Release 104:417-427 (2005).
Feener et al. Alternative splicing of human dystrophin mRNA generates isoforms at the carboxy terminus. Nature 338:509-511 (Apr. 6, 1989).
Flanary et al. Antigen delivery with poly(propylacrylic acid) conjugation enhanced MHC-1 presentation and T-cell activation. Bioconjugate Chem. 20:241-248 (2009).
Gaziova et al. Chemically defined polyethylene glycol siRNA conjugates with enhanced gene silencing effect. Bioorg Med Chem 22(7):2320-2326 (2014).

(56) References Cited

OTHER PUBLICATIONS

Giorgetti et al. Rescue of Metabolic Alterations in AR113Q Skeletal Muscle by Peripheral Androgen Receptor Gene Silencing. Cell Rep 17(1):125-136 (2016).
Goldmacher et al. Antibody-drug conjugates: using monoclonal antibodies for delivery of cytotoxic payloads to cancer cells. Therapeutic Delivery 2:397-416 (2011).
Goldspiel et al. Human gene therapy. Clin Pharm 12:488-505 (1993).
Griffey et al. 2'-0-aminopropyl ribonucleotides: a zwitterionic modification that enhances the exonuclease resistance and biological activity of antisense oligonucleotides, J. Med. Chem. 39(26):5100-5109 (1997).
Hackeng et al. Protein synthesis by native chemical ligation: Expanded scope by using straightforward methodology. PNAS USA 96:10068-10073 (1999).
Hanes et al. In vitro selection and evolution of functional proteins by using ribosome display. PNAS USA 94:4937-4942 (1997).
Hejesen et al. A traceless aryl-triazene linker for DNA-directed chemistry. Org Biomol Chem 11(15):2493-2497 (2013).
Henry et al. pH-responsive poly(styrene-alt-maleic anhydride) alkylamide copolymers for intracellular drug delivery. Biomacromolecules 7:2407-2414 (2006).
Hitachi et al. Role of microRNAs in skeletal muscle hypertrophy. Front Physiol 16(4):408 (2014).
Hoffman et al. Restoring Dystrophin Expression in Duchenne Muscular Dystrophy Muscle: Progress in Exon Skipping and Stop Codon Read Through. Am J Pathol 179(1):12-22 (2011).
*Homo sapiens* DM1 protein kinase (DMPK), transcript variant 7, mRNA. NCBI reference sequence NM_001288766 (Mar. 12, 2019).
Hu et al. Site-specific Antibody-polymer Conjugates for siRNA Delivery. J Am Chem Soc 135(37):13885-13891 (2013).
Huang et al. Mechanisms of resistance to EGFR tyrosine kinase inhibitors. Acta Pharma Sinica B 5(5):390-401 (2015).
Hudson et al. Cellular delivery of hammerhead ribozymes conjugated to a transferrin receptor antibody. Int J Pharmaceuticals 182(1):49-58 (1999).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85(16):5879-5883 (1988).
Ishikawa et al. Preparation of monomeric Fab'—horseradish peroxidase conjugate using thiol groups in the hinge and its evaluation in enzyme immunoassay and immunohistochemical staining. Ann N Y Acad Sci. 420:74-89 (1983).
Iversen et al. Optimized siRNA-PEG conjugates for extended blood circulation and reduced urine excretion in mice. Theranostics 3(3):201-209 (2013).
Jancik et al. Clinical relevance of KRAS in human cancers. J Biomed Biotechnol 2010:150960 (13 pgs.) (2010).
Jearawiriyapaisarn et al. Sustained Dystrophin Expression Induced by Peptide-conjugated Morpholino Oligomers in the Muscles of mdx Mice. Mol Ther. 16(9): 1624-1629 (2008).
Jones et al. Poly(2-alkylacrylic acid) polymers deliver molecules to the cytosol by pH-sensitive disruption of endosomal vesicles. Biochem J 372:65-75 (2003).
Karpeisky et al. Highly efficient synthesis of 2'-O-amino nucleosides and their incorporation in hammerhead ribozymes. Tetrahedron Lett 39:1131-1134 (1998).
Khormaee et al. Endosomolyticanionic polymer for the cytoplasmic delivery of siRNAs in localized in vivo applications. Adv Funct Mater 23:565-574 (2013).
Kim et al. PEG conjugated VEGF siRNA for anti-angiogenic gene therapy. J Cont Rel 116:123-129 (2006).
Kohler et al. Continuous cultures of fused cells secreting antibody of predefined specificity. Nature 256:495-497 (1975).
Koizumi. ENA oligonucleotides as therapeutics. Curr Opin Mol Ther 8(2):144-149 (2006).
Kontermann et al. Bispecific antibodies. Drug Discov Today 20(7):838-847 (2015).
Kozbor et al. The production of monoclonal antibodies from human lymphocytes. Immunology Today 4:72-79 (1983).
Kutmeier et al. Assembly of humanized antibody genes from synthetic oligonucleotides using a single-round PCR. BioTechniques 17:242 (1994).
Langlois et al. Cytoplasmic and Nuclear Retained DMPK mRNAS Are Targets for RNA Interference in Myotonic Dystrophy Cells. J biol Chem 280(17):16949-16954 (2005).
Lee et al. Antisense PMO cocktails effectively skip dystrophin exons 45-55 in myotubes transdifferentiated from DMD patient fibroblasts. PLoS One 13(5):e0197084 (2018).
Leigh et al. The Human Plasma Proteome: History, Character, and Diagnostic Prospects. Mol Cell Proteomics 1:845-867 (2002).
Leroy et al. Epidermal growth factor receptor down-regulation triggers human myoblast differentiation. PLOS One 8(8):e71770 (2013).
Levin. Targeting Therapeutic Oligonucleotides. N Engl J Med 376:86-88 (2017).
Loakes. Survey and summary: The applications of universal DNA base analogues. Nucleic Acids Research 29:2437-2447 (2001).
Loh et al. A Survey of siRNA Nanoscal Delivery Patents. 11 Nanotechnology Law & Bus. (pp. 29-37) (2014).
Lowy et al., Isolation of transforming DNA: Cloning the hamster aprt gene. Cell 22:817-823 (1980).
Lyon et al. Self-hydrolyzing maleimides improve the stability and pharmacological properties of antibody-drug conjugates. Nat. Biotechnol. 32(10):1059-1062 (2014).
Martinez et al. Single-stranded antisense siRNAs guide target RNA cleavage in RNAi. Cell 110(5):563-574 (2002).
Mcenaney et al. Antibody-recruiting molecules: an emerging paradigm for engaging immune function in treating human disease. ACS Chem Biol. 7(7):1139-1151 (2012).
Mei et al. FBXO32 Targets c-Myc for Proteasomal Degradation and Inhibits c-Myc Activity. J Biol Chem 290:16202-16214 (2015).
Miyata et al. Polymer nanotechnology for nucleic acid delivery. Drug Delivery System 31(1):44-53 (2016) (English Abstract).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulders et al. Molecular therapy in myotonic dystrophy: focus on RNA gain-of-function. Hum Mol Gen 19(R1):R90-R97 (2010).
Mulders et al. Triplet-repeat oligonucleotide-mediated reversal of RNA toxicity in myotonic dystrophy. PNAS 106(33):13915-13920 (2009).
Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science 260(5110):926-932 (1993).
Muratovska et al. Conjugate for efficient delivery of short interfering RNA (siRNA) into mammalian cells. FEBS Lett. 558(1-3):63-8 (2004).
Naisbitt et al. Disposition of amodiaquine and related antimalarial agents in human neutrophils: implications for drug design. J Pharmacol Exp Ther 280:884-893 (1997).
Neuberger et al. Recombinant antibodies possessing novel effector functions. Nature 312(5995):604-608 (1984).
Nielsen et al. Advances in targeted delivery of small interfering RNA using simple bioconjugates. Expert Opinion On Drug Delivery 11(5):791-822 (2014).
Normand-Sdiqui et al. Oligonucleotide delivery: Uptake of rat transferrin receptor antibody (OX / 26) conjugates into an in vitro immortalised cell line model of the blood, brain barrier. Int J Pharmaceuticals 163:63-71 (1998).
Obika et al. Synthesis of 2'-O,4'-C-methyleneuridine and -cytidine. Novel bicyclic nucleosides having a fixed C3'-endo sugar puckering. Tetrahedron Lett. 38(50):8735-8738 (1997).

(56) References Cited

OTHER PUBLICATIONS

O'Hare et al. Transformation of mouse fibroblasts to methotrexate resistance by a recombinant plasmid expressing a prokaryotic dihydrofolate reductase. PNAS USA 78:1527-1531 (1981).
Parmar et al. 5'-(E)-Vinylphosphonate: A Stable Phosphate Mimic Can Improve the RNAi Activity of siRNA-GalNAc Conjugates. Chembiochem 17(11):985-989 (2016).
PCT International Application No. PCT/JP2017/022509, Filed Jun. 19, 2017 (English counterpart US2019240346).
PCT/US2017/025608 International Search Report and Written Opinion dated Jul. 10, 2017.
PCT/US2018/012672 International Search Report and Written Opinion dated May 24, 2018.
PCT/US2018/012672 Invitation to Pay Additional Fees dated Mar. 20, 2018.
PCT/US2018/052289 International Search Report and Written Opinion dated Jan. 11, 2019.
PCT/US2018/054444 International Search Report and Written Opinion dated Feb. 15, 2019.
PCT/US2018/064359 Invitation to Pay Additional Fees dated Feb. 14, 2019.
PCT/US2018/064359 International Search Report and Written Opinion dated Apr. 11, 2019.
PCT/US2018/54444 Invitation to Pay Additional Fees dated Dec. 27, 2018.
Pei et al. Quantitative evaluation of siRNA delivery in vivo. RNA 16:2553-2563 (2010).
Perrault et al. Mixed deoxyribo- and ribo-oligonucleotides with catalytic activity. Nature 344:565-568 (1990).
Pieken et al. Kinetic characterization of ribonuclease-resistant 2'-modified hammerhead ribozymes. Science 253:314-317 (1991).
Rozema et al. Dynamic PolyConjugates for targeted in vivo delivery of siRNA to hepatocytes. PNAS USA 104(32):12982-12987 (2007).
Sacheck et al. Rapid disuse and denervation atrophy involve transcriptional changes similar to those of muscle wasting during systemic diseases. The FASEB Journal 21:140-155 (2007).
Santerre et al. Expression of prokaryotic genes for hygromycin B and G418 resistance as dominant-selection markers in mouse L cells. Gene 30(1-3):147-156 (1984).
Sartori et al. Smad2 and 3 transcription factors control muscle mass in adulthood. Am J Physiol Cell Physiol 296:C1248-C1257 (2009).
Schnyder et al. Targeting of skeletal muscle in vitro using biotinylated immunoliposomes. Biochem J 377(Pt.1):61-67 (2004).
Schwarz et al. Evidence that siRNAs function as guides, not primers, in the *Drosophila* and human RNAi pathways. Molecular Cell 10:537-548 (2002).
Sekyere et al. Examination of the distribution of the transferrin homologue, melanotransferrin (tumour antigen p97), in mouse and human. Biochimica et Biophysica Acta 1722(2):131-142 (2005).
Singh et al. Recent developments in oligonucleotide conjugation. Chem Soc Rev 39(6):2054-2070 (2010).
Skerra et al. Assembly of a functional Immunoglobulin Fv fragment in *Escherichia coli*. Science 240(4855):1038-1041 (1988).
Strop et al. Location matters: site of conjugation modulates stability and pharmacokinetics of antibody drug conjugates. Chem Biol 20(2):161-167 (2013).
Sugo et al. Development of antibody-siRNA conjugate targeted to cardiac and skeletal muscles. J Control release 237:1-13 (2016).
Summerton, et al. Morpholino antisense oligomers: design, preparation, and properties. Antisense Nucleic Acid Drug Dev. Jun. 1997;7(3):187-95.
Suñé-Pou et al. Targeting Splicing in the Treatment of Human Disease. Genes 8:E87 (2017).
Suriano et al. Beta-catenin (CTNNB1) gene amplification: a new mechanism of protein overexpression in cancer. Genes Chromosomes Cancer 42(3):238-246 (2005).
Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Talasila et al. EGFR Wild-type Amplification and Activation Promote Invasion and Development of Glioblastoma Independent of Angiogenesis. Acta Neuropathol. 125(5):683-698 (2013).
Tolstoshev. Gene Therapy, Concepts, Current Trials and Future Directions. Ann. Rev. Pharmacol. Toxicol. 32:573-596 (1993).
Turner et al. The myotonic dystrophies: diagnosis and management. J Neurol Neurosurg Psychiatry 81:358-367 (2010).
U.S. Appl. No. 15/473,849 1st Action Interview dated Nov. 24, 2017.
U.S. Appl. No. 15/476,849 1st Action Interview dated Sep. 11, 2017.
U.S. Appl. No. 15/476,849 Office Action dated Apr. 17, 2018.
U.S. Appl. No. 15/476,849 Office Action dated May 2, 2018.
U.S. Appl. No. 16/128,393 Office Action dated Aug. 26, 2019.
U.S. Appl. No. 16/128,417 Office Action dated Mar. 27, 2020.
U.S. Appl. No. 16/128,417 Office Action dated Sep. 30, 2019.
U.S. Appl. No. 16/128,428 Office Action dated Mar. 27, 2020.
U.S. Appl. No. 16/128,428 Office Action dated Oct. 1, 2019.
U.S. Appl. No. 16/128,440 Office Action dated May 30, 2019.
U.S. Appl. No. 16/128,440 Office Action dated Nov. 9, 2018.
U.S. Appl. No. 16/128,450 Miscellaneous Communication re: Third Party Submission dated Jul. 1, 2019.
U.S. Appl. No. 16/128,450 Office Action dated Apr. 19, 2019.
U.S. Appl. No. 16/128,450 Office Action dated Apr. 30, 2020.
U.S. Appl. No. 16/128,450 Office Action dated Dec. 16, 2020.
U.S. Appl. No. 16/128,450 Office Action dated Sep. 19, 2019.
U.S. Appl. No. 16/129,694 Office Action dated May 30, 2019.
U.S. Appl. No. 16/129,694 Office Action dated Nov. 19, 2018.
U.S. Appl. No. 16/129,696 Miscellaneous Communication re: Third Party Submission dated Jul. 3, 2019.
U.S. Appl. No. 16/129,696 Office Action dated Apr. 13, 2020.
U.S. Appl. No. 16/129,696 Office Action dated Apr. 17, 2019.
U.S. Appl. No. 16/129,696 Office Action dated Dec. 14, 2020.
U.S. Appl. No. 16/129,696 Office Action dated Sep. 19, 2019.
U.S. Appl. No. 16/152,324 Office Action dated Oct. 16, 2020.
U.S. Appl. No. 16/435,422 Miscellaneous Communication re: Third Party Submission dated Apr. 1, 2020.
U.S. Appl. No. 16/435,422 Office Action dated Jul. 2, 2020.
U.S. Appl. No. 16/435,422 Office Action dated Oct. 31, 2019.
U.S. Appl. No. 16/718,092 Miscellaneous Communication re: Third Party Submission dated Oct. 27, 2020.
U.S. Serial No. 17/024,624 Office Action dated Jul. 6, 2021.
U.S. Appl. No. 17/024,624 3rd Party Submission filed Feb. 23, 2021.
U.S. Appl. No. 17/024,624 Office Action dated Mar. 19, 2021.
U.S. Appl. No. 17/187,650 Office Action dated May 20, 2021.
U.S. Appl. No. 16/435,422 Office Action dated Apr. 15, 2020.
Usman et al. Exploiting the chemical synthesis of RNA. Trends Biochem Sci 17:334-339 (1992).
Valtorta et al. KRAS gene amplification in colorectal cancer and impact on response to EGFR-targeted therapy. Int J Cancer 133:1259-1266 (2013).
Van Deutekom et al. Antisense-induced exon skipping restores dystrophin expression in DMD patient derived muscle cells. Hum Mol Genet. 10(15):1547-54 (2001).
Van Vliet et al. Assessment of the feasibility of exon 45-55 multiexon skipping for duchenne muscular dystrophy. BMC Medical Genetics 9:105 (2008).
Verma et al. Modified oligonucleotides: synthesis and strategy for users. Annu Rev Biochem 67:99-134 (1998).
Vickers et al. Efficient Reduction of Target RNAs by Small Interfering RNA and RNase H-dependent Antisense Agents. J. Biol. Chem 278:7108-7118 (2003).
Walker et al. Improved cellular delivery of antisense oligonucleotides using transferrin receptor antibody-oligonucleotide conjugates. Pharmaceutical research 12(10):1548-1553 (1995).
Ward et al. Binding activities of a repertoire of single immunoglobulin variable domains secreted from *Escherichia coli*. Nature 341(6242):544-546 (1989).

(56) References Cited

OTHER PUBLICATIONS

Watts et al. Chemically modified siRNA: tools and applications. Drug Discov Today 13(19-20):842-855 (2008).

Wigler et al. Transfer of purified herpes virus thymidine kinase gene to cultured mouse cells. Cell 11:223-232 (1977).

Wigler et al. Transformation of mammalian cells with an amplifiable dominant-acting gene. PNAS USA 77:3567-3570 (1980).

Winkler. Oligonucleotide conjugates for therapeutic applications. Ther Del 4(7):791-809 (2013).

Wong et al. Co-injection of a targeted, reversibly masked endosomolytic polymer dramatically improves the efficacy of cholesterol-conjugated small interfering RNAs in vivo. Nucleic Acid Ther 22(6):380-390 (2012).

Wu et al. Building complex glycopeptides: Development of a cysteine-free native chemical ligation protocol. Angew. Chem. Int. Ed. 45:4116-4125 (2006).

Wu et al. Cell-penetrating peptides as transporters for morpholino oligomers: effects of amino acid composition on intracellular delivery and cytotoxicity. Nucleic Acids Res 35(15):5182-5191 (2007).

Wu et al. Delivery systems for gene therapy. Biotherapy 3:87-95 (1991).

Wu et al. Site-specific chemical modification of recombinant proteins produced in mammalian cells by using the genetically encoded aldehyde tag. PNAS USA 106(9):3000-3005 (2009).

Xia et al. Intravenous siRNA of brain cancer with receptor targeting and avidin-biotin technology. Pharm Res 24(12):2309-16 (2007).

Xu et al. Delivery systems for siRNA drug development in cancer therapy. Asian Journal of Pharmaceutical Sciences 10(1):1-12 (2015).

Yazdi et al. Influence of cellular trafficking on protein synthesis inhibition of immunotoxins directed against the transferrin receptor. Cancer Res 55:3763-3771 (1995).

Yessine et al. Characterization of the membrane-destabilizing properties of different pH-sensitive methacrylic acid copolymers. Biochimica et Biophysica Acta 1613:28-38 (2003).

Yuan et al. Development of siRNA payloads to target KRAS-mutant cancer. Cancer Discov 4(10):1182-1197 (2014).

Zhang et al. A remote arene-binding site on prostate specific membrane antigen revealed by antibody-recruiting small molecules. J Am Chem Soc. 132(36):12711-12716 (2010).

Khan et al. Silencing Myostatin Using Cholesterol-conjugated siRNAs Induces Muscle Growth. Molecular Therapy—Nucleic Acids 5:e342 (2016).

U.S. Appl. No. 16/649,572 Miscellaneous Communication re: Third Party Submission dated Mar. 19, 2021.

U.S. Appl. No. 17/214,525 Office Action dated Jan. 27, 2022.

U.S. Appl. No. 17/464,618 Office Action dated Jan. 31, 2022.

U.S. Appl. No. 17/499,796 Office Action dated Dec. 3, 2021.

U.S. Appl. No. 17/499,800 Office Action dated Feb. 10, 2022.

Vignaud et al. Progressive skeletal muscle weakness in transgenic mice expressing CTG expansions is associated with the activation of the ubiquitin-proteasome pathway. Neuromuscul Disord. 20(5):319-25 (2010).

\* cited by examiner

Cholesterol-siRNA conjugate with cholesterol at 5' end of the passanger strand

| Group | Test Article | N | siRNA Dose (mg/kg) | Dose Volume (mL/kg) | # of Doses | Harvest Time (h) |
|---|---|---|---|---|---|---|
| 1 | TfR-mAb-HPRT-PEG5k (n=1) | 4 | 3 | 5.0 | 1 | 96 |
| 2 | TfR-mAb-HPRT-PEG5k (n=1) | 4 | 1 | 5.0 | 1 | 96 |
| 3 | TfR-mAb-HPRT-PEG5k (n=1) | 4 | 0.3 | 5.0 | 1 | 96 |
| 4 | TfR-mAb-HPRT-PEG5k (n=1) | 4 | 0.1 | 5.0 | 1 | 96 |
| 5 | IgG2a-mAb-HPRT-PEG5k (n=1) | 4 | 3 | 5.0 | 1 | 96 |
| 6 | IgG2a-mAb-HPRT-PEG5k (n=1) | 4 | 1 | 5.0 | 1 | 96 |
| 7 | IgG2a-mAb-HPRT-PEG5k (n=1) | 4 | 0.3 | 5.0 | 1 | 96 |
| 8 | IgG2a-mAb-HPRT-PEG5k (n=1) | 4 | 0.1 | 5.0 | 1 | 96 |
| 9 | TfR-mAb-MSTN-PEG5k (n=1) | 4 | 3 | 5.0 | 1 | 96 |
| 10 | TfR-mAb-MSTN-PEG5k (n=1) | 4 | 1 | 5.0 | 1 | 96 |
| 11 | TfR-mAb-MSTN-PEG5k (n=1) | 4 | 0.3 | 5.0 | 1 | 96 |
| 12 | TfR-mAb-MSTN-PEG5k (n=1) | 4 | 0.1 | 5.0 | 1 | 96 |
| 13 | IgG2a-mAb-MSTN-PEG5k (n=1) | 4 | 3 | 5.0 | 1 | 96 |
| 14 | IgG2a-mAb-MSTN-PEG5k (n=1) | 4 | 1 | 5.0 | 1 | 96 |
| 15 | IgG2a-mAb-MSTN-PEG5k (n=1) | 4 | 0.3 | 5.0 | 1 | 96 |
| 16 | IgG2a-mAb-MSTN-PEG5k (n=1) | 4 | 0.1 | 5.0 | 1 | 96 |
| 17 | TfR-mAb-scramble-PEG5k (n=1) | 4 | 3 | 5.0 | 1 | 96 |
| 18 | TfR-mAb-scramble-PEG5k (n=1) | 4 | 1 | 5.0 | 1 | 96 |
| 19 | TfR-mAb-scramble-PEG5k (n=1) | 4 | 0.3 | 5.0 | 1 | 96 |
| 20 | TfR-mAb-scramble-PEG5k (n=1)=1) | 4 | 0.1 | 5.0 | 1 | 96 |
| 21 | PBS Control | 5 | - | 5.0 | 1 | 96 |

85  WT mice (CD-1)

FIG. 9A

| Group | Test Article | N | siRNA Dose (mg/kg) | # of Doses | Survival Bleed (h) | Terminal Bleed (h) | Harvest Time (h) |
|---|---|---|---|---|---|---|---|
| 1 | TfR-mAb-MSTN (n=1) | 4 | 3 | 1 | 0.25 | 24 | 24 |
| 2 | TfR-mAb-MSTN (n=1) | 4 | 3 | 1 | 1 | 96 | 96 |
| 3 | TfR-mAb-MSTN (n=1) | 4 | 3 | 1 | 2 | 168 | 168 |
| 4 | TfR-mAb-MSTN (n=1) | 4 | 3 | 1 | 4 | 336 | 336 |
| 5 | TfR-mAb-scramble (n=1) | 4 | 3 | 1 | 0.25 | 24 | 24 |
| 6 | TfR-mAb-scramble (n=1) | 4 | 3 | 1 | 1 | 96 | 96 |
| 7 | TfR-mAb-scramble (n=1) | 4 | 3 | 1 | 2 | 168 | 168 |
| 8 | TfR-mAb-scramble (n=1) | 4 | 3 | 1 | 4 | 336 | 336 |
| 9 | PBS Control | 4 | - | 1 | - | - | 24 |
| 10 | PBS Control | 4 | - | 1 | - | - | 96 |
| 11 | PBS Control | 4 | - | 1 | - | - | 168 |
| 12 | PBS Control | 4 | - | 1 | - | - | 336 |
| 13 | TfR-mAb-MSTN (n=1) | 5 | 3 | 1 | 504 | 840 | 840 |
| 14 | TfR-mAb-MSTN (n=1) | 5 | 3 | 1 | 672 | 1,008 | 1,008 |
| 15 | PBS Control | 5 | - | 1 | 504 | 840 | 840 |
| 16 | PBS control | 5 | - | 1 | 672 | 1,008 | 1,008 |

FIG. 10A

| Group | Test Article | N | siRNA Dose (mg/kg) | Dose Volume (mL/kg) | # of Doses | Dose Schedule | Harvest Time (h) |
|---|---|---|---|---|---|---|---|
| 1 | TfR-Fab-MSTN* (n=1) | 4 | 6 | 5.0 | 1 | t=0 | 96 |
| 2 | TfR-Fab-MSTN* (n=1) | 4 | 2 | 5.0 | 1 | t=0 | 96 |
| 3 | TfR-Fab-MSTN* (n=1) | 4 | 0.6 | 5.0 | 1 | t=0 | 96 |
| 4 | TfR-Fab-MSTN* (n=1) | 4 | 0.2 | 5.0 | 1 | t=0 | 96 |
| 5 | EGFR-Fab-MSTN* (n=1) | 4 | 6 | 5.0 | 1 | t=0 | 96 |
| 6 | EGFR-Fab-MSTN* (n=1) | 4 | 2 | 5.0 | 1 | t=0 | 96 |
| 7 | EGFR-Fab-MSTN* (n=1) | 4 | 0.6 | 5.0 | 1 | t=0 | 96 |
| 8 | EGFR-Fab-MSTN* (n=1) | 4 | 0.2 | 5.0 | 1 | t=0 | 96 |
| 9 | TfR-mAb-MSTN (n=1) | 4 | 3 | 5.0 | 1 | t=0 | 96 |
| 10 | TfR-mAb-MSTN (n=1) | 4 | 1 | 5.0 | 1 | t=0 | 96 |
| 11 | TfR-mAb-MSTN (n=1) | 4 | 0.3 | 5.0 | 1 | t=0 | 96 |
| 12 | TfR-mAb-MSTN (n=1) | 4 | 0.1 | 5.0 | 1 | t=0 | 96 |
| 13 | TfR-mAb-MSTN (n=2) | 4 | 6 | 5.0 | 1 | t=0 | 96 |
| 14 | TfR-mAb-MSTN (n=2) | 4 | 2 | 5.0 | 1 | t=0 | 96 |
| 15 | TfR-mAb-MSTN (n=2) | 4 | 0.6 | 5.0 | 1 | t=0 | 96 |
| 16 | TfR-mAb-MSTN (n=2) | 4 | 0.2 | 5.0 | 1 | t=0 | 96 |
| 17 | EGFR-mAb-MSTN* (n=1) | 4 | 2.6 | 5.0 | 1 | t=0 | 96 |
| 18 | EGFR-mAb-MSTN* (n=1) | 4 | 1 | 5.0 | 1 | t=0 | 96 |
| 19 | EGFR-mAb-MSTN* (n=2) | 4 | 3 | 5.0 | 1 | t=0 | 96 |
| 20 | EGFR-mAb-MSTN* (n=2) | 4 | 1 | 5.0 | 1 | t=0 | 96 |
| 21 | PBS Control | 5 | - | 5.0 | 1 | t=0 | 96 |

85 | WT mice (CD-1)

FIG. 11A

| Group | Test Article | N | siRNA Dose (mg/kg) | Dose Volume (mL/kg) | Dose Schedule | Harvest Time (h) |
|---|---|---|---|---|---|---|
| 1 | Chol-MSTN Control | 4 | 60 | 5.0 | t=0 | 96 |
| 2 | Chol-MSTN Control | 4 | 20 | 5.0 | t=0 | 96 |
| 3 | Chol-MSTN Control | 4 | 6 | 5.0 | t=0 | 96 |
| 4 | Chol-MSTN Control | 4 | 2 | 5.0 | t=0 | 96 |
| 5 | TfR-Fab-MSTN* (n=1) | 4 | 6 | 5.0 | t=0 | 96 |
| 6 | TfR-Fab-MSTN* (n=1) | 4 | 2 | 5.0 | t=0 | 96 |
| 7 | TfR-Fab-MSTN* (n=1) | 4 | 0.6 | 5.0 | t=0 | 96 |
| 8 | TfR-Fab-MSTN* (n=1) | 4 | 0.2 | 5.0 | t=0 | 96 |
| 9 | TfR-mAb-MSTN* (n=1) | 4 | 3 | 5.0 | t=0 | 96 |
| 10 | TfR-mAb-MSTN* (n=1) | 4 | 1 | 5.0 | t=0 | 96 |
| 11 | TfR-mAb-MSTN* (n=1) | 4 | 0.3 | 5.0 | t=0 | 96 |
| 12 | TfR-mAb-MSTN* (n=1) | 4 | 0.1 | 5.0 | t=0 | 96 |
| 13 | TfR-mAb-MSTN (n=1) | 4 | 3 | 5.0 | t=0 | 96 |
| 14 | TfR-mAb-MSTN (n=1) | 4 | 1 | 5.0 | t=0 | 96 |
| 15 | TfR-mAb-MSTN (n=1) | 4 | 0.3 | 5.0 | t=0 | 96 |
| 16 | TfR-mAb-MSTN (n=1) | 4 | 0.1 | 5.0 | t=0 | 96 |
| 17 | TfR-mAb-scramble (n=1) | 4 | 3 | 5.0 | t=0 | 96 |
| 18 | TfR-mAb-scramble (n=1) | 4 | 1 | 5.0 | t=0 | 96 |
| 19 | TfR-mAb-scramble (n=1) | 4 | 0.3 | 5.0 | t=0 | 96 |
| 20 | TfR-mAb-scramble (n=1) | 4 | 0.1 | 5.0 | t=0 | 96 |
| 21 | PBS Control | 5 | - | 5.0 | t=0 | 96 |

| 85 | WT mice (CD-1) |
|---|---|

FIG. 12A

| Group | Test Article | N | siRNA Dose (mg/kg) | Survival Bleed (day) | Terminal Bleed (day) | Harvest Time (day) |
|---|---|---|---|---|---|---|
| 1 | Chol-MSTN | 5 | 50 | 7 | 14 | 14 |
| 2 | Chol-MSTN | 5 | 50 | 21 | 28 | 28 |
| 3 | Chol-MSTN | 5 | 50 | 35 | 42 | 42 |
| 4 | Chol-MSTN | 5 | 50 | 49 | 56 | 56 |
| 5 | TfR-mAb-MSTN (n=1) | 5 | 3 | 7 | 14 | 14 |
| 6 | TfR-mAb-MSTN (n=1) | 5 | 3 | 21 | 28 | 28 |
| 7 | TfR-mAb-MSTN (n=1) | 5 | 3 | 35 | 42 | 42 |
| 8 | TfR-mAb-MSTN (n=1) | 5 | 3 | 49 | 56 | 56 |
| 9 | TfR-mAb-MSTN (n=2) | 5 | 3 | 7 | 14 | 14 |
| 10 | TfR-mAb-MSTN (n=2) | 5 | 3 | 21 | 28 | 28 |
| 11 | TfR-mAb-MSTN (n=2) | 5 | 3 | 35 | 42 | 42 |
| 12 | TfR-mAb-MSTN (n=2) | 5 | 3 | 49 | 56 | 56 |
| 13 | TfR-mAb-scramble (n=1) | 5 | 3 | 7 | 14 | 14 |
| 14 | TfR-mAb-scramble (n=1) | 5 | 3 | 21 | 28 | 28 |
| 15 | TfR-mAb-scramble (n=1) | 5 | 3 | 35 | 42 | 42 |
| 16 | TfR-mAb-scramble (n=1) | 5 | 3 | 49 | 56 | 56 |
| 17 | PBS Control | 5 | - | 7 | 14 | 14 |
| 18 | PBS Control | 5 | - | 21 | 28 | 28 |
| 19 | PBS Control | 5 | - | 35 | 42 | 42 |
| 20 | PBS Control | 5 | - | 49 | 56 | 56 |

FIG. 13A

| Group | Test Article | N | each siRNA Dose (mg/kg) | siRNA Mixture (mg/kg) | Harvest Time (h) | Final siRNA dose (mg/kg) |
|---|---|---|---|---|---|---|
| 1 | TfR-mAb-HPRT(n=1) | 4 | 3 | | 96 | 3 |
| 2 | TfR-mAb-HPRT(n=1) | 4 | 1 | | 96 | 1 |
| 3 | TfR-mAb-HPRT(n=1) | 4 | 0.3 | | 96 | 0.3 |
| 4 | TfR-mAb-HPRT(n=1) | 4 | 0.1 | | 96 | 0.1 |
| 5 | TfR-mAb-SSB (n=1) | 4 | 3 | | 96 | 3 |
| 6 | TfR-mAb-SSB (n=1) | 4 | 1 | | 96 | 1 |
| 7 | m TfR-mAb-SSB (n=1) | 4 | 0.3 | | 96 | 0.3 |
| 8 | TfR-mAb-SSB (n=1) | 4 | 0.1 | | 96 | 0.1 |
| 9 | TfR-mAb-HPRT (n=1) + TfR-mAb-SSB (n=1) | 4 | 3 | | 96 | 6 |
| 10 | TfR-mAb-HPRT (n=1) + TfR-mAb-SSB (n=1) | 4 | 1 | | 96 | 2 |
| 11 | TfR-mAb-HPRT (n=1) + TfR-mAb-SSB (n=1) | 4 | 0.3 | | 96 | 0.6 |
| 12 | TfR-mAb-HPRT (n=1) + TfR-mAb-SSB (n=1) | 4 | 0.1 | | 96 | 0.2 |
| 13 | TfR-mAb-HPRT/SSB(1:1) (n=2) | 4 | | 3 | 96 | 6 |
| 14 | TfR-mAb-HPRT/SSB(1:1) (n=2) | 4 | | 1 | 96 | 2 |
| 15 | TfR-mAb-HPRT/SSB(1:1) (n=2) | 4 | | 0.3 | 96 | 0.6 |
| 16 | TfR-mAb-HPRT/SSB(1:1) (n=2) | 4 | | 0.1 | 96 | 0.2 |
| | PBS Control | 5 | - | | 96 | |

FIG. 14A

| Group | Test Article | N | siRNA Dose (mg/kg) | Harvest Time (h) |
|---|---|---|---|---|
| 1 | TfR-mAb-mAtrogin#1179(n=1) | 4 | 3 | 96 |
| 2 | TfR-mAb-mAtrogin#1179(n=1) | 4 | 1 | 96 |
| 3 | TfR-mAb-mAtrogin#1179(n=1) | 4 | 0.3 | 96 |
| 4 | TfR-mAb-mAtrogin#1179(n=1) | 4 | 0.1 | 96 |
| 5 | TfR-mAb-mAtrogin#1504 (n=1) | 4 | 3 | 96 |
| 6 | TfR-mAb-mAtrogin#1504 (n=1) | 4 | 1 | 96 |
| 7 | TfR-mAb-mAtrogin#1504 (n=1) | 4 | 0.3 | 96 |
| 8 | TfR-mAb-mAtrogin#1504 (n=1) | 4 | 0.1 | 96 |
| 9 | TfR-mAb-m/hAtrogin#631 (n=1) | 4 | 3 | 96 |
| 10 | TfR-mAb-m/hAtrogin#631 (n=1) | 4 | 1 | 96 |
| 11 | TfR-mAb-m/hAtrogin#631 (n=1) | 4 | 0.3 | 96 |
| 12 | TfR-mAb-m/hAtrogin#631 (n=1) | 4 | 0.1 | 96 |
| 13 | TfR-mAb-m/hAtrogin#586 (n=1) | 4 | 3 | 96 |
| 14 | TfR-mAb-m/hAtrogin#586 (n=1) | 4 | 1 | 96 |
| 15 | TfR-mAb-m/hAtrogin#586 (n=1) | 4 | 0.3 | 96 |
| 16 | TfR-mAb-m/hAtrogin#586 (n=1) | 4 | 0.1 | 96 |
| 17 | PBS Control | 5 | - | 96 |

FIG. 15A

| Group | Test Article | N | siRNA Dose (mg/kg) | Harvest Time (h) |
|---|---|---|---|---|
| 1 | TfR-mAb-MuRF1#651(n=1) | 4 | 3 | 96 |
| 2 | TfR-mAb-MuRF1#651(n=1) | 4 | 1 | 96 |
| 3 | TfR-mAb-MuRF1#651(n=1) | 4 | 0.3 | 96 |
| 4 | TfR-mAb-MuRF1#651(n=1) | 4 | 0.1 | 96 |
| 5 | TfR-mAb-MuRF1#1387 (n=1) | 4 | 3 | 96 |
| 6 | TfR-mAb-MuRF1#1387 (n=1) | 4 | 1 | 96 |
| 7 | TfR-mAb-MuRF1#1387 (n=1) | 4 | 0.3 | 96 |
| 8 | TfR-mAb-MuRF1#1387 (n=1) | 4 | 0.1 | 96 |
| 9 | TfR-mAb-MuRF1#1454 (n=1) | 4 | 3 | 96 |
| 10 | TfR-mAb-MuRF1#1454 (n=1) | 4 | 1 | 96 |
| 11 | TfR-mAb-MuRF1#1454 (n=1) | 4 | 0.3 | 96 |
| 12 | TfR-mAb-MuRF1#1454 (n=1) | 4 | 0.1 | 96 |
| 13 | TfR-mAb-MuRF1#1660 (n=1) | 4 | 3 | 96 |
| 14 | TfR-mAb-MuRF1#1660 (n=1) | 4 | 1 | 96 |
| 15 | TfR-mAb-MuRF1#1660 (n=1) | 4 | 0.3 | 96 |
| 16 | TfR-mAb-MuRF1#1660 (n=1) | 4 | 0.1 | 96 |
| 17 | PBS Control | 5 | - | 96 |

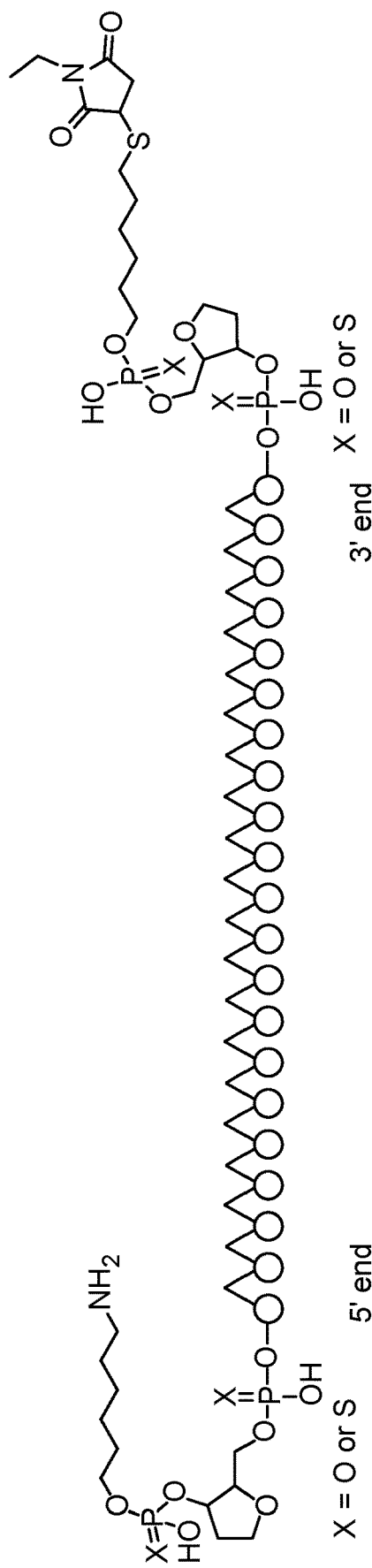
FIG. 20A
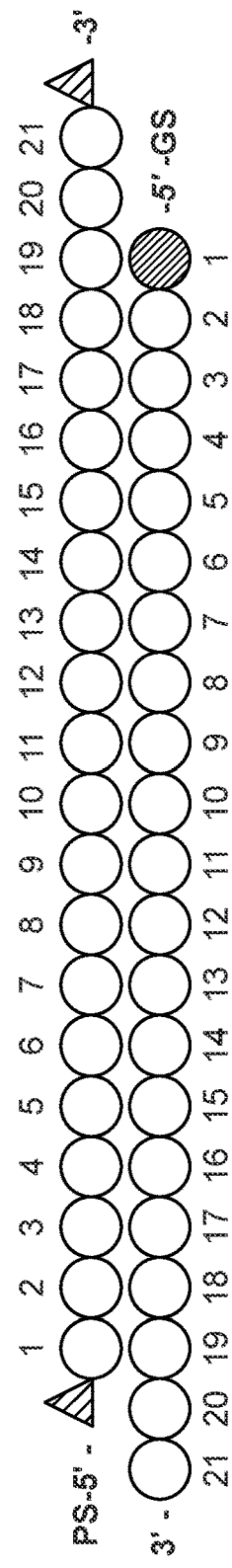
FIG. 20B

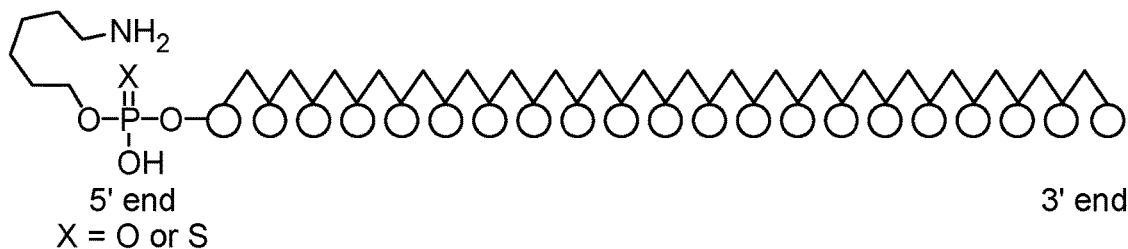
5' end  
X = O or S
3' end
FIG. 21A
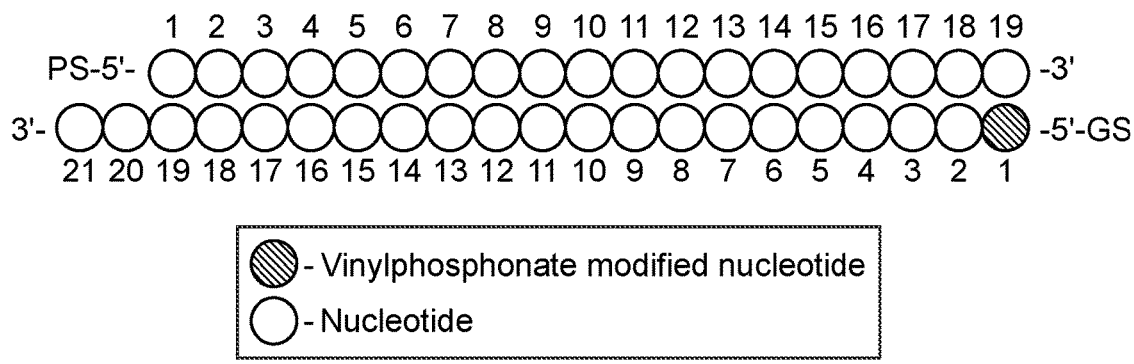
- Vinylphosphonate modified nucleotide
- Nucleotide
FIG. 21B
| Group | Test Article | N | siRNA Dose (mg/kg) | Dose Volume (mL/kg) | Harvest Time (h) |
|---|---|---|---|---|---|
| 1 | mTfR1-mAb-Atrogin-1 (DAR1) | 4 | 3 | 5.0 | 96 |
| 2 | mTfR1-mAb-Atrogin-1 (DAR1) | 4 | 3 | 5.0 | 7 days |
| 3 | mTfR1-mAb-Atrogin-1 (DAR1) | 4 | 3 | 5.0 | 14 days |
| 4 | mTfR1-mAb-Atrogin-1 (DAR1) | 4 | 3 | 5.0 | 21 days |
| 5 | PBS Control | 4 | - | 5.0 | 96 |
| 6 | PBS Control | 4 | - | 5.0 | 7 days |
| 7 | PBS Control | 4 | - | 5.0 | 14 days |
| 8 | PBS Control | 4 | - | 5.0 | 21 days |
FIG. 22

| Group | Test Article | N | siRNA Dose (mg/kg) | Dose Volume (mL/kg) | Harvest Time (h) |
|---|---|---|---|---|---|
| 1 | mTfR1-mAb-MuRF1(R2089) (DAR1) | 4 | 3 | 5.0 | 96 |
| 2 | mTfR1-mAb-MuRF1(R2089) (DAR1) | 4 | 1 | 5.0 | 96 |
| 3 | mTfR1-mAb-MuRF1(R2265) (DAR1) | 4 | 3 | 5.0 | 96 |
| 4 | mTfR1-mAb-MuRF1(R2265) (DAR1) | 4 | 1 | 5.0 | 96 |
| 5 | mTfR1-mAb-MuRF1(R2265) (DAR1) | 4 | 0.3 | 5.0 | 96 |
| 6 | mTfR1-mAb-MuRF1(R2265) (DAR1) | 4 | 0.1 | 5.0 | 96 |
| 7 | mTfR1-mAb-MuRF1(R2266) (DAR1) | 4 | 3 | 5.0 | 96 |
| 8 | mTfR1-mAb-MuRF1(R2266) (DAR1) | 4 | 1 | 5.0 | 96 |
| 9 | mTfR1-mAb-MuRF1(R2266) (DAR1) | 4 | 0.3 | 5.0 | 96 |
| 10 | mTfR1-mAb-MuRF1(R2266) (DAR1) | 4 | 0.1 | 5.0 | 96 |
| 11 | mTfR1-mAb-MuRF1(R2267) (DAR1) | 4 | 3 | 5.0 | 96 |
| 12 | mTfR1-mAb-MuRF1(R2267) (DAR1) | 4 | 1 | 5.0 | 96 |
| 13 | mTfR1-mAb-MuRF1(R2267) (DAR1) | 4 | 0.3 | 5.0 | 96 |
| 14 | mTfR1-mAb-MuRF1(R2267) (DAR1) | 4 | 0.1 | 5.0 | 96 |
| 15 | mTfR1-mAb-MuRF1(R2268) (DAR1) | 4 | 3 | 5.0 | 96 |
| 16 | mTfR1-mAb-MuRF1(R2268) (DAR1) | 4 | 1 | 5.0 | 96 |
| 27 | mTfR1-mAb-MuRF1(R2268) (DAR1) | 4 | 0.3 | 5.0 | 96 |
| 18 | mTfR1-mAb-MuRF1(R2268) (DAR1) | 4 | 0.1 | 5.0 | 96 |
| 19 | mTfR1-mAb-MuRF1(R2269) (DAR1) | 4 | 3 | 5.0 | 96 |
| 20 | mTfR1-mAb-MuRF1(R2269) (DAR1) | 4 | 1 | 5.0 | 96 |
| 21 | mTfR1-mAb-MuRF1(R2269) (DAR1) | 4 | 0.3 | 5.0 | 96 |
| 22 | mTfR1-mAb-MuRF1(R2269) (DAR1) | 4 | 0.1 | 5.0 | 96 |
| 23 | PBS Control | 5 | - | 5.0 | 96 |

FIG. 25

| Group | ASC | Atrophy | N | siRNA Dose (mg/kg) | siRNA:mAb Ratio (mol/mol) | Dose Volume (mL/kg) | # of Doses | Harvest Time (day post Dex) |
|---|---|---|---|---|---|---|---|---|
| 1 | TfR1-Atrogin-1 DAR1 | | 4 | 9 | 1.0 | 5.0 | 1 | 0 |
| 2 | TfR1-Atrogin-1 DAR1 | + PBS | 4 | 9 | 1.0 | 5.0 | 1 | 3 |
| 3 | TfR1-Atrogin-1 DAR1 | + Dex | 4 | 9 | 1.0 | 5.0 | 1 | 3 |
| 4 | TfR1-Atrogin-1 DAR1 | | 4 | 3 | 1.0 | 5.0 | 1 | 0 |
| 5 | TfR1-Atrogin-1 DAR1 | + PBS | 4 | 3 | 1.0 | 5.0 | 1 | 3 |
| 6 | TfR1-Atrogin-1 DAR1 | + Dex | 4 | 3 | 1.0 | 5.0 | 1 | 3 |
| 7 | TfR1-Atrogin-1 DAR1 | | 4 | 1 | 1.0 | 5.0 | 1 | 0 |
| 8 | TfR1-Atrogin-1 DAR1 | + PBS | 4 | 1 | 1.0 | 5.0 | 1 | 3 |
| 9 | TfR1-Atrogin-1 DAR1 | + Dex | 4 | 1 | 1.0 | 5.0 | 1 | 3 |
| 10 | TfR1-Scramble DAR1 | | 4 | 9 | 1.0 | 5.0 | 1 | 0 |
| 11 | TfR1-Scramble DAR1 | + PBS | 4 | 9 | 1.0 | 5.0 | 1 | 3 |
| 12 | TfR1-Scramble DAR1 | + Dex | 4 | 9 | 1.0 | 5.0 | 1 | 3 |
| 13 | TfR1-Scramble DAR1 | | 4 | 3 | 1.0 | 5.0 | 1 | 0 |
| 14 | TfR1-Scramble DAR1 | + PBS | 4 | 3 | 1.0 | 5.0 | 1 | 3 |
| 15 | TfR1-Scramble DAR1 | + Dex | 4 | 3 | 1.0 | 5.0 | 1 | 3 |
| 16 | PBS Control | | 5 | - | - | 5.0 | 1 | 0 |

FIG. 32

| Group | ASC | N | Total siRNA Dose (mg/kg) | Dose Volume (mL/kg) | Harvest Time (day post ASC) | Harvest Time (day post DEN) |
|---|---|---|---|---|---|---|
| 1 | TfR1-Atrogin-1 DAR1 | 4 | 4.5 | 5.0 | 7 | 0 |
| 2 | TfR1-Atrogin-1 DAR1 | 4 | 4.5 | 5.0 | 10 | 3 |
| 3 | TfR1-Atrogin-1 DAR1 | 4 | 4.5 | 5.0 | 17 | 10 |
| 4 | TfR1-Atrogin-1 DAR1 | 8 | 4.5 | 5.0 | 28 | 21 |
| 5 | TfR1-MuRF1 DAR1 | 4 | 4.5 | 5.0 | 7 | 0 |
| 6 | TfR1-MuRF1 DAR1 | 4 | 4.5 | 5.0 | 10 | 3 |
| 7 | TfR1-MuRF1 DAR1 | 4 | 4.5 | 5.0 | 17 | 10 |
| 8 | TfR1-MuRF1 DAR1 | 8 | 4.5 | 5.0 | 28 | 21 |
| 9 | TfR1-Atrogin-1 + TfR1-MuRF1 DAR1 | 4 | 9 | 5.0 | 7 | 0 |
| 10 | TfR1-Atrogin-1 + TfR1-MuRF1 DAR1 | 4 | 9 | 5.0 | 10 | 3 |
| 11 | TfR1-Atrogin-1 + TfR1-MuRF1 DAR1 | 4 | 9 | 5.0 | 17 | 10 |
| 12 | TfR1-Atrogin-1 + TfR1-MuRF1 DAR1 | 8 | 9 | 5.0 | 28 | 21 |
| 13 | TfR1-SC DAR1 | 4 | 4.5 | 5.0 | 7 | 0 |
| 14 | TfR1-SC DAR1 | 4 | 4.5 | 5.0 | 10 | 3 |
| 15 | TfR1-SC DAR1 | 4 | 4.5 | 5.0 | 17 | 10 |
| 16 | TfR1-SC DAR1 | 8 | 4.5 | 5.0 | 28 | 21 |
| 17 | PBS Control | 5 | - | 5.0 | 7 | 0 |

FIG. 38

Treatment-induced % Sparing of Muscle Wasting
(Leg muscle area)

| days post dose | days post denervation | MuRF1 | Atrogin-1 + MuRF1 |
|---|---|---|---|
| 16 | 9 | 29.0 | 34.7 |
| 20 | 13 | 32.0 | 33.4 |
| 23 | 16 | 31.0 | 24.5 |
| 27 | 20 | 24.5 | 26.3 |
| 32 | 25 | 20.2 | 16.2 |
| 34 | 27 | 14.2 | 18.2 |

FIG. 39E

Treatment-induced % Sparing of Muscle Wasting
(Gastrocnemius weight)

| days post dose | days post denervation | MuRF1 |
|---|---|---|
| 17 | 10 | 35.2 |
| 35 | 28 | 17.1 |

FIG. 39F

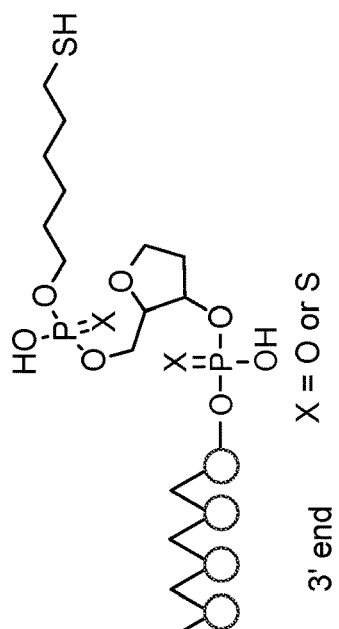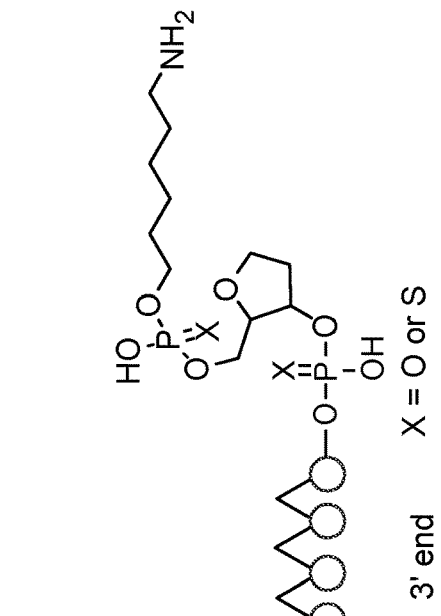
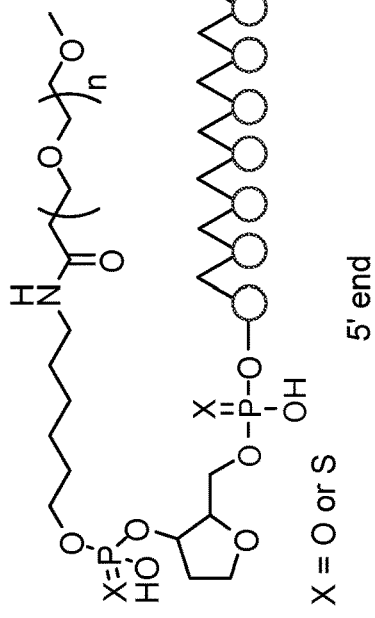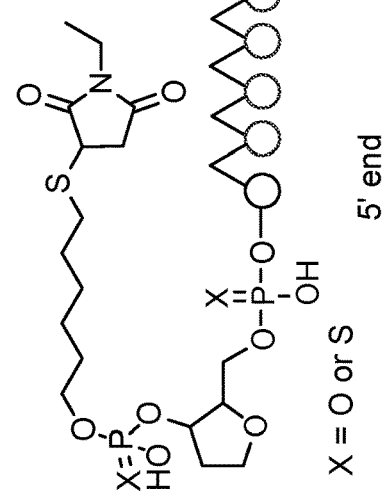
FIG. 40E
FIG. 40F

COMPOSITIONS AND METHODS OF TREATING MUSCLE ATROPHY AND MYOTONIC DYSTROPHY

CROSS-REFERENCE

This application is a divisional of U.S. application Ser. No. 17/024,624, filed on Sep. 17, 2020, which is a continuation of U.S. application Ser. No. 16/435,422, filed Jun. 7, 2019, which is a continuation of PCT Application No. PCT/US2018/064359, filed Dec. 6, 2018, which claims priority to U.S. Provisional Application No. 62/595,545, filed Dec. 6, 2017, and U.S. Provisional Application No. 62/725,883, filed Aug. 31, 2018, which each of the applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 7, 2019, is named 45532-722_402_SL txt and is 3,143,549 bytes in size.

BACKGROUND OF THE DISCLOSURE

Gene suppression by RNA-induced gene silencing provides several levels of control: transcription inactivation, small interfering RNA (siRNA)-induced mRNA degradation, and siRNA-induced transcriptional attenuation. In some instances, RNA interference (RNAi) provides long lasting effect over multiple cell divisions. As such, RNAi represents a viable method useful for drug target validation, gene function analysis, pathway analysis, and disease therapeutics.

SUMMARY OF THE DISCLOSURE

Disclosed herein, in certain embodiments, are polynucleic acid molecules and pharmaceutical compositions for modulating a gene associated with muscle atrophy (or an atrogene). In some embodiments, also described herein are methods of treating muscle atrophy with a polynucleic acid molecule or a polynucleic acid molecule conjugate disclosed herein.

Disclosed herein, in certain embodiments, is a molecule of Formula (I): A-$X_1$-B-$X_2$-C (Formula I) wherein, A is a binding moiety; B is a polynucleotide that hybridizes to a target sequence of an atrogene; C is a polymer, and $X_1$ and $X_2$ are each independently selected from a bond or a non-polymeric linker, wherein the polynucleotide comprises at least one 2' modified nucleotide, at least one modified internucleotide linkage, or at least one inverted abasic moiety; and wherein A and C are not attached to B at the same terminus. In some embodiments, the atrogene comprises a differentially regulated (e.g., an upregulated or downregulated) gene within the IGF1-Akt-FoxO pathway, the glucocorticoids-GR pathway, the PGC1α-FoxO pathway, the TNFα-NFκB pathway, or the myostatin-ActRIIb-Smad2/3 pathway. In some embodiments, the atrogene encodes an E3 ligase. In some embodiments, the atrogene encodes a Forkhead box transcription factor. In some embodiments, the atrogene comprises atrogin-1 gene (FBXO32), MuRF1 gene (TRIM63), FOXO1, FOXO3, or MSTN. In some embodiments, the atrogene comprises DMPK. In some embodiments, B consists of a polynucleotide that hybridizes to a target sequence of an atrogene. In some embodiments, C consists of a polymer. In some embodiments, the at least one 2' modified nucleotide comprises 2'-O-methyl, 2'-O-methoxyethyl (2'-O-MOE), 2'-O-aminopropyl, 2'-deoxy, T-deoxy-2-fluoro, 2-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2-O—N-methylacetamido (2'-O-NMA) modified nucleotide. In some embodiments, the at least one 2' modified nucleotide comprises locked nucleic acid (LNA) or ethylene nucleic acid (ENA). In some embodiments, the at least one modified internucleotide linkage comprises a phosphorothioate linkage or a phosphorodithioate linkage. In some embodiments, the at least one inverted abasic moiety is at at least one terminus. In some embodiments, the polynucleotide comprises a single strand which hybridizes to the target sequence of an atrogene. In some embodiments, the polynucleotide comprises a first polynucleotide and a second polynucleotide hybridized to the first polynucleotide to form a double-stranded polynucleic acid molecule, wherein either the first polynucleotide or the second polynucleotide also hybridizes to the target sequence of an atrogene. In some embodiments, the second polynucleotide comprises at least one modification. In some embodiments, the first polynucleotide and the second polynucleotide are RNA molecules. In some embodiments, the polynucleotide hybridizes to at least 8 contiguous bases of the target sequence of an atrogene. In some embodiments, the polynucleotide comprises a sequence that is at least 60%, 70%, 80%, 85%, 90%, 95%, or 99% complementary to a sequence as set forth in SEQ ID NOs: 28-141, 370-480, and 703-3406. In some embodiments, the polynucleotide is between about 8 and about 50 nucleotides in length. In some embodiments, the polynucleotide is between about 10 and about 30 nucleotides in length. In some embodiments, the first polynucleotide comprises a sequence having at least 80%, 85%, 90%, 95%, 96%, 97%, 98%, 99%, or 100% sequence identity to a sequence set forth in SEQ ID NOs: 142-255, 256-369, 481-591, 592-702, and 3407-14222. In some embodiments, the second polynucleotide comprises a sequence having at least 80%, 85%, 90%, 95%, 96%, 97%, 98%, 99%, or 100% sequence identity to a sequence as set forth in SEQ ID NOs: 142-255, 256-369, 481-591, 592-702, and 3407-14222. In some embodiments, $X_1$ and $X_2$ are independently a $C_1$-$C_6$ alkyl group. In some embodiments, $X_1$ and $X_2$ are independently a homobifunctional linker or a heterobifunctional linker, optionally conjugated to a $C_1$-$C_6$ alkyl group. In some embodiments, A is an antibody or binding fragment thereof. In some embodiments, A comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, A is an anti-transferrin receptor antibody or binding fragment thereof. In some embodiments, C is polyethylene glycol. In some embodiments, A-$X_1$ is conjugated to the 5' end of B and $X_2$—C is conjugated to the 3' end of B. In some embodiments, $X_2$—C is conjugated to the 5' end of B and A-$X_1$ is conjugated to the 3' end of B. In some embodiments, A is directly conjugated to $X_1$. In some embodiments, C is directly conjugated to $X_2$. In some embodiments, B is directly conjugated to $X_1$ and $X_2$. In some embodiments, the molecule further comprises D. In some embodiments, D is conjugated to C or to A. In some embodiments, D is an endosomolytic polymer.

Disclosed herein, in certain embodiments, is a polynucleic acid molecule conjugate comprising a binding moiety conjugated to a polynucleotide that hybridizes to a target sequence of an atrogene; wherein the polynucleotide optionally comprises at least one 2' modified nucleotide, at least one modified internucleotide linkage, or at least one inverted abasic moiety; and wherein the polynucleic acid molecule conjugate mediates RNA interference against the atrogene, thereby treating muscle atrophy in a subject. In some embodiments, the atrogene comprises a differentially regulated (e.g., an upregulated or downregulated)gene within the IGF1-Akt-FoxO pathway, the glucocorticoids-GR pathway, the PGC1α-FoxO pathway, the TNFα-NFκB pathway, or the myostatin-ActRIIb-Smad2/3 pathway. In some embodiments, the atrogene encodes an E3 ligase. In some embodiments, the atrogene encodes a Forkhead box transcription factor. In some embodiments, the atrogene comprises ligand of the TGF-beta (transforming growth factor-beta) superfamily of proteins. In some embodiments, the atrogene comprises DMPK. In some embodiments, the binding moiety is an antibody or binding fragment thereof. In some embodiments, the binding moiety comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, the binding moiety is an anti-transferrin receptor antibody or binding fragment thereof. In some embodiments, the binding moiety is cholesterol. In some embodiments, the polynucleotide comprises a single strand which hybridizes to the target sequence of an atrogene. In some embodiments, the polynucleotide comprises a first polynucleotide and a second polynucleotide hybridized to the first polynucleotide to form a double-stranded polynucleic acid molecule, wherein either the first polynucleotide or the second polynucleotide also hybridizes to the target sequence of an atrogene. In some embodiments, the second polynucleotide comprises at least one modification. In some embodiments, the first polynucleotide and the second polynucleotide are RNA molecules. In some embodiments, the polynucleotide hybridizes to at least 8 contiguous bases of the target sequence of an atrogene. In some embodiments, the polynucleotide comprises a sequence that is at least 60%, 70%, 80%, 85%, 90%, 95%, or 99% complementary to a sequence as set forth in SEQ ID NOs: 28-141, 370-480, and 703-3406. In some embodiments, the polynucleotide is between about 8 and about 50 nucleotides in length. In some embodiments, the polynucleotide is between about 10 and about 30 nucleotides in length. In some embodiments, the first poly nucleotide comprises a sequence having at least 80%, 85%, 90%, 95%, 96%, 97%, 98%, 99%, or 100% sequence identity to a sequence as set forth in SEQ ID NOs: 142-255, 256-369, 481-591, 592-702, and 3407-14222. In some embodiments, the second polynucleotide comprises a sequence having at least 80%, 85%, 90%, 95%, 96%, 97%, 98%, 99%, or 100% sequence identity to a sequence as set forth in SEQ ID NOs: 142-255, 256-369, 481-591, 592-702, and 3407-14222. In some embodiments, the polynucleic acid molecule conjugate optionally comprises a linker connecting the binding moiety to the polynucleotide. In some embodiments, the polynucleic acid molecule conjugate further comprises a polymer, optionally indirectly conjugated to the polynucleotide by an additional linker. In some embodiments, the linker and the additional linker are each independently a bond or a non-polymeric linker. In some embodiments, the polynucleic acid molecule conjugate comprises a molecule of Formula (I): A-X$_1$-B-X$_2$—C (Formula I) wherein, A is a binding moiety; B is a polynucleotide that hybridizes to a target sequence of an atrogene; C is a polymer, and X$_1$ and X$_2$ are each independently selected from a bond or a non-polymeric linker; wherein the polynucleotide comprises at least one 2' modified nucleotide, at least one modified internucleotide linkage, or at least one inverted abasic moiety; and wherein A and C are not attached to B at the same terminus. In some embodiments, the at least one 2' modified nucleotide comprises 2'-O-methyl, 2'-O-methoxyethyl (2'-O-MOE), 2'-O-aminopropyl, 2'-deoxy, T-deoxy-2'-fluoro, 2-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified nucleotide. In some embodiments, the at least one 2' modified nucleotide comprises locked nucleic acid (LNA) or ethylene nucleic acid (ENA). In some embodiments, the at least one modified internucleotide linkage comprises a phosphorothioate linkage or a phosphorodithioate linkage. In some embodiments, the at least one inverted abasic moiety is at at least one terminus. In some embodiments, the muscle atrophy is a diabetes-associated muscle atrophy. In some embodiments, the muscle atrophy is a cancer cachexia-associated muscle atrophy. In some embodiments, the muscle atrophy is associated with insulin deficiency. In some embodiments, the muscle atrophy is associated with chronic renal failure. In some embodiments, the muscle atrophy is associated with congestive heart failure. In some embodiments, the muscle atrophy is associated with chronic respiratory disease. In some embodiments, the muscle atrophy is associated with a chronic infection. In some embodiments, the muscle atrophy is associated with fasting. In some embodiments, the muscle atrophy is associated with denervation. In some embodiments, the muscle atrophy is associated with sarcopenia, glucocorticoid treatment, stroke, and/or heart attack. In some cases, myotonic dystrophy type 1 (DM1) is associated with an expansion of CTG repeats in the 3' UTR of the DMPK gene.

Disclosed herein, in certain embodiments, is a pharmaceutical composition comprising: a molecule described above or a polynucleic acid molecule conjugate described above; and a pharmaceutically acceptable excipient. In some embodiments, the pharmaceutical composition is formulated as a nanoparticle formulation. In some embodiments, the pharmaceutical composition is formulated for parenteral, oral, intranasal, buccal, rectal, or transdermal administration.

Disclosed herein, in certain embodiments, is a method of treating muscle atrophy or myotonic dystrophy in a subject in need thereof, comprising: administering to the subject a therapeutically effective amount of a polynucleic acid molecule conjugate comprising a binding moiety conjugated to a polynucleotide that hybridizes to a target sequence of an atrogene; wherein the polynucleotide optionally comprises at least one 2' modified nucleotide, at least one modified internucleotide linkage, or at least one inverted abasic moiety; and wherein the polynucleic acid molecule conjugate mediates RNA interference against the atrogene, thereby treating muscle atrophy or myotonic dystrophy in the subject. In some embodiments, the muscle atrophy is a diabetes-associated muscle atrophy. In some embodiments, the muscle atrophy is a cancer cachexia-associated muscle atrophy. In some embodiments, the muscle atrophy is associated with insulin deficiency. In some embodiments, the muscle atrophy is associated with chronic renal failure. In some embodiments, the muscle atrophy is associated with congestive heart failure. In some embodiments, the muscle atrophy is associated with chronic respiratory disease. In some embodiments, the muscle atrophy is associated with a chronic infection. In some embodiments, the muscle atrophy is associated with fasting. In some embodiments, the muscle atrophy is associated with denervation. In some embodiments, the muscle atrophy is associated with sarcopenia. In some embodiments, the myotonic dystrophy is DM1. In some embodiments, the atrogene comprises a differently regulated (e.g., an upregulated or downregulated) gene within the IGF1-Akt-FoxO pathway, the glucocorticoids-GR pathway, the PGC1α-FoxO pathway, the TNFα-NFκB pathway, or the myostatin-ActRIIb-Smad2/3 pathway. In some embodiments, the atrogene encodes an E3 ligase. In some embodiments, the atrogene encodes a Forkhead box transcription factor. In some embodiments, the atrogene comprises atrogin-1 gene (FBXO32), MuRF1 gene (TRIM63), FOXO1, FOXO3, or MSTN. In some embodiments, the atrogene comprises DMPK. In some embodiments, the polynucleic acid molecule conjugate comprises a molecule of Formula (I): A-$X_1$-B-$X_2$—C (Formula I) wherein, A is a binding moiety; B is a polynucleotide that hybridizes to the target sequence of an atrogene; C is a polymer; and $X_1$ and $X_2$ are each independently selected from a bond or a non-polymeric linker, wherein the polynucleotide comprises at least one 2' modified nucleotide, at least one modified internucleotide linkage, or at least one inverted abasic moiety; and wherein A and C are not attached to B at the same terminus. In some embodiments, B consists of a polynucleotide that hybridizes to the target sequence of an atrogene. In some embodiments, C consists of a polymer. In some embodiments, the at least one 2' modified nucleotide comprises 2'-O-methyl, 2'-O-methoxyethyl (2'-O-MOE), 2'-O-aminopropyl, 2'-deoxy, T-deoxy-2-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified nucleotide. In some embodiments, the at least one 2' modified nucleotide comprises locked nucleic acid (LNA) or ethylene nucleic acid (ENA). In some embodiments, the at least one modified internucleotide linkage comprises a phosphorothioate linkage or a phosphorodithioate linkage. In some embodiments, the at least one inverted abasic moiety is at at least one terminus. In some embodiments, the polynucleotide comprises a single strand which hybridizes to the target sequence of an atrogene. In some embodiments, the polynucleotide comprises a first polynucleotide and a second polynucleotide hybridized to the first polynucleotide to form a double-stranded polynucleic acid molecule, wherein either the first polynucleotide or the second polynucleotide also hybridizes to the target sequence of an atrogene. In some embodiments, the second polynucleotide comprises at least one modification. In some embodiments, the first polynucleotide and the second polynucleotide are RNA molecules. In some embodiments, the polynucleotide hybridizes to at least 8 contiguous bases of the target sequence of an atrogene. In some embodiments, the polynucleotide comprises a sequence that is at least 60%, 70%, 80%, 85%, 90%, 95%, or 99% complementary to a sequence as set forth in SEQ ID NOs: 28-141, 370-480, and 703-3406 In some embodiments, the polynucleotide is between about 8 and about 50 nucleotides in length. In some embodiments, the polynucleotide is between about 10 and about 30 nucleotides in length. In some embodiments, the first polynucleotide comprises a sequence having at least 80%, 854, 90%, 95%, %%, 97%, 98%, 99%, or 100% sequence identity to a sequence as set forth in SEQ ID NOs: 142-255, 256-369, 481-591, 592-702, and 3407-14222. In some embodiments, the second polynucleotide comprises a sequence having at least 80%, 85%, 90%, 95%, 96%, 97%, 98%, 99%, or 100% sequence identity to a sequence as set forth in SEQ ID NOs: 142-255, 256-369, 481-591, 592-702, and 3407-14222. In some embodiments, $X_1$ and $X_2$ are independently a $C_1$-$C_6$ alkyl group. In some embodiments, $X_1$ and $X_2$ are independently a homobifunctional linker or a heterobifunctional linker, optionally conjugated to a $C_1$-$C_6$ alkyl group. In some embodiments, A is an antibody or binding fragment thereof. In some embodiments, A comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, A is an anti-transferrin receptor antibody or binding fragment thereof. In some embodiments, C is polyethylene glycol. In some embodiments, A-$X_1$ is conjugated to the 5' end of B and $X_2$—C is conjugated to the 3' end of B. In some embodiments, $X_2$-C is conjugated to the 5' end of B and A-$X_1$ is conjugated to the 3' end of B. In some embodiments, A is directly conjugated to $X_1$. In some embodiments, C is directly conjugated to $X_2$. In some embodiments, B is directly conjugated to $X_1$ and $X_2$. In some embodiments, the method further comprises D. In some embodiments, D is conjugated to C or to A. In some embodiments, D is an endosomolytic polymer. In some embodiments, the polynucleic acid molecule conjugate is formulated for parenteral, oral, intranasal, buccal, rectal, or transdermal administration. In some embodiments, the subject is a human.

Disclosed herein, in certain embodiments, is a kit comprising a molecule described above or a polynucleic acid molecule conjugate described above.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below. The patent application file contains at least one drawing executed in color. Copies of this patent application publication with color drawing(s) will be provided by the Office upon request and payment of the necessary fee.

FIG. 9A illustrates in vivo study design to assess the ability of exemplary conjugates for their ability to mediate mRNA downregulation of myostatin (MSTN) in skeletal muscle.

FIG. 10A illustrates in vivo study design to assess the ability of exemplary conjugates for their ability to mediate mRNA downregulation of myostatin (MSTN) in skeletal muscle.

FIG. 11A illustrates an exemplary in viva study design.

FIG. 12A illustrates an exemplary in vivo study design.

FIG. 13A illustrates an exemplary in vivo study design.

FIG. 14A illustrates an exemplary in vivo study design.

FIG. 15A illustrates an exemplary in vivo study design.

FIG. 16A illustrates an exemplary in vivo study design.

FIG. 18A: gastrocnemius; FIG. 18B: Tibialis anterior, FIG. 18C: quadriceps; FIG. 18D: diaphragm; FIG. 18E: heart; and FIG. 18F: liver.

FIG. 20A-FIG. 20B illustrate an exemplary 21mer duplex utilized in Example 20. FIG. 20A shows a representative structure of siRNA passenger strand with C6-NH$_2$ conjugation handle at the 5' end and C6-S-NEM at 3' end. FIG. 20B shows a representative structure of a 21mer duplex with 19 bases of complementarity and 3' dinucleotide overhangs.

FIG. 21A-FIG. 21B illustrate a second exemplary 21 mer duplex utilized in Example 20. FIG. 21A shows a representative structure of siRNA passenger strand with a 5' conjugation handle. FIG. 21B shows a representative structure of a blunt ended duplex with 19 bases of complementarity and one 3' dinucleotide overhang.

FIG. 22 shows an illustrative in vivo study design.

FIG. 25 shows an illustrative in vivo study design.

FIG. 32 shows an illustrative in vivo study design.

Figure 33:
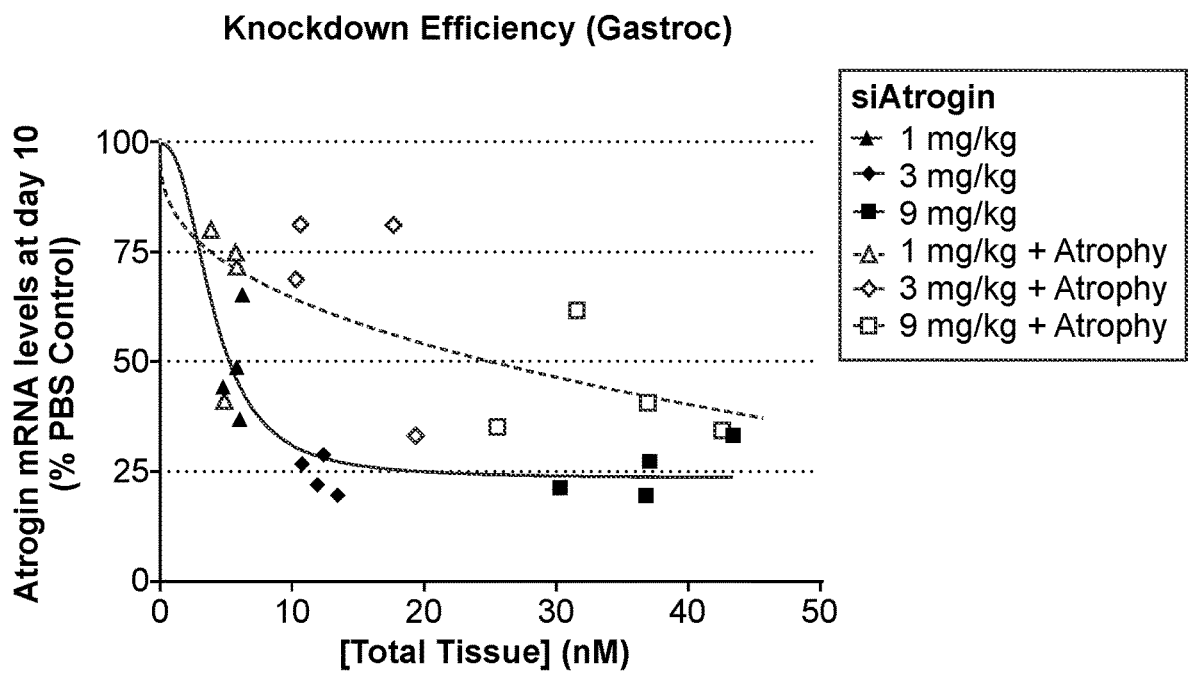

FIG. 33 shows Atrogin-1 mRNA downregulation in gastroc muscle, 10 days after TfR1 antibody siRNA conjugate, in the absence a presence of dexamethasone induced atrophy (initiated at day 7), relative to the measure concentration of siRNA in the tissue.

Figure 34:

FIG. 34 shows relative Atrogin-1 mRNA levels in gastroc muscle for the scrambled control groups in the absence (groups 10&13, and groups 11&14)) and presence of dexamethasone induced atrophy (groups 12&15).

Figure 35:
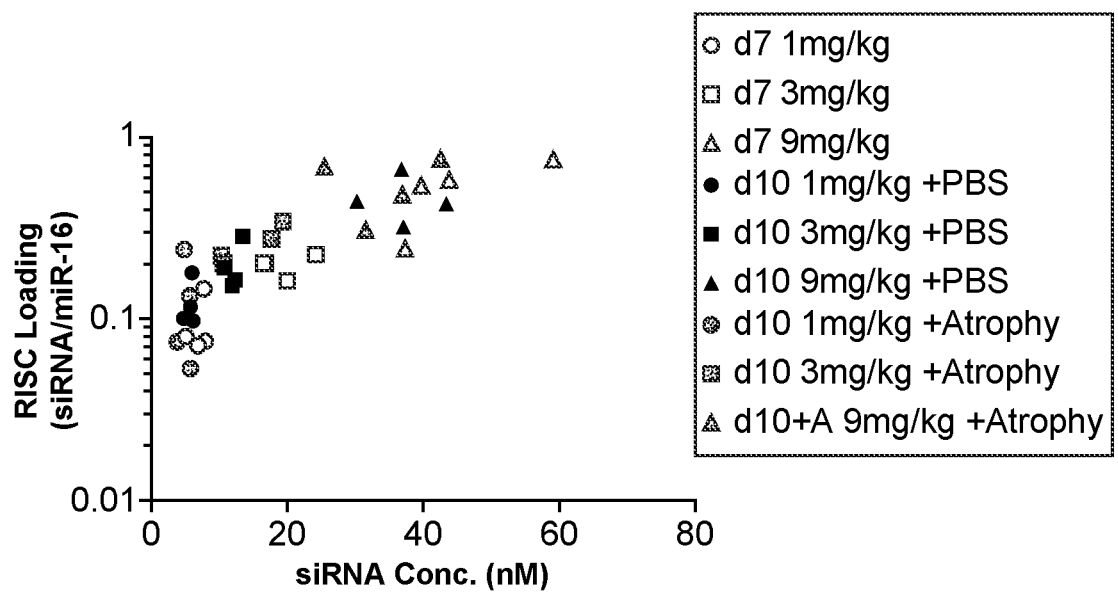

FIG. 35 shows relative RISC loading of the Atrogin-1 guide strand in mouse gastroc muscle after TfR1-mAb conjugate delivery in the absence and presence of dexamethasone induced atrophy.

Figure 36:
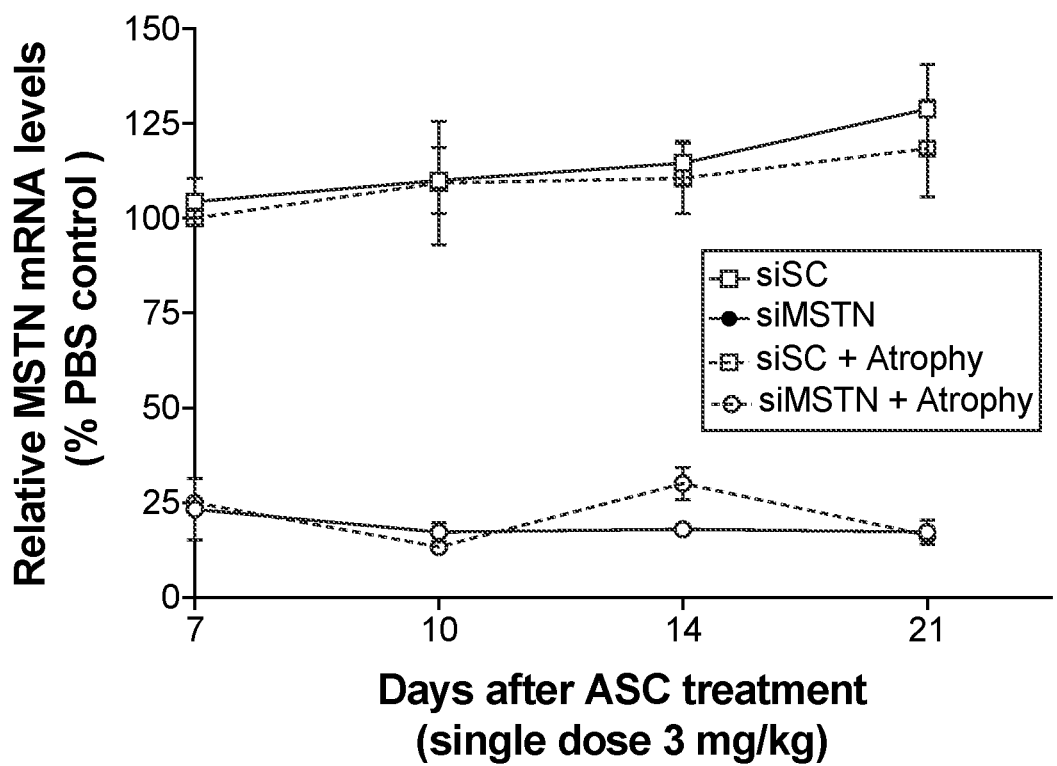

FIG. 36 shows a time course of MSTN mRNA downregulation in gastroc muscle after TfR1 antibody siRNA conjugate delivery, in the absence (solid lines) and presence (dotted lines) of dexamethasone induced atrophy (initiated at day 7), relative to the PBS control.

Figure 37:
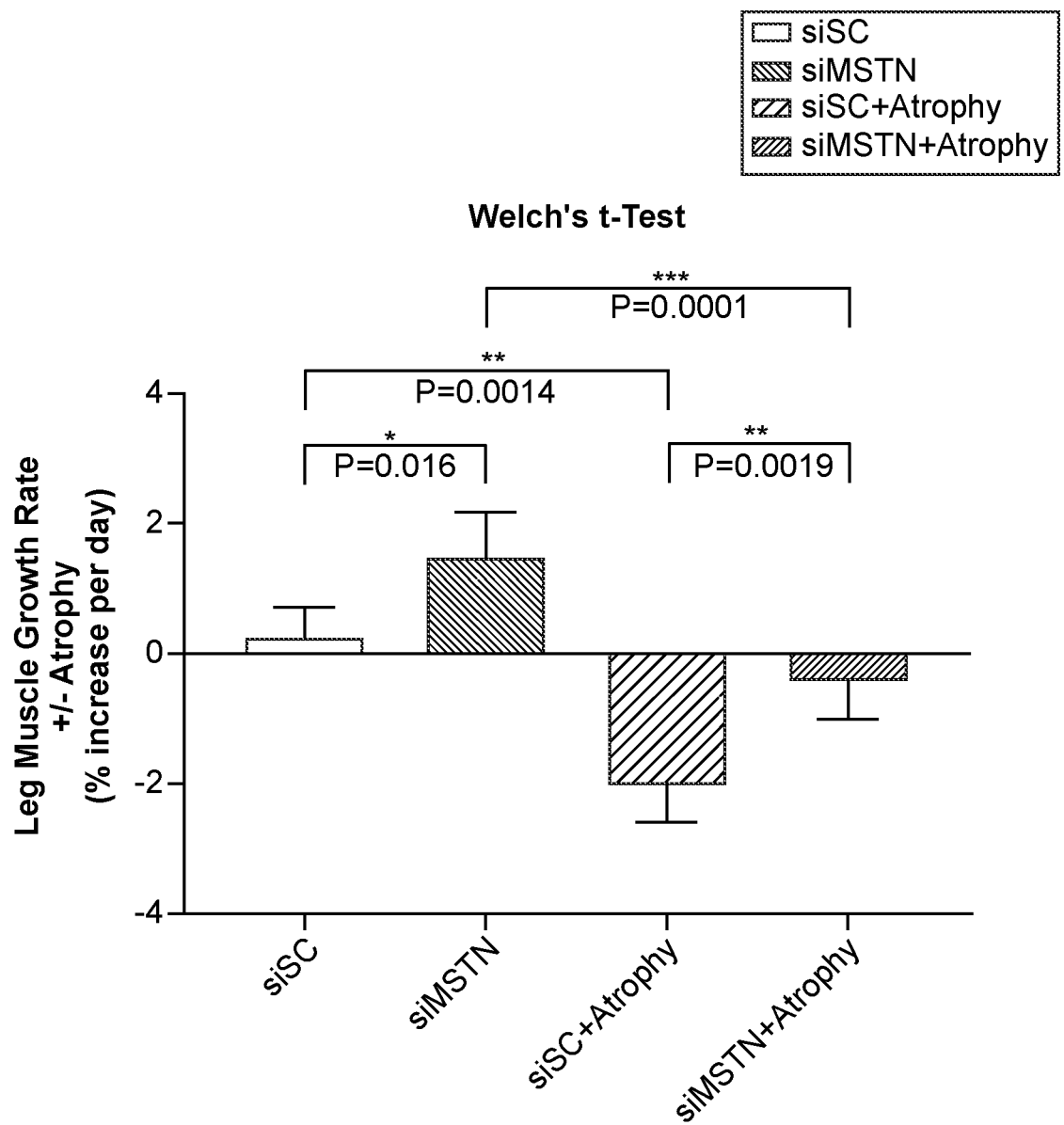

FIG. 37 shows leg muscle growth rate in gastroc muscle, after TfR1-mAb conjugate delivery in the absence and presence of dexamethasone induced atrophy.

FIG. 38 shows an illustrative in vivo study design.

Figure 39A:
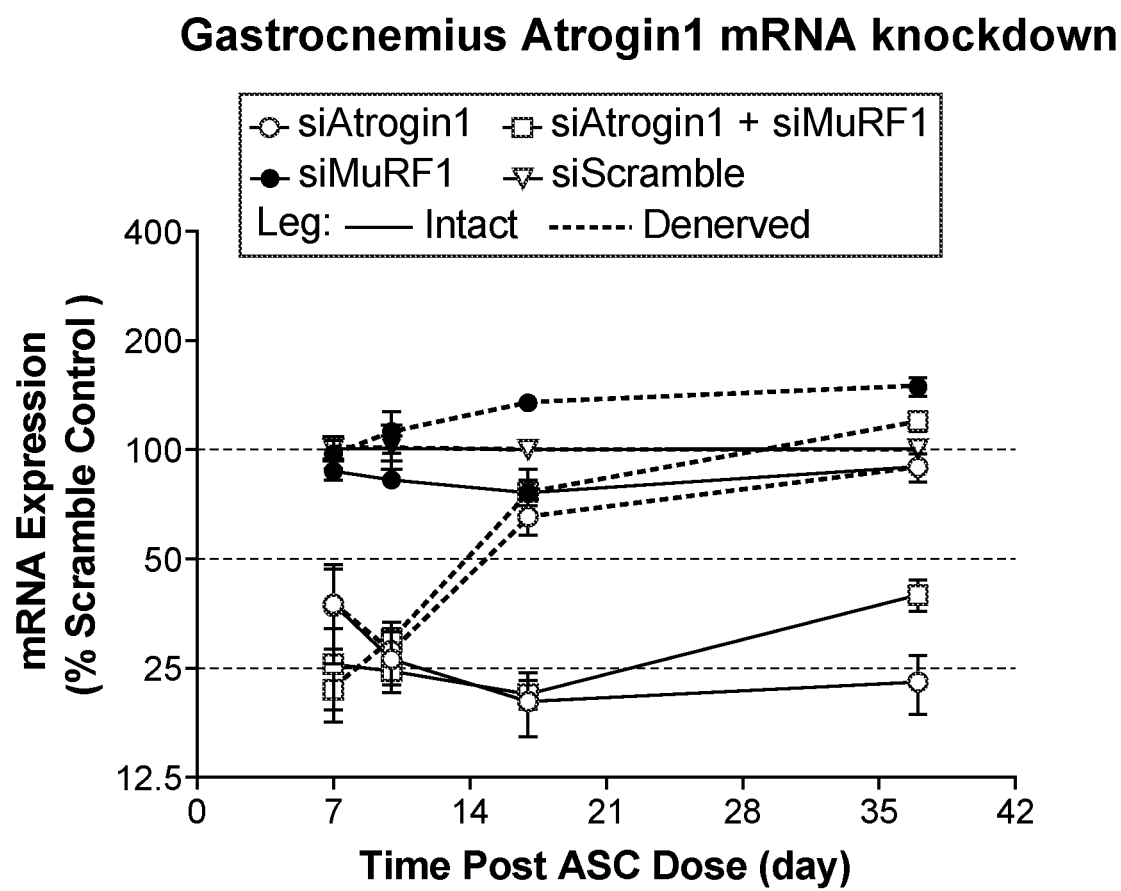

FIG. 39A shows a single treatment of 4.5 mg/kg (siRNA) of either Atrogin-1 siRNA or MuRF1 siRNA or a single dose of both siRNAs combined resulted in up to 75% downregulation of each target in the gastrocnemius.

Figure 39B:
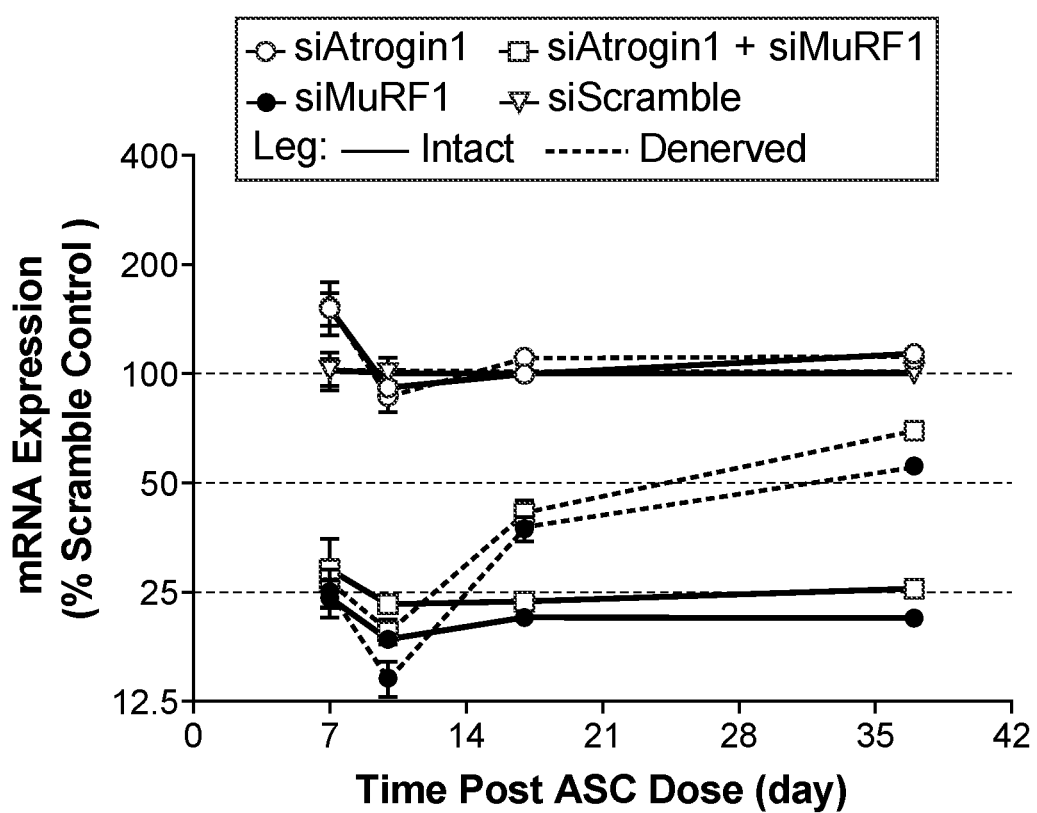

FIG. 39B shows mRNA knockdown of both targets in gastrocnemius is maintained at 75% in the intact leg out to 37 days post ASC dose.

Figure 39C:
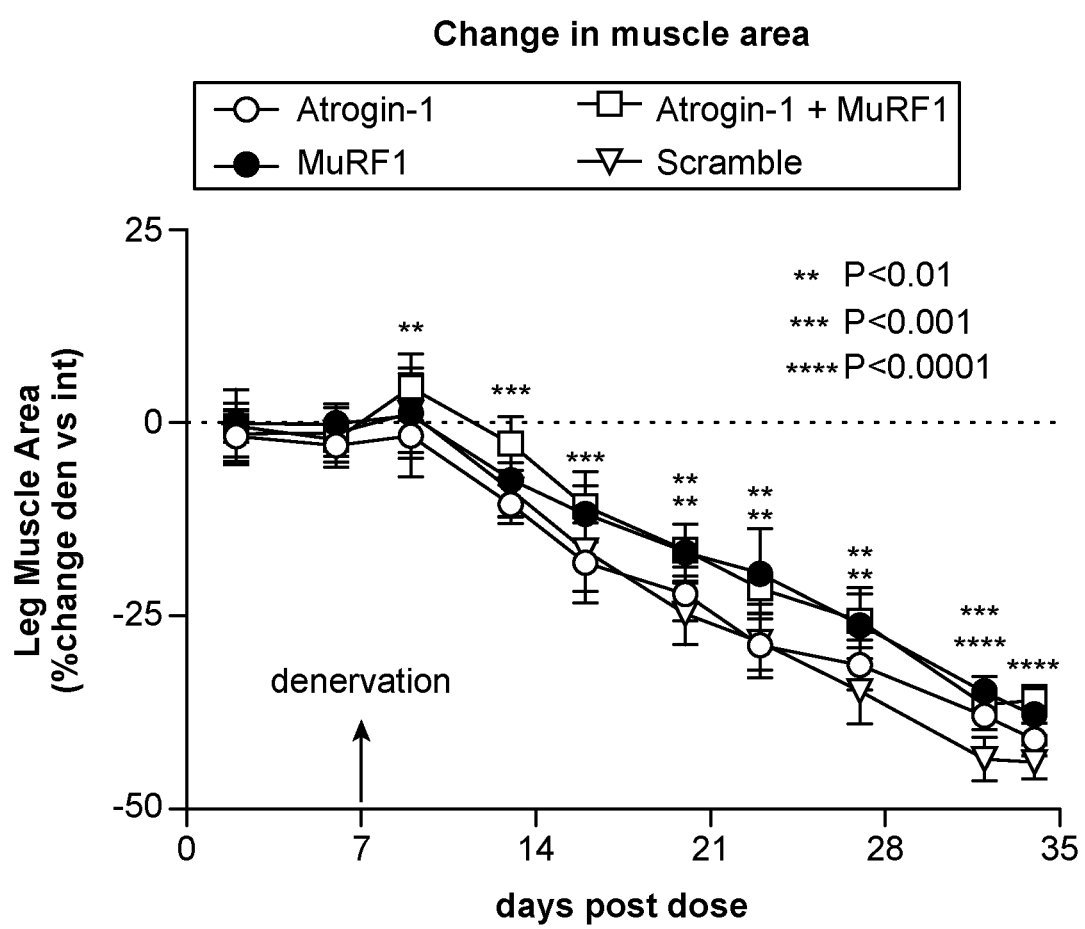

FIG. 39C shows changes in muscle area.

Figure 39D:
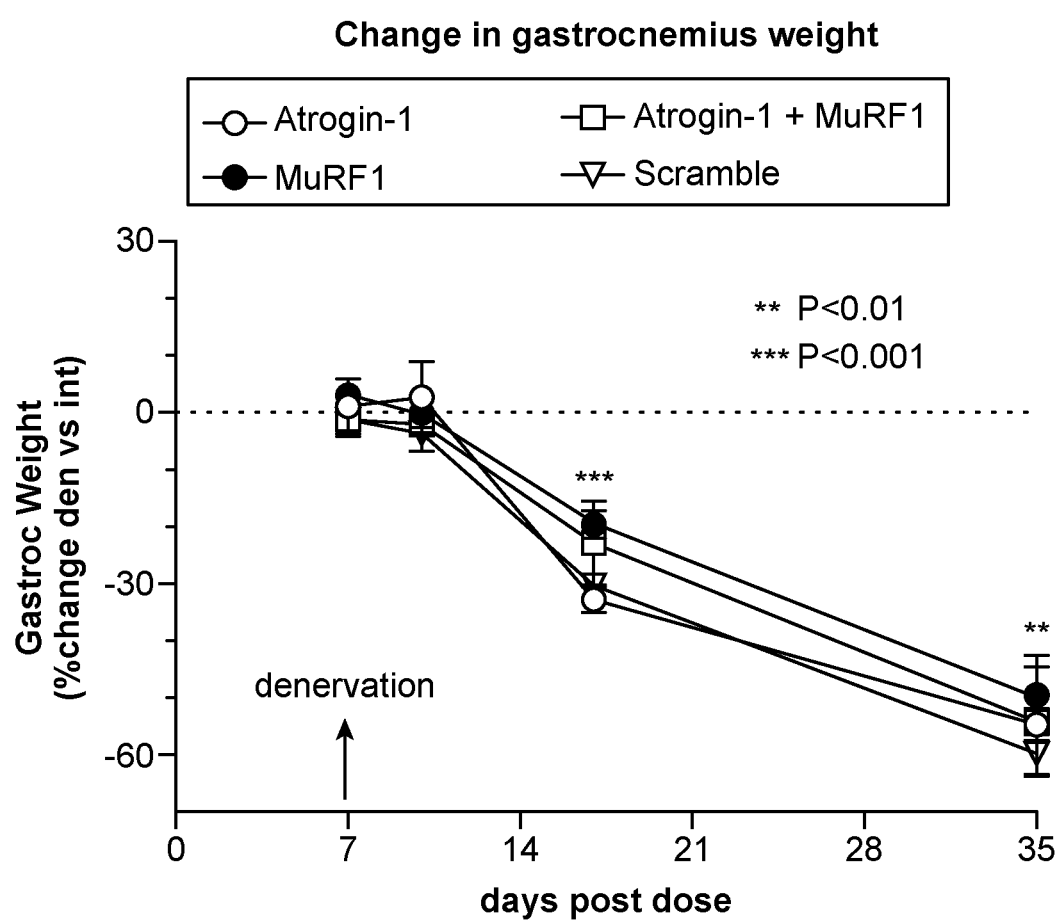

FIG. 39D shows changes in gastrocnemius weight.

FIG. 39E shows treatment-induced percentage sparing of muscle wasting in term of leg muscle area. The statistical analysis compared the treatment groups to the scramble siRNA control group using a Welch's TTest.

FIG. 39F shows the treatment-induced percentage sparing of muscle wasting in term of gastrocnemius weight.

Figure 40A:
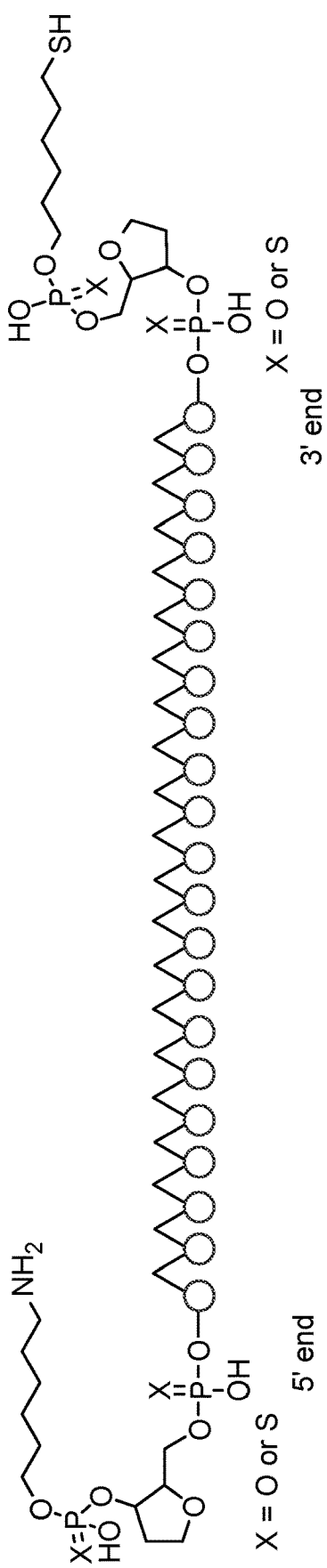

FIG. 40A shows a representative structure of siRNA with C6-NH$_2$ conjugation handle at the 5' end and C6-SH at 3'end of the passenger strand.

Figure 40B:
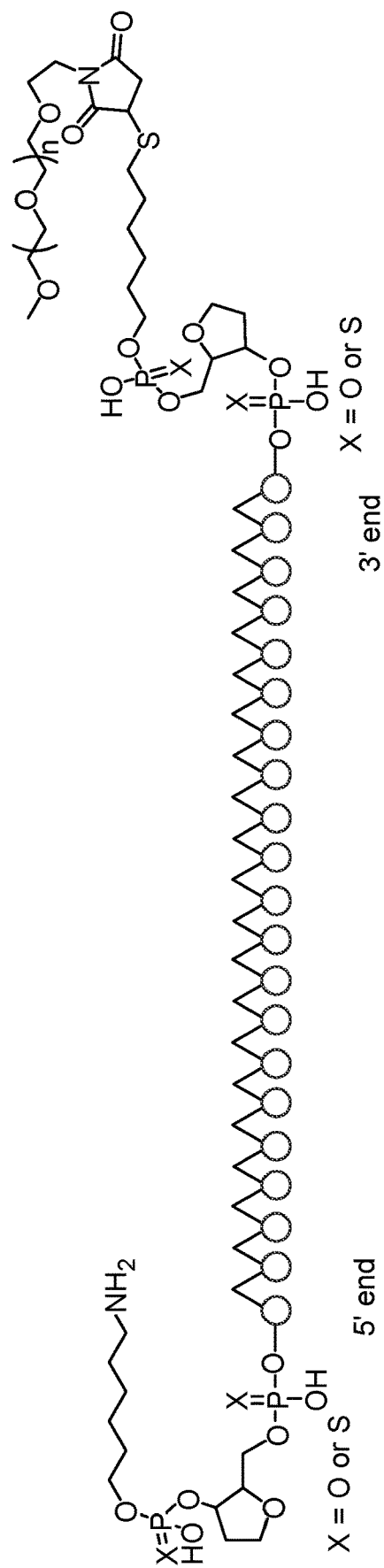

FIG. 40B shows a representative structure of siRNA passenger strand with C6-NH$_2$ conjugation handle at the 5' end and C6-S-PEG at 3' end.

Figure 40C:
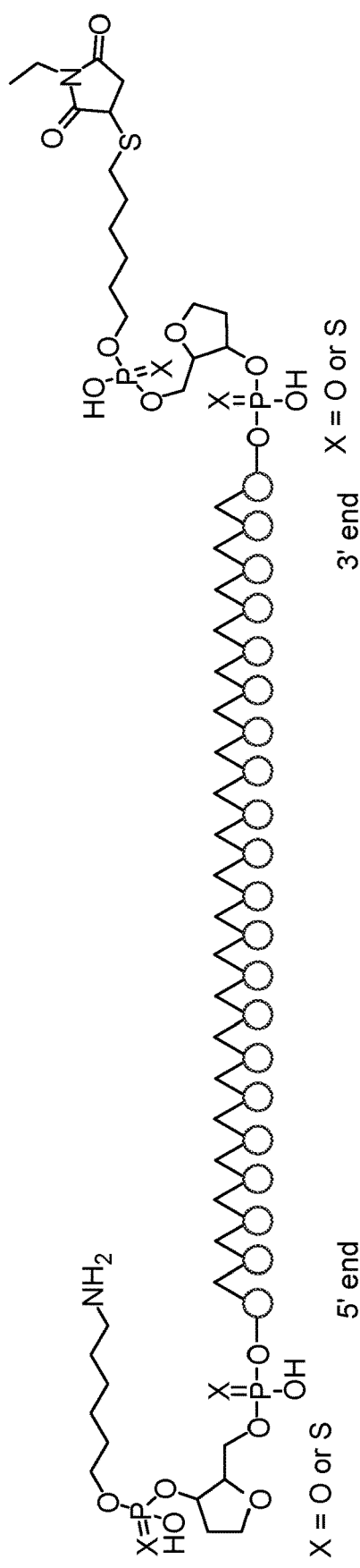

FIG. 40C shows a representative structure of siRNA passenger strand with C6-NH$_2$ conjugation handle at the 5' end and C6-S-NEM at 3' end.

Figure 40D:
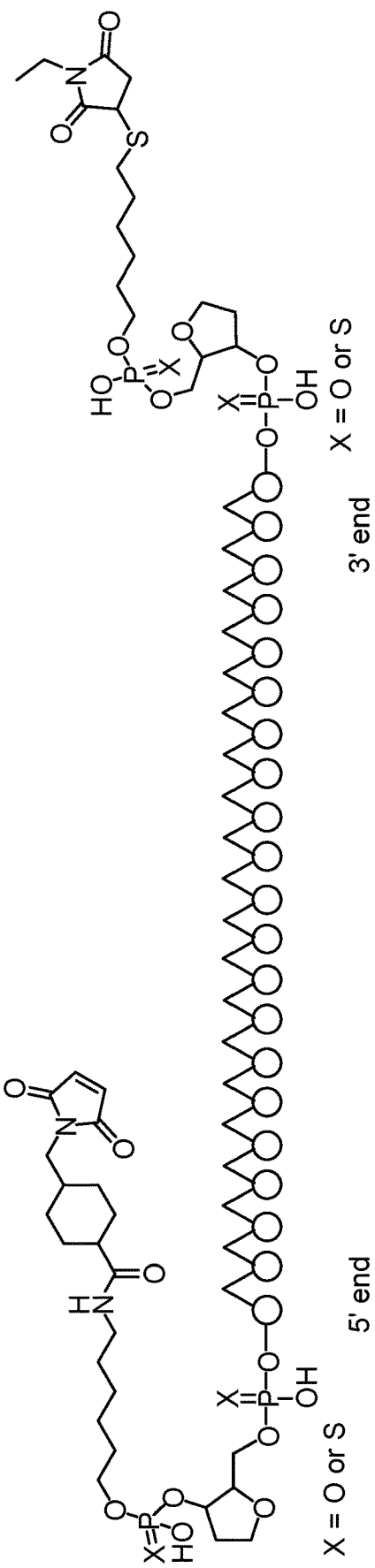

FIG. 40D shows a representative structure of siRNA passenger strand with C6-N-SMCC conjugation handle at the 5' end and C6-S-NEM at 3' end.

FIG. 40E shows a representative structure of siRNA passenger strand with PEG at the 5' end and C6-SH at 3' end.

FIG. 40F shows a representative structure of siRNA passenger strand with C6-S-NEM at the 5' end and C6-NH$_2$ conjugation handle at 3' end.

Figure 41A:
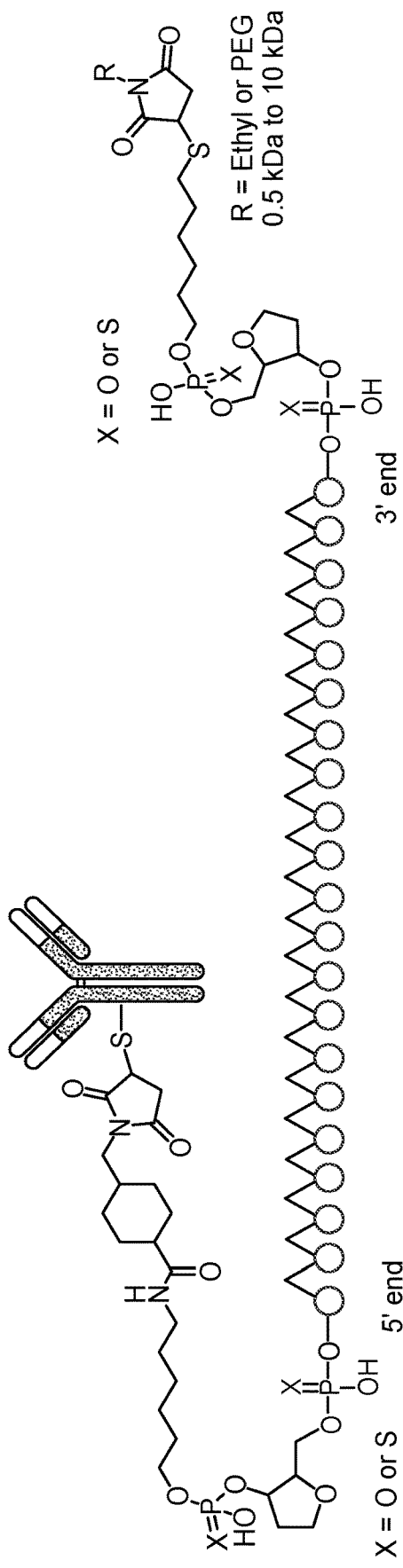

FIG. 41A shows Architecture-1: Antibody-Cys-SMCC-5'-passenger strand. This conjugate was generated by antibody inter-chain cysteine conjugation to maleimide (SMCC) at the 5' end of passenger strand.

Figure 41B:
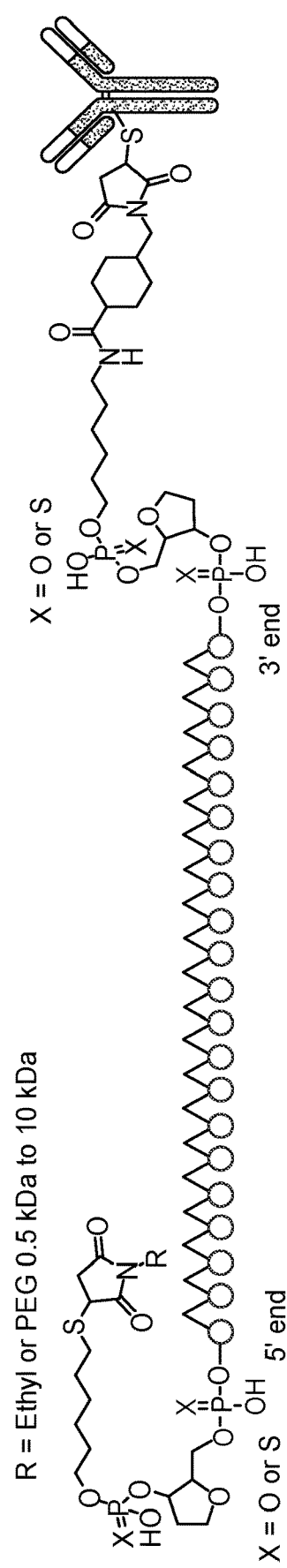

FIG. 41B shows Architecture-2: Antibody-Cys-SMCC-3'-Passenger strand. This conjugate was generated by antibody inter-chain cysteine conjugation to maleimide (SMCC) at the 3' end of passenger strand.

Figure 41C:
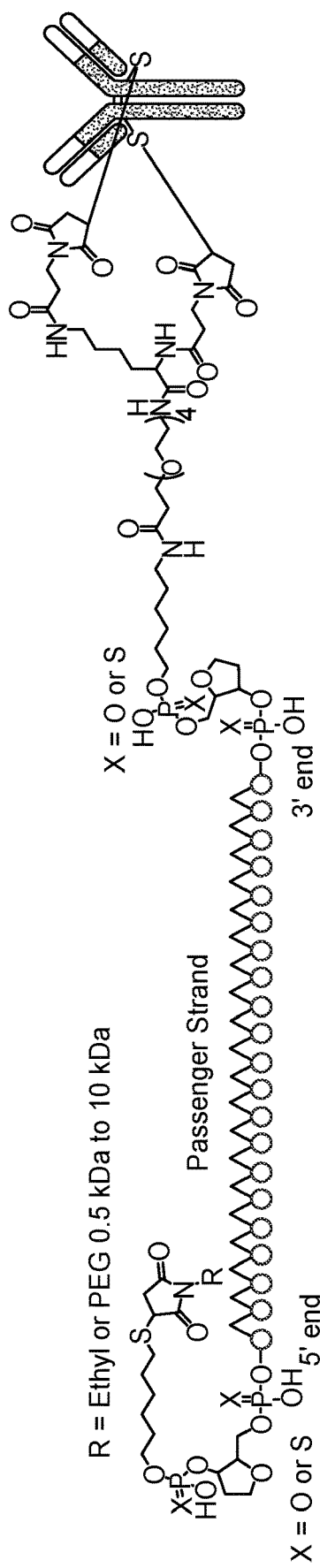

FIG. 41C shows ASC Architecture-3: Antibody-Cys-bis-Mal-3'-Passenger strand. This conjugate was generated by antibody inter-chain cysteine conjugation to bismaleimide (bisMal)linker at the 3' end of passenger strand.

Figure 41D:
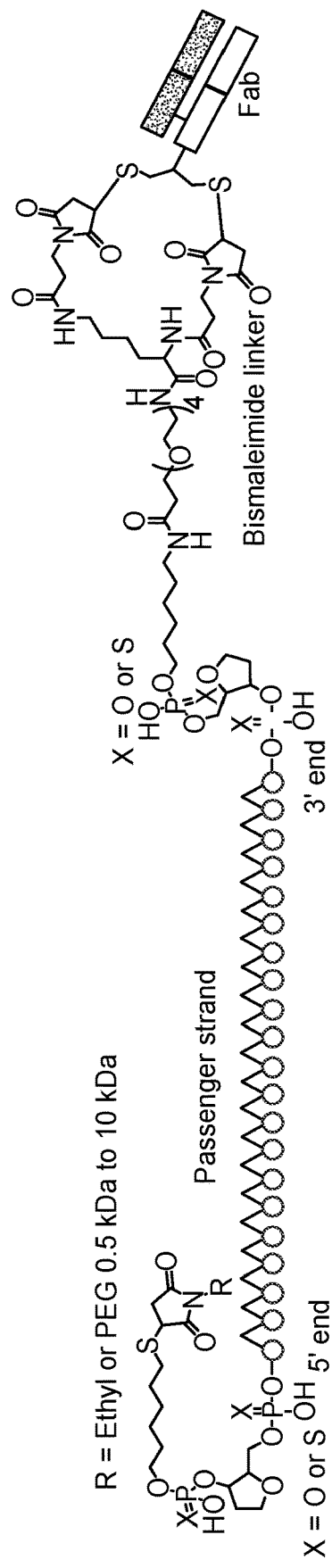

FIG. 41D shows ASC Architecture-4: A model structure of the Fab-Cys-bisMal-3'-Passenger strand. This conjugate was generated by Fab inter-chain cysteine conjugation to bismaleimide (bisMal) linker at the 3' end of passenger strand.

Figure 41E:
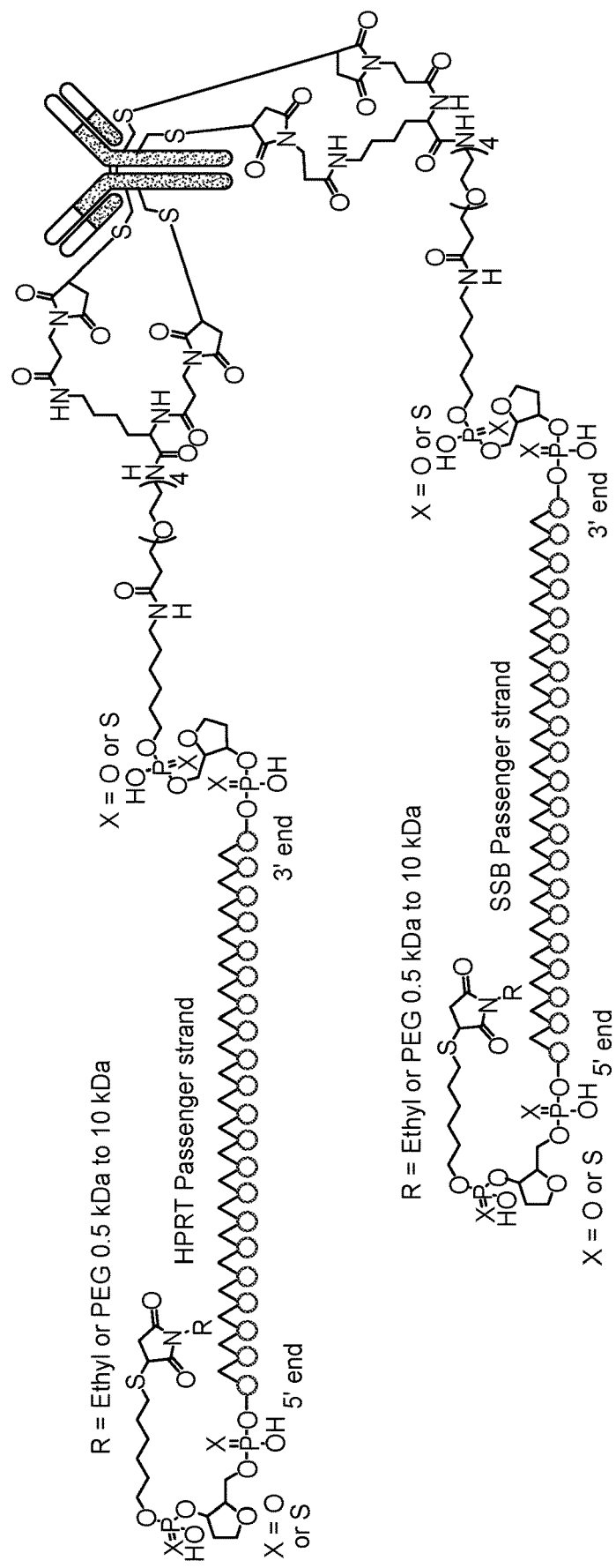

FIG. 41E shows ASC Architecture-5: A model structure of the antibody siRNA conjugate with two different siRNAs attached to one antibody molecule. This conjugate was generated by conjugating a mixture of SSB and HPRT siRNAs to the reduced mAb inter-chain cysteines to bismaleimide (bisMal) linker at the 3' end of passenger strand of each siRNA.

Figure 41F:
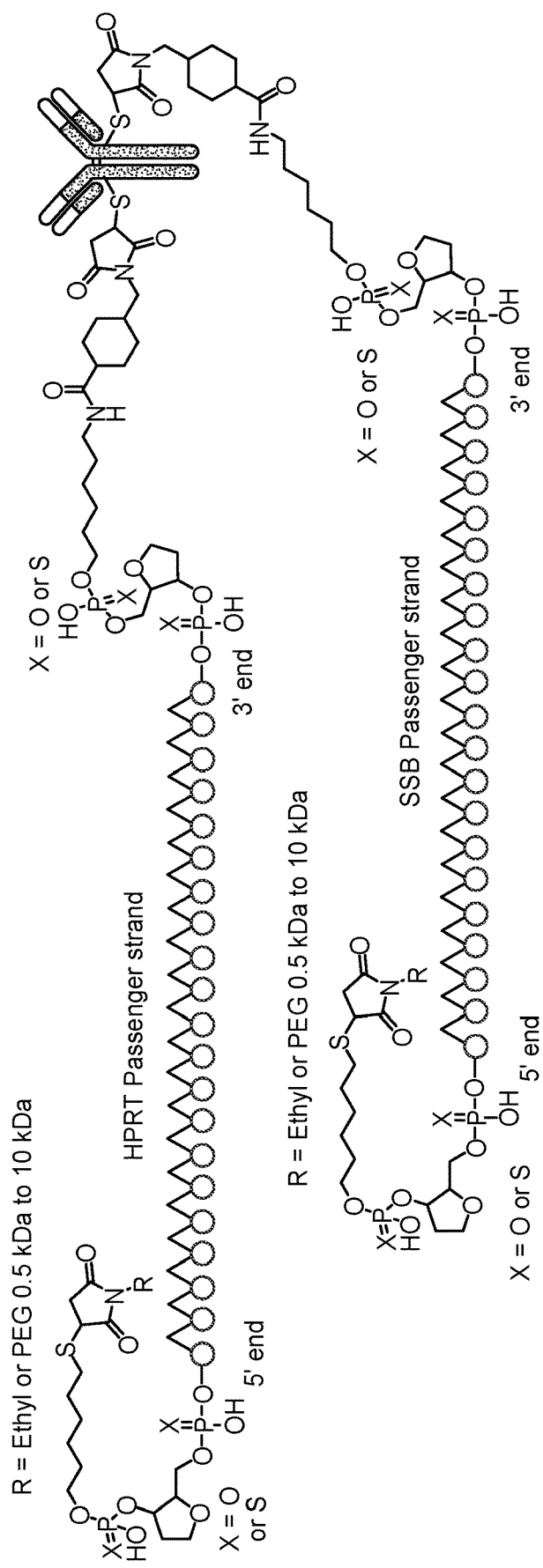

FIG. 41F shows ASC Architecture-6: A model structure of the antibody siRNA conjugate with two different siRNAs attached. This conjugate was generated by conjugating a mixture of SSB and HPRT siRNAs to the reduced mAb inter-chain cysteines to maleimide (SMCC) linker at the 3' end of passenger strand of each siRNA.

Figure 42:
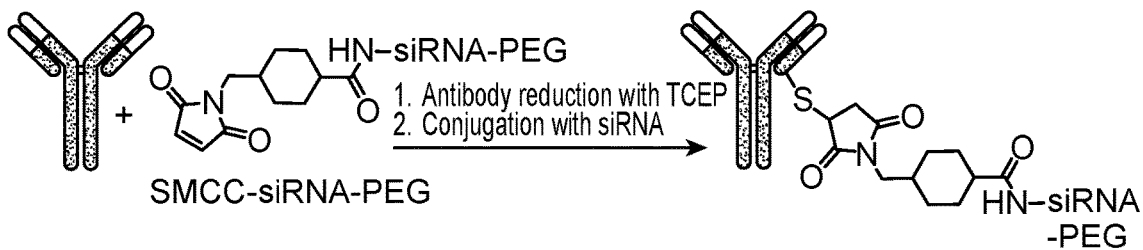

FIG. 42 shows Synthesis scheme-1: Antibody-Cys-SMCC-siRNA-PEG conjugates via antibody cysteine conjugation.

Figure 43:
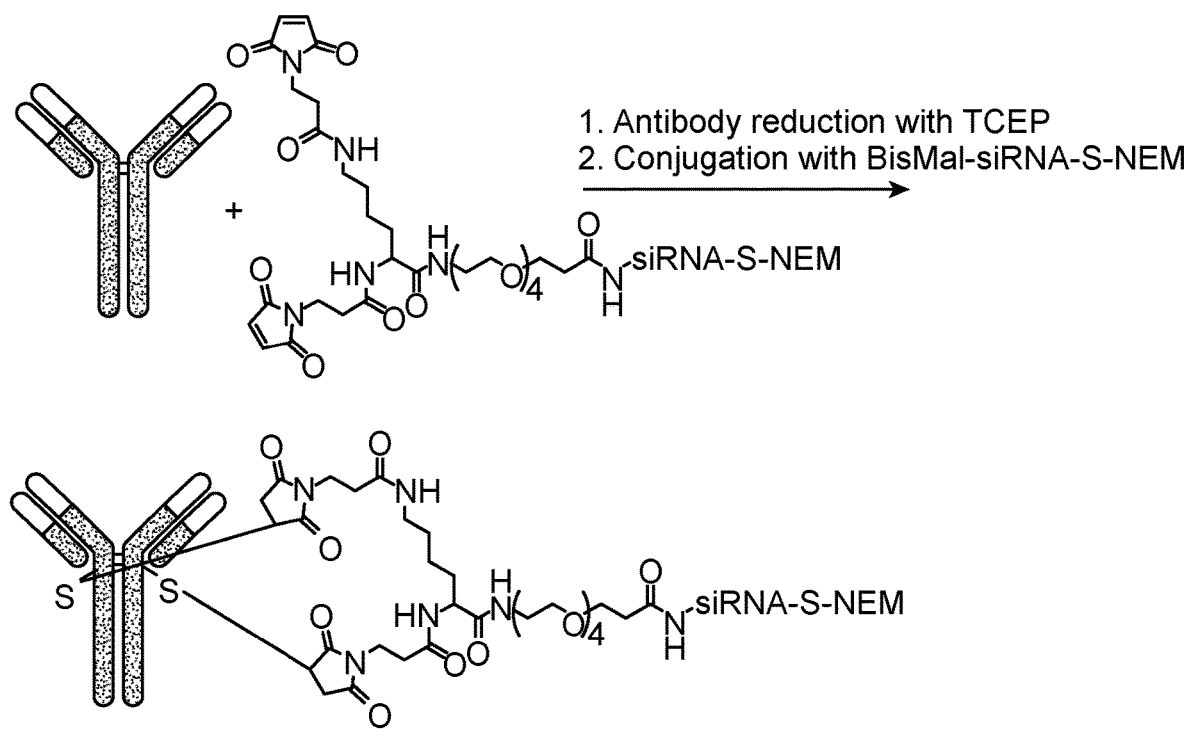

FIG. 43 shows Synthesis scheme-2: Antibody-Cys-Bis-Mal-siRNA-PEG conjugates.

Figure 44:
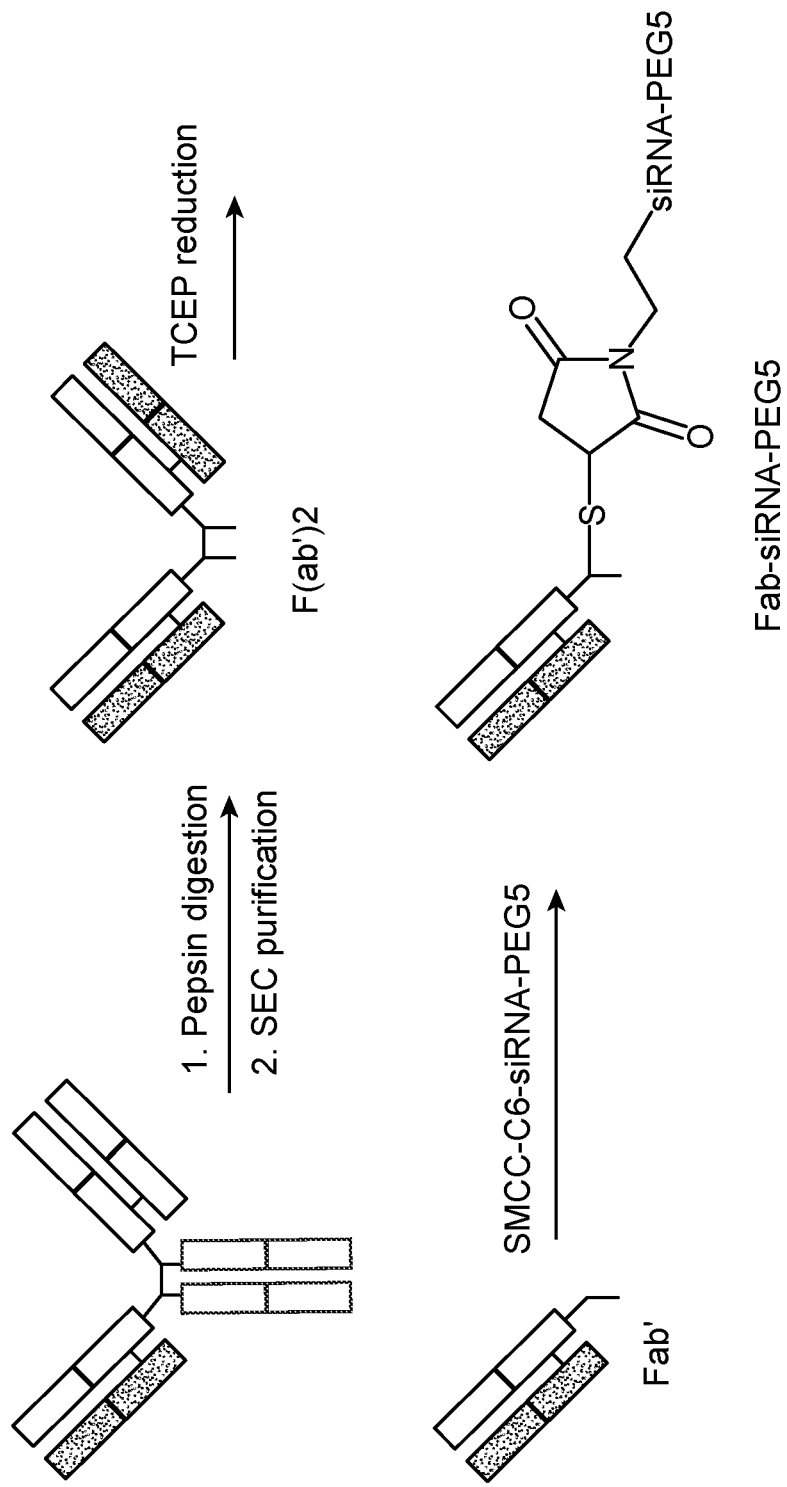

FIG. 44 shows Scheme-3: Fab-siRNA conjugate generation.

DETAILED DESCRIPTION OF THE DISCLOSURE

Muscle atrophy is the loss of muscle mass or the progressive weakening and degeneration of muscles, such as skeletal or voluntary muscles that controls movement, cardiac muscles, and smooth muscles. Various pathophysiological conditions including disuse, starvation, cancer, diabetes, and renal failure, or treatment with glucocorticoids result in muscle atrophy and loss of strength. The phenotypical effects of muscle atrophy are induced by various molecular events, including inhibition of muscle protein synthesis, enhanced turnover of muscle proteins, abnormal regulation of satellite cells differentiation, and abnormal conversion of muscle fibers types.

Extensive research has identified that muscle atrophy is an active process controlled by specific signaling pathways and transcriptional programs. Exemplary pathways involved in this process include, but are not limited to, IGF1-Akt-FoxO, glucocorticoids-GR, PGC1α-FoxO, TNFα-NFκB, and myostatin-ActRIIb-Smad2/3.

In some instances, therapeutic manipulation of mechanisms regulating muscle atrophy has focused on IGF1-Akt, TNFα-NfκB, and myostatin. While IGF1 analogs were shown to be effective in treating muscle atrophy, the involvement of the IGF1-Akt pathway in promoting tumorigenesis and hypertrophy prevents these therapies. Similar risks are involved in the use of β-adrenergic agonists for the regulation of the Akt-mTOR pathway. Inhibition of myostatin by using soluble ActRIIB or ligand blocking ActRIIb antibodies prevented and reversed skeletal muscle loss, and prolonged the survival of tumor-bearing animals. However the mechanism of the anti-atrophic effects of myostatin blockade remains uncertain as neither expression of a dominant-negative ActRIIb, nor knockdown of Smad2/3 prevented muscle loss following denervation (Satori et al., "Smad2 and 3 transcription factors control muscle mass in adulthood". *Am J Physiol Cell Physiol* 2%: C1248-C1257, 2009).

Comparing gene expression in different models of muscle atrophy (including diabetes, cancer cachexia, chronic renal failure, fasting and denervation) has led to the identification of atrophy-related genes, named atrogenes (Sacheck et al., "Rapid disuse and denervation atrophy involve transcriptional changes similar to those of muscle wasting during systemic diseases", *The FASEB Journal*, 21(1): 140-155, 2007), that are commonly up- or downregulated in atrophying muscle. Among genes that are strongly upregulated under atrophy conditions are muscle-specific ubiquitin-protein (E3) ligases (e.g. atrogin-1, MuRF1), Forkhead box transcription factors, and proteins mediating stress responses. In some cases, many of these effector proteins are difficult to regulate using traditional drugs.

Nucleic acid (e.g., RNAi) therapy is a targeted therapy with high selectivity and specificity. However, in some instances, nucleic acid therapy is also hindered by poor intracellular uptake, limited blood stability and non-specific immune stimulation. To address these issues, various modifications of the nucleic acid composition are explored, such as for example, novel linkers for better stabilizing and/or lower toxicity, optimization of binding moiety for increased target specificity and/or target delivery, and nucleic acid polymer modifications for increased stability and/or reduced off-target effect.

In some embodiments, the arrangement or order of the different components that make-up the nucleic acid composition further effects intracellular uptake, stability, toxicity, efficacy, and/or non-specific immune stimulation. For example, if the nucleic acid component includes a binding moiety, a polymer, and a polynucleic acid molecule (or polynucleotide), the order or arrangement of the binding moiety, the polymer, and/or the polynucleic acid molecule (or polynucleotide) (e.g., binding moiety-polynucleic acid molecule-polymer, binding moiety-polymer-polynucleic acid molecule, or polymer-binding moiety-polynucleic acid molecule) further effects intracellular uptake, stability, toxicity, efficacy, and/or non-specific immune stimulation.

In some embodiments, described herein include polynucleic acid molecules and polynucleic acid molecule conjugates for the treatment of muscle atrophy or myotonic dystrophy. In some instances, the polynucleic acid molecule conjugates described herein enhance intracellular uptake, stability, and/or efficacy. In some cases, the polynucleic acid molecule conjugates comprise a molecule of Formula (I): $A-X_1-B-X_2-C$. In some cases, the polynucleic acid molecules that hybridize to target sequences of one or more atrogenes.

Additional embodiments described herein include methods of treating muscle atrophy or myotonic dystrophy, comprising administering to a subject a polynucleic acid molecule or a polynucleic acid molecule conjugate described herein.

Atrogenes

Atrogenes, or atrophy-related genes, are genes that are upregulated or downregulated in atrophying muscle. In some instances, upregulated atrogenes include genes that encode ubiquitin ligases, Forkhead box transcription factors, growth factors, deubiquitinating enzymes, or proteins that are involved in glucocorticoid-induced atrophy.

Ubiquitin Ligases

In some embodiments, an atrogene described herein encodes an E3 ubiquitin ligase. Exemplary E3 ubiquitin ligases include, but are not limited to, Atrogin-1/MAFbx, muscle RING finger 1 (MuRF1), TNF receptor adaptor protein 6 (TRAF6), F-Box protein 30 (Fbxo30), F-Box protein 40 (Fbxo40), neural precursor cell expressed developmentally down-regulated protein 4 (Nedd4-1), and tripartite motif-containing protein 32 (Trim32). Exemplary mitochondrial ubiquitin ligases include, but are not limited to, Mitochondrial E3 ubiquitin protein ligase 1 (Mul1) and Carboxy terminus of Hsc70 interacting protein (CHIP).

In some embodiments, an atrogene described herein encodes Atrogin-1, also named Muscle Atrophy F-box (MAFbx), a member of the F-box protein family. Atrogin-1/MAFbx is one of the four subunits of the ubiquitin ligase complex SKP1-cullin-F-box (SCF) that promotes degradation of MyoD, a muscle transcription factor, and eukaryotic translation initiation factor 3 subunit F (eIF3-f). Atrogin-1/MAFbx is encoded by FBXO32.

In some embodiments, an atrogene described herein encodes muscle RING finger 1 (MuRF1). MuRF1 is a member of the muscle-specific RING finger proteins and along with family members MuRF2 and MuRF3 are found at the M-line and Z-line lattices of myofibrils. Further, several studies have shown that MuRF1 interacts with and/or modulates the half-life of muscle structural proteins such as troponin 1, myosin heavy chains, actin, myosin binding protein C, and myosin light chains 1 and 2. MuRF1 is encoded by TRIM63.

In some embodiments, an atrogene described herein encodes TNF receptor adaptor protein 6 (TRAF6) (also known as interleukin-I signal transducer, RING finger protein 85, or RNF85). TRAF6 is a member of the E3 ligase that mediates conjugation of Lys63-linked polyubiquitin chains to target proteins. The Lys63-linked polyubiquitin chains signal autophagy-dependent cargo recognition by scaffold protein p62 (SQSTM1). TRAF6 is encoded by the TRAF6 gene.

In some embodiments, an atrogene described herein encodes F-Box protein 30 (Fbxo30) (also known as F-Box only protein, helicase, 18; muscle ubiquitin ligase of SCF complex in atrophy-1; or MUSA1). Fbxo30 is a member of the SCF complex family of E3 ubiquitin ligases. In one study. Fbox30 is proposed to be inhibited by the bone morphogenetic protein (BMP) pathway and upon atrophy-inducing conditions, are upregulated and subsequently undergoes autoubiquitination. Fbxo30 is encoded by the FBXO30 gene.

In some embodiments, an atrogene described herein encodes F-Box protein 40 (Fbxo40) (also known as F-Box only protein 40 or muscle disease-related protein). A second member of the SCF complex family of E3 ubiquitin ligases, Fbxo40 regulates anabolic signals. In some instances. Fbxo40 ubiquitinates and affects the degradation of insulin receptor substrate 1, a downstream effector or insulin receptor-mediated signaling. Fbxo40 is encoded by the FBXO40 gene.

In some embodiments, an atrogene described herein encodes neural precursor cell expressed developmentally down-regulated protein 4 (Nedd4-1), a HECT domain E3 ubiquitin ligase which has been shown to be upregulated in muscle cells during disuse. Nedd4-1 is encoded by the NEDD4 gene.

In some embodiments, an atrogene described herein encodes tripartite motif-containing protein 32 (Trim32). Trim32 is a member of the E3 ubiquitin ligase that is involved in degradation of thin filaments such as actin, tropomyosin, and troponins; α-actinin; and desmin. Trim32 is encoded by the TRIM32 gene.

In some embodiments, an atrogene described herein encodes Mitochondrial E3 ubiquitin protein ligase 1 (Mul1) (also known as mitochondrial-anchored protein ligase. RING finger protein 218, RNF218, MAPL, MULAN, and GIDE). Mul1 is involved in the mitochondrial network remodeling and is up-regulated by the FoxO family of transcription factors under catabolic conditions, such as for example, denervation or fasting, and subsequently causes mitochondrial fragmentation and removal via autophagy (mitophagy). Furthermore. Mul1 ubiquitinates the mitochondrial pro-fusion protein mitofusin 2, a GTPase that is involved in mitochondrial fusion, leading to the degradation of mitofusin 2. Mul1 is encoded by the MUL1 gene.

In some embodiments, an atrogene described herein encodes Carboxy terminus of Hsc70 interacting protein (CHIP) (also known as STIP1 homology and U-Box containing protein 1, STUB1, CLL-associated antigen KW-8, antigen NY-CO-7, SCAR16. SDCCAG7, or UBOX1). CHIP is a mitochondrial ubiquitin ligase that regulates ubiquitination and lysosomal-dependent degradation of filamin C, a muscle protein found in the Z-line. Z-line or Z-disc is the structure formed between adjacent sarcomeres, and sarcomere is the basic unit of muscle. Alterations of filamin structure triggers binding of the co-chaperone BAG3, a complex that comprises chaperones Hsc70 and HspB8 with CHIP. Subsequent ubiquitination of BAG3 and filamin by CHIP activates the autophagy system, leading to degradation of filamin C. CHIP is encoded by the STUB1 gene.

Forkhead Box Transcription Factors

In some embodiments, an atrogene described herein encodes a Forkhead box transcription factor. Exemplary Forkhead box transcription factors include, but are not limited to, isoforms Forkhead box protein O1 (FoxO1) and Forkhead box protein O3 (FoxO3).

In some embodiments, an atrogene described herein encodes Forkhead box protein O1 (FoxO1) (also known as Forkhead homolog in Rhabdomyoscarcoma, FKHR, or FKH1). FoxO1 is involved in regulation of gluconeogenesis and glycogenolysis by insulin signaling, and the initiation of adipogenesis by preadipocytes. FoxO1 is encoded by the FOXO) gene.

In some embodiments, an atrogene described herein encodes Forkhead box protein O3 (FoxO3) (also known as Forkhead in Rhabdomyoscarcoma-like 1, FKHRL1, or FOXO3A). FoxO3 is activated by AMP-activated protein kinase AMPK, which in term induces expression of atrogin-1 and MuRF1. FoxO3 is encoded by the FOXO3 gene.

Growth Factors

In some embodiments, an atrogene described herein encodes a growth factor. An exemplary growth factor includes myostatin.

In some instances, an atrogene described herein encodes myostatin (Mstn), also known as growth/differentiation factor 8(GDF-8). Myostatin is intracellularly converted into an activator, and stimulates muscle degradation and suppresses muscle synthesis by inhibiting Akt through the phosphorylation/activation of Smad (small mothers against decapentaplegic). In some instances, myostatin has been found to be regulated by the Akt-FoxO signaling pathway. In additional instances, myostatin has been shown to suppress differentiation of satellite cells, stimulate muscle degradation through the inhibition of the Akt pathway, and suppress muscle synthesis via the mTOR pathway.

Deubiquitinating Enzymes

In some embodiments, an atrogene described herein encodes a deubiquitinating enzyme. Exemplary deubiquitinating enzymes include, but are not limited to, Ubiquitin specific peptidase 14 (USP14) and Ubiquitin specific peptidase 19 (USP19). In some instances, an atrogene described herein encodes USP14 (also known as deubiquitinating enzyme 14 or TGT). In other instances, an atrogene described herein encodes USP19 (also known as zinc finger MYND domain-containing protein 9, deubiquitinating enzyme 19, or ZMYND9). USP14 is encoded by the USP14 gene. USP19 is encoded by the USP19 gene.

Additional Atrogenes

In some embodiments, an atrogene described herein encodes regulated in development and DNA damage response 1 (Redd1), also known as DNA-damage-inducible transcript 4 (DDIT4) and HIF-1 responsive protein RTP801. Redd1 represses mTOR function by sequestering 14-3-3 and increases TSC1/2 activity. Furthermore, Redd1 decreases phosphorylation of 4E-BP1 and S6K1, which are involved in muscle protein synthesis. Redd1 is encoded by the DDIT4 gene.

In some embodiments, an atrogene described herein encodes cathepsin L2, also known as cathepsin V. Cathepsin L2 is a lysosomal cysteine proteinase. It is encoded by the CTSL2 gene.

In some embodiments, an atrogene described herein encodes TO interacting factor, or homeobox protein TGIF1. TG interacting factor is a transcription factor which regulates signaling pathways involved in embryonic development. This protein is encoded by the TGIF gene.

In some embodiments, an atrogene described herein encodes myogenin, also known as myogenic factor 4. Myogenin is a member of the MyoD family of muscle-specific basic-helix-loop-helix (bHLH) transcription factor involved in the coordination of skeletal muscle development and repair. Myogenin is encoded by the MYOG gene.

In some embodiments, an atrogene described herein encodes myotonin-protein kinase (MT-PK), also known as myolonic dystrophy protein kinase (MDPK) or dystrophia myotonica protein kinase (DMK). MT-PK is a Serine/Threonine kinase and further interacts with members of the Rho family of GTPases. In human, MT-PK is encoded by the DMPK gene.

In some embodiments, an atrogene described herein encodes histone deacetylase 2, a member of the histone deacetylase family. Histone deacetylase 2 is encoded by the HDAC2 gene.

In some embodiments, an atrogene described herein encodes histone deacetylase 3, another member of the histone deacetylase family. Histone deacetylase 3 is encoded by the HDAC3 gene.

In some embodiments, an atrogene described herein encodes metallothionein 1L, a member of the metallothionein family. Metallothioneins (MT) are cysteine-rish, low molecular weight proteins that is capable of binding heavy metals, thereby providing protection against metal toxicity and/or oxidative stress. Metallothionein 1L is encoded by the MT1L gene.

In some embodiments, an atrogene described herein encodes metallothionein 1B, a second member of the metallothionein family. Metallothionein 1B is encoded by the MT1B gene.

In some embodiments, an atrogene described herein is an atrogene listed in Table 14.

Polynucleic Acid Molecules

In certain embodiments, a polynucleic acid molecule hybridizes to a target sequence of an atrophy-related gene (also referred to as an atrogene). In some instances, a polynucleic acid molecule described herein hybridizes to a target sequence of an ubiquitin ligase (e.g., an E3 ubiquitin ligase or a mitochondrial ubiquitin ligase). In some instances, a polynucleic acid molecule described herein hybridizes to a target sequence of a Forkhead box transcription factor. In some instances, a poly nucleic acid molecule described herein hybridizes to a target sequence of a growth factor. In some instances, a polynucleic acid molecule described herein hybridizes to a target sequence of a deubiquitinating enzyme.

In some embodiments, a polynucleic acid molecule described herein hybridizes to a target sequence of FBXO32, TRIM63, TRAF6, FBXO30, FBXO40, NEDD4, TRIM32, MUL1, STUB1, FOXO1, FOXO3, MSTN, USP14, USP19, DDIT4, CTSL2, TGIF, MYOG, HDAC2, HDAC3, MT1L, MT1B, or DMPK. In some cases, a polynucleic acid molecule described herein hybridizes to a target sequence of FBXO32, TRIM63, FOXO1, FOXO3, or MSTN. In some cases, a polynucleic acid molecule described herein hybridizes to a target sequence of FBXO32. In some cases, a polynucleic acid molecule described herein hybridizes to a target sequence of TRIM63. In some cases, a polynucleic acid molecule described herein hybridizes to a target sequence of TRAF6. In some cases, a polynucleic acid molecule described herein hybridizes to a target sequence of FBXO30. In some cases, a polynucleic acid molecule described herein hybridizes to a target sequence of FBXO40. In some cases, a polynucleic acid molecule described herein hybridizes to a target sequence of NEDD4. In some cases, a polynucleic acid molecule described herein hybridizes to a target sequence of TRIM32. In some cases, a polynucleic acid molecule described herein hybridizes to a target sequence of MUL1. In some cases, a polynucleic acid molecule described herein hybridizes to a target sequence of STUB1. In some cases, a polynucleic acid molecule described herein hybridizes to a target sequence of FOXO1. In some cases, a polynucleic acid molecule described herein hybridizes to a target sequence of FOXO3. In some cases, a polynucleic acid molecule described herein hybridizes to a target sequence of MSTN. In some cases, a polynucleic acid molecule described herein hybridizes to a target sequence of USP14. In some cases, a polynucleic acid molecule described herein hybridizes to a target sequence of USP19. In some cases, a polynucleic acid molecule described herein hybridizes to a target sequence of DDIT4. In some cases, a polynucleic acid molecule described herein hybridizes to a target sequence of CTSL2. In some cases, a polynucleic acid molecule described herein hybridizes to a target sequence of TGIF. In some cases, a polynucleic acid molecule described herein hybridizes to a target sequence of MYOG. In some cases, a polynucleic acid molecule described herein hybridizes to a target sequence of HDAC2. In some cases, a polynucleic acid molecule described herein hybridizes to a target sequence of HDAC3. In some cases, a polynucleic acid molecule described herein hybridizes to a target sequence of MT1L. In some cases, a polynucleic acid molecule described herein hybridizes to a target sequence of MT1B. In some cases, a polynucleic acid molecule described herein hybridizes to a target sequence of of DMPK.

In some embodiments, the polynucleic acid molecule comprises a sequence having at least 50%, 55%, 60%, 65%, 70%, 75%, 80%, 85%, 90%, 95%, 96%, 97%, 97%, 98%, 99%, or 100% sequence identity to a target sequence as set forth in SEQ ID NOs: 28-141 and 370-480. In some embodiments, the polynucleic acid molecule comprises a sequence having at least 50% sequence identity to a target sequence as set forth in SEQ ID NOs: 28-141 and 370-480. In some embodiments, the polynucleic acid molecule comprises a sequence having at least 60% sequence identity to a target sequence as set forth in SEQ ID NOs: 28-141 and 370-480. In some embodiments, the polynucleic acid molecule comprises a sequence having at least 70% sequence identity to a target sequence as set forth in SEQ ID NOs: 28-141 and 370-480. In some embodiments, the polynucleic acid molecule comprises a sequence having at least 75% sequence identity to a target sequence as set forth in SEQ ID NOs: 28-141 and 370-480. In some embodiments, the polynucleic acid molecule comprises a sequence having at least 80% sequence identity to a target sequence as set forth in SEQ ID NOs: 28-141 and 370-480. In some embodiments, the polynucleic acid molecule comprises a sequence having at least 85% sequence identity to a target sequence as set forth in SEQ ID NOs: 28-141 and 370-480. In some embodiments, the polynucleic acid molecule comprises a sequence having at least 90% sequence identity to a target sequence as set forth in SEQ ID NOs: 28-141 and 370-480. In some embodiments, the polynucleic acid molecule comprises a sequence having at least 95% sequence identity to a target sequence as set forth in SEQ ID NOs: 28-141 and 370-480. In some embodiments, the polynucleic acid molecule comprises a sequence having at least 96% sequence identity to a target sequence as set forth in SEQ ID NOs: 28-141 and 370-480. In some embodiments, the polynucleic acid molecule comprises a sequence having at least 97% sequence identity to a target sequence as set forth in SEQ ID NOs: 28-141 and 370-480. In some embodiments, the polynucleic acid molecule comprises a sequence having at least 98% sequence identity to a target sequence as set forth in SEQ ID NOs: 28-141 and 370-480. In some embodiments, the polynucleic acid molecule comprises a sequence having at least 99% sequence identity to a target sequence as set forth in SEQ ID NOs: 28-141 and 370-480. In some embodiments, the polynucleic acid molecule consists of a target sequence as set forth in SEQ ID NOs: 28-141 and 370-480.

In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a target sequence as set forth in SEQ ID NOs: 703-3406. In some embodiments, the polynucleic acid molecule comprises a sequence having at least 50% sequence identity to a target sequence as set forth in SEQ ID NOs: 703-3406. In some embodiments, the polynucleic acid molecule comprises a sequence having at least 60% sequence identity to a target sequence as set forth in SEQ ID NOs: 703-3406. In some embodiments, the polynucleic acid molecule comprises a sequence having at least 70% sequence identity to a target sequence as set forth in SEQ ID NOs: 703-3406. In some embodiments, the polynucleic acid molecule comprises a sequence having at least 75% sequence identity to a target sequence as set forth in SEQ ID NOs: 703-3406. In some embodiments, the polynucleic acid molecule comprises a sequence having at least 80 sequence identity to a target sequence as set forth in SEQ ID NOs: 703-3406. In some embodiments, the polynucleic acid molecule comprises a sequence having at least 85% sequence identity to a target sequence as set forth in SEQ ID NOs: 703-3406. In some embodiments, the polynucleic acid molecule comprises a sequence having at least 90% sequence identity to a target sequence as set forth in SEQ ID NOs: 703-3406. In some embodiments, the polynucleic acid molecule comprises a sequence having at least 95% sequence identity to a target sequence as set forth in SEQ ID NOs: 703-3406. In some embodiments, the polynucleic acid molecule comprises a sequence having at least 96% sequence identity to a target sequence as set forth in SEQ ID NOs: 703-3406. In some embodiments, the polynucleic acid molecule comprises a sequence having at least 97% sequence identity to a target sequence as set forth in SEQ ID NOs: 703-3406. In some embodiments, the polynucleic acid molecule comprises a sequence having at least 98% sequence identity to a target sequence as set forth in SEQ ID NOs: 703-3406. In some embodiments, the polynucleic acid molecule comprises a sequence having at least 99% sequence identity to a target sequence as set forth in SEQ ID NOs: 703-3406. In some embodiments, the polynucleic acid molecule consists of a target sequence as set forth in SEQ ID NOs: 703-3406.

In some embodiments, the polynucleic acid molecule comprises a first polynucleotide and a second polynucleotide. In some instances, the first polynucleotide comprises a sequence having at least 50%, 55%, 60%, 65%, 70%, 75%, 80%, 85%, 90%, 95%, %%, 97%, 98%, 99%, or 100% sequence identity to a target sequence as set forth in SEQ ID NOs: 142-255, 256-369, 481-591, 592-702, and 3407-14222. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to a target sequence as set forth in SEQ ID NOs: 142-255, 256-369, 481-591, 592-702, and 3407-14222. In some cases, the poly nucleic acid molecule comprises a first polynucleotide having at least 50%, 55%, 60%, 65%, 70%, 75%, 80%, 85%, 90%, 95%, 96%, 97%, 98%, 99%, or 100% sequence identity to a target sequence as set forth in SEQ ID NOs: 142-255, 481-591, 3407-6110, and 8815-11518, and a second poly nucleotide having at least 50%, 55%, 60%, 65%, 70%, 75%, 80%, 85%, 90%, 95%, 96%, 97%, 98%, 99%, or 100% sequence identity to a target sequence as set forth in SEQ ID NOs: 256-369, 592-702, 6111-8814, and 11519-14222.

In some embodiments, the polynucleic acid molecule comprises a sense strand (e.g., a passenger strand) and an antisense strand (e.g., a guide strand). In some instances, the sense strand (e.g., the passenger strand) comprises a sequence having at least 50%, 55%, 60%, 65%, 70%, 75%, 80%, 85%, 90%, 95%, 96%, 97%, 98%, 99%, or 100% sequence identity to a target sequence as set forth in SEQ ID NOs: 142-255, 481-591, 3407-6110, and 8815-11518. In some instances, the antisense strand (e.g., the guide strand) comprises a sequence having at least 50%, 55%, 60%, 65%, 70%, 75%, 80%, 85%, 90%, 95%, 96%, 97%, 98%, 99%, or 100% sequence identity to a target sequence as set forth in SEQ ID NOs: 256-369, 592-702, 6111-8814, and 11519-14222.

In some embodiments, the polynucleic acid molecule described herein comprises RNA or DNA. In some cases, the polynucleic acid molecule comprises RNA. In some instances, RNA comprises short interfering RNA (siRNA), short hairpin RNA (shRNA), microRNA (miRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances, RNA comprises rRNA. In some instances, RNA comprises hnRNA. In some instances, the RNA comprises siRNA. In some instances, the polynucleic acid molecule comprises siRNA.

In some embodiments, the polynucleic acid molecule is from about 10 to about 50 nucleotides in length. In some instances, the polynucleic acid molecule is from about 10 to about 30, from about 15 to about 30, from about 18 to about 25, form about 18 to about 24, from about 19 to about 23, or from about 20 to about 22 nucleotides in length.

In some embodiments, the polynucleic acid molecule is about 50 nucleotides in length. In some instances, the polynucleic acid molecule is about 45 nucleotides in length. In some instances, the polynucleic acid molecule is about 40 nucleotides in length. In some instances, the polynucleic acid molecule is about 35 nucleotides in length. In some instances, the polynucleic acid molecule is about 30 nucleotides in length. In some instances, the polynucleic acid molecule is about 25 nucleotides in length. In some instances, the polynucleic acid molecule is about 20 nucleotides in length. In some instances, the polynucleic acid molecule is about 19 nucleotides in length. In some instances, the polynucleic acid molecule is about 18 nucleotides in length. In some instances, the polynucleic acid molecule is about 17 nucleotides in length. In some instances, the polynucleic acid molecule is about 16 nucleotides in length. In some instances, the polynucleic acid molecule is about 15 nucleotides in length. In some instances, the polynucleic acid molecule is about 14 nucleotides in length. In some instances, the polynucleic acid molecule is about 13 nucleotides in length. In some instances, the polynucleic acid molecule is about 12 nucleotides in length. In some instances, the polynucleic acid molecule is about 11 nucleotides in length. In some instances, the polynucleic acid molecule is about 10 nucleotides in length. In some instances, the polynucleic acid molecule is between about 10 and about 50 nucleotides in length. In some instances, the polynucleic acid molecule is between about 10 and about 45 nucleotides in length. In some instances, the polynucleic acid molecule is between about 10 and about 40 nucleotides in length. In some instances, the polynucleic acid molecule is between about 10 and about 35 nucleotides in length. In some instances, the polynucleic acid molecule is between about 10 and about 30 nucleotides in length. In some instances, the polynucleic acid molecule is between about 10 and about 25 nucleotides in length. In some instances, the polynucleic acid molecule is between about 10 and about 20 nucleotides in length. In some instances, the polynucleic acid molecule is between about 15 and about 25 nucleotides in length. In some instances, the polynucleic acid molecule is between about 15 and about 30 nucleotides in length. In some instances, the polynucleic acid molecule is between about 12 and about 30 nucleotides in length.

In some embodiments, the polynucleic acid molecule comprises a first polynucleotide. In some instances, the polynucleic acid molecule comprises a second polynucleotide. In some instances, the polynucleic acid molecule comprises a first polynucleotide and a second polynucleotide. In some instances, the first polynucleotide is a sense strand or passenger strand. In some instances, the second polynucleotide is an antisense strand or guide strand.

In some embodiments, the polynucleic acid molecule is a first polynucleotide. In some embodiments, the first polynucleotide is from about 10 to about 50 nucleotides in length. In some instances, the first polynucleotide is from about 10 to about 30, from about 15 to about 30, from about 18 to about 25, form about 18 to about 24, from about 19 to about 23, or from about 20 to about 22 nucleotides in length.

In some instances, the first polynucleotide is about 50 nucleotides in length. In some instances, the first polynucleotide is about 45 nucleotides in length. In some instances, the first polynucleotide is about 40 nucleotides in length. In some instances, the first polynucleotide is about 35 nucleotides in length. In some instances, the first polynucleotide is about 30 nucleotides in length. In some instances, the first polynucleotide is about 25 nucleotides in length. In some instances, the first polynucleotide is about 20 nucleotides in length. In some instances, the first polynucleotide is about 19 nucleotides in length. In some instances, the first polynucleotide is about 18 nucleotides in length. In some instances, the first polynucleotide is about 17 nucleotides in length. In some instances, the first polynucleotide is about 16 nucleotides in length. In some instances, the first polynucleotide is about 15 nucleotides in length. In some instances, the first polynucleotide is about 14 nucleotides in length. In some instances, the first polynucleotide is about 13 nucleotides in length. In some instances, the first polynucleotide is about 12 nucleotides in length. In some instances, the first polynucleotide is about 11 nucleotides in length. In some instances, the first polynucleotide is about 10 nucleotides in length. In some instances, the first polynucleotide is between about 10 and about 50 nucleotides in length. In some instances, the first polynucleotide is between about 10 and about 45 nucleotides in length. In some instances, the first polynucleotide is between about 10 and about 40 nucleotides in length. In some instances, the first polynucleotide is between about 10 and about 35 nucleotides in length. In some instances, the first polynucleotide is between about 10 and about 30 nucleotides in length. In some instances, the first polynucleotide is between about 10 and about 25 nucleotides in length. In some instances, the first polynucleotide is between about 10 and about 20 nucleotides in length. In some instances, the first polynucleotide is between about 15 and about 25 nucleotides in length. In some instances, the first polynucleotide is between about 15 and about 30 nucleotides in length. In some instances, the first polynucleotide is between about 12 and about 30 nucleotides in length.

In some embodiments, the polynucleic acid molecule is a second polynucleotide. In some embodiments, the second polynucleotide is from about 10 to about 50 nucleotides in length. In some instances, the second polynucleotide is from about 10 to about 30, from about 15 to about 30, from about 18 to about 25, form about 18 to about 24, from about 19 to about 23, or from about 20 to about 22 nucleotides in length.

In some instances, the second polynucleotide is about 50 nucleotides in length. In some instances, the second polynucleotide is about 45 nucleotides in length. In some instances, the second polynucleotide is about 40 nucleotides in length. In some instances, the second polynucleotide is about 35 nucleotides in length. In some instances, the second polynucleotide is about 30 nucleotides in length. In some instances, the second polynucleotide is about 25 nucleotides in length. In some instances, the second polynucleotide is about 20 nucleotides in length. In some instances, the second polynucleotide is about 19 nucleotides in length. In some instances, the second polynucleotide is about 18 nucleotides in length. In some instances, the second polynucleotide is about 17 nucleotides in length. In some instances, the second polynucleotide is about 16 nucleotides in length. In some instances, the second polynucleotide is about 15 nucleotides in length. In some instances, the second polynucleotide is about 14 nucleotides in length. In some instances, the second polynucleotide is about 13 nucleotides in length. In some instances, the second polynucleotide is about 12 nucleotides in length. In some instances, the second polynucleotide is about 11 nucleotides in length. In some instances, the second polynucleotide is about 10 nucleotides in length. In some instances, the second polynucleotide is between about 10 and about 50 nucleotides in length. In some instances, the second polynucleotide is between about 10 and about 45 nucleotides in length. In some instances, the second polynucleotide is between about 10 and about 40 nucleotides in length. In some instances, the second polynucleotide is between about 10 and about 35 nucleotides in length. In some instances, the second polynucleotide is between about 10 and about 30 nucleotides in length. In some instances, the second polynucleotide is between about 10 and about 25 nucleotides in length. In some instances, the second polynucleotide is between about 10 and about 20 nucleotides in length. In some instances, the second polynucleotide is between about 15 and about 25 nucleotides in length. In some instances, the second polynucleotide is between about 15 and about 30 nucleotides in length. In some instances, the second polynucleotide is between about 12 and about 30 nucleotides in length.

In some embodiments, the polynucleic acid molecule comprises a first polynucleotide and a second polynucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a 5' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides.

In some embodiments, the sequence of the polynucleic acid molecule is at least 40%, 50%, 55%, 60%, 65%, 70%, 75%, 80%, 85%, 90%, 95%, 98%, 99%, or 99.5% complementary to a target sequence described herein. In some embodiments, the sequence of the polynucleic acid molecule is at least 50% complementary to a target sequence described herein. In some embodiments, the sequence of the polynucleic acid molecule is at least 60% complementary to a target sequence described herein. In some embodiments, the sequence of the polynucleic acid molecule is at least 70% complementary to a target sequence described herein. In some embodiments, the sequence of the polynucleic acid molecule is at least 80% complementary to a target sequence described herein. In some embodiments, the sequence of the polynucleic acid molecule is at least 90% complementary to a target sequence described herein. In some embodiments, the sequence of the polynucleic acid molecule is at least 95% complementary to a target sequence described herein. In some embodiments, the sequence of the polynucleic acid molecule is at least 99% complementary to a target sequence described herein. In some instances, the sequence of the polynucleic acid molecule is 100% complementary to a target sequence described herein.

In some embodiments, the sequence of the polynucleic acid molecule has 5 or less mismatches to a target sequence described herein. In some embodiments, the sequence of the polynucleic acid molecule has 4 or less mismatches to a target sequence described herein. In some instances, the sequence of the polynucleic acid molecule has 3 or less mismatches to a target sequence described herein. In some cases, the sequence of the polynucleic acid molecule has 2 or less mismatches to a target sequence described herein. In some cases, the sequence of the polynucleic acid molecule has 1 or less mismatches to a target sequence described herein.

In some embodiments, the specificity of the polynucleic acid molecule that hybridizes to a target sequence described herein is a 95%, 98%, 99%, 99.5% or 100% sequence complementarity of the polynucleic acid molecule to a target sequence. In some instances, the hybridization is a high stringent hybridization condition.

In some embodiments, the polynucleic acid molecule has reduced off-target effect. In some instances. "off-target" or "off-target effects" refer to any instance in which a polynucleic acid polymer directed against a given target causes an unintended effect by interacting either directly or indirectly with another mRNA sequence, a DNA sequence or a cellular protein or other moiety. In some instances, an "off-target effect" occurs when there is a simultaneous degradation of other transcripts due to partial homology or complementarity between that other transcript and the sense and/or antisense strand of the polynucleic acid molecule.

In some embodiments, the polynucleic acid molecule comprises natural or synthetic or artificial nucleotide analogues or bases. In some cases, the polynucleic acid molecule comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some embodiments, nucleotide analogues or artificial nucleotide base comprise a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, and disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety. Exemplary chemical structures of a 2'-O-methyl modification of an adenosine molecule and 2'O-methoxyethyl modification of an uridine are illustrated below.

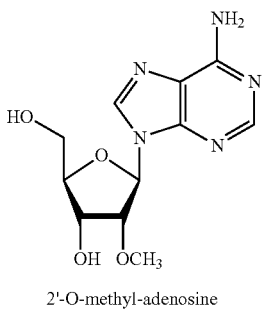

2'-O-methyl-adenosine

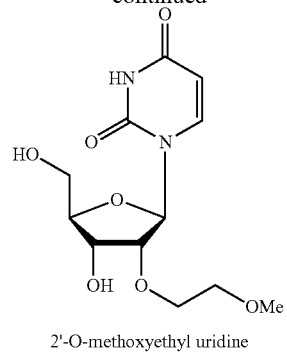

2'-O-methoxyethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

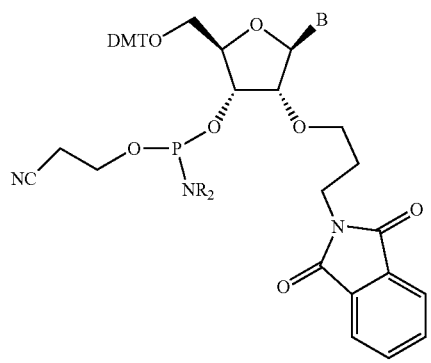

2'-O-aminopropyl nucleoside phosphoramidite

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^3$E) conformation of the furanose ring of an LNA monomer.

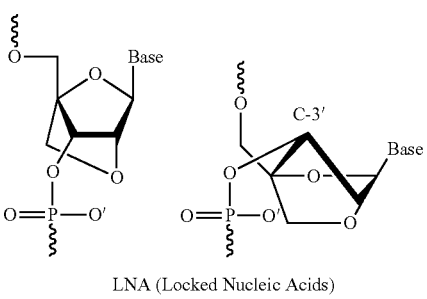

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a $C_3'$-endo sugar puckering conformation. ENA are part of the bridged nucleic acids class of modified nucleic acids that also comprises LNA. Exemplary chemical structures of the ENA and bridged nucleic acids are illustrated below.

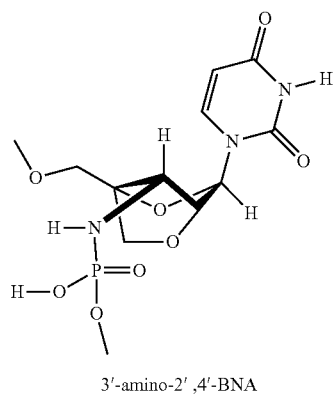

3'-amino-2',4'-BNA

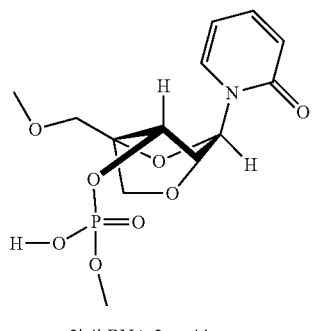

2',4'-BNA-2-pyridone

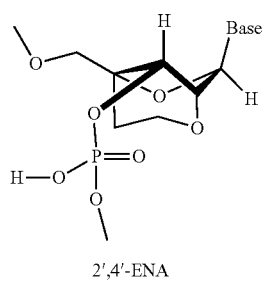

2',4'-ENA

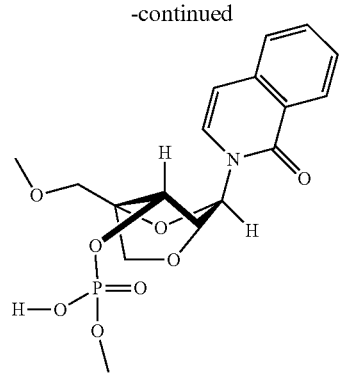

2',4'-BNA-1-isoquinolone

In some embodiments, additional modifications at the 2' hydroxyl group include 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA).

In some embodiments, nucleotide analogues comprise modified bases such as, but not limited to, 5-propynyluridine, 5-propynylcytidine, 6-methyladenine, 6-methylguanine, N,N,-dimethyladenine, 2-propyladenine, 2propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or be based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some embodiments, nucleotide analogues further comprise morpholinos, peptide nucleic acids (PNAs), methylphosphonate nucleotides, thiolphosphonate nucleotides, 2'-fluoro N3-P5'-phosphoramidites, 1',5'-anhydrohexitol nucleic acids (HNAs), or a combination thereof. Morpholino or phosphorodiamidate morpholino oligo (PMO) comprises synthetic molecules whose structure mimics natural nucleic acid structure by deviates from the normal sugar and phosphate structures. In some instances, the five member ribose ring is substituted with a six member morpholino ring containing four carbons, one nitrogen and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

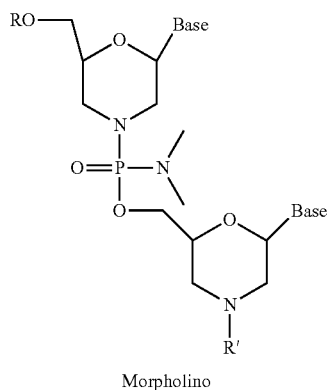

Morpholino

In some embodiments, peptide nucleic acid (PNA) does not contain sugar ring or phosphate linkage and the bases are attached and appropriately spaced by oligoglycine-like molecules, therefore, eliminating a backbone charge.

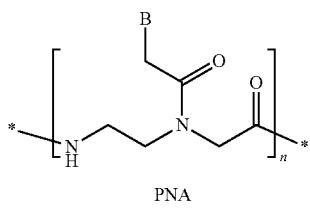

PNA

In some embodiments, one or more modifications optionally occur at the internucleotide linkage. In some instances, modified internucleotide linkage include, but is not limited to, phosphorothioates, phosphorodithioates, methylphosphonates, 5'-alkylenephosphonates, 5'-methylphosphonate, 3-alkylene phosphonates, borontrifluoridates, borano phosphate esters and selenophosphates of 3-5'linkage or 2-5'linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3-alkylphosphoramidates, aminoalkylphosphoramidates, thionophosphoramidates, phosphoropiperazidates, phosphoroanilothioates, phosphoranilidates, ketones, sulfones, sulfonamides, carbonates, carbamates, methylenehydrazos, methylknedimethylhvdrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof. Phosphorothioate antisense oligonucleotides (PS ASO) are antisense oligonucleotides comprising a phosphorothionate linkage. An exemplary PS ASO is illustrated below.

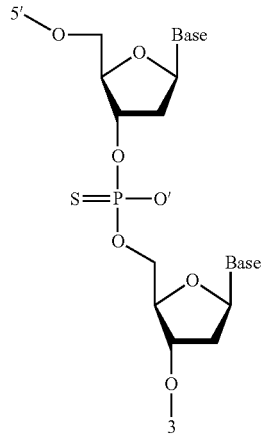

In some instances, the modification is a methyl or thiol modification such as methylphosphonate or thiolphosphonate modification. Exemplary thiolphosphonate nucleotide (left) and methylphosphonate nucleotide (right) are illustrated below.

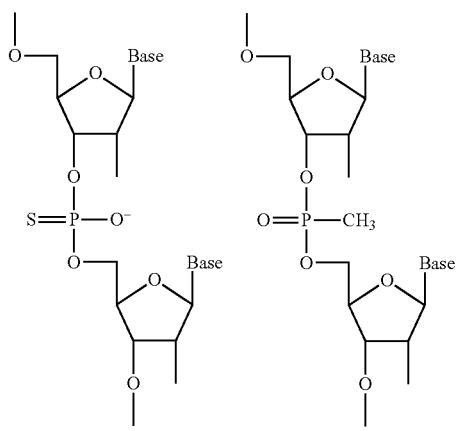

In some instances, a modified nucleotide includes, but is not limited to, 2'-fluoro N3-P5'-phosphoramidites illustrated as:

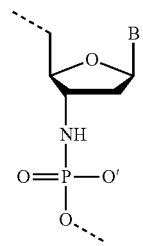

N3'-P5' Phosphoroamidate

In some instances, a modified nucleotide includes, but is not limited to, hexitol nucleic acid (or 1',5'-anhydrohexitol nucleic acids (HNA)) illustrated as:

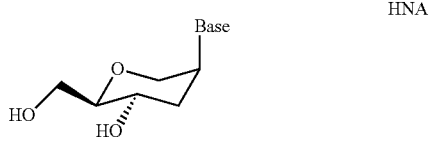

HNA

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g., a 3' C5-aminoalkyl dT. In an additional alternative, the 3'-terminus is optionally conjugated with an abasic site, e.g., with an apurinic or apyrimidinic site. In some instances, the 5'-terminus is conjugated with an aminoalkyl group. e.g., a 5'-O-alkylamino substituent. In some cases, the 5'-terminus is conjugated with an abasic site, e.g., with an apurmic or apyrimidinic site.

In some embodiments, the polynucleic acid molecule comprises one or more of the artificial nucleotide analogues described herein. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, T-deoxy-2'-fluoro, 2-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some instances, the polynucleic acid molecule comprises at least one of from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification.

In some cases, the polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification.

In some cases, the polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification.

In some instances, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification.

In some instances, the polynucleic acid molecule comprises at least one of: from about 10% to about 60% modification, from about 20% to about 60% modification, from about 30% to about 60% modification, from about 40% to about 60% modification, and from about 50% to about 60% modification.

In some cases, the polynucleic acid molecule comprises at least one of: from about 10% to about 50% modification, from about 20% to about 50% modification, from about 30% to about 50% modification, and from about 40% to about 50% modification.

In some cases, the polynucleic acid molecule comprises at least one of: from about 10% to about 40% modification, from about 20% to about 40% modification, and from about 30% to about 40% modification.

In some cases, the polynucleic acid molecule comprises at least one of: from about 10% to about 30% modification, and from about 20% to about 30% modification.

In some cases, the polynucleic acid molecule comprises from about 10% to about 20% modification.

In some cases, the polynucleic acid molecule comprises from about 15% to about 90%, from about 20% to about 80%, from about 30% to about 70%, or from about 40% to about 60% modifications.

In additional cases, the polynucleic acid molecule comprises at least about 15%, 20%, 30%, 40%, 50%, 60%, 70%, 80%, 90%, 95%, or 99% modification.

In some embodiments, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modifications.

In some instances, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modified nucleotides.

In some instances, from about 5 to about 100% of the polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95% or 100% of the polynucleic acid molecule comprise the artificial nucleotide analogues described herein. In some instances, about 5% of the polynucleic acid molecule comprises the artificial nucleotide analogues described herein. In some instances, about 10% of the polynucleic acid molecule comprises the artificial nucleotide analogues described herein. In some instances, about 15% of the polynucleic acid molecule comprises the artificial nucleotide analogues described herein. In some instances, about 20% of the polynucleic acid molecule comprises the artificial nucleotide analogues described herein. In some instances, about 25% of the polynucleic acid molecule comprises the artificial nucleotide analogues described herein. In some instances, about 30% of the polynucleic acid molecule comprises the artificial nucleotide analogues described herein. In some instances, about 35% of the polynucleic acid molecule comprises the artificial nucleotide analogues described herein. In some instances, about 40% of the polynucleic acid molecule comprises the artificial nucleotide analogues described herein. In some instances, about 45% of the polynucleic acid molecule comprises the artificial nucleotide analogues described herein. In some instances, about 50% of the polynucleic acid molecule comprises the artificial nucleotide analogues described herein. In some instances, about 55% of the polynucleic acid molecule comprises the artificial nucleotide analogues described herein. In some instances, about 60% of the polynucleic acid molecule comprises the artificial nucleotide analogues described herein. In some instances, about 65% of the polynucleic acid molecule comprises the artificial nucleotide analogues described herein. In some instances, about 70% of the polynucleic acid molecule comprises the artificial nucleotide analogues described herein. In some instances, about 75% of the polynucleic acid molecule comprises the artificial nucleotide analogues described herein. In some instances, about 80% of the polynucleic acid molecule comprises the artificial nucleotide analogues described herein. In some instances, about 85% of the polynucleic acid molecule comprises the artificial nucleotide analogues described herein. In some instances, about 90% of the polynucleic acid molecule comprises the artificial nucleotide analogues described herein. In some instances, about 95% of the polynucleic acid molecule comprises the artificial nucleotide analogues described herein. In some instances, about 96% of the polynucleic acid molecule comprises the artificial nucleotide analogues described herein. In some instances, about 97% of the polynucleic acid molecule comprises the artificial nucleotide analogues described herein. In some instances, about 98% of the polynucleic acid molecule comprises the artificial nucleotide analogues described herein. In some instances, about 99% of the polynucleic acid molecule comprises the artificial nucleotide analogues described herein. In some instances, about 100% of the polynucleic acid molecule comprises the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified. LNA, ENA, PNA. HNA, morpholino, methylphosphonate nucleotides, thiolphosphonate nucleotides, 2'-fluoro N3-P5'-phosphoramidites, or a combination thereof.

In some embodiments, the polynucleic acid molecule comprises from about 1 to about 25 modifications in which the modification comprises an artificial nucleotide analogues described herein. In some embodiments, the polynucleic acid molecule comprises about 1 modification in which the modification comprises an artificial nucleotide analogue described herein. In some embodiments, the polynucleic acid molecule comprises about 2 modifications in which the modifications comprise an artificial nucleotide analogue described herein. In some embodiments, the polynucleic acid molecule comprises about 3 modifications in which the modifications comprise an artificial nucleotide analogue described herein. In some embodiments, the polynucleic acid molecule comprises about 4 modifications in which the modifications comprise an artificial nucleotide analogue described herein. In some embodiments, the polynucleic acid molecule comprises about 5 modifications in which the modifications comprise an artificial nucleotide analogue described herein. In some embodiments, the polynucleic acid molecule comprises about 6 modifications in which the modifications comprise an artificial nucleotide analogue described herein. In some embodiments, the polynucleic acid molecule comprises about 7 modifications in which the modifications comprise an artificial nucleotide analogue described herein. In some embodiments, the polynucleic acid molecule comprises about 8 modifications in which the modifications comprise an artificial nucleotide analogue described herein. In some embodiments, the polynucleic acid molecule comprises about 9 modifications in which the modifications comprise an artificial nucleotide analogue described herein. In some embodiments, the polynucleic acid molecule comprises about 10 modifications in which the modifications comprise an artificial nucleotide analogue described herein. In some embodiments, the polynucleic acid molecule comprises about 11 modifications in which the modifications comprise an artificial nucleotide analogue described herein. In some embodiments, the polynucleic acid molecule comprises about 12 modifications in which the modifications comprise an artificial nucleotide analogue described herein. In some embodiments, the polynucleic acid molecule comprises about 13 modifications in which the modifications comprise an artificial nucleotide analogue described herein. In some embodiments, the polynucleic acid molecule comprises about 14 modifications in which the modifications comprise an artificial nucleotide analogue described herein. In some embodiments, the polynucleic acid molecule comprises about 15 modifications in which the modifications comprise an artificial nucleotide analogue described herein. In some embodiments, the polynucleic acid molecule comprises about 16 modifications in which the modifications comprise an artificial nucleotide analogue described herein. In some embodiments, the polynucleic acid molecule comprises about 17 modifications in which the modifications comprise an artificial nucleotide analogue described herein. In some embodiments, the polynucleic acid molecule comprises about 18 modifications in which the modifications comprise an artificial nucleotide analogue described herein. In some embodiments, the polynucleic acid molecule comprises about 19 modifications in which the modifications comprise an artificial nucleotide analogue described herein. In some embodiments, the polynucleic acid molecule comprises about 20 modifications in which the modifications comprise an artificial nucleotide analogue described herein. In some embodiments, the polynucleic acid molecule comprises about 21 modifications in which the modifications comprise an artificial nucleotide analogue described herein. In some embodiments, the polynucleic acid molecule comprises about 22 modifications in which the modifications comprise an artificial nucleotide analogue described herein. In some embodiments, the polynucleic acid molecule comprises about 23 modifications in which the modifications comprise an artificial nucleotide analogue described herein. In some embodiments, the polynucleic acid molecule comprises about 24 modifications in which the modifications comprise an artificial nucleotide analogue described herein. In some embodiments, the polynucleic acid molecule comprises about 25 modifications in which the modifications comprise an artificial nucleotide analogue described herein.

In some embodiments, a polynucleic acid molecule is assembled from two separate polynucleotides wherein one polynucleotide comprises the sense strand and the second polynucleotide comprises the antisense strand of the polynucleic acid molecule. In other embodiments, the sense strand is connected to the antisense strand via a linker molecule, which in some instances is a polynucleotide linker or a non-nucleotide linker.

In some embodiments, a polynucleic acid molecule comprises a sense strand and antisense strand, wherein pyrimidine nucleotides in the sense strand comprises 2'-O-methylpyrimidine nucleotides and purine nucleotides in the sense strand comprise 2'-deoxy purine nucleotides. In some embodiments, a polynucleic acid molecule comprises a sense strand and antisense strand, wherein pyrimidine nucleotides present in the sense strand comprise 2'-deoxy-2'-fluoro pyrimidine nucleotides and wherein purine nucleotides present in the sense strand comprise 2'-deoxy purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and the purine nucleotides when present in said antisense strand are 2'-O-methyl purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and wherein the purine nucleotides when present in said antisense strand comprise 2'-deoxy-purine nucleotides.

In some embodiments, a polynucleic acid molecule comprises a sense strand and antisense strand, wherein the sense strand includes a terminal cap moiety at the 5'-end, the 3'-end, or both of the 5' and 3' ends of the sense strand. In other embodiments, the terminal cap moiety is an inverted deoxy abasic moiety.

In some embodiments, a polynucleic acid molecule comprises a sense strand and an antisense strand, wherein the antisense strand comprises a phosphate backbone modification at the 3' end of the antisense strand. In some instances, the phosphate backbone modification is a phosphorothioate.

In some embodiments, a polynucleic acid molecule comprises a sense strand and an antisense strand, wherein the antisense strand comprises a glyceryl modification at the 3' end of the antisense strand.

In some embodiments, a polynucleic acid molecule comprises a sense strand and an antisense strand, in which the sense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and in which the antisense strand comprises about 1 to about 10 or more, specifically about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the sense strand comprises about 1 to about 25, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10, or more) 2'-deoxy, 2'-O-methyl, 2'-deoxy-2'-fluoro, and/or one or more (e.g., about 1, 2, 3, 4, 5, 6, 7, 8, 9, 10, or more) universal base modified nucleosides, and optionally a terminal cap molecule at the 3-end, the 5'-end, or both of the 3'- and 5'-ends of the sense strand; and in which the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the antisense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, 11, 12, 13, 14, 15, 16, 17, 18, 19, 20, or more pyrimidine nucleotides of the sense and/or antisense strand are chemically-modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In some embodiments, a polynucleic acid molecule comprises a sense strand and an antisense strand, in which the antisense strand comprises about 1 to about 25 or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10 or more pyrimidine nucleotides of the sense and/or antisense strand are chemically-modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In some embodiments, a polynucleic acid molecule described herein is a chemically-modified short interfering nucleic acid molecule having about 1 to about 25, for example, about 1, 2, 3, 4, 5, 6, 7, 8, 9, 10, 11, 12, 13, 14, 15, 16, 17, 18, 19, 20 or more phosphorothioate internucleotide linkages in each strand of the polynucleic acid molecule.

In another embodiment, a polynucleic acid molecule described herein comprises 2'-5' internucleotide linkages. In some instances, the 2'-5' internucleotide linkage(s) is at the 3'-end, the 5'-end, or both of the 3'- and 5'-ends of one or both sequence strands. In addition instances, the 2'-5' internucleotide linkage(s) is present at various other positions within one or both sequence strands, for example, about 1, 2, 3, 4, 5, 6, 7, 8, 9, 10, or more including every internucleotide linkage of a pyrimidine nucleotide in one or both strands of the polynucleic acid molecule comprise a 2'-5' internucleoside linkage, or about 1, 2, 3, 4, 5, 6, 7, 8, 9, 10, or more including every internucleotide linkage of a purine nucleotide in one or both strands of the polynucleic acid molecule comprise a 2'-5' internucleotide linkage.

In some embodiments, a polynucleic acid molecule is a single stranded polynucleic acid molecule that mediates RNAi activity in a cell or reconstituted in vitro system, wherein the polynucleic acid molecule comprises a single stranded polynucleotide having complementarity to a target nucleic acid sequence, and wherein one or more pyrimidine nucleotides present in the polynucleic acid are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the polynucleic acid are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, that is optionally present at the 3'-end, the 5'-end, or both of the 3' and 5'-ends of the antisense sequence, the polynucleic acid molecule optionally further comprising about 1 to about 4 (e.g., about 1, 2, 3, or 4) terminal 2'-deoxynucleotides at the 3'-end of the polynucleic acid molecule, wherein the terminal nucleotides further comprise one or more (e.g., 1, 2, 3, or 4) phosphorothioate internucleotide linkages, and wherein the polynucleic acid molecule optionally further comprises a terminal phosphate group, such as a 5'-terminal phosphate group.

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, T-deoxy-2-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribonuclease such as DNase, or exonuclease such as 5'-3' exonuclease and 3'-5' exonuclease. In some instances, 2'-O-methyl modified polynucleic acid molecule is nuclease resistance (e.g., RNase H, DNase, 5'-3' exonuclease or 3'-5' exonuclease resistance). In some instances, 2'O-methoxyethyl (2'-O-MOE) modified polynucleic acid molecule is nuclease resistance (e.g., RNase H. DNase, 5'-3' exonuclease or 3'-5' exonuclease resistance). In some instances, 2'-O-aminopropyl modified polynucleic acid molecule is nuclease resistance (e.g., RNase H, DNase, 5'-3' exonuclease or 3'-5' exonuclease resistance). In some instances, 2'-deoxy modified polynucleic acid molecule is nuclease resistance (e.g., RNase H, DNase, 5'-3' exonuclease or 3'-5' exonuclease resistance). In some instances, T-deoxy-2'-fluoro modified polynucleic acid molecule is nuclease resistance (e.g., RNase H. DNase, 5'-3' exonuclease or 3'-5' exonuclease resistance). In some instances, 2'-O-aminopropyl (2'-O-AP) modified polynucleic acid molecule is nuclease resistance (e.g., RNase H, DNase, 5'-3' exonuclease or 3'-5' exonuclease resistance). In some instances, 2'-dimethylaminoethyl (2'-O-DMAOE) modified polynucleic acid molecule is nuclease resistance (e.g., RNase H, DNase, 5'-3' exonuclease or 3'-5' exonuclease resistance). In some instances, 2'-O-dimethylaminopropyl (2'-O-DMAP) modified polynucleic acid molecule is nuclease resistance (e.g., RNase H. DNase, 5'-3' exonuclease or 3'-5' exonuclease resistance). In some instances. T-O-dimethylaminoethyloxyethyl (2'-O-DMAEOE) modified polynucleic acid molecule is nuclease resistance (e.g., RNase H, DNase, 5'-3' exonuclease or 3'-5' exonuclease resistance). In some instances, 2'-O—N-methylacetamido (2'-O-NMA) modified polynucleic acid molecule is nuclease resistance (e.g., RNase H, DNase, 5'-3' exonuclease or 3'-5' exonuclease resistance). In some instances, LNA modified poly nucleic acid molecule is nuclease resistance (e.g., RNase H, DNase, 5'-3' exonuclease or 3'-5' exonuclease resistance). In some instances. ENA modified polynucleic acid molecule is nuclease resistance (e.g., RNase H, DNase, 5'-3' exonuclease or 3'-5' exonuclease resistance). In some instances, HNA modified polynucleic acid molecule is nuclease resistance (e.g., RNase H, DNase, 5'-3' exonuclease or 3'-5' exonuclease resistance). In some instances, morpholinos is nuclease resistance (e.g., RNase H. DNase, 5'-3' exonuclease or 3'-5' exonuclease resistance). In some instances. PNA modified polynucleic acid molecule is resistant to nucleases (e.g., RNase H. DNase, 5'-3' exonuclease or 3'-5' exonuclease resistance). In some instances, methylphosphonate nucleotides modified polynucleic acid molecule is nuclease resistance (e.g., RNase H, DNase, 5'-3' exonuclease or 3'-5' exonuclease resistance). In some instances, thiolphosphonate nucleotides modified polynucleic acid molecule is nuclease resistance (e.g., RNase H. DNase, 5'-3' exonuclease or 3'-5' exonuclease resistance). In some instances, polynucleic acid molecule comprising 2'-fluoro N3-P5'-phosphoramidites is nuclease resistance (e.g., RNase H. DNase, 5'-3' exonuclease or 3'-5' exonuclease resistance). In some instances, the 5' conjugates described herein inhibit 5'-3' exonucleolytic cleavage. In some instances, the 3' conjugates described herein inhibit 3'-5' exonucleolytic cleavage.

In some embodiments, one or more of the artificial nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2-O-dimethylaminoethyl (2'-O-DMAOE), 2'-O-dimethylaminopropyl (2'-O-DMAP). T-O-dimethylaminoethyloxyethyl (2'-O-DMAEOE), or 2'-O—N-methylacetamido (2'-O-NMA) modified. LNA, ENA, PNA, HNA, morpholino, methylphosphonate nucleotides, thiolphosphonate nucleotides, or 2'-fluoro N3-P5'-phosphoramidites have increased binding affinity toward their mRNA target relative to an equivalent natural polynucleic acid molecule. In some instances, 2'-O-methyl modified polynucleic acid molecule has increased binding affinity toward their mRNA target relative to an equivalent natural polynucleic acid molecule. In some instances, 2'-O-methoxyethyl (2'-O-MOE) modified polynucleic acid molecule has increased binding affinity toward their mRNA target relative to an equivalent natural poly nucleic acid molecule. In some instances, 2'-O-aminopropyl modified polynucleic acid molecule has increased binding affinity toward their mRNA target relative to an equivalent natural polynucleic acid molecule. In some instances, 2'-deoxy modified polynucleic acid molecule has increased binding affinity toward their mRNA target relative to an equivalent natural polynucleic acid molecule. In some instances, T-deoxy-2'-fluoro modified polynucleic acid molecule has increased binding affinity toward their mRNA target relative to an equivalent natural polynucleic acid molecule. In some instances, 2'-O-aminopropyl (2'-O-AP) modified polynucleic acid molecule has increased binding affinity toward their mRNA target relative to an equivalent natural polynucleic acid molecule. In some instances, 2'-O-dimethylaminoethyl (2'-O-DMAOE) modified polynucleic acid molecule has increased binding affinity toward their mRNA target relative to an equivalent natural polynucleic acid molecule. In some instances, 2'-O-dimethylaminopropyl (2'-O-DMAP) modified polynucleic acid molecule has increased binding affinity toward their mRNA target relative to an equivalent natural polynucleic acid molecule. In some instances. T-O-dimethylaminoethyloxyethyl (2'-O-DMAEOE) modified polynucleic acid molecule has increased binding affinity toward their mRNA target relative to an equivalent natural polynucleic acid molecule. In some instances, 2'-O—N-methylacetamido (2'-O-NMA) modified polynucleic acid molecule has increased binding affinity toward their mRNA target relative to an equivalent natural polynucleic acid molecule. In some instances, LNA modified polynucleic acid molecule has increased binding affinity toward their mRNA target relative to an equivalent natural polynucleic acid molecule. In some instances. ENA modified polynucleic acid molecule has increased binding affinity toward their mRNA target relative to an equivalent natural polynucleic acid molecule. In some instances, PNA modified polynucleic acid molecule has increased binding affinity toward their mRNA target relative to an equivalent natural polynucleic acid molecule. In some instances. HNA modified polynucleic acid molecule has increased binding affinity toward their mRNA target relative to an equivalent natural polynucleic acid molecule. In some instances, morpholino modified polynucleic acid molecule has increased binding affinity toward their mRNA target relative to an equivalent natural polynucleic acid molecule. In some instances, methylphosphonate nucleotides modified polynucleic acid molecule has increased binding affinity toward their mRNA target relative to an equivalent natural polynucleic acid molecule. In some instances, thiolphosphonate nucleotides modified polynucleic acid molecule has increased binding affinity toward their mRNA target relative to an equivalent natural polynucleic acid molecule. In some instances, polynucleic acid molecule comprising 2'-fluoro N3-P5'-phosphoramidites has increased binding affinity toward their mRNA target relative to an equivalent natural polynucleic acid molecule. In some cases, the increased affinity is illustrated with a lower Kd, a higher melt temperature (Tm), or a combination thereof.

In some embodiments, a polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No.: WO2015107425.

In some embodiments, a polynucleic acid molecule described herein is further modified to include an aptamer conjugating moiety. In some instances, the aptamer conjugating moiety is a DNA aptamer conjugating moiety. In some instances, the aptamer conjugating moiety is Alphamer (Centauri Therapeutics), which comprises an aptamer portion that recognizes a specific cell-surface target and a portion that presents a specific epitopes for attaching to circulating antibodies. In some instance, a polynucleic acid molecule described herein is further modified to include an aptamer conjugating moiety as described in: U.S. Pat. Nos. 8,604,184, 8,591,910, and 7,850,975.

In additional embodiments, a polynucleic acid molecule described herein is modified to increase its stability. In some embodiment, the polynucleic acid molecule is RNA (e.g., siRNA). In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, T-deoxy-2'-fluoro, 2'-O-aminopropyl (2'-0-AP), 2'-4-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methyl-acetamido (2'-O-NMA) modification or by a locked or bridged ribose conformation (e.g., LNA or ENA). In some cases, the polynucleic acid molecule is modified by 2-O-methyl and/or 2'-O-methoxyethyl ribose. In some cases, the polynucleic acid molecule also includes morpholinos, PNAs. HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some instances, the polynucleic acid molecule is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. In some instances, the polynucleic acid molecule is assembled from two separate polynucleotides, where one strand is the sense strand and the other is the antisense strand, wherein the antisense and sense strands are self-complementary (e.g., each strand comprises nucleotide sequence that is complementary to nucleotide sequence in the other strand, such as where the antisense strand and sense strand form a duplex or double stranded structure, for example wherein the double stranded region is about 19, 20, 21, 22, 23, or more base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the polynucleic acid molecule is assembled from a single oligonucleotide, where the self-complementary sense and antisense regions of the polynucleic acid molecule are linked by means of a nucleic acid based or non-nucleic acid-based linker(s).

In some cases, the polynucleic acid molecule is a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. In other cases, the polynucleic acid molecule is a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide is processed either in vivo or in vitro to generate an active polynucleic acid molecule capable of mediating RNAi. In additional cases, the polynucleic acid molecule also comprises a single-stranded polynucleotide having nucleotide sequence complementary to nucleotide sequence in a target nucleic acid molecule or a portion thereof (for example, where such polynucleic acid molecule does not require the presence within the polynucleic acid molecule of nucleotide sequence corresponding to the target nucleic acid sequence or a portion thereof), wherein the single stranded polynucleotide further comprises a terminal phosphate group, such as a 5'-phosphate (see for example Martinez et al., 2002, *Cell.*, 110, 563-574 and Schwarz et al., 2002, *Molecular Cell*, 10, 537-568), or 5',3'-diphosphate.

In some instances, an asymmetric hairpin is a linear polynucleic acid molecule comprising an antisense region, a loop portion that comprises nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin polynucleic acid molecule comprises an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. In some cases, the asymmetric hairpin polynucleic acid molecule also comprises a 5'-terminal phosphate group that is chemically modified. In additional cases, the loop portion of the asymmetric hairpin polynucleic acid molecule comprises nucleotides, non-nucleotides, linker molecules, or conjugate molecules.

4 In some embodiments, an asymmetric duplex is a polynucleic acid molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex polynucleic acid molecule comprises an antisense region having length sufficient to mediate RNAi in a cell or in vitro system (e.g. about 19 to about 22 nucleotides) and a sense region having about 3 to about 18 nucleotides that are complementary to the antisense region.

In some cases, a universal base refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitrooxazole derivatives such as 3-nitropyrrole, 4-nitroindole, 5-nitroindole, and 6-nitroindole as known in the art (see for example Loakes, 2001, *Nucleic Acids Research*, 29, 2437-2447).

Polynucleic Acid Molecule Synthesis

In some embodiments, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication No. 1579015. Additional exemplary methods include those described in: Griffey et al., "2'-O-aminopropyl ribonucleotides: a zwitterionic modification that enhances the exonuclease resistance and biological activity of antisense oligonucleotides," J. Med Chem. 39(26):5100-5109 (1997)); Obika, et al. "Synthesis of 2-O4-C-methyleneuridine and -cytidine. Novel bicyclic nucleosides having a fixed C3,-endo sugar puckering". Tetrahedron Letters 38 (50): 8735 (1997); Koizumi, M. "ENA oligonucleotides as therapeutics". Current opinion in molecular therapeutics 8 (2): 144-149 (2006): and Abramova et al., "Novel oligonucleotide analogues based on morpholino nucleoside subunits-antisense technologies: new chemical possibilities," Indian Journal of Chemistry 48B:1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

In some embodiments, a polynucleic acid molecule is synthesized via a tandem synthesis methodology, wherein both strands are synthesized as a single contiguous oligonucleotide fragment or strand separated by a cleavable linker which is subsequently cleaved to provide separate fragments or strands that hybridize and permit purification of the duplex.

In some instances, a polynucleic acid molecule is also assembled from two distinct nucleic acid strands or fragments wherein one fragment includes the sense region and the second fragment includes the antisense region of the molecule.

Additional modification methods for incorporating, for example, sugar, base and phosphate modifications include: Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat. U.S. Pat. No. 5,334,711 and Beigelman et al., 1995, J. Biol. Chem., 27), 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med Chem., 5, 1999-2010. Such publications describe general methods and strategies to determine the location of incorporation of sugar, base and/or phosphate modifications and the like into nucleic acid molecules without modulating catalysis.

In some instances, while chemical modification of the polynucleic acid molecule internucleotide linkages with phosphorothioate, phosphorodithioate, and/or 5'-methylphosphonate linkages improves stability, excessive modifications sometimes cause toxicity or decreased activity. Therefore, when designing nucleic acid molecules, the amount of these internucleotide linkages in some cases is minimized. In such cases, the reduction in the concentration of these linkages lowers toxicity, increases efficacy and higher specificity of these molecules.

Polynucleic Acid Molecule Conjugates

In some embodiments, a polynucleic acid molecule is further conjugated to a polypeptide A for delivery to a site of interest. In some cases, a polynucleic acid molecule is conjugated to a polypeptide A and optionally a polymeric moiety.

In some instances, at least one polypeptide A is conjugated to at least one B. In some instances, the at least one polypeptide A is conjugated to the at least one B to form an A-B conjugate. In some embodiments, at least one A is conjugated to the 5' terminus of B, the 3' terminus of B, an internal site on B, or in any combinations thereof. In some instances, the at least one polypeptide A is conjugated to at least two B. In some instances, the at least one polypeptide A is conjugated to at least 2, 3, 4, 5, 6, 7, 8, or more B.

In some embodiments, at least one polypeptide A is conjugated at one terminus of at least one B while at least one C is conjugated at the opposite terminus of the at least one B to form an A-B-C conjugate. In some instances, at least one polypeptide A is conjugated at one terminus of the at least one B while at least one of C is conjugated at an internal site on the at least one B. In some instances, at least one polypeptide A is conjugated directly to the at least one C. In some instances, the at least one B is conjugated indirectly to the at least one polypeptide A via the at least one C to form an A-C-B conjugate.

In some instances, at least one B and/or at least one C, and optionally at least one D are conjugated to at least one polypeptide A. In some instances, the at least one B is conjugated at a terminus (e.g., a 5' terminus or a 3' terminus) to the at least one polypeptide A or are conjugated via an internal site to the at least one polypeptide A. In some cases, the at least one C is conjugated either directly to the at least one polypeptide A or indirectly via the at least one B. If indirectly via the at least one B, the at least one C is conjugated either at the same terminus as the at least one polypeptide A on B, at opposing terminus from the at least one polypeptide A, or independently at an internal site. In some instances, at least one additional polypeptide A is further conjugated to the at least one polypeptide A, to B, or to C. In additional instances, the at least one D is optionally conjugated either directly or indirectly to the at least one polypeptide A, to the at least one B, or to the at least one C. If directly to the at least one polypeptide A, the at least one D is also optionally conjugated to the at least one B to form an A-D-B conjugate or is optionally conjugated to the at least one B and the at least one C to form an A-D-B-C conjugate. In some instances, the at least one D is directly conjugated to the at least one polypeptide A and indirectly to the at least one B and the at least one C to form a D-A-B-C conjugate. If indirectly to the at least one polypeptide A, the at least one D is also optionally conjugated to the at least one B to form an A-B-D conjugate or is optionally conjugated to the at least one B and the at least one C to form an A-B-D-C conjugate. In some instances, at least one additional D is further conjugated to the at least one polypeptide A, to B, or to C.

Figure 19A:
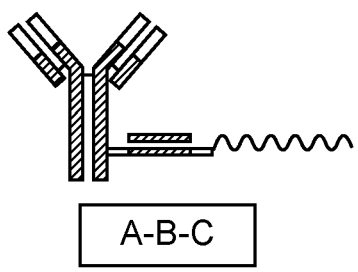
FIG. 19A-FIG. 19L show exemplary antibody-nucleic acid conjugates described herein.

In some embodiments, a polynucleic acid molecule conjugate comprises a construct as illustrated in FIG. 19A.

Figure 19B:
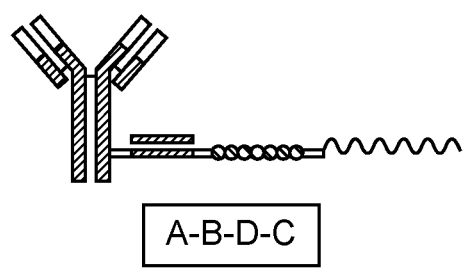

In some embodiments, a polynucleic acid molecule conjugate comprises a construct as illustrated in FIG. 19B.

Figure 19C:
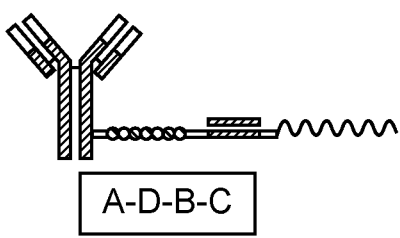

In some embodiments, a polynucleic acid molecule conjugate comprises a construct as illustrated in FIG. 19C.

Figure 19D:
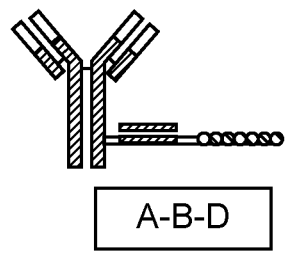

In some embodiments, a polynucleic acid molecule conjugate comprises a construct as illustrated in FIG. 19D.

Figure 19E:
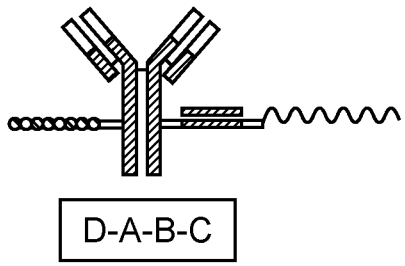

In some embodiments, a polynucleic acid molecule conjugate comprises a construct as illustrated in FIG. 19E.

Figure 19F:
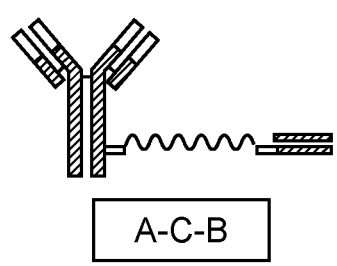

In some embodiments, a polynucleic acid molecule conjugate comprises a construct as illustrated in FIG. 19F.

Figure 19G:
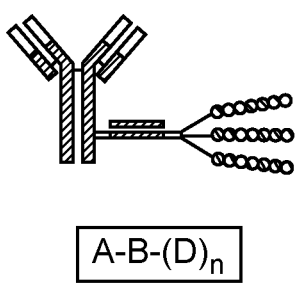

In some embodiments, a polynucleic acid molecule conjugate comprises a construct as illustrated in FIG. 19G.

Figure 19H:
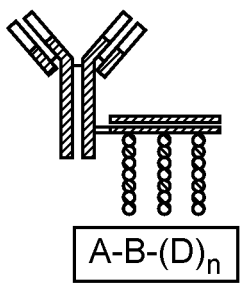

In some embodiments, a polynucleic acid molecule conjugate comprises a construct as illustrated in FIG. 19H.

Figure 19I:
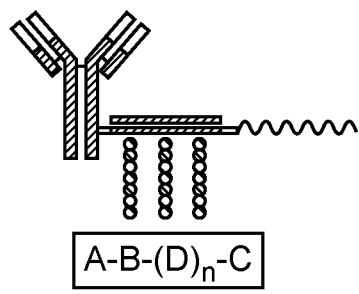

In some embodiments, a polynucleic acid molecule conjugate comprises a construct as illustrated in FIG. 19I.

Figure 19J:
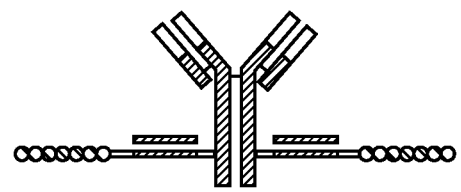

In some embodiments, a polynucleic acid molecule conjugate comprises a construct as illustrated in FIG. 19J.

Figure 19K:
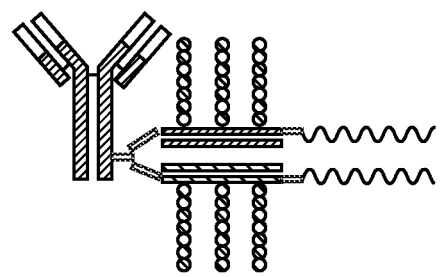

In some embodiments, a polynucleic acid molecule conjugate comprises a construct as illustrated in FIG. 19K.

Figure 19L:
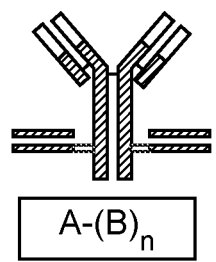

In some embodiments, a polynucleic acid molecule conjugate comprises a construct as illustrated in FIG. 19L.

Figure 19M:
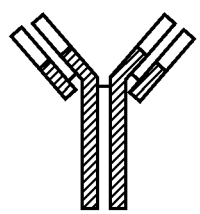
FIG. 19M presents an antibody cartoon utilized in FIG. 19A-FIG. 19L.

The antibody cartoon as illustrated in FIG. 19M is for representation purposes only and encompasses a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof.

Binding Moiety

In some embodiments, the binding moiety A is a polypeptide. In some instances, the polypeptide is an antibody or its fragment thereof. In some cases, the fragment is a binding fragment. In some instances, the antibody or binding fragment thereof comprises a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'s fragments, single-chain variable fragment (scFv), bis-scFv, (scFv), diabody, minibody, nanobody, triabody, tetrabody, disulfide stabilized Fv protein (dsFv), single-domain antibody (sdAb), Ig NAR, camelid antibody or binding fragment thereof, bispecific antibody or biding fragment thereof, or a chemically modified derivative thereof.

In some instances, A is an antibody or binding fragment thereof. In some instances, A is a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)$_3$ fragments, single-chain variable fragment (scFv), bis-scFv, (scFv)$_2$, diabody, minibody, nanobody, triabody, tetrabody, disulfide stabilized Fv protein ("dsFv"), single-domain antibody (sdAb), Ig NAR, camelid antibody or binding fragment thereof, bispecific antibody or biding fragment thereof, or a chemically modified derivative thereof. In some instances, A is a humanized antibody or binding fragment thereof. In some instances, A is a murine antibody or binding fragment thereof. In some instances, A is a chimeric antibody or binding fragment thereof. In some instances, A is a monoclonal antibody or binding fragment thereof. In some instances, A is a monovalent Fab'. In some instances. A is a divalent Fab$_2$. In some instances. A is a single-chain variable fragment (scFv).

In some embodiments, the binding moiety A is a bispecific antibody or binding fragment thereof. In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens.

In some cases, the bispecific antibody is a bispecific mini-antibody. In some instances, the bispecific mini-antibody comprises divalent Fab$_2$, F(ab)'$_3$ fragments, bis-scFv, (scFv)$_2$, diabody, minibody, triabody, tetrabody or a bi-specific T-cell engager (BiTE). In some embodiments, the bi-specific T-cell engager is a fusion protein that contains two single-chain variable fragments (scFvs) in which the two scFvs target epitopes of two different antigens.

In some embodiments, the binding moiety A is a bispecific mini-antibody. In some instances, A is a bispecific Fab$_2$. In some instances, A is a bispecific F(ab)$_3$ fragment. In some cases, A is a bispecific bis-scFv. In some cases, A is a bispecific (scFv)$_2$. In some embodiments. A is a bispecific diabody. In some embodiments, A is a bispecific minibody. In some embodiments, A is a bispecific triabody. In other embodiments, A is a bispecific tetrabody. In other embodiments. A is a bi-specific T-cell engager (BiTE).

In some embodiments, the binding moiety A is a trispecific antibody. In some instances, the trispecific antibody comprises F(ab)'$_3$ fragments or a triabody. In some instances, A is a trispecific F(ab)'$_3$ fragment. In some cases, A is a triabody. In some embodiments, A is a trispecific antibody as described in Dimas, et al., "Development of a trispecific antibody designed to simultaneously and efficiently target three different antigens on tumor cells," *Mol. Pharmaceutics*, 12(9): 3490-3501 (2015).

In some embodiments, the binding moiety A is an antibody or binding fragment thereof ta recognizes a cell surface protein. In some instances, the binding moiety A is an antibody or binding fragment thereof that recognizes a cell surface protein on a muscle cell. In some cases, the binding moiety A is an antibody or binding fragment thereof that recognizes a cell surface protein on a skeletal muscle cell.

In some embodiments, exemplary antibodies include, but are not limited to, an anti-myosin antibody, an anti-transferrin antibody, and an antibody that recognizes Muscle-Specific kinase (MuSK). In some instances, the antibody is an anti-transferrin (anti-CD71) antibody.

In some embodiments, the binding moiety A is conjugated to a polynucleic acid molecule (B) non-specifically. In some instances, the binding moiety A is conjugated to a polynucleic acid molecule (B) via a lysine residue or a cysteine residue, in a non-site specific manner. In some instances, the binding moiety A is conjugated to a polynucleic acid molecule (B) via a lysine residue in a non-site specific manner. In some cases, the binding moiety A is conjugated to a polynucleic acid molecule (B) via a cysteine residue in a non-site specific manner.

In some embodiments, the binding moiety A is conjugated to a polynucleic acid molecule (B) in a site-specific manner. In some instances, the binding moiety A is conjugated to a polynucleic acid molecule (B) through a lysine residue, a cysteine residue, at the 5'-terminus, at the 3'-terminus, an unnatural amino acid, or an enzyme-modified or enzyme-catalyzed residue, via a site-specific manner. In some instances, the binding moiety A is conjugated to a polynucleic acid molecule (B) through a lysine residue via a site-specific manner. In some instances, the binding moiety A is conjugated to a polynucleic acid molecule (B) through a cysteine residue via a site-specific manner. In some instances, the binding moiety A is conjugated to a polynucleic acid molecule (B) at the 5'-terminus via a site-specific manner. In some instances, the binding moiety A is conjugated to a polynucleic acid molecule (B) at the 3'-terminus via a site-specific manner. In some instances, the binding moiety A is conjugated to a polynucleic acid molecule (B) through an unnatural amino acid via a site-specific manner. In some instances, the binding moiety A is conjugated to a polynucleic acid molecule (B) through an enzyme-modified or enzyme-catalyzed residue via a site-specific manner.

In some embodiments, one or more polynucleic acid molecule (B) is conjugated to a binding moiety A. In some instances, about 1, 2, 3, 4, 5, 6, 7, 8, 9, 10, 11, 12, 13, 14, 15, 16, or more polynucleic acid molecules are conjugated to one binding moiety A. In some instances, about 1 polynucleic acid molecule is conjugated to one binding moiety A. In some instances, about 2 polynucleic acid molecules are conjugated to one binding moiety A. In some instances, about 3 polynucleic acid molecules are conjugated to one binding moiety A. In some instances, about 4 polynucleic acid molecules are conjugated to one binding moiety A. In some instances, about 5 polynucleic acid molecules are conjugated to one binding moiety A. In some instances, about 6 polynucleic acid molecules are conjugated to one binding moiety A. In some instances, about 7 polynucleic acid molecules are conjugated to one binding moiety A. In some instances, about 8 polynucleic acid molecules are conjugated to one binding moiety A. In some instances, about 9 polynucleic acid molecules are conjugated to one binding moiety A. In some instances, about 10 polynucleic acid molecules are conjugated to one binding moiety A. In some instances, about 11 polynucleic acid molecules are conjugated to one binding moiety A. In some instances, about 12 polynucleic acid molecules are conjugated to one binding moiety A. In some instances, about 13 polynucleic acid molecules are conjugated to one binding moiety A. In some instances, about 14 polynucleic acid molecules are conjugated to one binding moiety A. In some instances, about 15 polynucleic acid molecules are conjugated to one binding moiety A. In some instances, about 16 polynucleic acid molecules are conjugated to one binding moiety A. In some cases, the one or more polynucleic acid molecules are the same. In other cases, the one or more polynucleic acid molecules are different.

In some embodiments, the number of polynucleic acid molecule (B) conjugated to a binding moiety A forms a ratio. In some instances, the ratio is referred to as a DAR (drug-to-antibody) ratio, in which the drug as referred to herein is the polynucleic acid molecule (B). In some instances, the DAR ratio of the polynucleic acid molecule (B) to binding moiety A is about 1, 2, 3, 4, 5, 6, 7, 8, 9, 10, 11, 12, 13, 14, 15, 16, or greater. In some instances, the DAR ratio of the polynucleic acid molecule (B) to binding moiety A is about 1 or greater. In some instances, the DAR ratio of the polynucleic acid molecule (B) to binding moiety A is about 2 or greater. In some instances, the DAR ratio of the polynucleic acid molecule (B) to binding moiety A is about 3 or greater. In some instances, the DAR ratio of the polynucleic acid molecule (B) to binding moiety A is about 4 or greater. In some instances, the DAR ratio of the polynucleic acid molecule (B) to binding moiety A is about 5 or greater. In some instances, the DAR ratio of the polynucleic acid molecule (B) to binding moiety A is about 6 or greater. In some instances, the DAR ratio of the polynucleic acid molecule (B) to binding moiety A is about 7 or greater. In some instances, the DAR ratio of the polynucleic acid molecule (B) to binding moiety A is about 8 or greater. In some instances, the DAR ratio of the polynucleic acid molecule (B) to binding moiety A is about 9 or greater. In some instances, the DAR ratio of the polynucleic acid molecule (B) to binding moiety A is about 10 or greater. In some instances, the DAR ratio of the polynucleic acid molecule (B) to binding moiety A is about 11 or greater. In some instances, the DAR ratio of the polynucleic acid molecule (B) to binding moiety A is about 12 or greater.

In some instances, the DAR ratio of the polynucleic acid molecule (B) to binding moiety A is about 1, 2, 3, 4, 5, 6, 7, 8, 9, 10, 11, 12, 13, 14, 15, or 16. In some instances, the DAR ratio of the polynucleic acid molecule (B) to binding moiety A is about 1. In some instances, the DAR ratio of the polynucleic acid molecule (B) to binding moiety A is about 2. In some instances, the DAR ratio of the polynucleic acid molecule (B) to binding moiety A is about 3. In some instances, the DAR ratio of the polynucleic acid molecule (B) to binding moiety A is about 4. In some instances, the DAR ratio of the polynucleic acid molecule (B) to binding moiety A is about 5. In some instances, the DAR ratio of the polynucleic acid molecule (B) to binding moiety A is about 6. In some instances, the DAR ratio of the polynucleic acid molecule (B) to binding moiety A is about 7. In some instances, the DAR ratio of the polynucleic acid molecule (B) to binding moiety A is about 8. In some instances, the DAR ratio of the polynucleic acid molecule (B) to binding moiety A is about 9. In some instances, the DAR ratio of the polynucleic acid molecule (B) to binding moiety A is about 10. In some instances, the DAR ratio of the polynucleic acid molecule (B) to binding moiety A is about 11. In some instances, the DAR ratio of the polynucleic acid molecule (B) to binding moiety A is about 12. In some instances, the DAR ratio of the polynucleic acid molecule (B) to binding moiety A is about 13. In some instances, the DAR ratio of the polynucleic acid molecule (B) to binding moiety A is about 14. In some instances, the DAR ratio of the polynucleic acid molecule (B) to binding moiety A is about 13. In some instances, the DAR ratio of the polynucleic acid molecule (B) to binding moiety A is about 16.

In some instances, the DAR ratio of the polynucleic acid molecule (B) to binding moiety A is 1, 2, 3, 4, 5, 6, 7, 8, 9, 10, 11, 12, 13, 14, 15, or 16. In some instances, the DAR ratio of the polynucleic acid molecule (B) to binding moiety A is 1. In some instances, the DAR ratio of the polynucleic acid molecule (B) to binding moiety A is 2. In some instances, the DAR ratio of the polynucleic acid molecule (B) to binding moiety A is 4. In some instances, the DAR ratio of the polynucleic acid molecule (B) to binding moiety A is 6. In some instances, the DAR ratio of the polynucleic acid molecule (B) to binding moiety A is 8. In some instances, the DAR ratio of the polynucleic acid molecule (B) to binding moiety A is 12.

In some instances, a conjugate comprising polynucleic acid molecule (B) and binding moiety A has improved activity as compared to a conjugate comprising polynucleic acid molecule (B) without a binding moiety A. In some instances, improved activity results in enhanced biologically relevant functions, e.g., improved stability, affinity, binding, functional activity, and efficacy in treatment or prevention of a disease state. In some instances, the disease state is a result of one or more mutated exons of a gene. In some instances, the conjugate comprising polynucleic acid molecule (B) and binding moiety. A results in increased exon skipping of the one or more mutated exons as compared to the conjugate comprising polynucleic acid molecule (B) without a binding moiety A. In some instances, exon skipping is increased by at least or about 5%, 10%, 20%, 254, 30%, 40%, 50%, 60%, 70%, 80%, 90%, 95%, or more than 95% in the conjugate comprising polynucleic acid molecule (B) and binding moiety A as compared to the conjugate comprising polynucleic acid molecule (B) without a binding moiety A.

In some embodiments, an antibody or its binding fragment is further modified using conventional techniques known in the art, for example, by using amino acid deletion, insertion, substitution, addition, and/or by recombination and/or any other modification (e.g. posttranslational and chemical modifications, such as glycosylation and phosphorylation) known in the art either alone or in combination. In some instances, the modification further comprises a modification for modulating interaction with Fc receptors. In some instances, the one or more modifications include those described in, for example. International Publication No. WO97/34631, which discloses amino acid residues involved in the interaction between the Fc domain and the FcRn receptor. Methods for introducing such modifications in the nucleic acid sequence underlying the amino acid sequence of an antibody or its binding fragment is well known to the person skilled in the art.

In some instances, an antibody binding fragment further encompasses its derivatives and includes polypeptide sequences containing at least one CDR.

In some instances, the term "single-chain" as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such embodiments, bi-specific single chain antibody construct is tandem bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some embodiments, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to that the antibody or its binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further embodiments, the binding is exemplified by the specificity of a "key-lock-principle". Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well in a simple binding of the site to the antigen.

In some instances, specific interaction further refers to a reduced cross-reactivity of the antibody or its binding fragment or a reduced off-target effect. For example, the antibody or its binding fragment that bind to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Additional Binding Moieties

In some embodiments, the binding moiety is a plasma protein. In some instances, the plasma protein comprises albumin. In some instances, the binding moiety A is albumin. In some instances, albumin is conjugated by one or more of a conjugation chemistry described herein to a polynucleic acid molecule. In some instances, albumin is conjugated by native ligation chemistry to a polynucleic acid molecule. In some instances, albumin is conjugated by lysine conjugation to a polynucleic acid molecule.

In some instances, the binding moiety is a steroid. Exemplary steroids include cholesterol, phospholipids, di- and triacylglycerols, fatty acids, hydrocarbons that are saturated, unsaturated, comprise substitutions, or combinations thereof. In some instances, the steroid is cholesterol. In some instances, the binding moiety is cholesterol. In some instances, cholesterol is conjugated by one or more of a conjugation chemistry described herein to a polynucleic acid molecule. In some instances, cholesterol is conjugated by native ligation chemistry to a polynucleic acid molecule. In some instances, cholesterol is conjugated by lysine conjugation to a polynucleic acid molecule.

In some instances, the binding moiety is a polymer, including but not limited to polynucleic acid molecule aptamers that bind to specific surface markers on cells. In this instance the binding moiety is a polynucleic acid that does not hybridize to a target gene or mRNA, but instead is capable of selectively binding to a cell surface marker similarly to an antibody binding to its specific epitope of a cell surface marker.

In some cases, the binding moiety is a peptide. In some cases, the peptide comprises between about 1 and about 3 kDa. In some cases, the peptide comprises between about 1.2 and about 2.8 kDa, about 1.5 and about 2.5 kDa, or about 1.5 and about 2 kDa. In some instances, the peptide is a bicyclic peptide. In wine cases, the bicyclic peptide is a constrained bicyclic peptide. In some instances, the binding moiety is a bicyclic peptide (e.g., bicycles from Bicycle Therapeutics).

In additional cases, the binding moiety is a small molecule. In some instances, the small molecule is an antibody-recruiting small molecule. In some cases, the antibody-recruiting small molecule comprises a target-binding terminus and an antibody-binding terminus, in which the target-binding terminus is capable of recognizing and interacting with a cell surface receptor. For example, in some instances, the target-binding terminus comprising a glutamate urea compound enables interaction with PSMA, thereby, enhances an antibody interaction with a cell that expresses PSMA. In some instances, a binding moiety is a small molecule described in Zhang et al., "A remote arene-binding site on prostate specific membrane antigen revealed by antibody-recruiting small molecules." J Am Chem Soc. 132(36): 12711-12716 (2010): or McEnaney, et al., "Antibody-recruiting molecules: an emerging paradigm for engaging immune function in treating human disease," ACS Chem Biol. 7(7): 1139-1151 (2012).

Production of Antibodies or Binding Fragments Thereof

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a rabbit, to generate polyclonal antibodies or, more preferably, by generating monoclonal antibodies, e.g., as described by Kohler and Milstein (1975, *Nature* 256:495-497) or, as described by Kozbor et al. (1983, *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody is optionally obtained by screening Fab expression libraries (e.g., as described in Huse et al., 1989. Science 246:1275-1281) for clones of Fab fragments that bind the specific antigen or by screening antibody libraries (See. e.g., Clackson et al., 1991. Nature 352:624; Hane et al., 1997 *Proc. Natl. Acad. Sci. USA* 94:4937).

In some embodiments, techniques developed for the production of "chimeric antibodies" (Morrison et al., 1984, *Proc. Natl. Acad Sci.* 81:851-855; Neuberger et al., 1984, *Nature* 312:604-608; Takeda et al., 1985, *Nature* 314: 452454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region. e.g., humanized antibodies.

In some embodiments, techniques described for the production of single chain antibodies (U.S. Pat. No. 4,694,778; Bird, 1988, *Science* 242:42342; Huston et al., 1988, *Proc. Natl. Acad. Sci. USA* 85:5879-5883; and Ward et al., 1989. Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, Science 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences: plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter, the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk–, hgprt– or aprn– cells, respectively. Also, antimetabolite resistance are used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G418 (*Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993. *Science* 260:926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons. NY; Kriegler, 1990. *Gene Transfer and Expression, A Laboratory Manual*, Stockton Press. NY; and in Chapters 12 and 13, Dracopoli et al. (eds), 1994, *Current Protocols in Human Genetics*, John Wiley & Sons. NY.; Colberre-Garapin et al., 1981, *J. Mol. Biol.* 150:1).

In some instances, the expression levels of an antibody are increased by vector amplification (for a review, see Bebbington and Hentschel. *The use of vectors based on gene amplification for the expression of cloned genes in mammalian cells in DNA cloning*. Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, Mol. Cell Biol. 3:257).

In some instances, any method known in the art for purification or analysis of an antibody or antibody conjugates is used, for example, by chromatography (e.g., ion exchange, affinity, particularly by affinity for the specific antigen after Protein A, and sizing column chromatography), centrifugation, differential solubility, or by any other standard technique for the purification of proteins. Exemplary chromatography methods included, but are not limited to, strong anion exchange chromatography, hydrophobic interaction chromatography, size exclusion chromatography, and fast protein liquid chromatography.

Conjugation Chemistry

In some embodiments, a polynucleic acid molecule B is conjugated to a binding moiety. In some instances, the binding moiety comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of binding moiety also include steroids, such as cholesterol, phospholipids, di- and triacylglycerols, fatty acids, hydrocarbons (e.g., saturated, unsaturated, or contains substitutions), enzyme substrates, biotin, digoxigenin, and polysaccharides. In some instances, the binding moiety is an antibody or binding fragment thereof. In some instances, the polynucleic acid molecule is further conjugated to a polymer, and optionally an endosomolytic moiety.

In some embodiments, the polynucleic acid molecule is conjugated to the binding moiety by a chemical ligation process. In some instances, the polynucleic acid molecule is conjugated to the binding moiety by a native ligation. In some instances, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives," *J. Am. Chem. Soc.* 1997, 119, 4325-4329; Hackeng, et al. "Protein synthesis by native chemical ligation: Expanded scope by using straightforward methodology," *Proc. Natl. Acad Sci. USA* 1999, 96, 10068-10073; or Wu, et al. "Building complex glycopeptides: Development of a cysteine-free native chemical ligation protocol." *Angew. Chem. Int. Ed* 2006, 45, 4116-4125. In some instances, the conjugation is as described in U.S. Pat. No. 8,936,910. In some embodiments, the polynucleic acid molecule is conjugated to the binding moiety either site-specifically or non-specifically via native ligation chemistry.

In some instances, the polynucleic acid molecule is conjugated to the binding moiety by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," *JACS* 134(13): 5887-5892 (2012))

In some instances, the polynucleic acid molecule is conjugated to the binding moiety by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup el al., "Synthesis of site-specific antibody-drug conjugates using unnatural amino acids," *PNAS* 109(40): 16101-16106 (2012)).

In some instances, the polynucleic acid molecule is conjugated to the binding moiety by a site-directed method utilizing an enzyme-catalyzed process. In some instances, the site-directed method utilizes SMARTag™ technology (Catalent, Inc.). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydracino-Pictet-Spengler (HIPS) ligation. (see Wu el al., "Site-specific chemical modification of recombinant proteins produced in mammalian cells by using the genetically encoded aldehyde tag." *PNAS* 106(9): 3000-3005 (2009); Agarwal, el al., "A Pictet-Spengler ligation for protein chemical modification," PNAS 110(1): 46-51 (2013))

In some instances, the enzyme-catalyzed process comprises microbial transglutaminase (mTG). In some cases, the polynucleic acid molecule is conjugated to the binding moiety utilizing a microbial transglutaminase-catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop el al., "Location matters: site of conjugation modulates stability and pharmacokinetics of antibody drug conjugates," *Chemistry and Biology* 20(2) 161-167 (2013))

In some instances, the polynucleic acid molecule is conjugated to the binding moiety by a method as described in PCT Publication No. WO2014/140317, which utilizes a sequence-specific transpeptidase.

In some instances, the polynucleic acid molecule is conjugated to the binding moiety by a method as described in U.S. Patent Publication Nos. 2015/0105539 and 2015/0105540.

Polymer Conjugating Moiety

In some embodiments, a polymer moiety C is further conjugated to a polynucleic acid molecule described herein, a binding moiety described herein, or in combinations thereof. In some instances, a polymer moiety C is conjugated a polynucleic acid molecule. In some cases, a polymer moiety C is conjugated to a binding moiety. In other cases, a polymer moiety C is conjugated to a polynucleic acid molecule-binding moiety molecule. In additional cases, a polymer moiety C is conjugated, as illustrated supra.

In some instances, the polymer moiety C is a natural or synthetic polymer, consisting of long chains of branched or unbranched monomers, and/or cross-linked network of monomers in two or three dimensions. In some instances, the polymer moiety C includes a polysaccharide, lignin, rubber, or polyalkylene oxide (e.g., polyethylene glycol). In some instances, the at least one polymer moiety C includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylene terephthalate (also known as poly(ethylene terephthalate), PET, PETG, or PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer moiety C comprises polyalkylene oxide. In some instances, the polymer moiety C comprises PEG. In some instances, the polymer moiety C comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some embodiments, the polyalkylene oxide (e.g., PEG) is a polydisperse or monodisperse compound. In some instances, polydisperse material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, C is polyalkylene oxide (e.g., PEG) and has a molecular weight of about 200, 300, 40, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some embodiments. C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some embodiments, the polyalkylene oxide (e.g., PEG) comprises discrete ethylene oxide units (e.g., four to about 48 ethylene oxide units). In some instances, the polyalkylene oxide comprising the discrete ethylene oxide units is a linear chain. In other cases, the polyalkylene oxide comprising the discrete ethylene oxide units is a branched chain.

In some instances, the polymer moiety C is a polyalkylene oxide (e.g., PEG) comprising discrete ethylene oxide units. In some cases, the polymer moiety C comprises between about 4 and about 48 ethylene oxide units. In some cases, the polymer moiety C comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units.

In some instances, the polymer moiety C is a discrete PEG comprising, e.g., between about 4 and about 48 ethylene oxide units. In some cases, the polymer moiety C is a discrete PEG comprising, e.g., about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units. In some cases, the polymer moiety C is a discrete PEG comprising, e.g., about 4 ethylene oxide units. In some cases, the polymer moiety C is a discrete PEG comprising. e.g., about 5 ethylene oxide units. In some cases, the polymer moiety C is a discrete PEG comprising, e.g., about 6 ethylene oxide units. In some cases, the polymer moiety C is a discrete PEG comprising, e.g., about 7 ethylene oxide units. In some cases, the polymer moiety C is a discrete PEG comprising. e.g., about 8 ethylene oxide units. In some cases, the polymer moiety C is a discrete PEG comprising, e.g., about 9 ethylene oxide units. In some cases, the polymer moiety C is a discrete PEG comprising, e.g., about 10 ethylene oxide units. In some cases, the polymer moiety C is a discrete PEG comprising, e.g., about 11 ethylene oxide units. In some cases, the polymer moiety C is a discrete PEG comprising. e.g., about 12 ethylene oxide units. In some cases, the polymer moiety C is a discrete PEG comprising, e.g., about 13 ethylene oxide units. In some cases, the polymer moiety C is a discrete PEG comprising, e.g., about 14 ethylene oxide units. In some cases, the polymer moiety C is a discrete PEG comprising, e.g., about 15 ethylene oxide units. In some cases, the polymer moiety C is a discrete PEG comprising, e.g., about 16 ethylene oxide units. In some cases, the polymer moiety C is a discrete PEG comprising, e.g., about 17 ethylene oxide units. In some cases, the polymer moiety C is a discrete PEG comprising. e.g., about 18 ethylene oxide units. In some cases, the polymer moiety C is a discrete PEG comprising, e.g., about 19 ethylene oxide units. In some cases, the polymer moiety C is a discrete PEG comprising, e.g., about 20 ethylene oxide units. In some cases, the polymer moiety C is a discrete PEG comprising, e.g., about 21 ethylene oxide units. In some cases, the polymer moiety C is a discrete PEG comprising. e.g., about 22 ethylene oxide units. In some cases, the polymer moiety C is a discrete PEG comprising. e.g., about 23 ethylene oxide units. In some cases, the polymer moiety C is a discrete PEG comprising. e.g., about 24 ethylene oxide units. In some cases, the polymer moiety C is a discrete PEG comprising, e.g., about 25 ethylene oxide units. In some cases, the polymer moiety C is a discrete PEG comprising. e.g., about 26 ethylene oxide units. In some cases, the polymer moiety C is a discrete PEG comprising, e.g., about 27 ethylene oxide units. In some cases, the polymer moiety C is a discrete PEG comprising, e.g., about 28 ethylene oxide units. In some cases, the polymer moiety C is a discrete PEG comprising, e.g., about 29 ethylene oxide units. In some cases, the polymer moiety C is a discrete PEG comprising, e.g., about 30 ethylene oxide units. In some cases, the polymer moiety C is a discrete PEG comprising, e.g., about 31 ethylene oxide units. In some cases, the polymer moiety C is a discrete PEG comprising, e.g., about 32 ethylene oxide units. In some cases, the polymer moiety C is a discrete PEG comprising. e.g., about 33 ethylene oxide units. In some cases, the polymer moiety C is a discrete PEG comprising, e.g., about 34 ethylene oxide units. In some cases, the polymer moiety C is a discrete PEG comprising, e.g., about 35 ethylene oxide units. In some cases, the polymer moiety C is a discrete PEG comprising, e.g., about 36 ethylene oxide units. In some cases, the polymer moiety C is a discrete PEG comprising, e.g., about 37 ethylene oxide units. In some cases, the polymer moiety C is a discrete PEG comprising, e.g., about 38 ethylene oxide units. In some cases, the polymer moiety C is a discrete PEG comprising. e.g., about 39 ethylene oxide units. In some cases, the polymer moiety C is a discrete PEG comprising. e.g., about 40 ethylene oxide units. In some cases, the polymer moiety C is a discrete PEG comprising, e.g., about 41 ethylene oxide units. In some cases, the polymer moiety C is a discrete PEG comprising, e.g., about 42 ethylene oxide units. In some cases, the polymer moiety C is a discrete PEG comprising. e.g., about 43 ethylene oxide units. In some cases, the polymer moiety C is a discrete PEG comprising, e.g., about 44 ethylene oxide units. In some cases, the polymer moiety C is a discrete PEG comprising, e.g., about 45 ethylene oxide units. In some cases, the polymer moiety C is a discrete PEG comprising, e.g., about 46 ethylene oxide units. In some cases, the polymer moiety C is a discrete PEG comprising, e.g., about 47 ethylene oxide units. In some cases, the polymer moiety C is a discrete PEG comprising, e.g., about 48 ethylene oxide units.

In some cases, the polymer moiety C is dPEG® (Quanta Biodesign Ltd).

In some embodiments, the polymer moiety C comprises a cationic mucic acid-based polymer (cMAP). In some instances, cMAP comprises one or more subunit of at least one repeating subunit, and the subunit structure is represented as Formula (V):

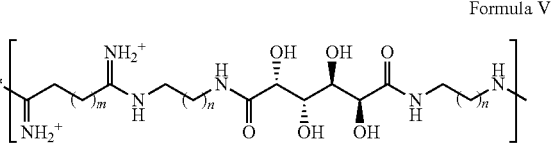

Formula V wherein m is independently at each occurrence 1, 2, 3, 4, 5, 6, 7, 8, 9, or 10, preferably 4-6 or 5; and n is independently at each occurrence 1, 2, 3, 4, or 5. In some embodiments, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In some instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or mom of these ranges.

In some instances, the polymer moiety C is cMAP-PEG copolymer, an mPEG-cMAP-PEGm triblock poly mer, or a cMAP-PEG-cMAP triblock polymer. In some cases, the polymer moiety C is cMAP-PEG copolymer. In other cases, the polymer moiety C is an mPEG-cMAP-PEGm triblock polymer. In additional cases, the polymer moiety C is a cMAP-PEG-cMAP triblock polymer.

In some embodiments, the polymer moiety C is conjugated to the polynucleic acid molecule, the binding moiety, and optionally to the endosomolytic moiety as illustrated supra.

Endosomolytic Moiety

In some embodiments, a molecule of Formula (I): A-$X_1$-B-$X_2$-C, further comprises an additional conjugating moiety. In some instances, the additional conjugating moiety is an endosomolytic moiety. In some cases, the endosomolytic moiety is a cellular compartmental release component, such as a compound capable of releasing from any of the cellular compartments known in the art, such as the endosome, lysosome, endoplasmic reticulum (ER), golgi apparatus, microtube, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer.

Endosomolytic Polypeptides

In some embodiments, a molecule of Formula (I): A-$X_1$-B-$X_2$-C, is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof.

In some instances, INF7 is a 24 residue polypeptide those sequence comprises CGIFGEIEELIEEGLENLIDWGNA (SEQ ID NO: 1), or GLFEAIEGFIENGWEGMIDGWYGC (SEQ ID NO: 2). In some instances, INF7 or its derivatives comprise a sequence or:

```
                                  (SEQ ID NO: 3)
GLFEAIEGFIENGWEGMIWDYGSGSCG, (SEQ ID NO: 4)
GLFEAIEGFIENGWEGMIDG WYG-(PEG)6-NH2,
or (SEQ ID NO: 5)
GLFEAIEGFIENGWEGMIWDYG-SGSC-K(GalNAc)2.
```

In some cases, melittin is a 26 residue polypeptide those sequence comprises CLTGAILKVLATGLPTLISWIKNK-RKQ (SEQ ID NO: 6), or GIGAVLKVLTTGLPAL-ISWIKRKRQQ (SEQ ID NO: 7). In some instances, melittin comprises a polypeptide sequence as described in U.S. Pat. No. 8,501,930.

In some instances, meucin is an antimicrobial peptide (AMP) derived from the venom gland of the scorpion *Mesobuthus eupeus*. In some instances, meucin comprises of meucin-13 those sequence comprises IFGAIAGLLKNIF-$NH_2$ (SEQ ID NO: 8) and meucin-18 those sequence comprises FFGHLFKLATKIIPSLFQ (SEQ ID NO: 9).

In some instances, the endosomolytic polypeptide comprises a polypeptide in which its sequence is at least 50%, 60%, 70%, 80%, 90%, 95%, or 99% sequence identity to INF7 or its derivatives thereof, melittin or its derivatives thereof, or meucin or its derivatives thereof. In some instances, the endosomolytic moiety comprises INF7 or its derivatives thereof, melittin or its derivatives thereof, or meucin or its derivatives thereof.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1-5. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 1. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 2-5. In some cases, the endosomolytic moiety comprises SEQ ID NO: 1. In some cases, the endosomolytic moiety comprises SEQ ID NO: 2-5. In some cases, the endosomolytic moiety consists of SEQ ID NO: 1. In some cases, the endosomolytic moiety consists of SEQ ID NO: 2-5.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 6 or 7. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 6. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 7. In some cases, the endosomolytic moiety comprises SEQ ID NO: 6. In some cases, the endosomolytic moiety comprises SEQ ID NO: 7. In some cases, the endosomolytic moiety consists of SEQ ID NO: 6. In some cases, the endosomolytic moiety consists of SEQ ID NO: 7.

In some instances, the endosomolytic moiety is meucin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100%, sequence identity to SEQ ID NOs: 8 or 9. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 8. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 9. In some cases, the endosomolytic moiety comprises SEQ ID NO: 8. In some cases, the endosomolytic moiety comprises SEQ ID NO: 9. In some cases, the endosomolytic moiety consists of SEQ ID NO: 8. In some cases, the endosomolytic moiety consists of SEQ ID NO: 9.

In some instances, the endosomolytic moiety comprises a sequence as illustrated in Table 1.

| NAME | ORIGIN | AMINO ACID SEQUENCE | SEQ ID NO: | TYPE |
|---|---|---|---|---|
| Pep-1 | NLS from Simian Virus 40 large antigen and Reverse transcriptase of HIV | KETWWETWWTE WSQPKKKRKV | 10 | Primary amphipathic |
| pVEC | VE-cadherin | LLIILRRRRIR KQAHAHSK | 11 | Primary amphipathic |
| VT5 | Synthetic peptide | DPKGDPKGVTV TVTVTVTGKGD PKPD | 12 | β-sheet amphipathic |
| C105Y | 1-antitrypsin | CSIPPEVKFNK PFVYLI | 13 | — |
| Transportan | Galanin and mastoparan | GWTLNSAGYLL GKINLKALAAL AKKIL | 14 | Primary amphipathic |
| TP10 | Galanin and mastoparan | AGYLLGKINLK ALAALAKKIL | 15 | Primary amphipathic |
| MPG | A hydrofobic domain from the fusion sequence of HIV gp41 and NLS of SV40 T antigen | GALFLGFLGAA GSTMGA | 16 | β-sheet amphipathic |
| gH625 | Glycoprotein gH of HSV type I | HGLASTLTRWA HYNALIRAF | 17 | Secondary amphipathic α-helical |
| CADY | PPTG1 peptide | GLWRALWRLLR SLWRLLWRA | 18 | Secondary amphipathic α-helical |
| GALA | Synthetic peptide | WEAALAEALAE ALAEHLAEALA EALEALAA | 19 | Secondary amphipathic α-helical |
| INF | Influenza HA2 fusion peptide | GLFEAIEGFIE NGWEGMIDGWY GC | 20 | Secondary amphipathic α-helical/ pH-dependent membrane active peptide |
| HA2E5-TAT | Influenza HA2 subunit of influenza virus X31 strain fusion peptide | GLFGAIAGFIE NGWEGMIDGWY G | 21 | Secondary amphipathic α-helical/ pH-dependent membrane active peptide |
| HA2-penetratin | Influenza HA2 subunit of influenza virus X31 strain fusion peptide | GLFGAIAGFIE NGWEGMIDGRQ IKIWFQNRRMK KK-amide | 22 | pH-dependent membrane active peptide |
| HA-K4 | Influenza HA2 subunit of influenza virus X31 strain fusion peptide | GLFGAIAGFIE NGWEGMIDG-SSKKKK | 23 | pH-dependent membrane active peptide |
| HA2E4 | Influenza HA2 subunit of influenza virus X31 strain fusion peptide | GLFEAIAGFIE NGWEGMIDGGG YC | 24 | pH-dependent membrane active peptide |
| H5WYG | HA2 analogue | GLFHAIAHFIH GGWHGLIHGWY G | 25 | pH-dependent membrane active peptide |
| GALA-INF3-(PEG)6-NH | INF3 fusion peptide | GLFEAIEGFIE NGWEGLAEALA EALEALAA-(PEG)6-NH2 | 26 | pH-dependent membrane active peptide |
| CM18-TAT11 | Cecropin-A-Melittin$_{2-12}$ (CM$_{18}$) fusion peptide | KWKLFKKIGAV LKVLTTG-YGRKKRRQRRR | 27 | pH-dependent membrane active peptide |

In some cases, the endosomolytic moiety comprises a Bak BH3 polypeptide which induces apoptosis through antagonization of suppressor targets such as Bcl-2 and/or Bcl-x$_L$. In some instances, the endosomolytic moiety comprises a Bak BH3 polypeptide described in Albarran, et al., "Efficient intracellular delivery of a pro-apoptotic peptidic with a pH-responsive carrier," Reactive & Functional Polymers 71: 261-265 (2011).

In some instances, the endosomolytic moiety comprises a polypeptide (e.g., a cell-penetrating polypeptide) as described in PCT Publication Nos. WO2013/166155 or WO2015/069587.

Endosomolytic Lipids

In some embodiments, the endosomolytic moiety is a lipid (e.g., a fusogenic lipid). In some embodiments, a molecule of Formula (I): A-X$_1$-B-X$_2$-C, is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmiloylolcoylphosphatidykholine (POPC), (6Z, 9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (XTC).

In some instances, an endosomolytic moiety is a lipid (e.g., a fusogenic lipid) described in PCT Publication No. WO09/126,933.

Endosomolytic Small Molecules

In some embodiments, the endosomolytic moiety is a small molecule. In some embodiments, a molecule of Formula (I): A-X$_1$-B-X$_2$-C, is further conjugated with an endosomolytic small molecule. Exemplary small molecules suitable as endosomolytic moieties include, but are not limited to, quinine, chloroquine, hydroxychloroquine, amodiaquins (carnoquines), amopyroquines, primaquines, mefloquine, nivaquines, halofantrines, quinone imines, or a combination thereof. In some instances, quinoline endosomolytic moieties include, but are not limited to, 7-chloro-4-(4-diethyl-amino-1-methylbutyl-amino)quinoline (chloroquine); 7-chloro-4-(4-ethyl-(2-hydroxyethyl)-amino-1-methylbutyl-amino)quinoline (hydroxychloroquine); 7-fluoro-4-(4-diethyl-amino-1-methylbutyl-amino)quinoline; 4-(4-diethylamino-1-methylbutylamino) quinoline; 7-hydroxy-4-(4-diethyl-amino-1-methylbutylamino)quinoline; 7-chloro-4-(4-diethylamino-1-butylamino)quinoline (desmethylchloroquine); 7-fluoro-4-(4-diethylamino-1-butylamino)quinoline); 4-(4-diethyl-amino-1-butylamino)quinoline; 7-hydroxy-4-(4-diethylamino-1-butylamino)quinoline; 7-chloro-4-(1-carboxy-4-diethylamino-1-butylamino)quinoline; 7-fluoro-4-(1-carboxy-4-diethyl-amino-1-butylamino)quinoline; 4-(1-carboxy-4-diethylamino-1-butylamino) quinoline; 7-hydroxy-4-(1-carboxy-4-diethylamino-1-butylamino)quinoline: 7-chloro-4-(1-carboxy-4-diethylamino-1-methylbutylamino)quinoline; 7-fluoro-4-(1-carboxy-4-diethyl-amino-1-methylbutylamino)quinoline; 4-(1-carboxy-4-diethylamino-1-methylbutylamino)quinoline; 7-hydroxy-4-(1-carboxy-4-diethylamino-1-methylbutylamino)quinoline; 7-fluoro-4-(4-ethyl-(2-hydroxyethyl)-amino-1-methylbutylamino)quinoline; 4-(4-ethyl-(2-hydroxy-ethyl)-amino-1-methylbutylamino-)quinoline; 7-hydroxy-4-(4-ethyl-(2-hydroxyethyl)-amino-1-methylbutylamino)quinoline; hydroxychloroquine phosphate; 7-chloro-4-(4-ethyl-(2-hydroxyethyl-1)-amino-1-butylamino)quinoline (desmethylhydroxychloroquine); 7-fluoro-4-(4-ethyl-(2-hydroxyethyl)-amino-1-butylamino) quinoline: 4-(4-ethyl-(2-hydroxyethyl)-amino-1-butylamino)quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino)quinoline; 7-fluoro-4-(l-carboxy-4-ethyl-(2-hydroxyethyl)-amino-1-butylamino)quinoline; 4-(l-carboxy-4-ethyl-(2-hydroxyethyl)-amino-1-butylamino)quinoline; 7-hydroxy-4-(1-carboy-4-ethyl-(2-hydroxyethyl)-amino-1-butylamino)quinoline; 7-chloro-4-(l-carboxy-4-ethyl-(2-hydroxyethyl)-amino-1-methylbutylamino)quinoline; 7-fluoro-4-(1-carboxy-4-ethyl-(2-hydroxyethyl)-amino-1-methylbutylamino)quinoline; 4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino)quinoline; 8-1 (4-aminopentyl)amino-6-methoxydihydrochloride quinoline; 1-acetyl-1,2,3,4-tetrahydroquinoline; 8-[(4-aminopentyl)amino]-6-methoxyquinoline dihydrochloride; I-butyryl-1,2,3,4-tetrahydroquinoline; 3-chloro-4-(4-hydroxy-alpha,alpha'-bis(2-methyl-1-pyrrolidinyl)-2,5-xylidinoquinoline, 4-[(4-diethyl-amino)-1-methylbutyl-amino]-6-methoxyquinoline; 3-fluoro-4-(4-hydroxy-alpha,alpha'-bis(2-methyl-1-pyrrolidinyl)-2,5-xylidinoquinoline, 4-[(4-diethylamino)-1-methylbutyl-amino]-6-methoxyquinoline; 4-(4-hydroxy-alpha,alpha'-bis(2-methyl-1-pyrrolidinyl)-2,5-xylidinoquinoline; 4-[(4-diethylamino)-1-methylbutyl-amino]-6-methoxyquinoline; 3,4-dihydro-1-(2H)-quinolinecarboxaldehyde; 1,1'-pentamethylene diquinoleinium diiodide; 8-quinolinol sulfate and amino, aldehyde, carboxylic, hydroxyl, halogen, keto, sulfhydryl and vinyl derivatives or analogs thereof. In some instances, an endosomolytic moiety is a small molecule described in Naisbitt et al (1997, J Pharmacol Exp Therapy 280:884-893) and in U.S. Pat. No. 5,736,557.

Linkers

In some embodiments, a linker described herein is a cleavable linker or a non-cleavable linker. In some instances, the linker is a cleavable linker. In other instances, the linker is a non-cleavable linker.

In some cases, the linker is a non-polymeric linker. A non-polymeric linker refers to a linker that does not contain a repeating unit of monomers generated by a polymerization process. Exemplary non-polymeric linkers include, but are not limited to, $C_1$-$C_6$ alkyl group (e.g., a $C_5$, $C_4$, $C_3$, $C_2$, or $C_1$ alkyl group), homobifunctional cross linkers, heterobifunctional cross linkers, peptide linkers, traceless linkers, self-immolative linkers, maleimide-based linkers, or combinations thereof. In some cases, the non-polymeric linker comprises a C-Ct alkyl group (e.g., a $C_5$, $C_4$, $C_3$, $C_2$, or $C_1$ alkyl group), a homobifunctional cross linker, a heterobifunctional cross linker, a peptide linker, a traceless linker, a self-immolative linker, a maleimide-based linker, or a combination thereof. In additional cases, the non-polymeric linker does not comprise more than two of the same type of linkers, e.g., more than two homobifunctional cross linkers, or more than two peptide linkers. In further cases, the non-polymeric linker optionally comprises one or more reactive functional groups.

In some instances, the non-polymeric linker does not encompass a polymer that is described above. In some instances, the non-polymeric linker does not encompass a polymer encompassed by the polymer moiety C. In some cases, the non-polymeric linker does not encompass a polyalkylene oxide (e.g., PEG). In some cases, the non-polymeric linker does not encompass a PEG.

In some instances, the linker comprises a homobifunctional linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis (sulfosuccinimidyl)suberate (BS), disuccinimidyl tartrate; (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[a-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs). N-succinimidyl(4-iodoactyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl]amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 (M$_2$C$_2$H), 3-(2-pyridyldithio)propionyl hydrazide (PDPH), amine-reactive and photoreactive cross-linkers such as N-hydroxysuccinimidyl-4-azidosalicylic acid (NHs-AsA). N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)bexanoate (sANPAH), sulfosuccinimidyl-6-(4'-azido-2'-nitrophenylamino)hexanoate (sulfo-sANPAH), N-5-azido-2-nitrobenzoyloxysuccinimide (AN-B-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumarin-3-acetate (sulfo-sAMCA), ρ-nitrophenyl diazopyruvate (ρNPDP), ρ-nitrophenyl-2-diazo-3,3,3-trifluoropropionate (PNP-DTP), sulfhydryl-reactive and photoreactive cross-linkers such as 1-(p-Azidosalicylamido)-4-(iodoacetamido)butane (AsIB). N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido)butylamine (AsBA), and arginine-reactive and photoreactive cross-linkers such as ρ-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et. al., "Self-hydrolyzing maleimides improve the stability and pharmacological properties of antibody-drug conjugates," *Nat. Biotechnol.* 32(10):1059-1062 (2014). In some instances, the linker comprises a self-stabilizing maleimide. In some instances, the linker is a self-stabilizing maleimide.

In some embodiments, the linker comprises a peptide moiety. In some instances, the peptide moiety comprises at least 2, 3, 4, 5, or 6 more amino acid residues. In some instances, the peptide moiety comprises at most 2, 3, 4, 5, 6, 7, or 8 amino acid residues. In some instances, the peptide moiety comprises about 2, about 3, about 4, about 5, or about 6 amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 14223). Phe-Lys. Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 14224), or Gly-Phe-Leu-Gly (SEQ ID NO: 14225). In some instances, the linker comprises a peptide moiety such as: Val-Cit (valine-citrulline). Gly-Gly-Phe-Gly (SEQ ID NO: 14223). Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 14224), or Gly-Phe-Leu-Gly (SEQ ID NO: 14225). In some cases, the linker comprises Val-Cit. In some cases, the linker is Val-Cit.

In some embodiments, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a me-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication No. WO2015038426.

In some embodiments, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some embodiments, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et. al., "A traceless aryl-triazene linker for DNA-directed chemistry," *Org Biomol Chem* 11(15): 2493-2497 (2013). In some instances, the linker is a traceless linker described in Blaney, et. al., "Traceless solid-phase organic synthesis," *Chem. Rev.* 102: 2607-2024 (2002). In some instances, a linker is a traceless linker as described in U.S. Pat. No. 6,821,783.

In some instances, the linker is a linker described in U.S. Pat. Nos. 6,884,869; 7,498,298; 8,288,352; 8,609,105; or 8,697,688; U.S. Patent Publication Nos. 2014/0127239; 20131/028919; 2014/286970, 2013/0309256; 2015/037360; or 2014/0294851; or PCT Publication Nos. WO2015057699; WO2014080251; WO2014197854; WO2014145090; or WO2014177042.

In some embodiments. $X_1$ and $X_2$ are each independently a bond or a non-polymeric linker. In some instances, $X_1$ and $X_2$ are each independently a bond. In some cases, $X_1$ and $X_2$ are each independently a non-polymeric linker.

In some instances, $X_1$ is a bond or a non-polymeric linker. In some instances, $X_1$ is a bond. In some instances, $X_1$ is a non-polymeric linker. In some instances, the linker is a $C_1$-$C_6$ alkyl group. In some cases. $X_1$ is a $C_1$-$C_6$ alkyl group, such as for example, a $C_5$, $C_4$, $C_3$, $C_2$, or $C_1$ alkyl group. In some cases, the $C_1$-$C_6$ alkyl group is an unsubstituted $C_1$-$C_6$ alkyl group. As used in the context of a linker, and in particular in the context of $X_1$, alkyl means a saturated straight or branched hydrocarbon radical containing up to six carbon atoms. In some instances. $X_1$ includes a homobifunctional linker or a heterobifunctional linker described supra. In some cases. $X_1$ includes a heterobifunctional linker. In some cases, $X_1$ includes sMCC. In other instances, $X_1$ includes a heterobifunctional linker optionally conjugated to a $C_1$-$C_6$ alkyl group. In other instances, $X_1$ includes sMCC optionally conjugated to a $C_1$-$C_6$ alkyl group. In additional instances, $X_1$ does not include a homobifunctional linker or a heterobifunctional linker described supra.

In some instances, $X_2$ is a bond or a linker. In some instances. $X_2$ is a bond. In other cases, $X_2$ is a linker. In additional cases, $X_2$ is a non-polymeric linker. In some embodiments, $X_2$ is a $C_1$-$C_6$ alkyl group. In some instances, $X_2$ is a homobifunctional linker or a heterobifunctional linker described supra. In some instances. $X_2$ is a homobifunctional linker described supra. In some instances, $X_2$ is a heterobifunctional linker described supra. In some instances, $X_2$ comprises a maleimide group, such as maleimidocaproyl (me) or a self-stabilizing maleimide group described above. In some instances, $X_2$ comprises a peptide moiety, such as Val-Cit. In some instances. $X_1$ comprises a benzoic acid group, such as PABA. In additional instances, $X_2$ comprises a combination of a maleimide group, a peptide moiety, and/or a benzoic acid group. In additional instances, $X_2$ comprises a mc group. In additional instances, $X_2$ comprises a mc-val-cit group. In additional instances, $X_2$ comprises a val-cit-PABA group. In additional instances, $X_2$ comprises a mc-val-cit-PABA group.

Methods of Use

Muscle atrophy refers to a loss of muscle mass and/or to a progressive weakening and degeneration of muscles. In some cases, the loss of muscle mass and/or the progressive weakening and degeneration of muscles occurs due to a high rate of protein degradation, a low rate of protein synthesis, or a combination of both. In some cases, a high rate of muscle protein degradation is due to muscle protein catabolism (i.e., the breakdown of muscle protein in order to use amino acids as substrates for gluconeogenesis).

In one embodiment, muscle atrophy refers to a significant loss in muscle strength. By significant loss in muscle strength is meant a reduction of strength in diseased, injured, or unused muscle tissue in a subject relative to the same muscle tissue in a control subject. In an embodiment, a significant loss in muscle strength is a reduction in strength of at least 10%, at least 15%, at least 20%, at least 25%, at least 30%, at least 35%, at least 40%, at least 45%, at least 50%, or more relative to the same muscle tissue in a control subject. In another embodiment, by significant loss in muscle strength is meant a reduction of strength in unused muscle tissue relative to the muscle strength of the same muscle tissue in the same subject prior to a period of nonuse. In an embodiment, a significant loss in muscle strength is a reduction of at least 10%, at least 15%, at least 20%, at least 25%, at least 30%, at least 35%, at least 40%, at least 45%, at least 50%, or more relative to the muscle strength of the same muscle tissue in the same subject prior to a period of nonuse.

In another embodiment, muscle atrophy refers to a significant loss in muscle mass. By significant loss in muscle mass is meant a reduction of muscle volume in diseased, injured, or unused muscle tissue in a subject relative to the same muscle tissue in a control subject. In an embodiment, a significant loss of muscle volume is at least 10%, at least 15%, at least 20%, at least 25%, at least 30%, at least 35%, at least 40%, at least 45%, at least 50%, or more relative to the same muscle tissue in a control subject. In another embodiment, by significant loss in muscle mass is meant a reduction of muscle volume in unused muscle tissue relative to the muscle volume of the same muscle tissue in the same subject prior to a period of nonuse. In an embodiment, a significant loss in muscle tissue is at least 10%, at least 15%, at least 20%, at least 25%, at least 30%, at least 35%, at least 40%, at least 45%, at least 50%, or more relative to the muscle volume of the same muscle tissue in the same subject prior to a period of nonuse. Muscle volume is optionally measured by evaluating the cross-section area of a muscle such as by Magnetic Resonance Imaging (e.g., by a muscle volume/cross-section area (CSA) MRI method).

Myotonic dystrophy is a multisystemic neuromuscular disease comprising two main types: myotonic dystrophy type 1 (DM1) and myotonic dystrophy type 2 (DM2). DM1 is caused by a dominantly inherited "CTG" repeat expansion in the gene DM protein kinase (DMPK), which when transcribed into mRNA, forms hairpins that bind with high affinity to the Muscleblind-like (MBNL) family of proteins. MBNL proteins are involved in post-transcriptional splicing and polyadenylation site regulation and loss of the MBNL protein functions lead to downstream accumulation of nuclear foci and increase in mis-splicing events and subsequently to myotonia and other clinical symptoms.

In some embodiments, described herein is a method of treating muscle atrophy or myotonic dystrophy in a subject, which comprises administering to the subject a therapeutically effective amount of a polynucleic acid molecule described herein or a polynucleic acid molecule conjugate described herein. In some instances, the muscle atrophy is associated and/or induced by cachexia (e.g., cancer cachexia), denervation, myopathy, motor neuron diseases, diabetes, chronic obstructive pulmonary disease, liver disease, congestive heart failure, chronic renal failure, chronic infection, sepsis, fasting, sarcopenia, glucocorticoid-induced atrophy, disuse, or space flight. In some cases, myotonic dystrophy is DM1.

Cachexia

Cachexia is an acquired, accelerated loss of muscle caused by an underlying disease. In some instances, cachexia refers to a loss of body mass that cannot be reversed nutritionally, and is generally associated with an underlying disease, such as cancer, COPD, AIDS, heart failure, and the like. When cachexia is seen in a patient with end-stage cancer, it is called "cancer cachexia". Cancer cachexia affects the majority of patients with advanced cancer and is associated with a reduction in treatment tolerance, response to therapy, quality of life and duration of survival. It some instances, cancer cachexia is defined as a multifactorial syndrome characterized by an ongoing loss of skeletal muscle mass, with or without loss of fat mass, which cannot be fully reversed by conventional nutritional support and leads to progressive functional impairment. In some cases, skeletal muscle loss appears to be the most significant event in cancer cachexia. In addition, the classification of cancer cachexia suggests that the diagnostic criteria takes into account not only that weight loss is a signal event of the cachectic process but that the initial reserve of the patient should also be considered, such as low BMI or low level of muscularity.

In some embodiments, described herein is a method of treating cachexia-associated muscle atrophy in a subject, which comprises administering to the subject a therapeutically effective amount of a polynucleic acid molecule described herein or a polynucleic acid molecule conjugate described herein. In additional embodiments, described herein is a method of treating cancer cachexia-associated muscle atrophy in a subject, which comprises administering to the subject a therapeutically effective amount of a polynucleic acid molecule described herein or a polynucleic acid molecule conjugate described herein.

Denervation

Denervation is an injury to the peripheral motoneurons with a partial or complete interruption of the nerve fibers between an organ and the central nervous system, resulting in an interruption of nerve conduction and motoneuron firing which, in turn, prevents the contractability of skeletal muscles. This loss of nerve function is either localized or generalized due to the loss of an entire motor neuron unit. The resulting inability of skeletal muscles to contract leads to muscle atrophy. In some instances, denervation is associated with or as a result of degenerative, metabolic, or inflammatory neuropathy (e.g., Guillain-Barre syndrome, peripheral neuropathy, or exposure to environmental toxins or drugs). In additional instances, denervation is associated with a physical injury, e.g., a surgical procedure.

In some embodiments, described herein is a method of treating muscle atrophy associated with or induced by denervation in a subject, which comprises administering to the subject a therapeutically effective amount of a polynucleic acid molecule described herein. In other embodiments, described herein is a method of treating muscle atrophy associated with or induced by denervation in a subject, which comprises administering to the subject a therapeutically effective amount of a polynucleic acid molecule conjugate described herein.

Myopathy

Myopathy is an umbrella term that describes a disease of the muscle. In some instances, myopathy includes myotonia; congenital myopathy such as nemaline myopathy, multi/minicore myopathy and myotubular (centronuclear) myopathy; mitochondrial myopathy; familial periodic paralysis; inflammatory myopathy; metabolic myopathy, for example, caused by a glycogen or lipid storage disease; dermatomyositis; polymyositis; inclusion body myositis; myositis ossificans; rhabdomyolysis; and myoglobinurias. In some instances, myopathy is caused by a muscular dystrophy syndrome, such as Duchenne, Becker, myotonic, fascioscapulohumeral, Emery-Dreifuss, oculopharyngeal, scapulohumeral, limb girdle. Fukuyama, a congenital muscular dystrophy, or hereditary distal myopathy. In some instances, myopathy is caused by myotonic dystrophy (e.g., myotonic dystrophy type 1 or DM1). In some instances, myopathy is caused by DM1.

In some embodiments, described herein is a method of treating muscle atrophy associated with or induced by myopathy in a subject, which comprises administering to the subject a therapeutically effective amount of a polynucleic acid molecule described herein. In other embodiments, described herein is a method of treating muscle atrophy associated with or induced by myopathy in a subject, which comprises administering to the subject a therapeutically effective amount of a polynucleic acid molecule conjugate described herein.

Motor Neuron Diseases

Motor neuron disease (MND) encompasses a neurological disorder that affects motor neurons, cells that control voluntary muscles of the body. Exemplary motor neuron diseases include, but are not limited to, adult motor neuron diseases, infantile spinal muscular atrophy, amyotrophic lateral sclerosis, juvenile spinal muscular atrophy, autoimmune motor neuropathy with multifocal conductor block, paralysis due to stroke or spinal cord injury, or skeletal immobilization due to trauma.

In some embodiments, described herein is a method of treating muscle atrophy associated with or induced by a motor neuron disease in a subject, which comprises administering to the subject a therapeutically effective amount of a polynucleic acid molecule described herein. In other embodiments, described herein is a method of treating muscle atrophy associated with or induced by a motor neuron disease in a subject, which comprises administering to the subject a therapeutically effective amount of a polynucleic acid molecule conjugate described herein.

Diabetes

Diabetes (diabetes mellitus. DM) comprises type 1 diabetes, type 2 diabetes, type 3 diabetes, type 4 diabetes, double diabetes, latent autoimmune diabetes (LAD), gestational diabetes, neonatal diabetes mellitus (NDM), maturity onset diabetes of the young (MODY), Wolfram syndrome, Alström syndrome, prediabetes, or diabetes insipidus. Type 2 diabetes, also called non-insulin dependent diabetes, is the most common type of diabetes accounting for 95% of all diabetes cases. In some instances, type 2 diabetes is caused by a combination of factors, including insulin resistance due to pancreatic beta cell dysfunction, which in turn leads to high blood glucose levels. In some cases, increased glucagon levels stimulate the liver to produce an abnormal amount of unneeded glucose, which contributes to high blood glucose levels.

Type 1 diabetes, also called insulin-dependent diabetes, comprises about 5% to 10% of all diabetes cases. Type 1 diabetes is an autoimmune disease where T cells attack and destroy insulin-producing beta cells in the pancreas. In some embodiments, Type 1 diabetes is caused by genetic and environmental factors.

Type 4 diabetes is a recently discovered type of diabetes affecting about 20% of diabetic patients age 65 and over. In some embodiments, type 4 diabetes is characterized by age-associated insulin resistance.

In some embodiments, type 3 diabetes is used as a term for Alzheimer's disease resulting in insulin resistance in the brain.

In some embodiments, described herein is a method of treating diabetes-associated muscle atrophy in a subject, which comprises administering to the subject a therapeutically effective amount of a polynucleic acid molecule described herein or a polynucleic acid molecule conjugate described herein. In additional embodiments, described herein is a method of treating cancer diabetes-associated muscle atrophy in a subject, which comprises administering to the subject a therapeutically effective amount of a polynucleic acid molecule described herein or a polynucleic acid molecule conjugate described herein.

Chronic Obstructive Pulmonary Disease

Chronic obstructive pulmonary disease (COPD) is a type of obstructive lung disease characterized by long-term breathing problems and poor airflow. Chronic bronchitis and emphysema are two different types of COPD. In some instances, described herein is a method of treating muscle atrophy associated with or induced by COPD (e.g., chronic bronchitis or emphysema) in a subject, which comprises administering to the subject a therapeutically effective amount of a polynucleic acid molecule described herein. In other embodiments, described herein is a method of treating muscle atrophy associated with or induced by COPD (e.g., chronic bronchitis or emphysema) in a subject, which comprises administering to the subject a therapeutically effective amount of a polynucleic acid molecule conjugate described herein.

Liver Diseases

Liver disease (or hepatic disease) comprises fibrosis, cirrhosis, hepatitis, alcoholic liver disease, hepatic steatosis, a hereditary disease, or primary liver cancer. In some instances, described herein is a method of treating muscle atrophy associated with or induced by a liver disease in a subject, which comprises administering to the subject a therapeutically effective amount of a polynucleic acid molecule described herein. In other embodiments, described herein is a method of treating muscle atrophy associated with or induced by a liver disease in a subject, which comprises administering to the subject a therapeutically effective amount of a polynucleic acid molecule conjugate described herein.

Congestive Heart Failure

Congestive heart failure is a condition in which the heart is unable to pump enough blood and oxygen to the body's tissues. In some instances, described herein is a method of treating muscle atrophy associated with or induced by congestive heart failure in a subject, which comprises administering to the subject a therapeutically effective amount of a polynucleic acid molecule described herein. In other embodiments, described herein is a method of treating muscle atrophy associated with or induced by congestive heart failure in a subject, which comprises administering to the subject a therapeutically effective amount of a polynucleic acid molecule conjugate described herein.

Chronic Renal Failure

Chronic renal failure or chronic kidney disease is a condition characterized by a gradual loss of kidney function over time. In some instances, described herein is a method of treating muscle atrophy associated with or induced by a chronic renal failure in a subject, which comprises administering to the subject a therapeutically effective amount of a polynucleic acid molecule described herein. In other embodiments, described herein is a method of treating muscle atrophy associated with or induced by a chronic renal failure in a subject, which comprises administering to the subject a therapeutically effective amount of a polynucleic acid molecule conjugate described herein.

Chronic Infections

In some embodiments, chronic infection such as AIDS further leads to muscle atrophy. In some instances, described herein is a method of treating muscle atrophy associated with or induced by a chronic infection (e.g., AIDS) in a subject, which comprises administering to the subject a therapeutically effective amount of a polynucleic acid molecule described herein. In other embodiments, described herein is a method of treating muscle atrophy associated with or induced by a chronic infection (e.g., AIDS) in a subject, which comprises administering to the subject a therapeutically effective amount of a polynucleic acid molecule conjugate described herein.

Sepsis

Sepsis is an immune response to an infection leading to tissue damage, organ failure, and/or death. In some embodiments, described herein is a method of treating muscle atrophy associated with or induced by sepsis in a subject, which comprises administering to the subject a therapeutically effective amount of a polynucleic acid molecule described herein. In other embodiments, described herein is a method of treating muscle atrophy associated with or induced by sepsis in a subject, which comprises administering to the subject a therapeutically effective amount of a polynucleic acid molecule conjugate described herein.

Fasting

Fasting is a willing abstinence or reduction from some or all food, drinks, or both, for a period of time. In some embodiments, described herein is a method of treating muscle atrophy associated with or induced by fasting in a subject, which comprises administering to the subject a therapeutically effective amount of a polynucleic acid molecule described herein. In other embodiments, described herein is a method of treating muscle atrophy associated with or induced by fasting in a subject, which comprises administering to the subject a therapeutically effective amount of a polynucleic acid molecule conjugate described herein.

Sarcopenia

Sarcopenia is the continuous process of muscle atrophy in the course of regular aging that is characterized by a gradual loss of muscle mass and muscle strength over a span of months and years. A regular aging process means herein an aging process that is not influenced or accelerated by the presence of disorders and diseases which promote skeletomuscular neurodegeneration.

In some embodiments, described herein is a method of treating muscle atrophy associated with or induced by sarcopenia in a subject, which comprises administering to the subject a therapeutically effective amount of a polynucleic acid molecule described herein. In other embodiments, described herein is a method of treating muscle atrophy associated with or induced by sarcopenia in a subject, which comprises administering to the subject a therapeutically effective amount of a polynucleic acid molecule conjugate described herein.

Glucocorticoid-Associated Muscle Atrophy

In some embodiments, treatment with a glucocorticoid further results in muscle atrophy. Exemplary glucocorticoids include, but are not limited to, cortisol, dexamethasone, betamethasone, prednisone, methylprednisolone, and prednisolone.

In some embodiments, described herein is a method of treating glucocorticoid-associated muscle atrophy in a subject, which comprises administering to the subject a therapeutically effective amount of a polynucleic acid molecule described herein. In other embodiments, described herein is a method of treating glucocorticoid-associated muscle atrophy in a subject, which comprises administering to the subject a therapeutically effective amount of a polynucleic acid molecule conjugate described herein.

Disuse-Associated Muscle Atrophy

Disuse-associated muscle atrophy results when a limb is immobilized (e.g., due to a limb or joint fracture or an orthopedic surgery such as a hip or knee replacement surgery). As used herein, "immobilization" or "immobilized" refers to the partial or complete restriction of movement of limbs, muscles, bones, tendons, joints, or any other body parts for an extended period of time (e.g., for 2 days, 3 days, 4 days, 5 days, 6 days, a week, two weeks, or more). In some instances, a period of immobilization includes short periods or instances of unrestrained movement, such as to bathe, to replace an external device, or to adjust an external device. Limb immobilization is optionally carried out by any variety of external devices including, but are not limited to, braces, slings, casts, bandages, and splints (any of which is optionally composed of hard or soft material including but not limited to cloth, gauze, fiberglass, plastic, plaster, or metal), as well as any variety of internal devices including surgically implanted splints, plates, braces, and the like. In the context of limb immobilization, the restriction of movement involves a single joint or multiple joints (e.g., simple joints such as the shoulder joint or hip joint, compound joints such as the radiocarpal joint, and complex joints such as the knee joint, including but not limited to one or more of the following: articulations of the hand, shoulder joints, elbow joints, wrist joints, auxiliary articulations, sternoclavicular joints, vertebral articulations, temporomandibular joints, sacroiliac joints, hip joints, knee joints, and articulations of the foot), a single tendon or ligament or multiple tendons or ligaments (e.g., including but not limited to one or more of the following: the anterior cruciate ligament, the posterior cruciate ligament, rotator cuff tendons, medial collateral ligaments of the elbow and knee, flexor tendons of the hand, lateral ligaments of the ankle, and tendons and ligaments of the jaw or temporomandibular joint), a single bone or multiple bones (e.g., including but not limited to one or more of the Wowing: the skull, mandible, clavicle, ribs, radius, ulna, humorous, pelvis, sacrum, femur, patella, phalanges, carpals, metacarpals, tarsals, metatarsals, fibula, tibia, scapula, and vertebrae), a single muscle or multiple muscles (e.g., including but not limited to one or more of the following: latissimus dorsi, trapezius, deltoid, pectorals, biceps, triceps, external obliques, abdominals, gluteus maximus, hamstrings, quadriceps, gastrocnemius, and diaphragm); a single limb or multiple limbs one or more of the arms and legs), or the entire skeletal muscle system or portions thereof (e.g., in the case of a full body cast or spica cast).

In some embodiments, described herein is a method of treating disuse-associated muscle atrophy in a subject, which comprises administering to the subject a therapeutically effective amount of a polynucleic acid molecule described herein. In other embodiments, described herein is a method of treating disuse-associated muscle atrophy in a subject, which comprises administering to the subject a therapeutically effective amount of a polynucleic acid molecule conjugate described herein.

Pharmaceutical Formulation

In some embodiments, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular, intra-arterial, intraperitoneal, intrathecal, intracerebral, intracerebroventricular, or intracranial) administration. In other instances, the pharmaceutical composition describe herein is formulated for oral administration. In still other instances, the pharmaceutical composition describe herein is formulated for intranasal administration.

In some embodiments, the pharmaceutical formulations include, but are not limited to, aqueous, liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle. e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some embodiments, the pharmaceutical formulation comprises a delivery vector, e.g., a recombinant vector, the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some embodiments, the pharmaceutical formulation includes a carrier or carrier materials selected on the basis of compatibility with the composition disclosed herein, and the release profile properties of the desired dosage form. Exemplary carrier materials include. e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*. Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A, and Lachman, L., Eds., Pharmaceutical Dosage Forms. Marcel Decker. New York, N.Y., 1980; and Pharmaceutical Dosage Forms and Drug Delivery Systems, Seventh Ed. (Lippincott Williams & Wilkins 1999).

In some instances, the pharmaceutical formulation further includes pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions: suitable salts include sodium chloride, potassium chloride, sodium thiosulfate, sodium bisulfite and ammonium sulfate.

In some instances, the pharmaceutical formulation further includes diluent which are used to stabilize compounds because they provide a more stable environment. Salts dissolved in buffered solutions (which also provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®, dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulation includes disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked poly vinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulation includes filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium olate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium docusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxy propylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, poloxamers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium docusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are coadministered. In some instances, the two or more different pharmaceutical compositions are coadministered simultaneously. In some cases, the two or more different pharmaceutical compositions are coadministered sequentially without a gap of time between administrations. In other cases, the two or more different pharmaceutical compositions are coadministered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or mom of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include target nucleic acid molecule described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the at to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of"or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

The term "therapeutically effective amount" relates to an amount of a polynucleic acid molecule conjugate that is sufficient to provide a desired therapeutic elect in a mammalian subject. In some cases, the amount is single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. Naturally, dosage levels of the particular polynucleic acid molecule conjugate employed to provide a therapeutically effective amount vary in dependence of the type of injury, the age, the weight, the gender, the medical condition of the subject, the severity of the condition, the route of administration, and the particular inhibitor employed. In some instances, therapeutically effective amounts of polynucleic acid molecule conjugate, as described herein, is estimated initially from cell culture and animal models. For example, $IC_{50}$ values determined in cell culture methods optionally serve as a starting point in animal models, while $IC_{50}$ values determined in animal models are optionally used to find a therapeutically effective dose in humans.

Skeletal muscle, or voluntary muscle, is generally anchored by tendons to bone and is generally used to effect skeletal movement such as locomotion or in maintaining posture. Although some control of skeletal muscle is generally maintained as an unconscious reflex (e.g., postural muscles or the diaphragm), skeletal muscles react to conscious control. Smooth muscle, or involuntary muscle, is found within the walls of organs and structures such as the esophagus, stomach, intestines, uterus, urethra, and blood vessels.

Skeletal muscle is further divided into two broad types: Type I (or "slow twitch") and Type II (or "fast twitch"). Type I muscle fibers are dense with capillaries and are rich in mitochondria and myoglobin, which gives Type I muscle tissue a characteristic red color. In some cases, Type I muscle fibers carries more oxygen and sustain aerobic activity using fats or carbohydrates for fuel. Type I muscle fibers contract for long periods of time but with little force. Type II muscle fibers are further subdivided into three major subtypes (IIa, IIx, and IIb) that vary in both contractile speed and force generated. Type II muscle fibers contract quickly and powerfully but fatigue very rapidly, and therefore produce only short, anaerobic bursts of activity before muscle contraction becomes painful.

Unlike skeletal muscle, smooth muscle is not under conscious control.

Cardiac muscle is also an involuntary muscle but more closely resembles skeletal muscle in structure and is found only in the heart. Cardiac and skeletal muscles are striated in that they contain sarcomeres that are packed into highly regular arrangements of bundles. By contrast, the myofibrils of smooth muscle cells are not arranged in sarcomeres and therefore are not striated.

Muscle cells encompass any cells that contribute to muscle tissue. Exemplary muscle cells include myoblasts, satellite cells, myotubes, and myofibril tissues.

As used here, muscle force is proportional to the cross-sectional area (CSA), and muscle velocity is proportional to muscle fiber length. Thus, comparing the cross-sectional areas and muscle fibers between various kinds of muscles is capable of providing an indication of muscle atrophy. Various methods are known in the art to measure muscle strength and muscle weight, see, for example, "Musculoskeletal assessment: Joint range of motion and manual muscle strength" by Hazel M. Clarkson, published by Lippincott Williams & Wilkins, 2000. The production of tomographic images from selected muscle tissues by computed axial tomography and sonographic evaluation are additional methods of measuring muscle mass.

EXAMPLES

These examples are provided for illustrative purposes only and not to limit the scope of the claims provided herein.

Example 1. siRNA Sequences and Synthesis

All siRNA single strands were fully assembled on solid phase using standard phosphoramidite chemistry and purified over HPLC. Purified single strands were duplexed to get the double stranded siRNA. All the siRNA passenger strand contains conjugation handles in different formats, C6-NH$_7$ and/or C6-SH, one at each end of the strand. The conjugation handle or handles were connected to siRNA passenger strand via inverted abasic phosphodiester or phosphorothioate. FIGS. 40A-40F are representative structures of the formats used in the in vivo experiments.

Cholesterol-Myostatin siRNA Conjugate

Figure 1:
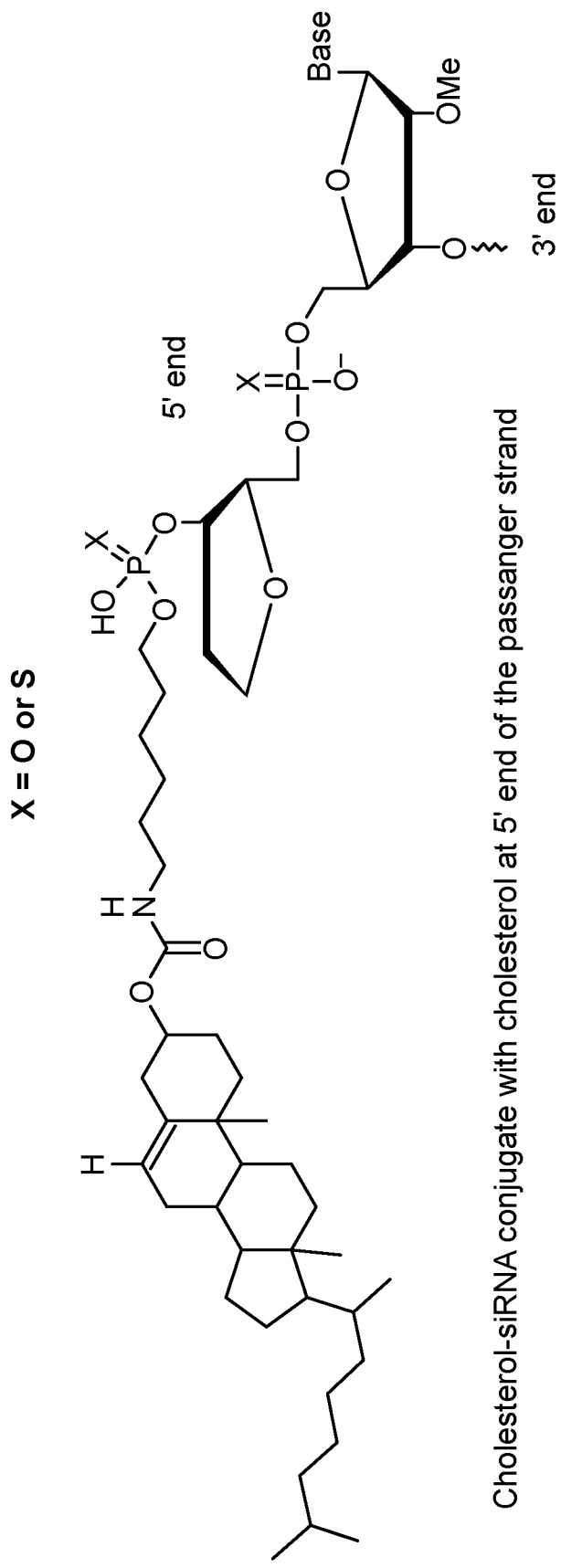
FIG. 1 illustrates an exemplary structure of cholesterol-myostatin siRNA conjugate.

The sequence of the guide/antisense strand was complementary to the gene sequence starting a base position 1169 for the mouse mRNA transcript for MSTN (UUAUUAUUUGUUCUUUGCCUU; SEQ ID NO: 14226). Base, sugar and phosphate modifications were used to optimize the potency of the duplex and reduce immunogenicity. All siRNA single strands were fully assembled on solid phase using standard phospharamidite chemistry and purified over HPLC. Purified single strands were duplexed to get the double stranded siRNA. The passenger strand contained a 5' cholesterol which was conjugated as described below in FIG. 1.

Example 2. General Experimental Protocol and Materials

Animals

All animal studies were conducted following protocols in accordance with the Institutional Animal Care and Use Committee (IACUC) at Explora BioLabs, which adhere to the regulations outlined in the USDA Animal Welfare Act as well as the "Guide for the Care and Use of Laboratory Animals" (National Research Council publication, 8th Ed., revised in 2011). All mice were obtained from either Charles River Laboratories or Harlan Laboratories.

Wild type CD-1 mice (4-6 week old) were dosed via intravenous (iv) injection with the indicated ASCs (or antibody-nucleic acid conjugate) and doses.

Anti-Transferrin Receptor Antibody

Anti-mouse transferrin receptor antibody or CD71 mAb is a rat IgG2a subclass monoclonal antibody that binds mouse CD71 or mouse transferrin receptor 1 (mTfR1). The antibody was produced by BioXcell and it is commercially available (Catalog #BE0175).

IgG2a Isotype Control Antibody

Rat IgG2a isotype control antibody was purchased from BioXcell (Clone 2A3, Catalog #BEM089) and this antibody is specific to trinitrophenol and does not have any known antigens in mouse.

Anti-EGFR Antibody

Anti-EGFR antibody is a fully human IgG1κ monoclonal antibody directed against the human epidermal growth factor receptor (EGFR). It is produced in the Chinese Hamster Ovary cell line DJT33, which has been derived from the CHO cell line CHO-K1SV by transfection with a GS vector carrying the antibody genes derived from a human anti-EGFR antibody producing hybridoma cell line (2F8). Standard mammalian cell culture and purification technologies are employed in the manufacturing of anti-EGFR antibody.

The theoretical molecular weight (MW) of anti-EGFR antibody without glycans is 146.6 kDa. The experimental MW of the major glycosylated isoform of the antibody is 149 kDa as determined by mass spectrometry. Using SDS-PAGE under reducing conditions the MW of the light chain was found to be approximately 25 kDa and the MW of the heavy chain to be approximately 50 kDa. The heavy chains are connected to each other by two inter-chain disulfide bonds, and one light chain is attached to each heavy chain by a single inter-chain disulfide bond. The light chain has two intra-chain disulfide bonds and the heavy chain has four intra-chain disulfide bonds. The antibody is N-linked glycosylated at Asn305 of the heavy chain with glycans composed of N-acetyl-glucosamine, mannose, fucose and galactose. The predominant glycans present are fucosylated bi-antennary structures containing zero or one terminal galactose residue.

The charged isoform pattern of the IgG1κ antibody has been investigated using imaged capillary IEF, agarose IEF and analytical cation exchange HPLC. Multiple charged isoforms are found, with the main isoform having an isoelectric point of approximately 8.7.

The major mechanism of action of anti-EGFR antibody is a concentration dependent inhibition of EGF-induced EGFR phosphorylation in A431 cancer cells. Additionally, induction of antibody-dependent cell-mediated cytotoxicity (ADCC) at low antibody concentrations has been observed in pre-clinical cellular in vitro studies.

In Vitro Evaluation of siRNA Potency and Efficacy

C2C12 myoblasts (ATCC) were grown in DMEM supplemented with 10% v/v FBS. For transfection, cells were plated at a density of 10,000 cells/well in 24-well plates, and transfected within 24 hours. C2C12 myotubes were generated by incubating confluent C2C12 myoblast cultures in DMEM supplemented with 2% v/v horse serum for 3-4 days. During and after differentiation the medium was changed daily. Pre-differentiated primary human skeletal muscle cells were obtained from ThermoFisher and plated in DMEM with 2% v/v horse serum according to recommendations by the manufacturer. Human SJCRH30 rhabdomyosarcoma myoblasts (ATCC) were grown in DMEM supplemented with 10% v/v heat-inactivated fetal calf serum, 4.5 mg/mL glucose, 4 mM L-glutamine, 10 mM HEPES, and 1 mM sodium pyruvate. For transfections cells were plated in a density of 10,000-20,000 cells/well in 24-well plates and transfected within 24 hours. All cells were transfected with various concentrations of the siRNAs (0.0001-100 nM: 10-fold dilutions) using RNAiMax (ThermoFisher) according to the recommendation by the manufacturer. Transfected cells were incubated in 5% CO2 at 37° C. for 2 days, then washed with PBS, and harvested in 300 ul TRizol (ThermoFisher) and stored at −80° C. RNA was prepared using a ZYMO 96-well RNA kit (ThermoFisher) and relative RNA expression levels quantified by RT-qPCR using commercially available TaqMan probes (LifeTechnology). Expression data were analyzed using the □□CT method normalized to Ppib expression, and are presented as % KD relative to mock-transfected cells. Data were analyzed by nonlinear regression using a 3 parameter dose response inhibition function (GraphPad Prism 7.02). All knock down results present the maximal observed KD under these experimental conditions.

Myostatin ELISA

Myostatin protein in plasma was quantified using the GDF-8 (Myostatin) Quantikine ELISA Immunoassay (part #DGDF80) from R&D Systems according to the manufacturer's instructions.

RISC Loading Assay

Specific immunoprecipitation of the RISC from tissue lysates and quantification of small RNAs in the immunoprecipitates were determine by stem-loop PCR, using an adaptation of the assay described by Pei et al. Quantitative evaluation of siRNA delivery in vivo. RNA (2010), 16:2553-2563.

Example 3. Conjugate Synthesis

The structures in FIGS. 41A-41F illustrate exemplary A-$X_1$-B-$X_2$-Y (Formula I) architectures described herein.

Example 3.1 Antibody siRNA Conjugate Synthesis Using SMCC Linker

FIG. 42 illustrates synthesis scheme-1: Antibody-Cys-SMCC-siRNA-PEG conjugates via antibody cysteine conjugation.

Step 1: Antibody Interchain Disulfide Reduction with TCEP

Antibody was buffer exchanged with borax buffer (pH 8) and made up to 10 mg/ml concentration. To this solution, 2 equivalents of TCEP in water was added and rotated for 2 hours at RT. The resultant reaction mixture was buffer exchanged with pH 7.4 PBS containing 5 mM EDTA and added to a solution of SMCC-C6-siRNA or SMCC-C6-siRNA-C6-NHCO-PEG-XkDa (2 equivalents) (X=0.5 kDa to 10 kDa) in pH 7.4 PBS containing 5 mM EDTA at RT and rotated overnight. Analysis of the reaction mixture by analytical SAX column chromatography showed antibody siRNA conjugate along with unreacted antibody and siRNA.

Step 2: Purification

The crude reaction mixture was purified by AKTA explorer FPLC using anion exchange chromatography method-1 as described in Example 3.4. Fractions containing DAR1 and DAR>2 antibody-siRNA-PEG conjugates were separated, concentrated and buffer exchanged with pH 7.4 PBS.

Step-3: Analysis of the Purified Conjugate

The isolated conjugates were characterized by SEC, SAX chromatography and SDS-PAGE. The purity of the conjugate was assessed by analytical HPLC using either anion exchange chromatography method-2 or anion exchange chromatography method-3. Both methods are described in Example 3.4. Isolated DAR1 conjugates are typically eluted at 9.0±0.3 min on analytical SAX method and are greater than 90% pure. The typical DAR>2 cysteine conjugate contains more than 85% DAR2 and less than 15% DAR3.

Figure 2:
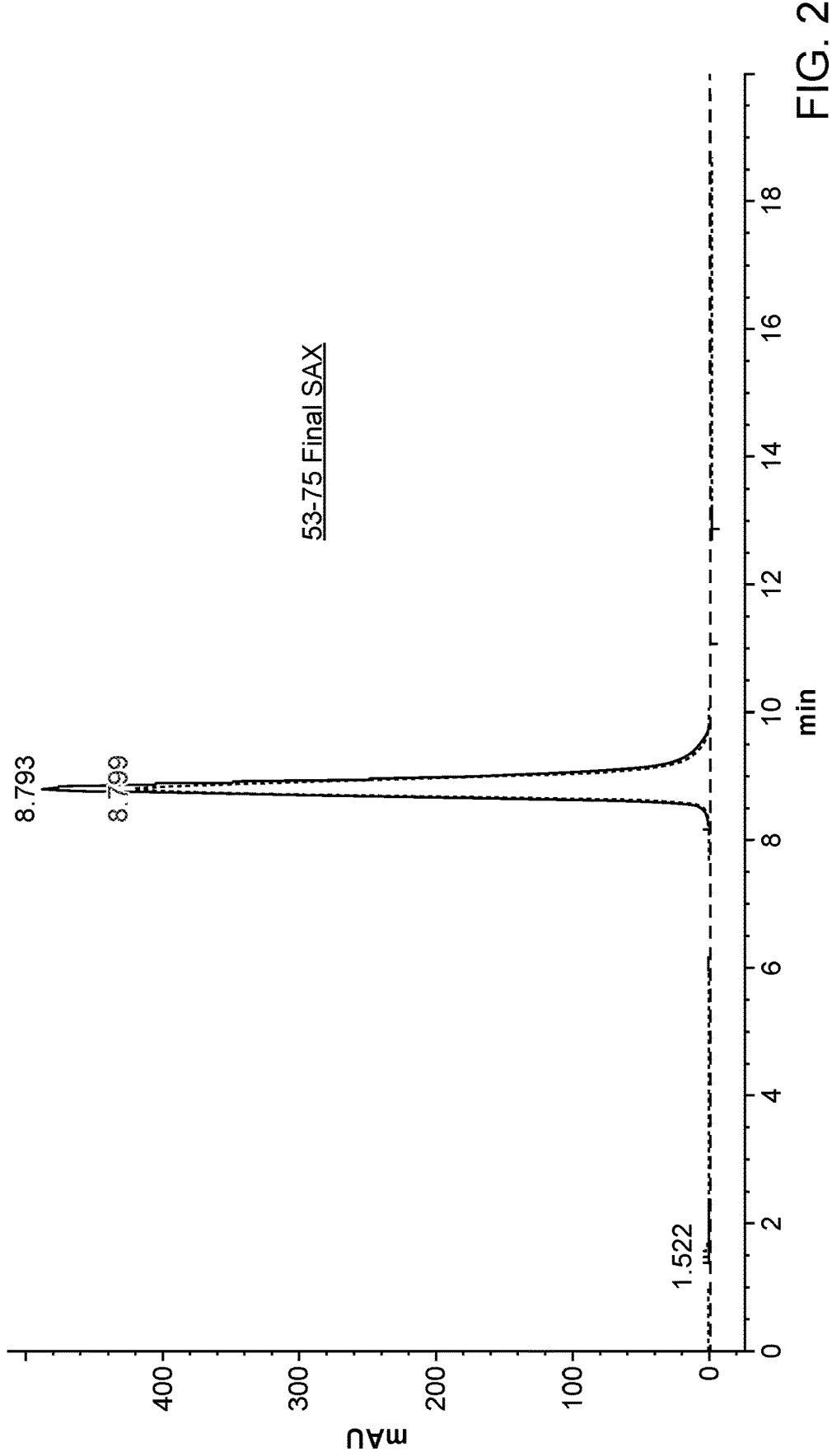
FIG. 2 illustrates SAX HPLC chromatogram of TfR mAb-(Cys)-HPRT-PEG5k, DAR1.

FIG. 2 illustrates SAX HPLC chromatogram of TfR mAb-(Cys)-HPRT-PEG5k, DAR1.

Figure 3:
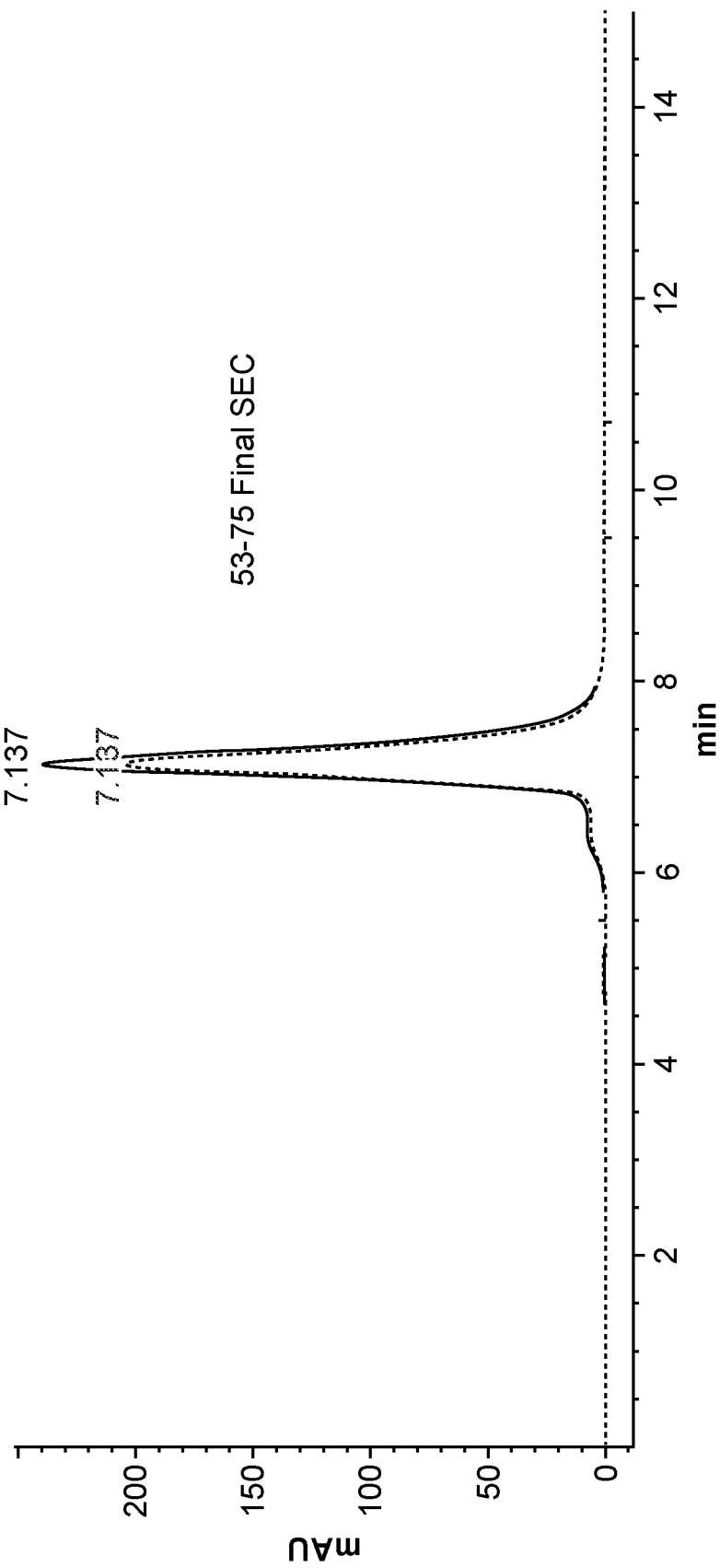
FIG. 3 illustrates SEC HPLC chromatogram of TfR mAb-(Cys)-HPRT-PEG5k, DAR1.

FIG. 3 illustrates SEC HPLC chromatogram of TfR mAb-(Cys)-HPRT-PEG5k, DAR1.

Example 3.2. Antibody siRNA Conjugate Synthesis Using Bis-Maleimide (BisMal) Linker FIG. 43 shows synthesis scheme-2: Antibody-Cys-Bis-Mal-siRNA-PEG conjugates.

Step 1: Antibody Reduction with TCEP

Antibody was buffer exchanged with borax buffer (pH 8) and made up to 5 mg/ml concentration. To this solution, 2 equivalents of TCEP in water was added and rotated for 2 hours at RT. The resultant reaction mixture was exchanged with pH 7.4 PBS containing 5 mM EDTA and added to a solution of BisMal-C6-siRNA-C6-S-NEM (2 equivalents) in pH 7.4 PBS containing 5 mM EDTA at RT and kept at 4° C. overnight. Analysis of the reaction mixture by analytical SAX column chromatography showed antibody siRNA conjugate along with unreacted antibody and siRNA.

Step 2: Purification

The crude reaction mixture was purified by AKTA explorer FPLC using anion exchange chromatography method-1. Fractions containing DAR1 and DAR2 antibody-siRNA conjugates were separated, concentrated and buffer exchanged with pH 7.4 PBS.

Step-3: Analysis of the Purified Conjugate

The isolated conjugates were characterized by either mass spec or SDS-PAGE. The purity of the conjugate was assessed by analytical HPLC using either anion exchange chromatography method-2 or 3 as well as size exclusion chromatography method-1.

Figure 4:
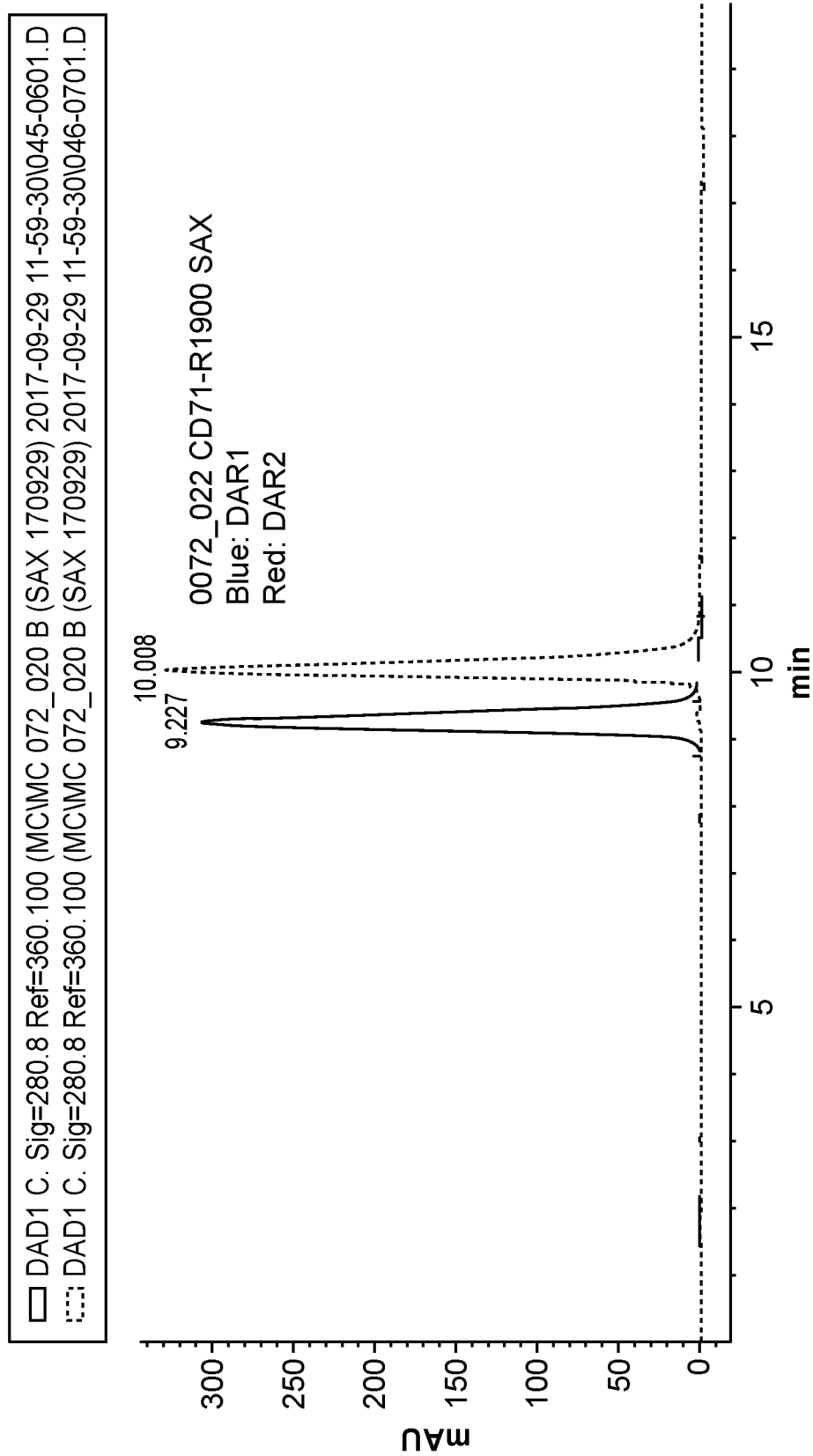
FIG. 4 illustrates an overlay of DAR1 and DAR2 SAX HPLC chromatograms of TfR1mAb-Cys-BisMal-siRNA conjugates.

FIG. 4 illustrates an overlay of DAR1 and DAR2 SAX HPLC chromatograms of TfR1mAb-Cys-BisMal-siRNA conjugates.

Figure 5:
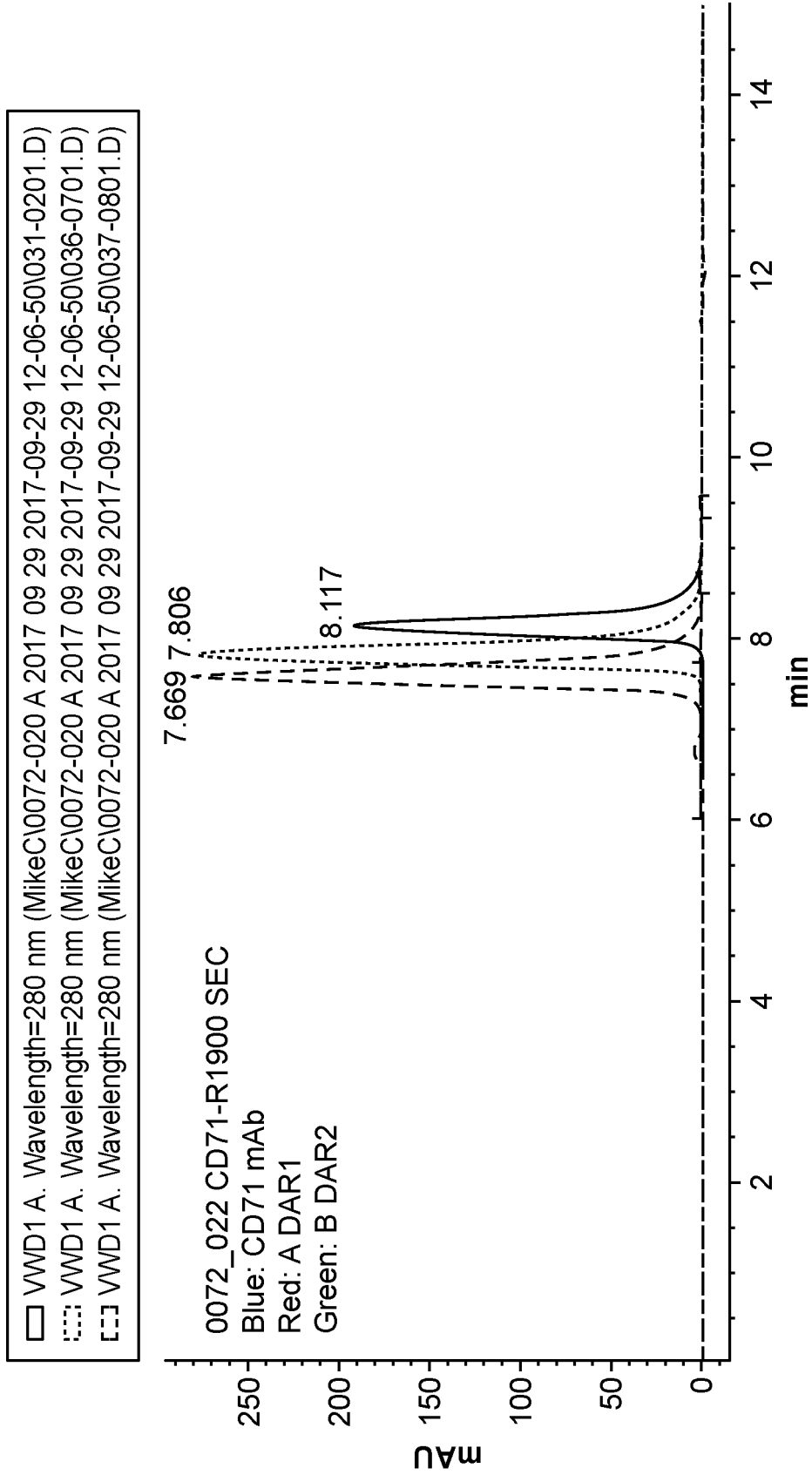
FIG. 5 illustrates an overlay of DAR1 and DAR2 SEC HPLC chromatograms of TfR1mAb-Cys-BisMal-siRNA conjugates.

FIG. 5 illustrates an overlay of DAR1 and DAR2 SEC HPLC chromatograms of TfR1mAb-Cys-BisMal-siRNA conjugates.

Example 3.3. Fab' Generation from mAb and Conjugation to siRNA

FIG. 44 shows scheme-3: Fab-siRNA conjugate generation.

Step 1: Antibody Digestion with Pepsin

Antibody was buffer exchanged with pH 4.0, 20 mM sodium acetate/acetic acid buffer and made up to 5 mg/ml concentration. Immobilized pepsin (Thermo Scientific, Prod #20343) was added and incubated for 3 hours at 37'C. The reaction mixture was filtered using 30 kDa MWCO Amicon spin filters and pH 7.4 PBS. The retentate was collected and purified using size exclusion chromatography to isolate F(ab')2. The collected F(ab')2 was then reduced by 10 equivalents of TCEP and conjugated with SMCC-C6-siRNA-PEG5 at room temperature in pH 7.4 PBS. Analysis of reaction mixture on SAX chromatography showed Fab-siRNA conjugate along with unreacted Fab and siRNA-PEG.

Step 2: Purification

The crude reaction mixture was purified by AKTA explorer FPLC using anion exchange chromatography method-1. Fractions containing DAR1 and DAR2 Fab-siRNA conjugates were separated, concentrated and buffer exchanged with pH 7.4 PBS.

Step-3: Analysis of the Purified Conjugate

The characterization and purity of the isolated conjugate was assessed by analytical HPLC using anion exchange chromatography method-2 or 3 as well as by SEC method-1.

Figure 6:
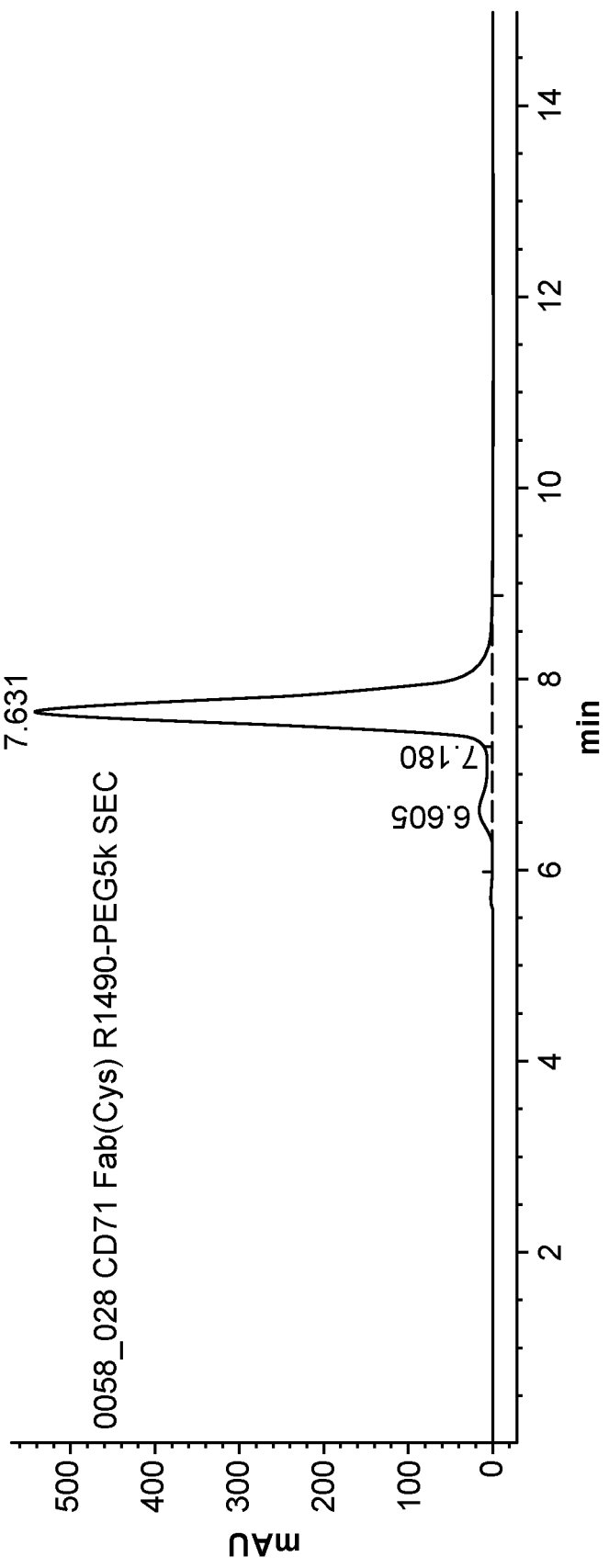
FIG. 6 illustrates SEC chromatogram of CD71 Fab-Cys-HPRT-PEG5.

FIG. 6 illustrates SEC chromatogram of CD71 Fab-Cys-HPRT-PEG5.

Figure 7:
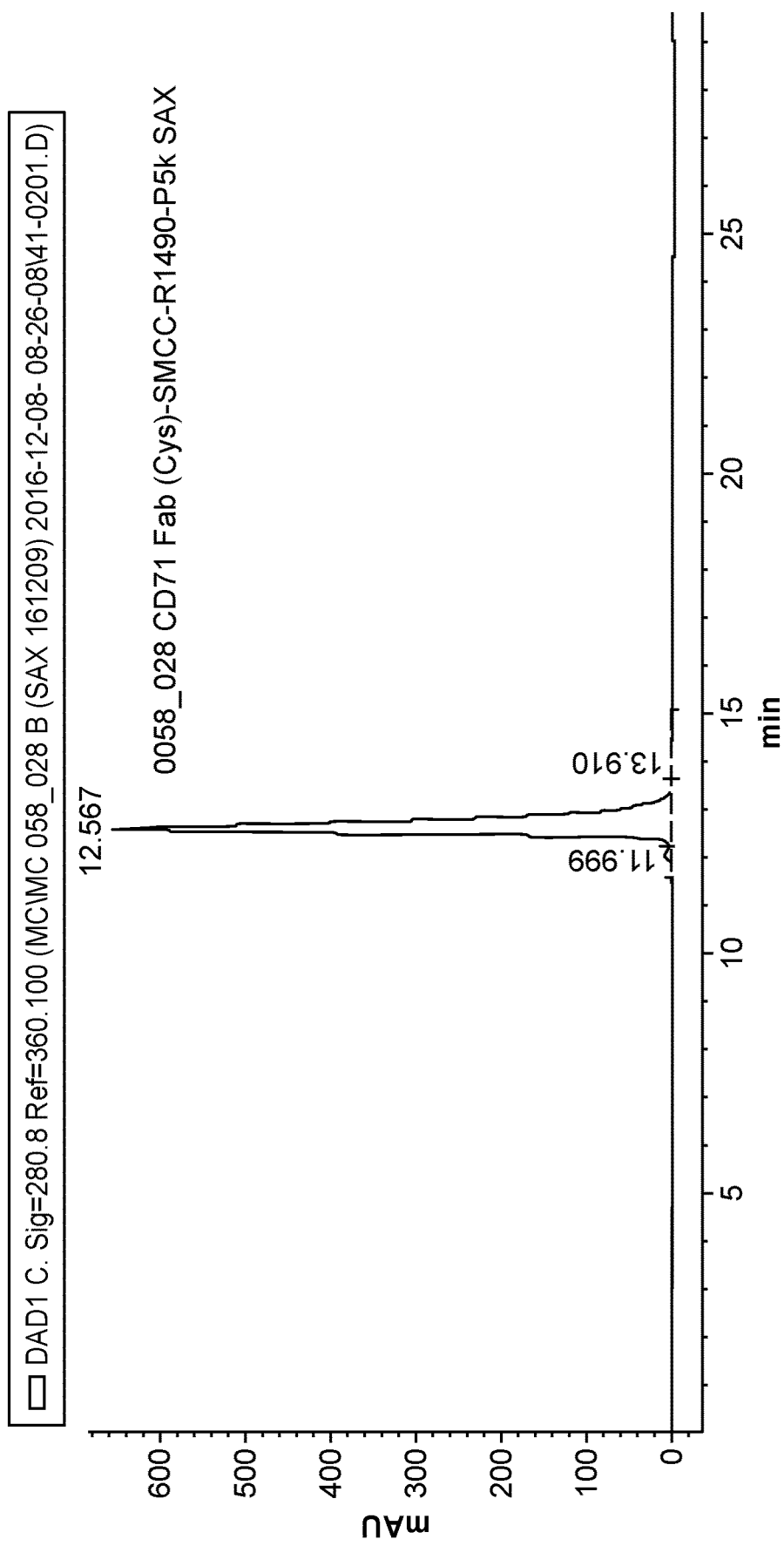
FIG. 7 illustrates SAX chromatogram of CD71 Fab-Cys-HPRT-PEG5.

FIG. 7 illustrates SAX chromatogram of CD71 Fab-Cys-HPRT-PEG5.

Example 3.4. Purification and Analytical Methods

Anion Exchange Chromatography Method (SAX)-1.
1. Column: Tosoh Bioscience, TSKGel SuperQ-5PW, 21.5 mm ID×15 cm, 13 um
2. Solvent A: 20 mM TRIS buffer, pH 8.0; Solvent B: 20 mM TRIS, 1.5 M NaCl, pH 8.0; Flow Rate: 6.0 ml/min
3. Gradient:

|    | % A | % B | Column Volume |
|----|-----|-----|---------------|
| a. |     |     |               |
| b. | 100 | 0   | 1.00          |
| c. | 60  | 40  | 18.00         |
| d. | 40  | 60  | 2.00          |
| e. | 40  | 60  | 5.00          |
| f. | 0   | 100 | 2.00          |
| g. | 100 | 0   | 2.00          |

Anion Exchange Chromatography (SAX) method-2

1. Column: Thermo Scientific, ProPac™ SAX-10, Bio LC™, 4×250 mm
2. Solvent A: 80% 10 mM TRIS pH 8, 20% ethanol; Solvent B: 80% 10 mM TRIS pH 8, 20% ethanol, 1.5 M NaCl: Flow Rate: 0.75 ml/min
3. Gradient:

|    | Time  | % A | % B |    |
|----|-------|-----|-----|----|
| a. |       |     |     |    |
| b. | 0.0   | 90  | 10  |    |
| c. | 3.00  |     | 90  | 10 |
| d. | 11.00 | 40  | 60  |    |
| e. | 13.00 | 40  | 60  |    |
| f. | 15.00 | 90  | 10  |    |
| g. | 20.00 | 90  | 10  |    |

Anion Exchange Chromatography (SAX) Method-3

1. Column: Thermo Scientific, ProPac™ SAX-10, Bio LC™, 4×250 mm
2. Solvent A: 80% 10 mM TRIS pH 8, 20% ethanol; Solvent B: 80% 10 mM TRIS pH 8, 20% ethanol, 1.5 M NaCl
3. Flow Rate: 0.75 ml/min
4. Gradient:

|    | Time  | % A | % B |
|----|-------|-----|-----|
| a. |       |     |     |
| b. | 0.0   | 90  | 10  |
| c. | 3.00  | 90  | 10  |
| d. | 11.00 | 40  | 60  |
| e. | 23.00 | 40  | 60  |
| f. | 25.00 | 90  | 10  |
| g. | 30.00 | 90  | 10  |

Size Exclusion Chromatography (SEC) Method-1

1. Column: TOSOH Biosciences, TSKgelG3000SW XL, 7.8×300 mm, 5 μM
2. Mobile phase: 150 mM phosphate buffer
3. Flow Rate: 1.0 ml/min for 15 mins Example 4. In Vitro Screen: Atrogin-1

Identification of siRNAs for the Regulation of Mouse and Human/NHP Atrogin-1

A bioinformatics screen conducted identified 56 siRNAs (19mers) that bind specifically to mouse atrogin-1 (Fbxo32; NM_026346.3). In addition, 6 siRNAs were identified that target mouse atrogin-1 and human atrogin-1 (FBXO32; NM_058229.3). A screen for siRNAs (19mers) targeting specifically human/NHP atrogin-1 (FBXO32; NM_058229.3) yielded 52 candidates (Table 2A-Table 2B). All selected siRNA target sites do not harbor SNPs (pos. 2-18).

Tables 2A and 2B illustrate identified siRNA candidates for the regulation of mouse and human/NHP atrogin-1.

TABLE 2A

| 19mer pos. in NM_026346.3 | exon # | mouse | mouse x human | sequence of total 23mer target site in NM_026346.3 | SEQ ID NO: |
|---|---|---|---|---|---|
| 7 | 1 | X | | GGGCAGCGGCCCGGGAUAAAUAC | 28 |
| 8 | 1 | X | | GGCAGCGGCCCGGGAUAAAUACU | 29 |
| 499 | 3-Feb | X | | AACCAAAACUCAGUACUUCCAUC | 30 |
| 553 | 4-Mar | X | | UACGAAGGAGCGCCAUGGAUACU | 31 |
| 590 | 4 | X | X | GCUUUCAACAGACUGGACUUCUC | 32 |
| 631 | 4 | X | | CAGAAGAUUCAACUACGUAGUAA | 33 |
| 694 | 5 | X | | GAGUGGCAUCGCCCAAAAGAACU | 34 |
| 772 | 6 | X | | AAGACUUAUACGGGAACUUCUCC | 35 |
| 1178 | 8 | X | | AAGCUUGUACGAUGUUACCCAAG | 36 |
| 1179 | 8 | X | | AGCUUGUACGAUGUUACCCAAGA | 37 |
| 1256 | 9-Aug | X | X | UGGAAGGGCACUGACCAUCCGUG | 38 |
| 1258 | 9-Aug | X | X | GAAGGGCACUGACCAUCCGUGCA | 39 |
| 1260 | 9 | X | X | AGGGCACUGACCAUCCGUGCACG | 40 |
| 1323 | 9 | X | | AAGACUUUAUCAAUUUGUUCAAG | 41 |
| 1401 | 9 | X | | GGGAGUCGGGACACUUCAUUUGU | 42 |
| 1459 | 9 | X | | CGGGGGAUACGUCAUUGAGGAGA | 43 |
| 1504 | 9 | X | | UUGCCGAUGGAAAUUUACAAAUG | 44 |
| 1880 | 9 | X | X | CCACACAAUGGUCUACCUCUAAA | 45 |
| 1884 | 9 | X | X | ACAAUGGUCUACCUCUAAAAGCA | 46 |
| 2455 | 9 | X | | CUGAUAGAUGUGUUCGUCUUUAAA | 47 |
| 2570 | 9 | X | | AUCUCAGGGCUUAAGGAGUUAAU | 48 |
| 2572 | 9 | X | | CUCAGGGCUUAAGGAGUUAAUUC | 49 |
| 2936 | 9 | X | | CUGAUUUGCAGGGUCUUACAUCU | 50 |
| 3006 | 9 | X | | CUGGUGGCCAAAUUAAGUUGAAU | 51 |
| 3007 | 9 | X | | UGGUGGCCAAAUUAAGUUGAAUU | 52 |
| 3115 | 9 | X | | GAGAUUACAAACAUUGUAACAGA | 53 |
| 3668 | 9 | X | | CAGCGCAAAACUAGUUAGCCAGU | 54 |
| 3676 | 9 | X | | AACUAGUUAGCCAGUCUUACAGA | 55 |
| 3715 | 9 | X | | AAGUCAUAUAGCAUCCAUACACC | 56 |
| 3800 | 9 | X | | UAGUAGGUGCUUGCAGGUUCUCC | 57 |
| 3845 | 9 | X | | AUGGUAUGUGACACAACCGAAGA | 58 |
| 3856 | 9 | X | | CACAACCGAAGAAUCGUUUGACG | 59 |
| 4026 | 9 | X | | GGCAAGCAAGAUACCCAUAUUAG | 60 |
| 4095 | 9 | X | | AGCUCUUAGGACAUUAAUAGUCU | 61 |
| 4139 | 9 | X | | UGCAGGACUCCCAGACUUAAAAC | 62 |
| 4183 | 9 | X | | CCCAGAACUGCUAGUACAAAAGC | 63 |
| 4203 | 9 | X | | AGCAAGAGGGGUGUGGCUAUAGA | 64 |
| 4208 | 9 | X | | GAGGGGUGUGGCUAUAGAAGUUG | 65 |

TABLE 2A-continued

| | | | | |
|---|---|---|---|---|
| 4548 | 9 | X | GACCAUGUCGCUACUACCAUUGC | 66 |
| 4554 | 9 | X | GUCGCUACUACCAUUGCUUCAAG | 67 |
| 4563 | 9 | X | ACCAUUGCUUCAAGUGGGUAUCU | 68 |
| 4567 | 9 | X | UUGCUUCAAGUGGGUAUCUCAGU | 69 |
| 4673 | 9 | X | CUGGUUAGUGAUGAUCAACUUCA | 70 |
| 4858 | 9 | X | UGCCGCUUCAUACGGGAGAAAAA | 71 |
| 4970 | 9 | X | UCGGCUUCAACGCAUUGUUUAUU | 72 |
| 5022 | 9 | X | CUGCCUGGUUAUAAAGCAAUAAC | 73 |
| 5235 | 9 | X | ACCUGUUAGUGCUUAAACAGACU | 74 |
| 5237 | 9 | X | CUGUUAGUGCUUAAACAGACUCA | 75 |
| 5279 | 9 | X | GGGGCAAACGCAGGGGUGUUACU | 76 |
| 5292 | 9 | X | GGGUGUUACUCUUUGAUAUAUCA | 77 |
| 5443 | 9 | X | AUCCCAGACUUUAGACCAAAAGG | 78 |
| 5640 | 9 | X | UUGUGGACGUGUGUAAAUUCAUG | 79 |
| 6000 | 9 | X | UUCAUUGACCAACCAGUCUUAAG | 80 |
| 6105 | 9 | X | UGCCGCAACCUCCCAAGUCAUAU | 81 |
| 6530 | 9 | X | GAGUAUAGACAUGCGUGUUAACU | 82 |
| 6537 | 9 | X | GACAUGCGUGUUAACUAUGCACA | 83 |
| 6608 | 9 | X | UUGGUUCCAUCUUUAUACCAAAU | 84 |
| 6668 | 9 | X | GUGUCUAAGCUUAGAAGCUUUAA | 85 |
| 6720 | 9 | X | UGGGUUGAACACUUUAACUAAAC | 86 |
| 6797 | 9 | X | AUCUGAAUCCUGUAUAACUUAUU | 87 |
| 6799 | 9 | X | CUGAAUCCUGUAUAACUUAUUUG | 88 |
| 6803 | 9 | X | AUCCUGUAUAACUUAUUUGCACA | 89 |

| 19mer pos. in NM_058229.3 | human + NHP | sequence of total 23mer target site in NM_058229.3 | |
|---|---|---|---|
| 586 | x | UUCCAGAAGAUUUAACUACGUGG | 90 |
| 589 | x | CAGAAGAUUUAACUACGUGGUCC | 91 |
| 1068 | x | AGCGGCAGAUCCGCAAACGAUUA | 92 |
| 1071 | x | GGCAGAUCCGCAAACGAUUAAUU | 93 |
| 1073 | x | CAGAUCCGCAAACGAUUAAUUCU | 94 |
| 1075 | x | GAUCCGCAAACGAUUAAUUCUGU | 95 |
| 1076 | x | AUCCGCAAACGAUUAAUUCUGUC | 96 |
| 1077 | x | UCCGCAAACGAUUAAUUCUGUCA | 97 |
| 1079 | x | CGCAAACGAUUAAUUCUGUCAGA | 98 |
| 1083 | x | AACGAUUAAUUCUGUCAGACAAA | 99 |
| 1127 | x | AUGUAUUUCAAACUUGUCCGAUG | 100 |
| 1142 | x | GUCCGAUGUUACCCAAGGAAAGA | 101 |
| 1164 | x | AGCAGUAUGGAGAUACCCUUCAG | 102 |
| 1228 | x | CCAUCCGUGCACUGCCAAUAACC | 103 |

TABLE 2A-continued

| | | | |
|---|---|---|---|
| 1254 | x | AGAGCUGCUCCGUUUCACUUUCA | 104 |
| 1361 | x | UGGGAAUAUGGCAUUUGGACACU | 105 |
| 1492 | x | UGUGAACUUCUCACUAGAAUUGG | 106 |
| 1500 | x | UCUCACUAGAAUUGGUAUGGAAA | 107 |
| 1563 | x | CAGCAAGACUAUAAGGGCAAUAA | 108 |
| 1566 | x | CAAGACUAUAAGGGCAAUAAUUC | 109 |
| 1635 | x | UCUUAUAGUUCCCUAGGAAGAAA | 110 |
| 1679 | x | AUAGGACGCUUUGUUUACAAUGU | 111 |
| 2487 | x | UUUUCUUUAGGUCCAACAUCAAA | 112 |
| 2488 | x | UUUCUUUAGGUCCAACAUCAAAA | 113 |
| 2582 | x | AGGAGAGGUACCACAAGUUCAUC | 114 |
| 2661 | x | GAGGCAAAUAUCAGCAGGUAACU | 115 |
| 2663 | x | GGCAAAUAUCAGCAGGUAACUGU | 116 |
| 2790 | x | UUUCCUACAACAAUGUACAUAUA | 117 |
| 2999 | x | AAGAGACAAGCUAUGAUACAACA | 118 |
| 3875 | x | GAAAUCAACCUUUAUGGUUCUCU | 119 |
| 4036 | x | GUGCCACGUGGUAUCUGUUAAGU | 120 |
| 4039 | x | CCACGUGGUAUCUGUUAAGUAUG | 121 |
| 4059 | x | AUGGCCAGAGCCUCACAUAUAAG | 122 |
| 4062 | x | GCCAGAGCCUCACAUAUAAGUGA | 123 |
| 4065 | x | AGAGCCUCACAUAUAAGUGAAGA | 124 |
| 4117 | x | AUAAUAGUCUAUAGAAUUUCUAU | 125 |
| 4444 | x | GCCUAGAGUCUCUUGAGAGUAAA | 126 |
| 4653 | x | GAAAGCAUCCCCAAUGUAUCAGU | 127 |
| 4665 | x | AAUGUAUCAGUUGUGAGAUGAUU | 128 |
| 4787 | x | CUACUAGCACUUGGGCAGUAAGG | 129 |
| 5162 | x | UUAACUAAACUCUAUCAUCAUUU | 130 |
| 5261 | x | CUGGCCUAAAAUCCUAUUAGUGC | 131 |
| 5270 | x | AAUCCUAUUAGUGCUUAAACAGA | 132 |
| 5272 | x | UCCUAUUAGUGCUUAAACAGACC | 133 |
| 5338 | x | UUUGAUAUAUCUUGGGUCCUUGA | 134 |
| 5737 | x | UGGCUGUUAACGUUUCCAUUUCA | 135 |
| 5739 | x | GCUGUUAACGUUUCCAUUUCAAG | 136 |
| 6019 | x | CUCAGAGGUACAUUUAAUCCAUC | 137 |
| 6059 | x | CAGGACCAGCUAUGAGAUUCAGU | 138 |
| 6140 | x | GGGGGAUUAUUCCAUGAGGCAGC | 139 |
| 6431 | x | GGCUCCAAGCUGUAUUCUAUACU | 140 |
| 6720 | x | UUUGUACCAGACGGUGGCAUAUU | 141 |

TABLE 2B

| 19mer pos. in NM_026346.3 | exon # | sense strand sequence (5'-3') | SEQ ID NO: | antisense strand sequence (5'-3') | SEQ ID NO: |
|---|---|---|---|---|---|
| 7 | 1 | GCAGCGGCCCGGGAUAAAU | 142 | AUUUAUCCCGGGCCGCUGC | 256 |
| 8 | 1 | CAGCGGCCCGGGAUAAAUA | 143 | UAUUUAUCCCGGGCCGCUG | 257 |
| 499 | 3-Feb | CCAAAACUCAGUACUUCCA | 144 | UGGAAGUACUGAGUUUUGG | 258 |
| 553 | 4-Mar | CGAAGGAGCGCCAUGGAUA | 145 | UAUCCAUGGCGCUCCUUCG | 259 |
| 590 | 4 | UUUCAACAGACUGGACUUC | 146 | GAAGUCCAGUCUGUUGAAA | 260 |
| 631 | 4 | GAAGAUUCAACUACGUAGU | 147 | ACUACGUAGUUGAAUCUUC | 261 |
| 694 | 5 | GUGGCAUCGCCCAAAAGAA | 148 | UUCUUUUGGGCGAUGCCAC | 262 |
| 772 | 6 | GACUUAUACGGGAACUUCU | 149 | AGAAGUUCCCGUAUAAGUC | 263 |
| 1178 | 8 | GCUUGUACGAUGUUACCCA | 150 | UGGGUAACAUCGUACAAGC | 264 |
| 1179 | 8 | CUUGUACGAUGUUACCCAA | 151 | UUGGGUAACAUCGUACAAG | 265 |
| 1256 | 9-Aug | GAAGGGCACUGACCAUCCG | 152 | CGGAUGGUCAGUGCCCUUC | 266 |
| 1258 | 9-Aug | AGGGCACUGACCAUCCGUG | 153 | CACGGAUGGUCAGUGCCCU | 267 |
| 1260 | 9 | GGCACUGACCAUCCGUGCA | 154 | UGCACGGAUGGUCAGUGCC | 268 |
| 1323 | 9 | GACUUUAUCAAUUUGUUCA | 155 | UGAACAAAUUGAUAAAGUC | 269 |
| 1401 | 9 | GAGUCGGGACACUUCAUUU | 156 | AAAUGAAGUGUCCCGACUC | 270 |
| 1459 | 9 | GGGGAUACGUCAUUGAGGA | 157 | UCCUCAAUGACGUAUCCCC | 271 |
| 1504 | 9 | GCCGAUGGAAAUUUACAAA | 158 | UUUGUAAAUUUCCAUCGGC | 272 |
| 1880 | 9 | ACACAAUGGUCUACCUCUA | 159 | UAGAGGUAGACCAUUGUGU | 273 |
| 1884 | 9 | AAUGGUCUACCUCUAAAAG | 160 | CUUUUAGAGGUAGACCAUU | 274 |
| 2455 | 9 | GAUAGAUGUGUUCGUCUUA | 161 | UAAGACGAACACAUCUAUC | 275 |
| 2570 | 9 | CUCAGGGCUUAAGGAGUUA | 162 | UAACUCCUUAAGCCCUGAG | 276 |
| 2572 | 9 | CAGGGCUUAAGGAGUUAAU | 163 | AUUAACUCCUUAAGCCCUG | 277 |
| 2936 | 9 | GAUUUGCAGGGUCUUACAU | 164 | AUGUAAGACCCUGCAAAUC | 278 |
| 3006 | 9 | GGUGGCCAAAUUAAGUUGA | 165 | UCAACUUAAUUUGGCCACC | 279 |
| 3007 | 9 | GUGGCCAAAUUAAGUUGAA | 166 | UUCAACUUAAUUUGGCCAC | 280 |
| 3115 | 9 | GAUUACAAACAUUGUAACA | 167 | UGUUACAAUGUUUGUAAUC | 281 |
| 3668 | 9 | GCGCAAAACUAGUUAGCCA | 168 | UGGCUAACUAGUUUUGCGC | 282 |
| 3676 | 9 | CUAGUUAGCCAGUCUUACA | 169 | UGUAAGACUGGCUAACUAG | 283 |
| 3715 | 9 | GUCAUAUAGCAUCCAUACA | 170 | UGUAUGGAUGCUAUAUGAC | 284 |
| 3800 | 9 | GUAGGUGCUUGCAGGUUCU | 171 | AGAACCUGCAAGCACCUAC | 285 |
| 3845 | 9 | GGUAUGUGACACAACCGAA | 172 | UUCGGUUGUGUCACAUACC | 286 |
| 3856 | 9 | CAACCGAAGAAUCGUUUGA | 173 | UCAAACGAUUCUUCGGUUG | 287 |
| 4026 | 9 | CAAGCAAGAUACCCAUAUU | 174 | AAUAUGGGUAUCUUGCUUG | 288 |
| 4095 | 9 | CUCUUAGGACAUUAAUAGU | 175 | ACUAUUAAUGUCCUAAGAG | 289 |
| 4139 | 9 | CAGGACUCCCAGACUUAAA | 176 | UUUAAGUCUGGGAGUCCUG | 290 |
| 4183 | 9 | CAGAACUGCUAGUACAAAA | 177 | UUUUGUACUAGCAGUUCUG | 291 |
| 4203 | 9 | CAAGAGGGGUGUGGCUAUA | 178 | UAUAGCCACACCCCUCUUG | 292 |
| 4208 | 9 | GGGGUGUGGCUAUAGAAGU | 179 | ACUUCUAUAGCCACACCCC | 293 |
| 4548 | 9 | CCAUGUCGCUACUACCAUU | 180 | AAUGGUAGUAGCGACAUGG | 294 |

TABLE 2B-continued

| | | | | | |
|---|---|---|---|---|---|
| 4554 | 9 | CGCUACUACCAUUGCUUCA | 181 | UGAAGCAAUGGUAGUAGCG | 295 |
| 4563 | 9 | CAUUGCUUCAAGUGGGUAU | 182 | AUACCCACUUGAAGCAAUG | 296 |
| 4567 | 9 | GCUUCAAGUGGGUAUCUCA | 183 | UGAGAUACCCACUUGAAGC | 297 |
| 4673 | 9 | GGUUAGUGAUGAUCAACUU | 184 | AAGUUGAUCAUCACUAACC | 298 |
| 4858 | 9 | CCGCUUCAUACGGGAGAAA | 185 | UUUCUCCCGUAUGAAGCGG | 299 |
| 4970 | 9 | GGCUUCAACGCAUUGUUUA | 186 | UAAACAAUGCGUUGAAGCC | 300 |
| 5022 | 9 | GCCUGGUUAUAAAGCAAUA | 187 | UAUUGCUUUAUAACCAGGC | 301 |
| 5235 | 9 | CUGUUAGUGCUUAAACAGA | 188 | UCUGUUUAAGCACUAACAG | 302 |
| 5237 | 9 | GUUAGUGCUUAAACAGACU | 189 | AGUCUGUUUAAGCACUAAC | 303 |
| 5279 | 9 | GGCAAACGCAGGGGUGUUA | 190 | UAACACCCCUGCGUUUGCC | 304 |
| 5292 | 9 | GUGUUACUCUUUGAUAUAU | 191 | AUAUAUCAAAGAGUAACAC | 305 |
| 5443 | 9 | CCCAGACUUUAGACCAAAA | 192 | UUUUGGUCUAAAGUCUGGG | 306 |
| 5640 | 9 | GUGGACGUGUGUAAAUUCA | 193 | UGAAUUUACACACGUCCAC | 307 |
| 6000 | 9 | CAUUGACCAACCAGUCUUA | 194 | UAAGACUGGUUGGUCAAUG | 308 |
| 6105 | 9 | CCGCAACCUCCCAAGUCAU | 195 | AUGACUUGGGAGGUUGCGG | 309 |
| 6530 | 9 | GUAUAGACAUGCGUGUUAA | 196 | UUAACACGCAUGUCUAUAC | 310 |
| 6537 | 9 | CAUGCGUGUUAACUAUGCA | 197 | UGCAUAGUUAACACGCAUG | 311 |
| 6608 | 9 | GGUUCCAUCUUUAUACCAA | 198 | UUGGUAUAAAGAUGGAACC | 312 |
| 6668 | 9 | GUCUAAGCUUAGAAGCUUU | 199 | AAAGCUUCUAAGCUUAGAC | 313 |
| 6720 | 9 | GGUUGAACACUUUAACUAA | 200 | UUAGUUAAAGUGUUCAACC | 314 |
| 6797 | 9 | CUGAAUCCUGUAUAACUUA | 201 | UAAGUUAUACAGGAUUCAG | 315 |
| 6799 | 9 | GAAUCCUGUAUAACUUAUU | 202 | AAUAAGUUAUACAGGAUUC | 316 |
| 6803 | 9 | CCUGUAUAACUUAUUUGCA | 203 | UGCAAAUAAGUUAUACAGG | 317 |

| 19mer pos. in NM_058229.3 | sense strand sequence (5'-3') | | antisense strand sequence (5'-3') | |
|---|---|---|---|---|
| 586 | CCAGAAGAUUUAACUACGU | 204 | ACGUAGUUAAAUCUUCUGG | 318 |
| 589 | GAAGAUUUAACUACGUGGU | 205 | ACCACGUAGUUAAAUCUUC | 319 |
| 1068 | CGGCAGAUCCGCAAACGAU | 206 | AUCGUUUGCGGAUCUGCCG | 320 |
| 1071 | CAGAUCCGCAAACGAUUAA | 207 | UUAAUCGUUUGCGGAUCUG | 321 |
| 1073 | GAUCCGCAAACGAUUAAUU | 208 | AAUUAAUCGUUUGCGGAUC | 322 |
| 1075 | UCCGCAAACGAUUAAUUCU | 209 | AGAAUUAAUCGUUUGCGGA | 323 |
| 1076 | CCGCAAACGAUUAAUUCUG | 210 | CAGAAUUAAUCGUUUGCGG | 324 |
| 1077 | CGCAAACGAUUAAUUCUGU | 211 | ACAGAAUUAAUCGUUUGCG | 325 |
| 1079 | CAAACGAUUAAUUCUGUCA | 212 | UGACAGAAUUAAUCGUUUG | 326 |
| 1083 | CGAUUAAUUCUGUCAGACA | 213 | UGUCUGACAGAAUUAAUCG | 327 |
| 1127 | GUAUUUCAAACUUGUCCGA | 214 | UCGGACAAGUUUGAAAUAC | 328 |
| 1142 | CCGAUGUUACCCAAGGAAA | 215 | UUUCCUUGGGUAACAUCGG | 329 |
| 1164 | CAGUAUGGAGAUACCCUUC | 216 | GAAGGGUAUCUCCAUACUG | 330 |
| 1228 | AUCCGUGCACUGCCAAUAA | 217 | UUAUUGGCAGUGCACGGAU | 331 |
| 1254 | AGCUGCUCCGUUUCACUUU | 218 | AAAGUGAAACGGAGCAGCU | 332 |

TABLE 2B-continued

| | | | | |
|---|---|---|---|---|
| 1361 | GGAAUAUGGCAUUUGGACA | 219 | UGUCCAAAUGCCAUAUUCC | 333 |
| 1492 | UGAACUUCUCACUAGAAUU | 220 | AAUUCUAGUGAGAAGUUCA | 334 |
| 1500 | UCACUAGAAUUGGUAUGGA | 221 | UCCAUACCAAUUCUAGUGA | 335 |
| 1563 | GCAAGACUAUAAGGGCAAU | 222 | AUUGCCCUUAUAGUCUUGC | 336 |
| 1566 | AGACUAUAAGGGCAAUAAU | 223 | AUUAUUGCCCUUAUAGUCU | 337 |
| 1635 | UUAUAGUUCCUAGGAAGA | 224 | UCUUCCUAGGGAACUAUAA | 338 |
| 1679 | AGGACGCUUUGUUUACAAU | 225 | AUUGUAAACAAAGCGUCCU | 339 |
| 2487 | UUCUUUAGGUCCAACAUCA | 226 | UGAUGUUGGACCUAAAGAA | 340 |
| 2488 | UCUUUAGGUCCAACAUCAA | 227 | UUGAUGUUGGACCUAAAGA | 341 |
| 2582 | GAGAGGUACCACAAGUUCA | 228 | UGAACUUGUGGUACCUCUC | 342 |
| 2661 | GGCAAAUAUCAGCAGGUAA | 229 | UUACCUGCUGAUAUUUGCC | 343 |
| 2663 | CAAAUAUCAGCAGGUAACU | 230 | AGUUACCUGCUGAUAUUUG | 344 |
| 2790 | UCCUACAACAAUGUACAUA | 231 | UAUGUACAUUGUUGUAGGA | 345 |
| 2999 | GAGACAAGCUAUGAUACAA | 232 | UUGUAUCAUAGCUUGUCUC | 346 |
| 3875 | AAUCAACCUUUAUGGUUCU | 233 | AGAACCAUAAAGGUUGAUU | 347 |
| 4036 | GCCACGUGGUAUCUGUUAA | 234 | UUAACAGAUACCACGUGGC | 348 |
| 4039 | ACGUGGUAUCUGUUAAGUA | 235 | UACUUAACAGAUACCACGU | 349 |
| 4059 | GGCCAGAGCCUCACAUAUA | 236 | UAUAUGUGAGGCUCUGGCC | 350 |
| 4062 | CAGAGCCUCACAUAUAAGU | 237 | ACUUAUAUGUGAGGCUCUG | 351 |
| 4065 | AGCCUCACAUAUAAGUGAA | 238 | UUCACUUAUAUGUGAGGCU | 352 |
| 4117 | AAUAGUCUAUAGAAUUUCU | 239 | AGAAAUUCUAUAGACUAUU | 353 |
| 4444 | CUAGAGUCUCUUGAGAGUA | 240 | UACUCUCAAGAGACUCUAG | 354 |
| 4653 | AAGCAUCCCCAAUGUAUCA | 241 | UGAUACAUUGGGGAUGCUU | 355 |
| 4665 | UGUAUCAGUUGUGAGAUGA | 242 | UCAUCUCACAACUGAUACA | 356 |
| 4787 | ACUAGCACUUGGGCAGUAA | 243 | UUACUGCCCAAGUGCUAGU | 357 |
| 5162 | AACUAAACUCUAUCAUCAU | 244 | AUGAUGAUAGAGUUUAGUU | 358 |
| 5261 | GGCCUAAAAUCCUAUUAGU | 245 | ACUAAUAGGAUUUUAGGCC | 359 |
| 5270 | UCCUAUUAGUGCUUAAACA | 246 | UGUUUAAGCACUAAUAGGA | 360 |
| 5272 | CUAUUAGUGCUUAAACAGA | 247 | UCUGUUUAAGCACUAAUAG | 361 |
| 5338 | UGAUAUAUCUUGGGUCCUU | 248 | AAGGACCCAAGAUAUAUCA | 362 |
| 5737 | GCUGUUAACGUUUCCAUUU | 249 | AAAUGGAAACGUUAACAGC | 363 |
| 5739 | UGUUAACGUUUCCAUUUCA | 250 | UGAAAUGGAAACGUUAACA | 364 |
| 6019 | CAGAGGUACAUUUAAUCCA | 251 | UGGAUUAAAUGUACCUCUG | 365 |
| 6059 | GGACCAGCUAUGAGAUUCA | 252 | UGAAUCUCAUAGCUGGUCC | 366 |
| 6140 | GGGAUUAUUCCAUGAGGCA | 253 | UGCCUCAUGGAAUAAUCCC | 367 |
| 6431 | CUCCAAGCUGUAUUCUAUA | 254 | UAUAGAAUACAGCUUGGAG | 368 |
| 6720 | UGUACCAGACGGUGGCAUA | 255 | UAUGCCACCGUCUGGUACA | 369 |

Evaluation of Selected Atrogin-1 siRNAs in Transfected Mouse C2C12 Myoblasts, Mouse C2C12 Myotubes, Pre-Differentiated Myotubes of Primary Human Skeletal Muscle Cells, and Human SJCRH30 Rhabdomyosarcoma Myoblasts.

From the 62 identified siRNAs targeting mouse atrogin-1 and 52 targeting human atrogin-1, 30 and 20 siRNAs were selected for synthesis and functional analysis, respectively. The activity of these siRNAs was analyzed in transfected mouse C2C12 myoblasts, mouse C2C12 myotubes, pre-differentiated myotubes of primary human skeletal muscle cells, and human SJCRH30 rhabdomyosarcoma myoblasts.

Figure 8:
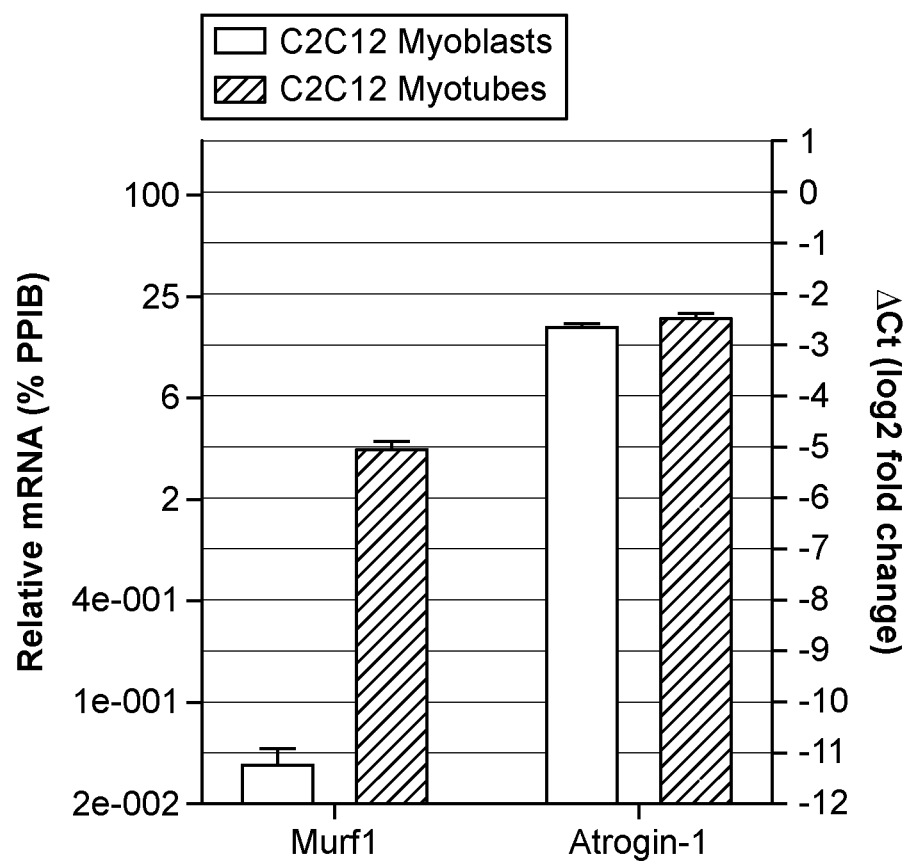
FIG. 8 illustrates relative expression levels of Murf1 and atrogin-1 in C2C12 myoblasts and myotubes C2C12 myoblasts and myotubes were generated as described in Example 4, mRNA levels were determined as described in Example 4.

None of the tested siRNAs targeting mouse atrogin-1 showed significant activity in mouse C2C12 myotubes (at 10 nM), however 3 siRNAs downregulated mouse atrogin-1 mRNA by >75% in C2C12 myoblasts (Table 3). In contrast, siRNAs targeting Murf1, which is exclusively expressed in C2C12 myotubes (FIG. 8), were active in C2C12 myotubes, demonstrating that siRNAs can be transfected into C2C12 myotubes. To determine whether atrogin-1 might be alternatively spliced in C2C12 myoblasts and myotubes, various positions in the atrogin-1 mRNA were probed by RT-qPCR, but yielded similar results. Among the 20 tested siRNAs targeting human atrogin-1 only four yielded >75% KD. For both, mouse and human atrogin-1, active siRNAs localized either within or close to the coding region. One of the siRNAs targeting mouse atrogin-1 (1179) was strongly cross-reactive with human atrogin-1. While this siRNA failed to show significant activity in mouse C2C12 myotubes, it effectively downregulated human atrogin-1 in myotubes of primary human skeletal muscle cells. All efficacious siRNAs downregulated their respective targets with sub-nanomolar potency.

TABLE 3 illustrates activity of selected atrogin-1 siRNAs in transfected mouse C2C12 myoblasts, mouse C2C12 myotubes, pre-differentiated myotubes of primary human skeletal muscle cells, and human SJCRH30 rhabdomyosarcoma myoblasts. For experimental procedures see Example 2.

| mu atrogin-1 NM_026346.3 ID # | muC2C12 myotubes % KD (10 nM) | muC2C12 myoblasts % KD | muC2C12 myoblasts IC50 (nM) | huSkMC myoblasts % KD | huSkMC myotubes IC50 (nM) | huSJCRH30 myotubes % KD | huSJCRH30 myoblasts IC50 (nM) |
|---|---|---|---|---|---|---|---|
| 8 | no KD | no KD | | | | | |
| 499 | 8.5 | 34.4 | | | | | |
| 553 | 9.7 | 10.6 | | | | | |
| 590 | 10.1 | 30.5 | 0.628 | 62.8 | | | |
| 631 | 14.4 | 83.7 | 0.159 | 81.5 | 0.129 | 54.5 | 0.614 |
| 694 | 10.2 | 50.5 | 1.228 | 72.4 | 0.011 | 64.6 | 0.004 |
| 772 | 8.8 | 64.7 | 0.872 | | | | 0.084 |
| 1179 | 7.2 | 76.6 | 0.160 | 88.5 | 0.010 | 86.0 | 0.015 |
| 1256 | 2.7 | 32.5 | | | | | |
| 1260 | no KD | 13.6 | | | | | |
| 1459 | 16.1 | 60.8 | 0.258 | 24.4 | 1.714 | | |
| 1504 | 12.8 | 76.8 | 0.092 | 29.1 | 0.433 | 17.3 | 0.423 |
| 1880 | 14.3 | 58.6 | 0.192 | 66.5 | | | |
| 1884 | 7.7 | 54.6 | 0.135 | 54.8 | | | 0.002 |
| 2572 | 13.7 | 61.5 | 0.928 | 16.0 | 2.664 | 18.4 | 0.027 |
| 3007 | 14.4 | 32.7 | | | | | |
| 3668 | 1.4 | 6.9 | | | | | |
| 3715 | 0.7 | 17.2 | | | | | |
| 3856 | no KD | 5.9 | | | | | |
| 4139 | 2.7 | 10.5 | | | | | |
| 4567 | 12.8 | 56.1 | 1.589 | 0.0 | | 37.2 | 1.028 |
| 4673 | 11.6 | 34.9 | | | | | |
| 4970 | 15.6 | 35.7 | | | | | |
| 5292 | 20.3 | 49.6 | 0.106 | 19.3 | 0.441 | 11.2 | 0.02 |
| 5640 | 13.6 | 40.4 | | | | | |
| 6000 | 19.7 | 21.2 | | | | | |
| 6530 | 3.5 | no KD | | | | | |
| 6608 | 7.4 | no KD | | | | | |
| 6720 | 17.5 | no KD | | | | | |
| 6799 | 15.4 | no KD | | | | | |

| mu atrogin-1 NM_058229.3 ID # | muC2C12 myotubes % KD (10 nM) | muC2C12 myoblasts % KD | muC2C12 myoblasts IC50 (nM) | huSkMC myoblasts % KD | huSkMC myotubes IC50 (nM) | huSJCRH30 myotubes % KD | huSJCRH30 myoblasts IC50 (nM) |
|---|---|---|---|---|---|---|---|
| 586 | | 66.1 | 0.326 | 89.9 | 0.008 | 90.6 | 0.011 |
| 1071 | | 0.0 | no KD | 55.9 | | | |
| 1077 | | 14.4 | 1.774 | 93.9 | 0.009 | 93.9 | 0.016 |
| 1083 | | no KD | no KD | 92.8 | 0.047 | 92.2 | 0.056 |
| 1361 | | | | 80.1 | 0.003 | 81.4 | 0.118 |
| 1566 | | | | 49.9 | | | |
| 1679 | | 15.1 | 1.471 | 55.8 | | | |
| 2582 | | | | 46.2 | | | |
| 2663 | | no KD | no KD | 64.2 | | | |
| 2999 | | no KD | no KD | 55.0 | | | |
| 4036 | | no KD | 0.200 | 64.7 | | | |
| 4059 | | | | 3.2 | | | |
| 4117 | | 24.2 | 1.541 | 68.0 | | | |
| 5162 | | | | 15.7 | | | |
| 5261 | | | | 44.4 | | | |

TABLE 3-continued illustrates activity of selected atrogin-1 siRNAs in transfected mouse C2C12 myoblasts, mouse C2C12 myotubes, pre-differentiated myotubes of primary human skeletal muscle cells, and human SJCRH30 rhabdomyosarcoma myoblasts. For experimental procedures see Example 2.

| | | | |
|---|---|---|---|
| 5272 | | | 47.4 |
| 5737 | no KD | no KD | 60.8 |
| 6019 | | | 44.4 |
| 6059 | no KD | no KD | 57.6 |
| 6431 | no KD | no KD | 65.0 |

Example 5. In Vitro Screen: MuRF-1

Identification of siRNAs Targeting Mouse Murf1 (Trim63) and/or Human/NHP MuRF1 (TRIM63)

A bioinformatics screen was conducted and identified of siRNAs (29mers) that bind specifically to mouse Murf1 sequences that show >3 sequence derivations from mouse Murf2 (Trim55; NM_001039048.2) or Murf3 (Trim54). In addition, 9 siRNAs were identified that target mouse MU and human MuRF1 (TRIM63; NM_032588.3). A screen for siRNAs (19mers) targeting specifically human and NHP MuRF1 (NM_032588.3) yielded 52 candidates (Table 4A-Table 4B3). All selected siRNA target sites do not harbor SNPs (pos. 2-18).

Tables 4A and 4B illustrate identified siRNA candidates for the regulation of mouse and human/NHP MuRF1.

TABLE 4A

| 19mer pos. in NM_001039048.2 | exon # | mouse | mouse x human | sequence of total 23mer target site in NM_001039048.2 | SEQ ID NO: |
|---|---|---|---|---|---|
| 33 | 1 | x | | GAGGAUCCGAGUGGGUUUGGAGA | 370 |
| 82 | 1 | x | | CGAGACAGUCGCAUUUCAAAGCA | 371 |
| 109 | 1 | x | | GGAUUAUAAAUCUAGCCUGAUUC | 372 |
| 130 | 1 | x | | UCCUGAUGGAAACGCUAUGGAGA | 373 |
| 264 | 2 | x | | AGGCUGCGAAUCCCUACUGGACC | 374 |
| 318 | 2 | x | | GUCGUUUCCGUUGCCCCUCGUGC | 375 |
| 328 | 2 | x | | UUGCCCCUCGUGCCGCCAUGAAG | 376 |
| 329 | 2 | x | | UGCCCCUCGUGCCGCCAUGAAGU | 377 |
| 330 | 2 | x | | GCCCCUCGUGCCGCCAUGAAGUG | 378 |
| 337 | 2 | x | | GUGCCGCCAUGAAGUGAUCAUGG | 379 |
| 346 | 2 | x | | UGAAGUGAUCAUGGACCGGCACG | 380 |
| 423 | 3-Feb | x | X | AGCAGGAGUGCUCCAGUCGGCCC | 381 |
| 457 | 3 | x | | CAGCCACCCGAUGUGCAAGGAAC | 382 |
| 460 | 3 | x | | CCACCCGAUGUGCAAGGAACACG | 383 |
| 495 | 3 | x | X | UCAACAUCUACUGUCUCACGUGU | 384 |
| 497 | 3 | x | | AACAUCUACUGUCUCACGUGUGA | 385 |
| 499 | 3 | x | X | CAUCUACUGUCUCACGUGUGAGG | 386 |
| 500 | 3 | x | X | AUCUACUGUCUCACGUGUGAGGU | 387 |
| 502 | 3 | x | X | CUACUGUCUCACGUGUGAGGUGC | 388 |
| 505 | 3 | x | X | CUGUCUCACGUGUGAGGUGCCUA | 389 |
| 507 | 3 | x | | GUCUCACGUGUGAGGUGCCUACU | 390 |
| 511 | 3 | x | | CACGUGUGAGGUGCCUACUUGCU | 391 |
| 538 | 3 | x | | GUGCAAGGUGUUUGGGGCUCACC | 392 |
| 609 | 4 | x | | CUGAGCUGAGUAACUGCAUCUCC | 393 |
| 616 | 4 | x | | GAGUAACUGCAUCUCCAUGCUGG | 394 |
| 646 | 4 | x | | CAACGACCGAGUGCAGACGAUCA | 395 |

TABLE 4A-continued

| | | | | | |
|---|---|---|---|---|---|
| 651 | 4 | x | | ACCGAGUGCAGACGAUCAUCUCU | 396 |
| 787 | 5 | x | X | GCUGCAGCGGAUCACGCAGGAGC | 397 |
| 790 | 5 | x | | GCAGCGGAUCACGCAGGAGCAGG | 398 |
| 911 | 5 | x | | GAGCCCGGAGGGGCUACCUUCCU | 399 |
| 1012 | 7 | x | | UGAGAACAUGGACUACUUUACUC | 400 |
| 1016 | 7 | x | | AACAUGGACUACUUUACUCUGGA | 401 |
| 1018 | 7 | x | | CAUGGACUACUUUACUCUGGACU | 402 |
| 1022 | 7 | x | | GACUACUUUACUCUGGACUUAGA | 403 |
| 1130 | 8 | x | | GAGGAAGAGGGCGUGACCACAGA | 404 |
| 1266 | 9 | x | | UACAAUAGGGAAGUGUGUCUUCU | 405 |
| 1351 | 9 | x | | ACACAAUUGGAAAUGUAUCCAAA | 406 |
| 1364 | 9 | x | | UGUAUCCAAAACGUCACAGGACA | 407 |
| 1366 | 9 | x | | UAUCCAAAACGUCACAGGACACU | 408 |
| 1369 | 9 | x | | CCAAAACGUCACAGGACACUUUU | 409 |
| 1380 | 9 | x | | CAGGACACUUUUCUACGUUGGUG | 410 |
| 1386 | 9 | x | | ACUUUUCUACGUUGGUGCGAAAU | 411 |
| 1387 | 9 | x | | CUUUUCUACGUUGGUGCGAAAUG | 412 |
| 1390 | 9 | x | | UUCUACGUUGGUGCGAAAUGAAA | 413 |
| 1391 | 9 | x | | UCUACGUUGGUGCGAAAUGAAAU | 414 |
| 1393 | 9 | x | | UACGUUGGUGCGAAAUGAAAUAU | 415 |
| 1397 | 9 | x | | UUGGUGCGAAAUGAAAUAUUUUG | 416 |
| 1454 | 9 | x | X | UAUAUGUAUGCCAAUUUGGUGCU | 417 |
| 1458 | 9 | x | X | UGUAUGCCAAUUUGGUGCUUUUU | 418 |
| 1460 | 9 | x | | UAUGCCAAUUUGGUGCUUUUUGU | 419 |
| 1462 | 9 | x | | UGCCAAUUUGGUGCUUUUUGUAC | 420 |
| 1466 | 9 | x | | AAUUUGGUGCUUUUUGUACGAGA | 421 |
| 1478 | 9 | x | | UUUGUACGAGAACUUUUGUAUGA | 422 |
| 1480 | 9 | x | | UGUACGAGAACUUUUGUAUGAUC | 423 |
| 1481 | 9 | x | | GUACGAGAACUUUUGUAUGAUCA | 424 |
| 1483 | 9 | x | | ACGAGAACUUUUGUAUGAUCACG | 425 |
| 1520 | 9 | x | | GACUGGCGAUUGUCACAAAGUGG | 426 |
| 1658 | 9 | x | | GGAUAGGACUGAAUUUGUGUUAU | 427 |
| 1660 | 9 | x | | AUAGGACUGAAUUUGUGUUAUAU | 428 |

| 19mer pos. in NM_032588.3 | human + NHP | sequence of total 23mer target site in NM_032588.3 | |
|---|---|---|---|
| 28 | X | GGAAGCCAACAGGAUCCGACCCG | 429 |
| 75 | X | CCCAGGUCUACUUAGAGCAAAGU | 430 |
| 77 | X | CAGGUCUACUUAGAGCAAAGUUA | 431 |
| 153 | X | AGUCGAGCCUGAUCCAGGAUGGG | 432 |
| 239 | X | CCAGUGGUCAUCUUGCCGUGCCA | 433 |

TABLE 4A-continued

| | | | |
|---|---|---|---|
| 245 | X | GUCAUCUUGCCGUGCCAGCACAA | 434 |
| 248 | X | AUCUUGCCGUGCCAGCACAACCU | 435 |
| 249 | X | UCUUGCCGUGCCAGCACAACCUG | 436 |
| 259 | X | CCAGCACAACCUGUGCCGGAAGU | 437 |
| 339 | X | UGUCCAUGUCUGGAGGCCGUUUC | 438 |
| 367 | X | CCCCACCUGCCGCCACGAGGUGA | 439 |
| 368 | X | CCCACCUGCCGCCACGAGGUGAU | 440 |
| 370 | X | CACCUGCCGCCACGAGGUGAUCA | 441 |
| 371 | X | ACCUGCCGCCACGAGGUGAUCAU | 442 |
| 372 | X | CCUGCCGCCACGAGGUGAUCAUG | 443 |
| 373 | X | CUGCCGCCACGAGGUGAUCAUGG | 444 |
| 374 | X | UGCCGCCACGAGGUGAUCAUGGA | 445 |
| 375 | X | GCCGCCACGAGGUGAUCAUGGAU | 446 |
| 379 | X | CCACGAGGUGAUCAUGGAUCGUC | 447 |
| 380 | X | CACGAGGUGAUCAUGGAUCGUCA | 448 |
| 381 | X | ACGAGGUGAUCAUGGAUCGUCAC | 449 |
| 384 | X | AGGUGAUCAUGGAUCGUCACGGA | 450 |
| 385 | X | GGUGAUCAUGGAUCGUCACGGAG | 451 |
| 386 | X | GUGAUCAUGGAUCGUCACGGAGU | 452 |
| 387 | X | UGAUCAUGGAUCGUCACGGAGUG | 453 |
| 451 | X | CAUCUACAAACAGGAGUGCUCCA | 454 |
| 458 | X | AAACAGGAGUGCUCCAGUCGGCC | 455 |
| 459 | X | AACAGGAGUGCUCCAGUCGGCCG | 456 |
| 461 | X | CAGGAGUGCUCCAGUCGGCCGCU | 457 |
| 491 | X | GGCAGUCACCCCAUGUGCAAGGA | 458 |
| 499 | X | CCCCAUGUGCAAGGAGCACGAAG | 459 |
| 503 | X | AUGUGCAAGGAGCACGAAGAUGA | 460 |
| 531 | X | UCAACAUCUACUGUCUCACGUGU | 461 |
| 535 | X | CAUCUACUGUCUCACGUGUGAGG | 462 |
| 539 | X | UACUGUCUCACGUGUGAGGUGCC | 463 |
| 564 | X | CCUGCUCCAUGUGCAAGGUGUUU | 464 |
| 568 | X | CUCCAUGUGCAAGGUGUUUGGGA | 465 |
| 610 | X | GGCCCCAUUGCAGAGUGUCUUCC | 466 |
| 612 | X | CCCCAUUGCAGAGUGUCUUCCAG | 467 |
| 645 | X | CUGAACUGAAUAACUGUAUCUCC | 468 |
| 647 | X | GAACUGAAUAACUGUAUCUCCAU | 469 |
| 670 | X | GCUGGUGGCGGGGAAUGACCGUG | 470 |
| 671 | X | CUGGUGGCGGGGAAUGACCGUGU | 471 |
| 672 | X | UGGUGGCGGGGAAUGACCGUGUG | 472 |
| 673 | X | GGUGGCGGGGAAUGACCGUGUGC | 473 |

TABLE 4A-continued

| | | | |
|---|---|---|---|
| 812 | X | AAAAGUGAGUUGCUGCAGCGGAU | 474 |
| 860 | X | AGCUUCAUCGAGGCCCUCAUCCA | 475 |
| 968 | X | CUCUUGACUGCCAAGCAACUCAU | 476 |
| 970 | X | CUUGACUGCCAAGCAACUCAUCA | 477 |
| 977 | X | GCCAAGCAACUCAUCAAAAGCAU | 478 |
| 979 | X | CAAGCAACUCAUCAAAAGCAUUG | 479 |
| 980 | X | AAGCAACUCAUCAAAAGCAUUGU | 480 |

TABLE 4B

| 19mer pos. in NM_001039048.2 | exon # | sense strand sequence (5'-3') | SEQ ID NO: | antisense strand sequence (5'-3') | SEQ ID NO: |
|---|---|---|---|---|---|
| 33 | 1 | GGAUCCGAGUGGGUUUGGA | 481 | UCCAAACCCACUCGGAUCC | 592 |
| 82 | 1 | AGACAGUCGCAUUUCAAAG | 482 | CUUUGAAAUGCGACUGUCU | 593 |
| 109 | 1 | AUUAUAAAUCUAGCCUGAU | 483 | AUCAGGCUAGAUUUAUAAU | 594 |
| 130 | 1 | CUGAUGGAAACGCUAUGGA | 484 | UCCAUAGCGUUUCCAUCAG | 595 |
| 264 | 2 | GCUGCGAAUCCCUACUGGA | 485 | UCCAGUAGGGAUUCGCAGC | 596 |
| 318 | 2 | CGUUUCCGUUGCCCCUCGU | 486 | ACGAGGGGCAACGGAAACG | 597 |
| 328 | 2 | GCCCCUCGUGCCGCCAUGA | 487 | UCAUGGCGGCACGAGGGGC | 598 |
| 329 | 2 | CCCCUCGUGCCGCCAUGAA | 488 | UUCAUGGCGGCACGAGGGG | 599 |
| 330 | 2 | CCCUCGUGCCGCCAUGAAG | 489 | CUUCAUGGCGGCACGAGGG | 600 |
| 337 | 2 | GCCGCCAUGAAGUGAUCAU | 490 | AUGAUCACUUCAUGGCGGC | 601 |
| 346 | 2 | AAGUGAUCAUGGACCGGCA | 491 | UGCCGGUCCAUGAUCACUU | 602 |
| 423 | 3-Feb | CAGGAGUGCUCCAGUCGGC | 492 | GCCGACUGGAGCACUCCUG | 603 |
| 457 | 3 | GCCACCCGAUGUGCAAGGA | 493 | UCCUUGCACAUCGGGUGGC | 604 |
| 460 | 3 | ACCCGAUGUGCAAGGAACA | 494 | UGUUCCUUGCACAUCGGGU | 605 |
| 495 | 3 | AACAUCUACUGUCUCACGU | 495 | ACGUGAGACAGUAGAUGUU | 606 |
| 497 | 3 | CAUCUACUGUCUCACGUGU | 496 | ACACGUGAGACAGUAGAUG | 607 |
| 499 | 3 | UCUACUGUCUCACGUGUGA | 497 | UCACGUGAGACAGUAGA | 608 |
| 500 | 3 | CUACUGUCUCACGUGUGAG | 498 | CUCACGUGAGACAGUAG | 609 |
| 502 | 3 | ACUGUCUCACGUGUGAGGU | 499 | ACCUCACGUGAGACAGU | 610 |
| 505 | 3 | GUCUCACGUGUGAGGUGCC | 500 | GGCACCUCACACGUGAGAC | 611 |
| 507 | 3 | CUCACGUGUGAGGUGCCUA | 501 | UAGGCACCUCACACGUGAG | 612 |
| 511 | 3 | CGUGUGAGGUGCCUACUUG | 502 | CAAGUAGGCACCUCACACG | 613 |
| 538 | 3 | GCAAGGUGUUUGGGGCUCA | 503 | UGAGCCCCAAACACCUUGC | 614 |
| 609 | 4 | GAGCUGAGUAACUGCAUCU | 504 | AGAUGCAGUUACUCAGCUC | 615 |
| 616 | 4 | GUAACUGCAUCUCCAUGCU | 505 | AGCAUGGAGAUGCAGUUAC | 616 |
| 646 | 4 | ACGACCGAGUGCAGACGAU | 506 | AUCGUCUGCACUCGGUCGU | 617 |
| 651 | 4 | CGAGUGCAGACGAUCAUCU | 507 | AGAUGAUCGUCUGCACUCG | 618 |
| 787 | 5 | UGCAGCGGAUCACGCAGGA | 508 | UCCUGCGUGAUCCGCUGCA | 619 |
| 790 | 5 | AGCGGAUCACGCAGGAGCA | 509 | UGCUCCUGCGUGAUCCGCU | 620 |

TABLE 4B-continued

| | | | | | |
|---|---|---|---|---|---|
| 911 | 5 | GCCCGGAGGGGCUACCUUC | 510 | GAAGGUAGCCCCUCCGGGC | 621 |
| 1012 | 7 | AGAACAUGGACUACUUUAC | 511 | GUAAAGUAGUCCAUGUUCU | 622 |
| 1016 | 7 | CAUGGACUACUUUACUCUG | 512 | CAGAGUAAAGUAGUCCAUG | 623 |
| 1018 | 7 | UGGACUACUUUACUCUGGA | 513 | UCCAGAGUAAAGUAGUCCA | 624 |
| 1022 | 7 | CUACUUUACUCUGGACUUA | 514 | UAAGUCCAGAGUAAAGUAG | 625 |
| 1130 | 8 | GGAAGAGGGCGUGACCACA | 515 | UGUGGUCACGCCCUCUUCC | 626 |
| 1266 | 9 | CAAUAGGGAAGUGUGUCUU | 516 | AAGACACACUUCCCUAUUG | 627 |
| 1351 | 9 | ACAAUUGGAAAUGUAUCCA | 517 | UGGAUACAUUUCCAAUUGU | 628 |
| 1364 | 9 | UAUCCAAAACGUCACAGGA | 518 | UCCUGUGACGUUUUGGAUA | 629 |
| 1366 | 9 | UCCAAAACGUCACAGGACA | 519 | UGUCCUGUGACGUUUUGGA | 630 |
| 1369 | 9 | AAAACGUCACAGGACACUU | 520 | AAGUGUCCUGUGACGUUUU | 631 |
| 1380 | 9 | GGACACUUUCUACGUUGG | 521 | CCAACGUAGAAAAGUGUCC | 632 |
| 1386 | 9 | UUUUCUACGUUGGUGCGAA | 522 | UUCGCACCAACGUAGAAAA | 633 |
| 1387 | 9 | UUUCUACGUUGGUGCGAAA | 523 | UUUCGCACCAACGUAGAAA | 634 |
| 1390 | 9 | CUACGUUGGUGCGAAAUGA | 524 | UCAUUUCGCACCAACGUAG | 635 |
| 1391 | 9 | UACGUUGGUGCGAAAUGAA | 525 | UUCAUUUCGCACCAACGUA | 636 |
| 1393 | 9 | CGUUGGUGCGAAAUGAAAU | 526 | AUUUCAUUUCGCACCAACG | 637 |
| 1397 | 9 | GGUGCGAAAUGAAAUAUUU | 527 | AAAUAUUUCAUUUCGCACC | 638 |
| 1454 | 9 | UAUGUAUGCCAAUUUGGUG | 528 | CACCAAAUUGGCAUACAUA | 639 |
| 1458 | 9 | UAUGCCAAUUUGGUGCUUU | 529 | AAAGCACCAAAUUGGCAUA | 640 |
| 1460 | 9 | UGCCAAUUUGGUGCUUUUU | 530 | AAAAAGCACCAAAUUGGCA | 641 |
| 1462 | 9 | CCAAUUUGGUGCUUUUUGU | 531 | ACAAAAAGCACCAAAUUGG | 642 |
| 1466 | 9 | UUUGGUGCUUUUUGUACGA | 532 | UCGUACAAAAAGCACCAAA | 643 |
| 1478 | 9 | UGUACGAGAACUUUUGUAU | 533 | AUACAAAAGUUCUCGUACA | 644 |
| 1480 | 9 | UACGAGAACUUUUGUAUGA | 534 | UCAUACAAAAGUUCUCGUA | 645 |
| 1481 | 9 | ACGAGAACUUUUGUAUGAU | 535 | AUCAUACAAAAGUUCUCGU | 646 |
| 1483 | 9 | GAGAACUUUUGUAUGAUCA | 536 | UGAUCAUACAAAAGUUCUC | 647 |
| 1520 | 9 | CUGGCGAUUGUCACAAAGU | 537 | ACUUUGUGACAAUCGCCAG | 648 |
| 1658 | 9 | AUAGGACUGAAUUUGUGUU | 538 | AACACAAAUUCAGUCCUAU | 649 |
| 1660 | 9 | AGGACUGAAUUUGUGUUAU | 539 | AUAACACAAAUUCAGUCCU | 650 |

| 19mer pos. in NM_032588.3 | sense strand sequence (5'-3') | | antisense strand sequence (5'-3') | |
|---|---|---|---|---|
| 28 | AAGCCAACAGGAUCCGACC | 540 | GGUCGGAUCCUGUUGGCUU | 651 |
| 75 | CAGGUCUACUUAGAGCAAA | 541 | UUUGCUCUAAGUAGACCUG | 652 |
| 77 | GGUCUACUUAGAGCAAAGU | 542 | ACUUUGCUCUAAGUAGACC | 653 |
| 153 | UCGAGCCUGAUCCAGGAUG | 543 | CAUCCUGGAUCAGGCUCGA | 654 |
| 239 | AGUGGUCAUCUUGCCGUGC | 544 | GCACGGCAAGAUGACCACU | 655 |
| 245 | CAUCUUGCCGUGCCAGCAC | 545 | GUGCUGGCACGGCAAGAUG | 656 |
| 248 | CUUGCCGUGCCAGCACAAC | 546 | GUUGUGCUGGCACGGCAAG | 657 |
| 249 | UUGCCGUGCCAGCACAACC | 547 | GGUUGUGCUGGCACGGCAA | 658 |

TABLE 4B-continued

| | | | | |
|---|---|---|---|---|
| 259 | AGCACAACCUGUGCCGGAA | 548 | UUCCGGCACAGGUUGUGCU | 659 |
| 339 | UCCAUGUCUGGAGGCCGUU | 549 | AACGGCCUCCAGACAUGGA | 660 |
| 367 | CCACCUGCCGCCACGAGGU | 550 | ACCUCGUGGCGGCAGGUGG | 661 |
| 368 | CACCUGCCGCCACGAGGUG | 551 | CACCUCGUGGCGGCAGGUG | 662 |
| 370 | CCUGCCGCCACGAGGUGAU | 552 | AUCACCUCGUGGCGGCAGG | 663 |
| 371 | CUGCCGCCACGAGGUGAUC | 553 | GAUCACCUCGUGGCGGCAG | 664 |
| 372 | UGCCGCCACGAGGUGAUCA | 554 | UGAUCACCUCGUGGCGGCA | 665 |
| 373 | GCCGCCACGAGGUGAUCAU | 555 | AUGAUCACCUCGUGGCGGC | 666 |
| 374 | CCGCCACGAGGUGAUCAUG | 556 | CAUGAUCACCUCGUGGCGG | 667 |
| 375 | CGCCACGAGGUGAUCAUGG | 557 | CCAUGAUCACCUCGUGGCG | 668 |
| 379 | ACGAGGUGAUCAUGGAUCG | 558 | CGAUCCAUGAUCACCUCGU | 669 |
| 380 | CGAGGUGAUCAUGGAUCGU | 559 | ACGAUCCAUGAUCACCUCG | 670 |
| 381 | GAGGUGAUCAUGGAUCGUC | 560 | DACGAUCCAUGAUCACCUC | 671 |
| 384 | GUGAUCAUGGAUCGUCACG | 561 | CGUGACGAUCCAUGAUCAC | 672 |
| 385 | UGAUCAUGGAUCGUCACGG | 562 | CCGUGACGAUCCAUGAUCA | 673 |
| 386 | GAUCAUGGAUCGUCACGGA | 563 | UCCGUGACGAUCCAUGAUC | 674 |
| 387 | AUCAUGGAUCGUCACGGAG | 564 | CUCCGUGACGAUCCAUGAU | 675 |
| 451 | UCUACAAACAGGAGUGCUC | 565 | GAGCACUCCUGUUUGUAGA | 676 |
| 458 | ACAGGAGUGCUCCAGUCGG | 566 | CCGACUGGAGCACUCCUGU | 677 |
| 459 | CAGGAGUGCUCCAGUCGGC | 567 | GCCGACUGGAGCACUCCUG | 678 |
| 461 | GGAGUGCUCCAGUCGGCCG | 568 | CGGCCGACUGGAGCACUCC | 679 |
| 491 | CAGUCACCCCAUGUGCAAG | 569 | CUUGCACAUGGGGUGACUG | 680 |
| 499 | CCAUGUGCAAGGAGCACGA | 570 | UCGUGCUCCUUGCACAUGG | 681 |
| 503 | GUGCAAGGAGCACGAAGAU | 571 | AUCUUCGUGCUCCUUGCAC | 682 |
| 531 | AACAUCUACUGUCUCACGU | 572 | ACGUGAGACAGUAGAUGUU | 683 |
| 535 | UCUACUGUCUCACGUGUGA | 573 | UCACACGUGAGACAGUAGA | 684 |
| 539 | CUGUCUCACGUGUGAGGUG | 574 | CACCUCACACGUGAGACAG | 685 |
| 564 | UGCUCCAUGUGCAAGGUGU | 575 | ACACCUUGCACAUGGAGCA | 686 |
| 568 | CCAUGUGCAAGGUGUUUGG | 576 | CCAAACACCUUGCACAUGG | 687 |
| 610 | CCCCAUUGCAGAGUGUCUU | 577 | AAGACACUCUGCAAUGGGG | 688 |
| 612 | CCAUUGCAGAGUGUCUUCC | 578 | GGAAGACACUCUGCAAUGG | 689 |
| 645 | GAACUGAAUAACUGUAUCU | 579 | AGAUACAGUUAUUCAGUUC | 690 |
| 647 | ACUGAAUAACUGUAUCUCC | 580 | GGAGAUACAGUUAUUCAGU | 691 |
| 670 | UGGUGGCGGGGAAUGACCG | 581 | CGGUCAUUCCCCGCCACCA | 692 |
| 671 | GGUGGCGGGGAAUGACCGU | 582 | ACGGUCAUUCCCCGCCACC | 693 |
| 672 | GUGGCGGGGAAUGACCGUG | 583 | CACGGUCAUUCCCCGCCAC | 694 |
| 673 | UGGCGGGGAAUGACCGUGU | 584 | ACACGGUCAUUCCCCGCCA | 695 |
| 812 | AAGUGAGUUGCUGCAGCGG | 585 | CCGCUGCAGCAACUCACUU | 696 |
| 860 | CUUCAUCGAGGCCCUCAUC | 586 | GAUGAGGGCCUCGAUGAAG | 697 |
| 968 | CUUGACUGCCAAGCAACUC | 587 | GAGUUGCUUGGCAGUCAAG | 698 |

TABLE 4B-continued

| | | | | |
|---|---|---|---|---|
| 970 | UGACUGCCAAGCAACUCAU | 588 | AUGAGUUGCUUGGCAGUCA | 699 |
| 977 | CAAGCAACUCAUCAAAAGC | 589 | GCUUUUGAUGAGUUGCUUG | 700 |
| 979 | AGCAACUCAUCAAAAGCAU | 590 | AUGCUUUUGAUGAGUUGCU | 701 |
| 980 | GCAACUCAUCAAAAGCAUU | 591 | AAUGCUUUUGAUGAGUUGC | 702 |

Activity of Selected MuRF1 siRNAs in Transfected Mouse C2C12 Myotubes and Pre-Differentiated Myotubes of Primary Human Skeletal Muscle Cells From the 60 identified siRNAs targeting mouse Murf1 and 25 siRNAs targeting human MuRF1, 35 and 25 siRNAs were selected for synthesis, respectively. The activity of these siRNAs was analyzed in transfected mouse C2C12 myotubes and pre-differentiated primary human skeletal muscle cells (Table 5). Among the siRNAs targeting mouse MurF1, 14 displayed >70% knock down of Murf1, but <20% knock down of Murf2 and Murf3 in C2C12 myotubes. At least 6 of these 14 siRNAs were cross reactive with human MuRF1. Among the tested siRNAs targeting human MuRF1, 8 displayed >70% knock down of MuRF1, but <20% knock down of MuRF2 and MuRF3 in pre-differentiated myotubes of primary human skeletal muscle cells. Only 1 of these 8 siRNAs showed significant cross-reactivity with mouse Muf1. All efficacious siRNAs downregulated their respective targets with subnanomolar potency.

TABLE 5 illustrates activity of selected MuRF1 siRNAs in transfected mouse C2C12 myotubes and pre-differentiated myotubes of primary human skeletal muscle cells. Cells were grown and transfected and RNAs isolated and analyzed as described in Example 5.

| 19 mer position in NM_026346.3 | muC2C 12 myotubes mMuRF1 KD (%) | muC2C 12 myotubes mMuRF2 KD (%) | muC2C 12 myotubes mMuRF3 KD (%) | muC2C 12 myotubes mMuRF1 IC50 (nM) | huSkMC myotubes hMuRF1 KD (%) | huSkMC myotubes hMuRF2 KD (%) | huSkMC myotubes hMuRF3 KD (%) | huSkMC myotubes hMuRfl IC50 (nM) |
|---|---|---|---|---|---|---|---|---|
| 33 | 24.3 | 0.0 | 5.5 | | | | | |
| 109 | 73.4 | 0.0 | 6.0 | 0.073 | | | | |
| 130 | 45.8 | 10.4 | 16.0 | | | | | |
| 264 | 79.6 | 3.7 | 22.0 | 0.172 | 80.9 | 5.6 | 0.0 | 0.018 |
| 337 | 42.9 | 10.4 | 7.9 | | | | | |
| 423 | 65.9 | 15.5 | 8.9 | 0.288 | 64.5 | | | |
| 460 | 56.4 | 16.6 | 17.8 | | | | | |
| 495 | 70.7 | 9.6 | 31.9 | 0.495 | 76.1 | 49.0 | 4.4 | 0.105 |
| 499 | 73.8 | 12.7 | 7.0 | 0.116 | 76.0 | 11.3 | 24.0 | 0.150 |
| 500 | 69.0 | 20.7 | 11.5 | 0.167 | 92.5 | 23.3 | 50.0 | |
| 538 | 48.6 | 10.7 | 16.5 | | | | | |
| 651 | 78.3 | 5.8 | 0.0 | 0.082 | 53.9 | 0.0 | 4.2 | 0.150 |
| 787 | 26.0 | 13.5 | 7.9 | | | | | |
| 911 | 43.5 | 0.0 | 10.0 | | | | | |
| 1012 | 74.1 | 0.0 | 27.5 | 0.014 | 83.1 | 6.6 | 0.0 | 0.019 |
| 1018 | 72.6 | 12.3 | 6.3 | 0.121 | | | | |
| 1022 | 70.9 | 26.5 | 22.9 | 0.042 | | | | |
| 1130 | 60.6 | 22.0 | 16.3 | 0.206 | | | | |
| 1266 | 73.5 | 27.1 | 19.6 | 0.007 | 83.8 | 7.5 | 42.3 | 0.184 |
| 1351 | 77.5 | 44.2 | 0.0 | 0.008 | 79.0 | 6.6 | 52.4 | 0.509 |
| 1364 | 71.6 | 0.8 | 2.8 | 0.012 | 27.9 | | | |
| 1387 | 79.1 | 9.5 | 14.9 | 0.007 | 66.7 | 15.0 | 13.3 | 0.059 |
| 1390 | 73.6 | 33.1 | 10.0 | 0.012 | | | | |
| 1393 | 75.2 | 28.4 | 4.5 | 0.044 | 73.3 | 34.0 | 12.1 | 0.141 |
| 1397 | 78.8 | 5.2 | 16.4 | 0.008 | 74.9 | 23.0 | 12.3 | 0.009 |
| 1454 | 73.8 | 6.5 | 8.7 | 0.019 | 68.2 | 7.0 | 1.7 | 0.004 |
| 1458 | 73.1 | 0.0 | 6.4 | 0.016 | 85.8 | 13.7 | 42.7 | 0.008 |
| 1462 | 69.9 | 17.2 | 19.8 | 0.017 | 63.8 | 3.8 | 0.0 | 0.005 |
| 1466 | 75.0 | 17.8 | 19.1 | 0.012 | 68.4 | 6.2 | 0.0 | 0.045 |
| 1480 | 71.1 | 11.9 | 6.9 | 0.022 | | | | |
| 1481 | 65.8 | 12.2 | 0.4 | 0.266 | | | | |
| 1483 | 74.6 | 1.1 | 4.0 | 0.030 | | | | |
| 1520 | 72.8 | 1.6 | 8.8 | 0.012 | 30.6 | | | |
| 1658 | 73.7 | 21.6 | 9.8 | 0.028 | 26.0 | 15.6 | 6.6 | 0.005 |
| 1660 | 76.2 | 0.0 | 0.0 | 0.017 | | | | |
| 75 | 25.8 | | | | 69.6 | 0.0 | 0.0 | |
| 77 | 14.5 | 17.4 | 13.8 | | 83.7 | 7.1 | 13.9 | 0.152 |
| 245 | 60.3 | | | 0.905 | 70.9 | 33.1 | 14.3 | |
| 259 | 49.7 | | | 2.759 | 75.1 | 84.5 | 71.1 | 0.053 |
| 339 | | | | | 52.7 | 1.2 | 14.3 | |
| 367 | | | | | 0.0 | 0.0 | 0.0 | |
| 370 | 8.8 | | | 0.033 | 21.2 | 25.0 | 4.1 | |
| 373 | | | | | 64.6 | 21.8 | 14.1 | |
| 374 | 33.7 | 7.0 | 14.8 | 0.659 | 89.7 | 10.0 | 19.7 | 0.110 |
| 380 | 19.5 | | | 0.013 | 70.6 | 8.5 | 0.4 | |
| 386 | | | | | 69.9 | 19.9 | 16.4 | 0.002 |

TABLE 5-continued illustrates activity of selected MuRF1 siRNAs in transfected mouse C2C12 myotubes and pre-differentiated myotubes of primary human skeletal muscle cells. Cells were grown and transfected and RNAs isolated and analyzed as described in Example 5.

| 19 mer position in NM_026346.3 | muC2C 12 myotubes mMuRF1 KD (%) | muC2C 12 myotubes mMuRF2 KD (%) | muC2C 12 myotubes mMuRF3 KD (%) | muC2C 12 myotubes mMuRF1 IC50 (nM) | huSkMC myotubes hMuRF1 KD (%) | huSkMC myotubes hMuRF2 KD (%) | huSkMC myotubes hMuRF3 KD (%) | huSkMC myotubes hMuRfl IC50 (nM) |
|---|---|---|---|---|---|---|---|---|
| 459 | 66.7 | | | 0.148 | 78.1 | 25.2 | 7.1 | |
| 491 | | | | | 57.1 | 16.3 | 1.3 | |
| 503 | 56.4 | | | 0.101 | 52.0 | 89.9 | 86.1 | |
| 535 | 70.8 | 32.4 | 13.4 | 0.074 | 82.1 | 24.0 | 9.5 | 0.008 |
| 564 | 8.2 | | | 0.002 | 72.4 | 26.1 | 0.6 | |
| 610 | 6.5 | 18.7 | 17.0 | | 89.6 | 9.4 | 15.2 | 0.107 |
| 645 | 46.2 | 13.9 | 2.3 | 3.475 | 85.2 | 0.0 | 0.0 | 0.007 |
| 647 | 77.5 | 20.1 | 0.0 | 0.211 | 94.6 | 4.4 | 19.4 | 0.006 |
| 673 | | | | | 35.5 | 13.4 | 4.5 | |
| 860 | | | | | 77.1 | 22.5 | 0.0 | |
| 970 | 8.8 | 29.3 | 10.6 | | 84.9 | 12.9 | 7.3 | 0.056 |
| 977 | 19.9 | 5.9 | 0.0 | 2.838 | 93.6 | 51.0 | 12.6 | 0.117 |
| 979 | | | | | 87.4 | 29.6 | 17.4 | 0.058 |
| 980 | 0.0 | 36.0 | 2.1 | | 93.6 | 4.7 | 20.5 | 0.118 |

Example 6, 2017-PK-279-WT-CD71 vs IgG2A Isotype, HPRT vs MSTN siRNA Design and Synthesis MSTN: A 21mer duplex with 19 bases of complementarity and 3' dinucleotide overhangs was designed against mouse MSTN. The sequence (5' to 3') of the guide/antisense strand was UUAUUAUUUGUUCUUUGCCUU (SEQ ID NO: 14226). Base, sugar and phosphate modifications were used to optimize the potency of the duplex and reduce immunogenicity. All siRNA single strands were fully assembled on solid phase using standard phosphoramidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphorothioate-inverted abasic-phosphorothioate linker.

HPRT: A 21mer duplex with 19 bases of complementarity and 3' dinucleotide overhangs was designed against mouse MSTN. The sequence (5' to 3') of the guide/antisense strand was UUAAAAUCUACAGUCAUAGUU (SEQ ID NO: 14227). Base, sugar and phosphate modifications were used to optimize the potency of the duplex and reduce immunogenicity. All siRNA single strands were fully assembled on solid phase using standard phosphoramidite chemistry and purified over HPLC. Purified single strands were duplexed to get the double stranded siRNA. The passenger strand contained two conjugation handles, a C6-NH$_2$ at the 3' end and a C6-SH at the 5' end. Both conjugation handles were connected to siRNA passenger strand via phosphorothioate-inverted abasic-phosphorothioate linker.

Negative control siRNA sequence (scramble): A published (Burke et al. (2014) Pharm. Res., 31(12):3445-60) 21mer duplex with 19 bases of complementarity and 3' dinucleotide overhangs was used. The sequence (5' to 3') of the guide/antisense strand was UAUCGACGUGUCCAGCUAGUU (SEQ ID NO: 14228). The same base, sugar and phosphate modifications that were used for the active MSTN siRNA duplex were used in the negative control siRNA. All siRNA single strands were fully assembled on solid phase using standard phosphoramidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via a phosphodiester-inverted abasic-phosphodiester linker.

ASC synthesis and Characterization

The CD71 mAb-siRNA DAR1 conjugates were made, purified and characterized as described in Example 3. All conjugates were made through cysteine conjugation, a SMCC linker and the PEG was attached at the thiol using architecture 1 for MSTN and the scrambled siRNA and architecture 2 for the HPRT siRNA, see Example 3. Conjugates were characterized chromatographically as described in Table 6.

TABLE 6

HPLC retention time (RT) in minutes

| Groups | Conjugate | RT, SAX Method-2 | RT, SEC Method-1 |
|---|---|---|---|
| 1-4 | TfR-mAb-HPRT-PEG5k; DAR1 | 8.8 | 7.1 |
| 5-8 | IgG2a-mAb-HPRT-PEG5k; DAR1 | 8.9 | 7.7 |
| 9-12 | TfR-mAb-MSTN-PEG5k; DAR1 | 8.7 | 7.2 |
| 13-16 | IgG2a-mAb-MSTN-PEG5k; DAR1 | 8.9 | 7.7 |
| 17-20 | TfR-mAb-scrambled-PEG5k; DAR1 | 8.4 | 7.2 |

In Vivo Study Design

The conjugates were assessed for their ability to mediate mRNA downregulation of myostatin (MSTN) in skeletal muscle in vivo in wild type CD-1 mice. Mice were dosed via intravenous (iv) injection with PBS vehicle control and the indicated ASCs and doses, see FIG. 9A. After 96 hours, gastrocnemius (gastroc) muscle tissues were harvested and snap-frozen in liquid nitrogen, mRNA knockdown in target tissue was determined using a comparative qPCR assay. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct).

Results

Figure 9B:
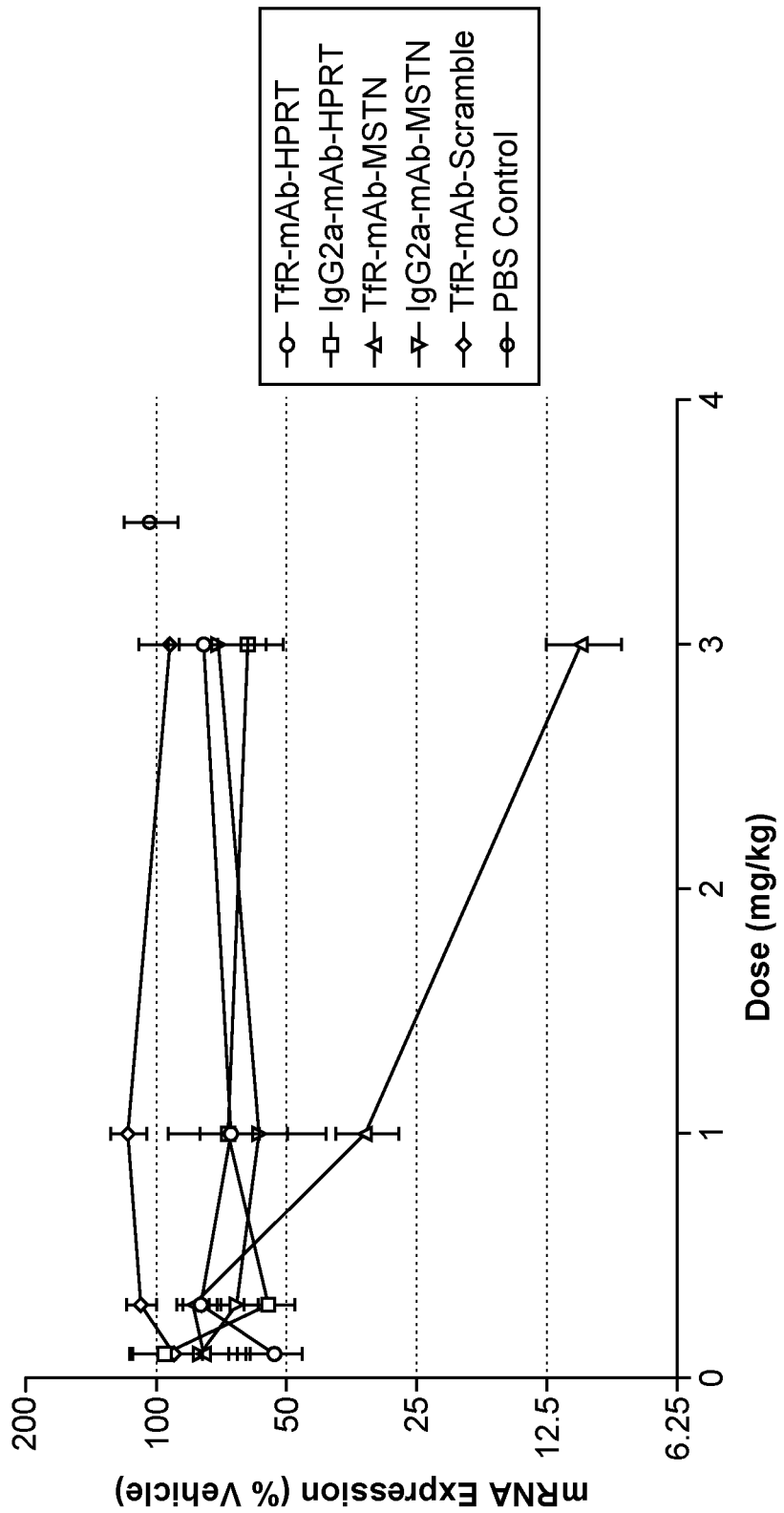
FIG. 9B shows siRNA-mediated mRNA knockdown of mouse MSTN in mouse gastrocnemius (gastroc) muscle.

For gastrocnemius muscle harvested 96 hours post-dose, maximum MSTN mRNA downregulation of greater than 90% was observed after a single intravenous dose of 3 mg/kg of siRNA, see FIG. 9B. In addition, a dose response was also observed (dose range: 0.3 to 3.0 mg/kg siRNA) and no significant mRNA downregulation was observed for the control groups.

Conclusions

In gastrocnemius muscle, it was demonstrated that an ASC is able to downregulate a muscle specific gene. The ASC was made with an anti-transferrin antibody conjugated to an siRNA designed to down regulate MSTN mRNA. Mouse gastroc muscle expresses the transferrin receptor and the conjugate has a mouse specific anti-transferrin antibody to target the siRNA, resulting in accumulation of the conjugates in gastroc muscle. Receptor mediate uptake resulted in siRNA mediated knockdown of the MSTN mRNA.

Example 7, 2017-PK-289-WT-CD71 mAb MSTN Time Course for Phenotype siRNA Design and Synthesis MSTN: A 21mer duplex with 19 bases of complementarity and 3' dinucleotide overhangs was designed against mouse MSTN. The sequence (5' to 3") of the guide/antisense strand was UUAUUAUUUGUUCUUUGCCUU (SEQ ID NO: 14226). Base, sugar and phosphate modifications were used to optimize the potency of the duplex and reduce immunogenicity. All siRNA single strands were fully assembled on solid phase using standard phosphoramidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphorothioate-inverted abasic-phosphorothioate linker. Because the free thiol was not being used for conjugation, it was end capped with N-ethylmaleimide.

Negative control siRNA sequence (scramble): A published (Burke et al. (2014) Pharm. Res., 31(12):3445-60) 21mer duplex with 19 bases of complementarity and 3' dinucleotide overhangs was used. The sequence (5' to 3') of the guide/antisense strand was UAUCGACGUGUCCAGC-UAGUU (SEQ ID NO: 14228). The same base, sugar and phosphate modifications that were used for the active MSTN siRNA duplex were used in the negative control siRNA. All siRNA single strands were fully assembled on solid phase using standard phosphoramidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphorothioate-inverted abasic-phosphorothioate linker. Because the free thiol was not being used for conjugation, it was end capped with N-ethylmaleimide.

ASC Synthesis and Characterization

The CD71 mAb-siRNA DAR1 conjugates were made and characterized as described in Example 3. All conjugates were made through cysteine conjugation, a SMCC linker and the thiol was end capped with NEM using architecture 1. Conjugates were characterized chromatographically as described in Table 7.

TABLE 7

| Groups | Conjugate | HPLC retention time (RT) in minutes | |
|---|---|---|---|
| | | RT, SAX Method-2 | RT, SEC Method-1 |
| 1-4, 13 & 14 | TfR-mAb-MSTN-NEM; DAR1 | 8.7 | 10.0 |
| 5-8 | TfR-mAb-scrambled-NEM; DAR1 | 8.9 | 10.0 |

In Vivo Study Design

The conjugates were assessed for their ability to mediate mRNA downregulation of myostatin (MSTN) in skeletal muscle n vivo in wild type CD-1 mice. Mice were dosed via intravenous (iv) injection with PBS vehicle control and the indicated ASCs at the doses indicated in FIG. 10A. Plasma and tissue samples were also taken as indicated in FIG. 10A. Muscle tissues were harvested and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct). Quantitation of tissue siRNA concentrations was determined using a stem-loop qPCR assay as described in the methods section. The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

Plasma myostatin levels were determined using an ELISA, see Example 2 for full experimental details. Changes in leg muscle area were determined: The leg-to-be-measured were shaved and a line was drawn using indelible ink to mark region of measurement. Mice were restrained in a cone restraint and the right leg was held by hand. Digital calipers were used to take one measurement on the sagittal plane and another on the coronal plane. The procedure was repeated twice per week.

Results

Figure 10B:
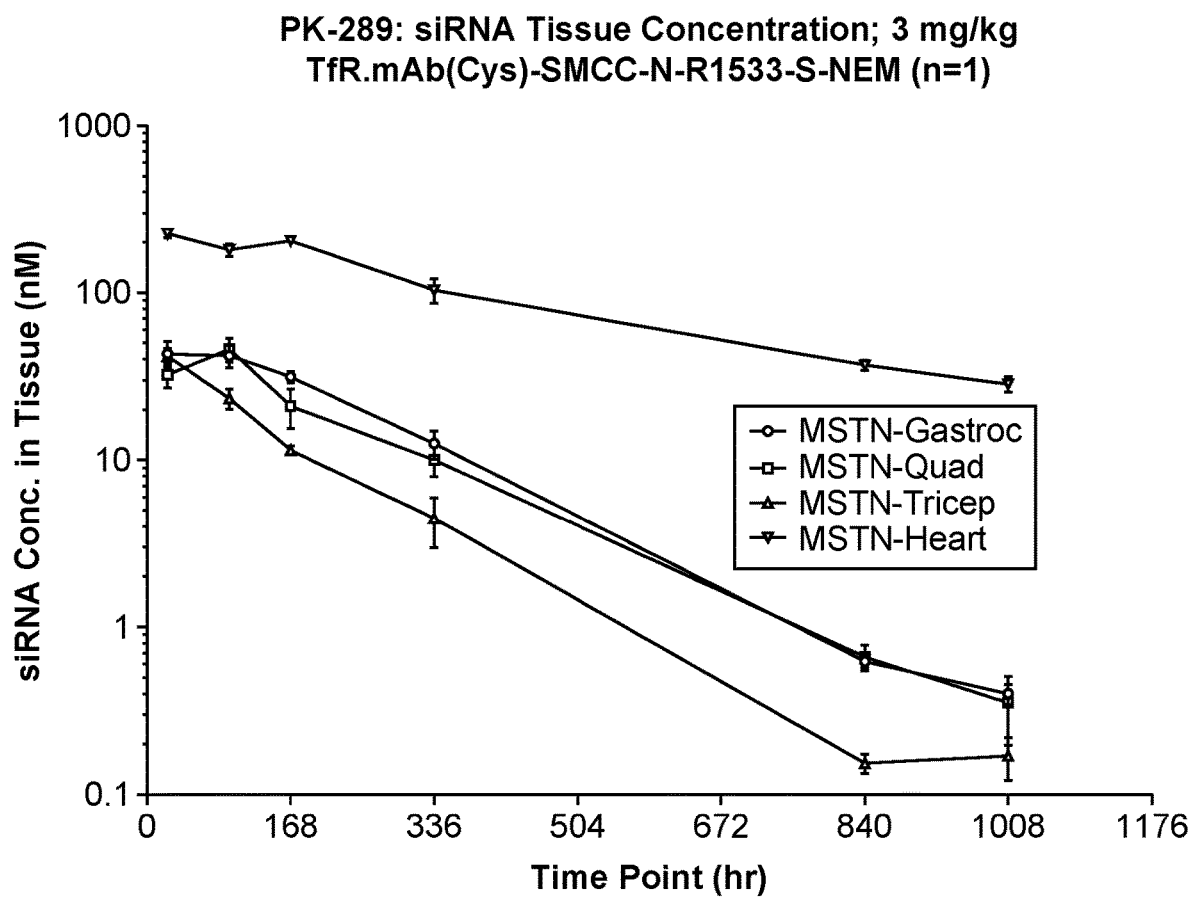
FIG. 10B shows tissue concentration-time profiles out to 1008 h post-dose of an exemplary molecule of Formula (I).
Figure 10C:
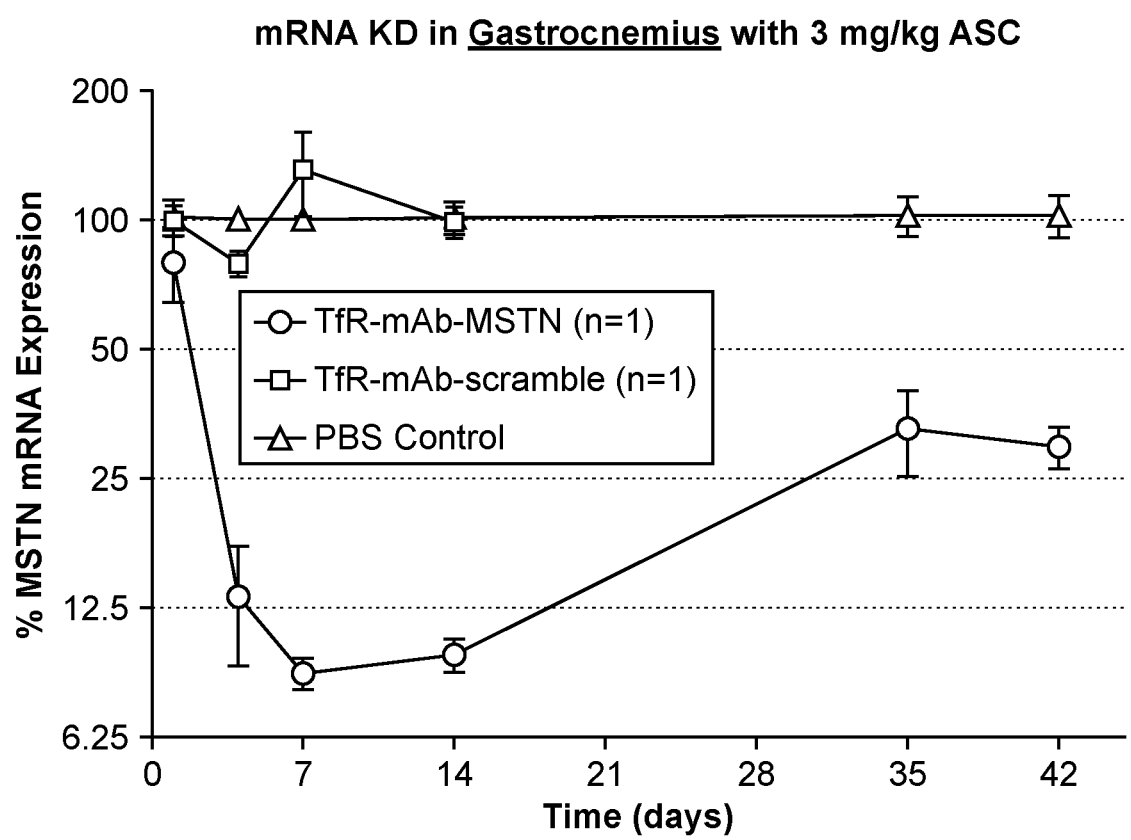
FIG. 10C shows siRNA-mediated mRNA knockdown of mouse MSTN in mouse gastrocnemius (gastroc) muscle.
Figure 10D:
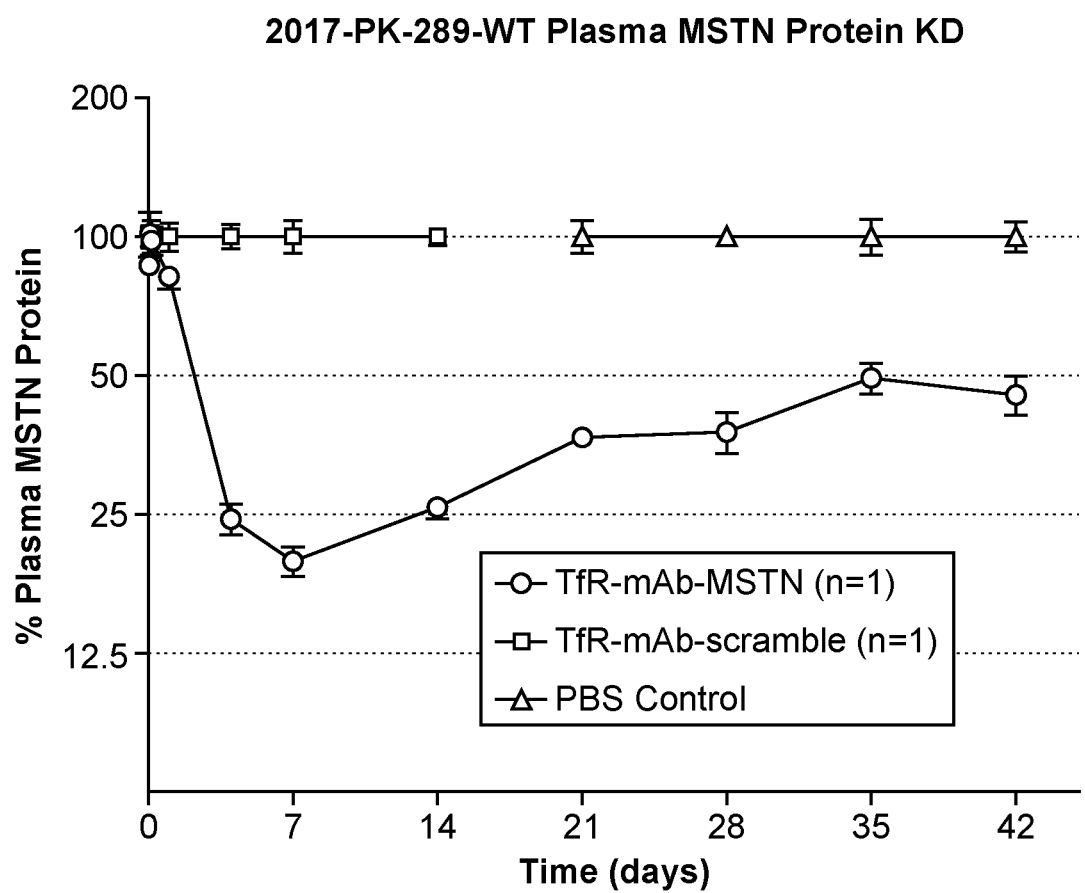
FIG. 10D shows plasma MSTN protein reduction after siRNA-mediated mRNA knockdown of mouse MSTN in mouse gastrocnemius (gastroc) muscle.
Figure 10E:
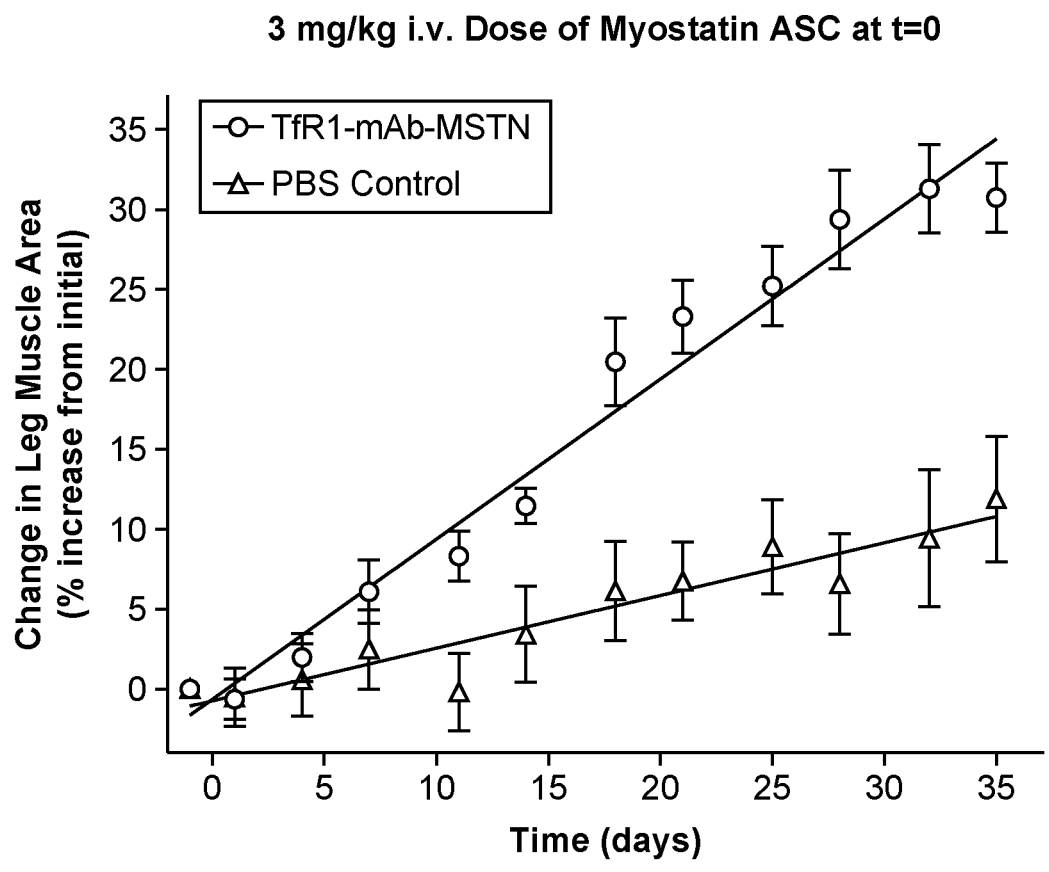
FIG. 10E shows changes in muscle size after siRNA-mediated mRNA knockdown of mouse MSTN in mouse gastrocnemius (gastroc) muscle.
Figure 10F:
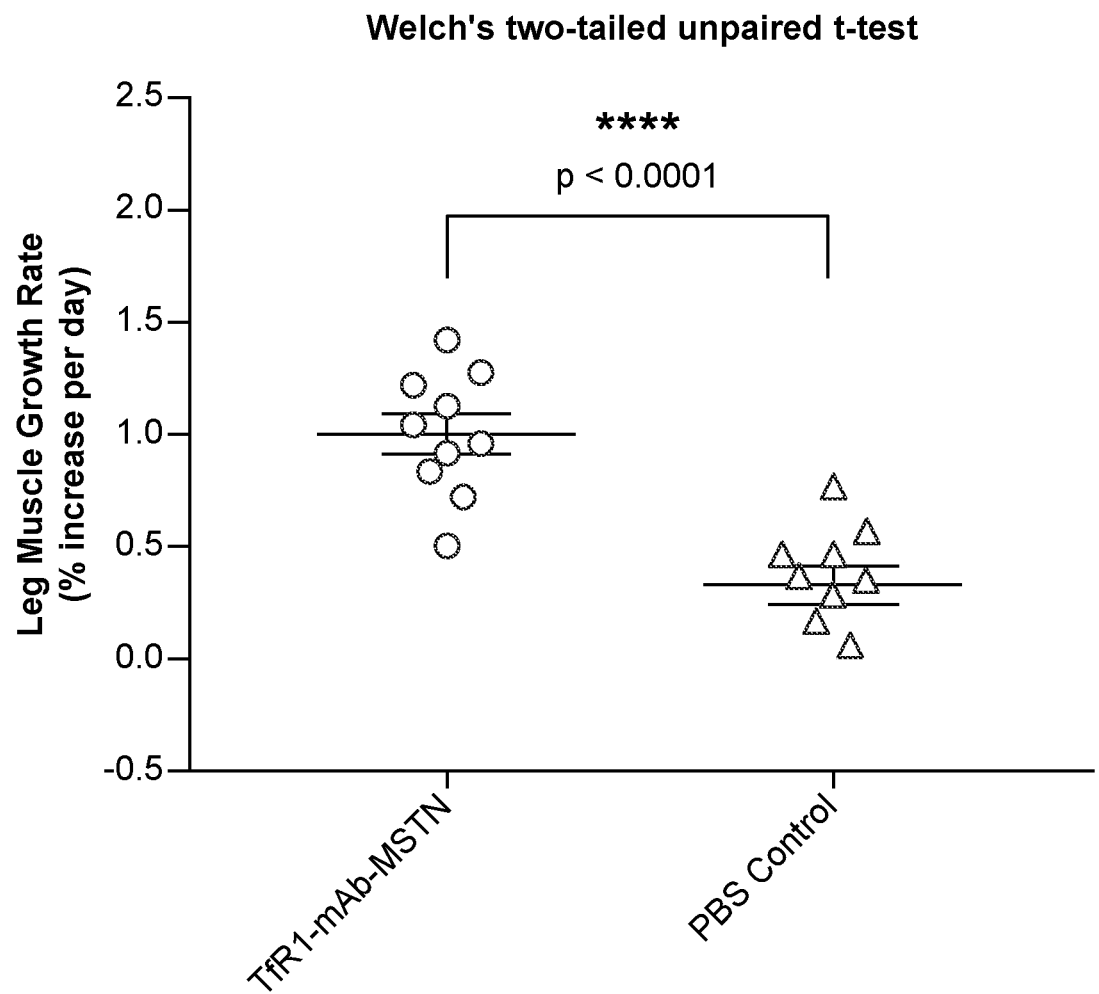
FIG. 10F shows Welch's two-tailed unpaired t-test of FIG. 10E.

Quantifiable levels of siRNA accumulated in muscle tissue after a single intravenous dose of the antibody siRNA conjugates, see FIG. 10B. Robust MSTN mRNA downregulation was observed in gastrocnemius muscle, which resulted in a reduction in the levels of MSTN protein in the plasma, after a single intravenous dose of 3 mg/kg of siRNA, see FIG. 10C and FIG. 10D. Maximum mRNA downregulation of ~90% was observed between 7-14 days post-dose. At 6 weeks post-dose gastroc muscle had approximately 75% mRNA downregulation, which corresponded to about a 50% reduction in plasma protein levels relative to the PBS or anti-transferrin antibody conjugated scrambled controls. Downregulation of MSTN resulted in statistically significant increases in muscle size, see FIG. 10E and FIG. 10F.

Conclusions

In this example it was demonstrated that accumulation of siRNA in various muscle tissues after a single dose of an anti-transferrin antibody targeted siRNA conjugate. In Gastroc muscle, significant and long-lasting siRNA mediated MSTN mRNA downregulation was observed. Mouse gastroc muscle expresses transferrin receptor and the conjugate has a mouse specific anti-transferrin antibody to target the siRNA, resulting in accumulation of the conjugates in gastroc muscle. Receptor mediate uptake resulted in siRNA mediated knockdown of the MSTN gene.

Example 8: 2017-PK-299-WT-MSTN Zalu vs Ti, mAb vs Fab, DAR1 vs DAR2 siRNA Design and Synthesis MSTN: A 21mer duplex with 19 bases of complementarity and 3' dinucleotide overhangs was designed against mouse MSTN. The sequence (5' to 3') of the guide/antisense strand was UUAUUAUUUGUUCUUUGCCUU (SEQ ID NO: 14226). Base, sugar and phosphate modifications were used to optimize the potency of the duplex and reduce immunogenicity. All siRNA single strands were fully assembled on solid phase using standard phospharamidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphorothioate-inverted abasic-phosphorothioate linker. Because the free thiol was not being used for conjugation, it was end capped with N-ethylmaleimide.

MSTN*: MSTN: A 21mer duplex with 19 bases of complementarity and 3' dinucleotide overhangs was designed against mouse MSTN. The sequence (5' to 3') of the guide/antisense strand was UUAUUALUUUGUUC-UUUGCCUU (SEQ ID NO: 14226). Base, sugar and phosphate modifications were used to optimize the potency of the duplex and reduce immunogenicity. All siRNA single strands were fully assembled on solid phase using standard phospharamidite chemistry and purified over HPLC. Purified single strands were duplexed to get the double stranded siRNA. The passenger strand contained one conjugation handle, a C6-NH$_2$ at the 5' end, which was connected to siRNA passenger strand via phosphorothioate-inverted abasic-phosphorothioate linker.

ASC Synthesis and Characterization

The CD71 mAb-siRNA DAR1 and DAR2 conjugates were made and characterized as described in Example 3. Groups 1-8 and 17-20 were made through cysteine conjugation and a BisMal linker using architecture 3. Groups 9-16 were made through cysteine conjugation, a SMCC linker and the free thiol was end capped with NEM PEG using architecture 1. Conjugates were characterized chromatographically as described in Table 8.

TABLE 8

HPLC retention time (RT) in minutes

| Groups | Conjugate | RT, SAX Method-2 | RT, SEC Method-1 |
|---|---|---|---|
| 1-4 | TfR-Fab-MSTN; DAR1 | 8.7 | 10.0 |
| 5-8 | EGFR-Fab-MSTN; DAR1 | 8.9 | 10.0 |
| 9-12 | TfR-mAb-MSTN-NEM; DAR1 | 9.5 | 7.9 |
| 13-16 | TfR-mAb-MSTN-nEM; DAR2 | 10.3 | 8.1 |
| 17-18 | EGFR-mAb-MSTN; DAR1 | 9.3 | NT |
| 19-20 | EGFR-mAb-MSTN; DAR2 | 10.2 | NT |

In Vivo Study Design

The conjugates were assessed for their ability to mediate mRNA downregulation of myostatin (MSTN) in skeletal muscle in vivo in wild type CD-1 mice. Mice were dosed via intravenous (iv) injection with PBS vehicle control and the indicated ASCs at the doses indicated in FIG. 11A. Plasma and tissue samples were also taken as indicated in FIG. 11A. Gastrocnemius (gastroc) muscle tissues were harvested and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct). Quantitation of tissue siRNA concentrations was determined using a stem-loop qPCR assay as described in the methods section. The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

Results

Figure 11B:
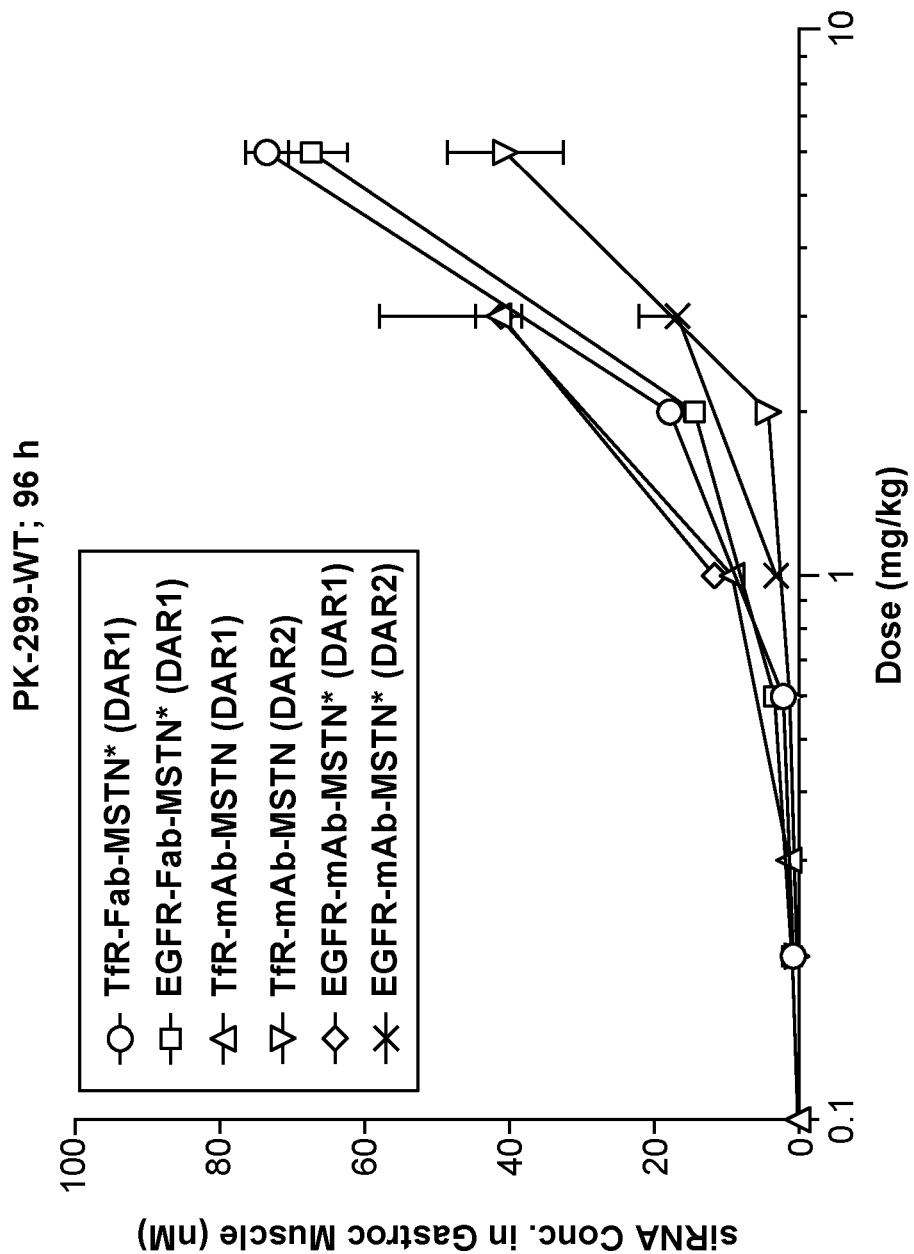
FIG. 11B shows tissue accumulation of siRNA in mouse gastrocnemius (gastroc) muscle after a single i.v. administration of an exemplary molecule of Formula (I) at the doses indicated.
Figure 11C:
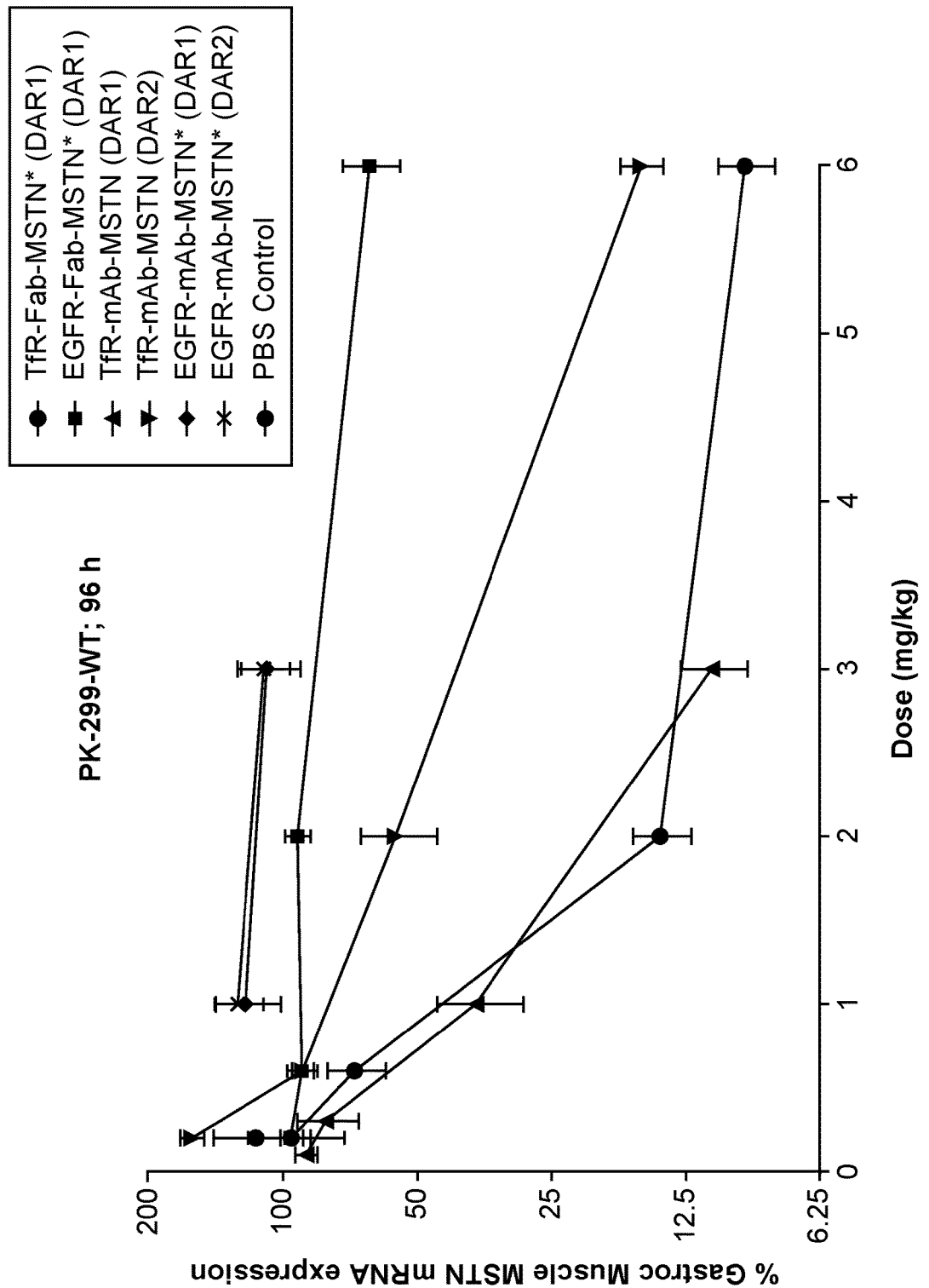
FIG. 11C shows siRNA-mediated mRNA knockdown of mouse MSTN in mouse gastrocnemius (gastroc) muscle.

Quantifiable levels of siRNA accumulated in muscle tissue after a single intravenous dose of the antibody and Fab siRNA conjugates, see FIG. 11B. Robust MSTN mRNA downregulation was observed in gastroc muscle, when the anti-transferrin antibody conjugate was administered as a DAR1 or DAR2, or as a Fab DAR1 conjugate, see FIG. 11C.

Conclusions

In this example it was demonstrated that accumulation of siRNA in gastroc muscle tissue after a single dose of an anti-transferrin antibody and Fab targeted siRNA conjugates. In Gastroc muscle. siRNA mediated MSTN mRNA downregulation with DAR1 and DAR2 antibody conjugates were observed, in addition to the DAR1 Fab conjugate. Mouse gastroc muscle expresses transferrin receptor and the conjugate has a mouse specific anti-transferrin antibody or Fab to target the siRNA, resulting in accumulation of the conjugates in gastroc muscle. Receptor mediate uptake resulted in siRNA mediated knockdown of the MSTN gene.

Example 9: 2017-PK-303-WT-Dose Response MSTN mAb vs Fab vs Chol siRNA Design and Synthesis MSTN: A 21mer duplex with 19 bases of complementarity and 3' dinucleotide overhangs was designed against mouse MSTN. The sequence (5' to 3') of the guide/antisense strand was UUAUUAUUUGUUCUUUGCCUU (SEQ ID NO: 14226). Base, sugar and phosphate modifications were used to optimize the potency of the duplex and reduce immunogenicity. All siRNA single strands were fully assembled on solid phase using standard phospharamidite chemistry and purified over HPLC. Purified single strands were duplexed to get the double stranded siRNA. The passenger strand contained two conjugation handles, a C6-NH$_2$ at the 3' end and a C6-SH at the 3' end. Both conjugation handles were connected to siRNA passenger strand via phosphorothioate-inverted abasic-phosphorothioate linker. Because the free thiol was not being used for conjugation, it was end capped with N-ethylmaleimide.

MSTN*: MSTN: A 21mer duplex with 19 bases of complementarity and 3' dinucleotide overhangs was designed against mouse MSTN. The sequence (5' to 3') of the guide/antisense strand was UUAUUAUUUGUUC-UUUGCCUU (SEQ ID NO: 14226). Base, sugar and phosphate modifications were used to optimize the potency of the duplex and reduce immunogenicity. All siRNA single strands were fully assembled on solid phase using standard phospharamidite chemistry and purified over HPLC. Purified single strands were duplexed to get the double stranded siRNA. The passenger strand contained one conjugation handle, a C6-NH$_2$ at the 5' end, which was connected to siRNA passenger strand via phosphothioate-inverted abasic-phosphorothioate linker.

Negative control siRNA sequence (scramble): A published (Burke et al. (2014) Pharm. Res., 31(12):3445-60) 21mer duplex with 19 bases of complementarity and 3' dinucleotide overhangs was used. The sequence (5' to 3') of the guide/antisense strand was UAUCGACGUGUCCAGC-UAGUU (SEQ ID NO: 14228). The same base, sugar and phosphate modifications that were used for the active MSTN siRNA duplex were used in the negative control siRNA. All siRNA single strands were fully assembled on solid phase using standard phospharamidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphorothioate-inverted abasic-phosphorothioate linker. Because the free thiol was not being used for conjugation, it was end capped with N-ethylmaleimide.

ASC Synthesis and Characterization

The CD71 mAb-siRNA DAR1 and DAR2 conjugates were made and characterized as described in Example 3. Groups 5-12 made through cysteine conjugation, a BisMal linker using architecture 3. Groups 13-16 were made through cysteine conjugation, a SMCC linker, the free thiol was end capped with NEM using architecture 1. Groups 17-20 were made through cysteine conjugation, a BisMal linker, the free thiol was end capped with NEM using architecture 3. Conjugates were characterized chromatographically as described Table 9.

TABLE 9

HPLC retention time (RT) in minutes

| Groups | Conjugate | RT, SAX Method-2 | RT, SEC Method-1 |
|---|---|---|---|
| 5-8 | TfR-Fab-MSTN*; DAR1 | 8.7 | 10.0 |
| 9-12 | TfR-mAb-MSTN*; DAR1 | 9.3 | 7.8 |
| 13-16 | TfR-mAb-MSTN; DAR1 | 9.5 | 7.9 |
| 17-20 | TfR-mAb-scramble; DAR1 | 9.1 | 7.3 |

In Vivo Study Design

The conjugates were assessed for their ability to mediate mRNA downregulation of myostatin (MSTN) in skeletal muscle in vivo in wild type CD-1 mice. Mice were dosed via intravenous (iv) injection with PBS vehicle control and the indicated ASCs at the doses indicated in FIG. 12A. Tissue samples were also taken as indicated in FIG. 12A. Gastrocnemius (gastroc) muscle tissues were harvested and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct). Quantitation of tissue siRNA concentrations was determined using a stem-loop qPCR assay as described in the methods section. The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

Intracellular RISC loading was determined as described in Example 2.

Results

Figure 12B:
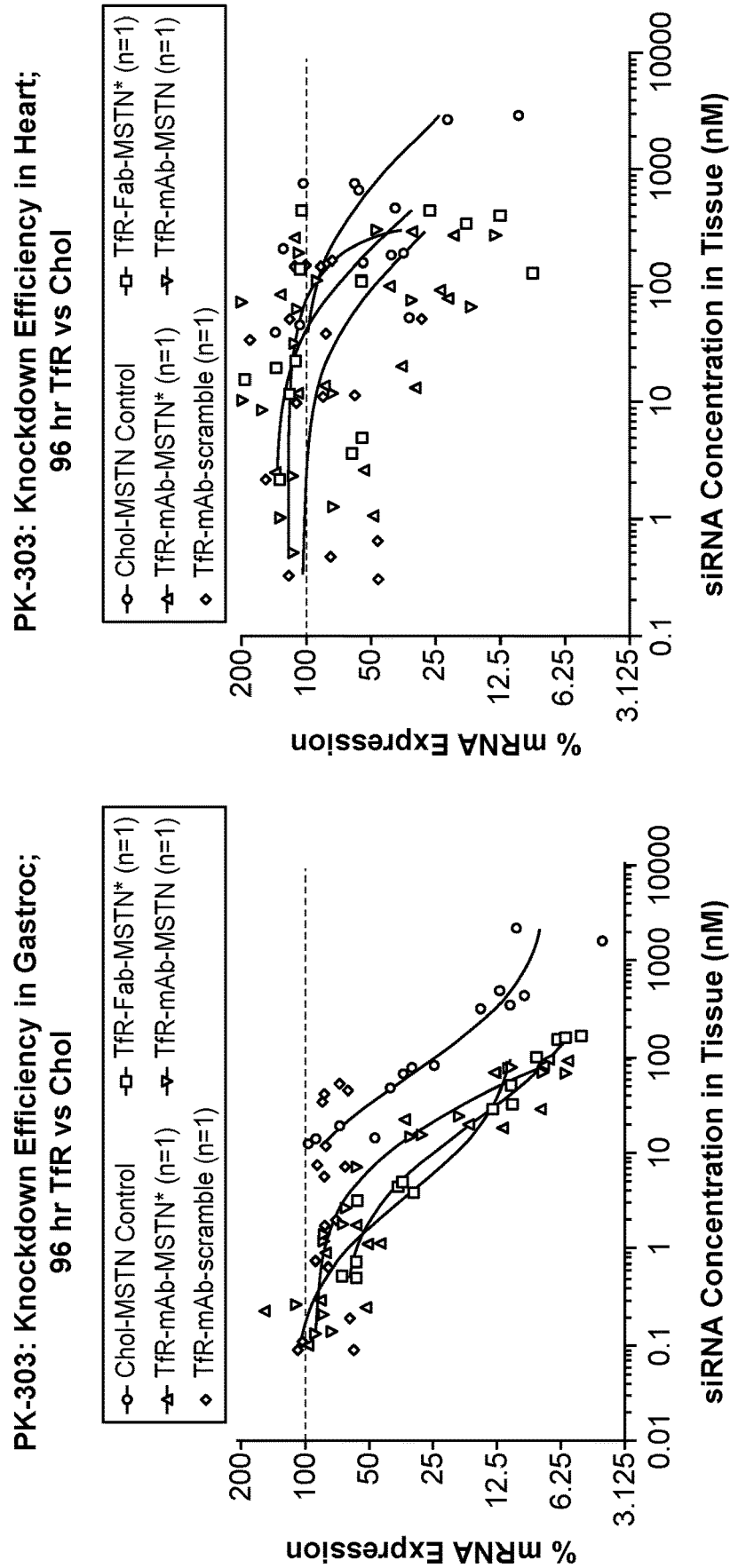
FIG. 12B shows accumulation of siRNA in various muscle tissue.
Figure 12C:
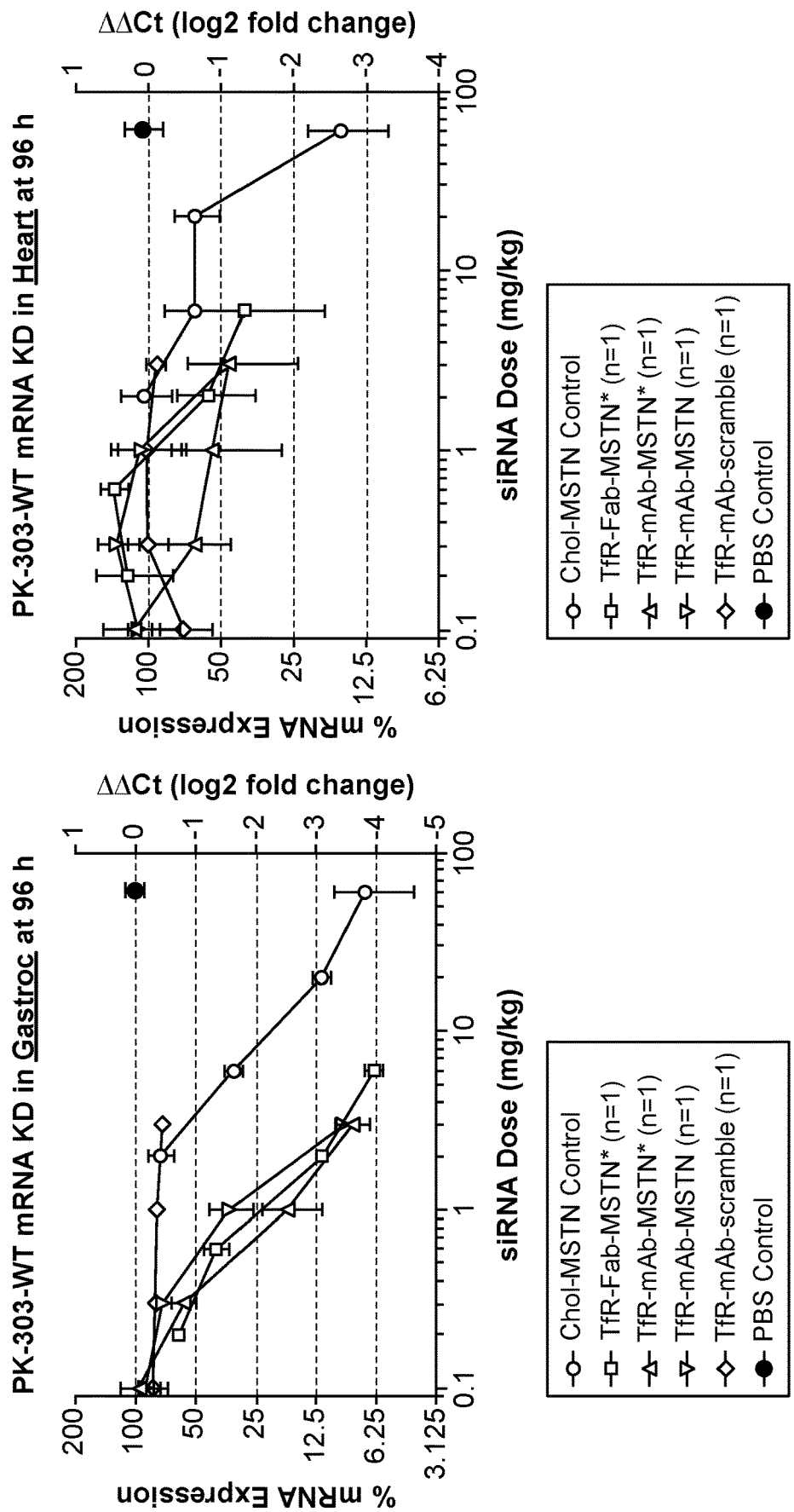
FIG. 12C shows siRNA-mediated mRNA knockdown of mouse MSTN in mouse gastrocnemius (gastroc) and heart muscle.
Figure 12D:
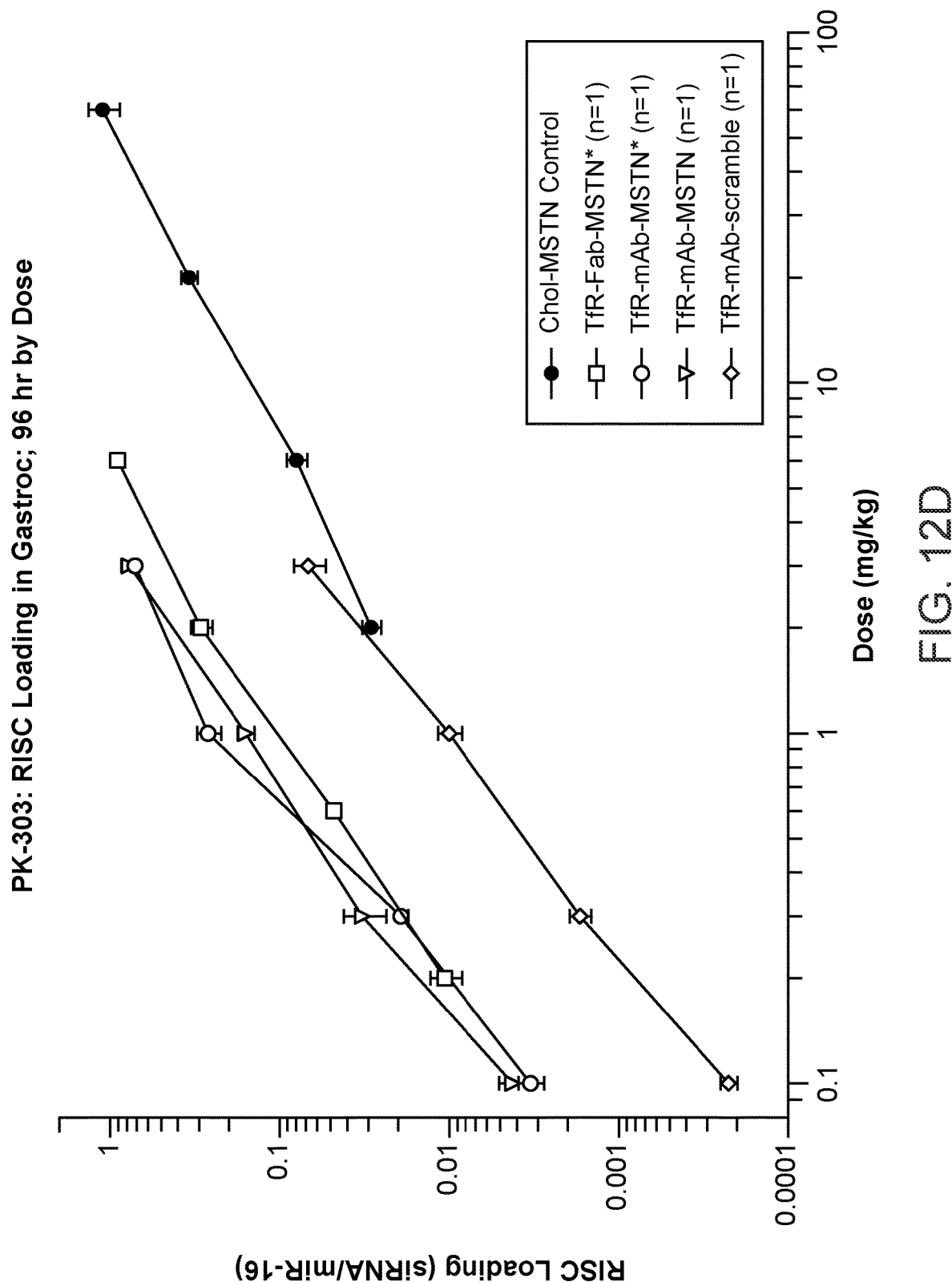
FIG. 12D shows RISC loading of the MSTN guide strand in mouse gastrocnemius (gastroc) muscle.

Quantifiable levels of siRNA accumulated in gastroc and heart tissue, see FIG. 12B, after a single intravenous dose of the antibody and Fab siRNA conjugates. Robust MSTN mRNA downregulation was observed in gastroc muscle, when the ASC was targeted with either the anti-transferrin receptor antibody or Fab see FIG. 12B and FIG. 12C. Much higher concentrations of siRNA were delivered to heart tissue, but this did not result in robust myostatin mRNA downregulation, see FIG. 12B. Compared to the cholesterol siRNA conjugate, much lower doses of the ASCs were required to achieve equivalent mRNA downregulation. The amount of RISC loading of the MSTN siRNA guide strand correlated with downregulation of the mRNA, see FIG. 12D.

Conclusions

In this example it was demonstrated that accumulation of siRNA in gastrocnemius muscle tissue after a single dose of an anti-transferrin antibody and Fab targeted siRNA conjugates. In Gastroc muscle. siRNA mediated MSTN mRNA downregulation with the DAR1 anti-transferrin antibody or Fab conjugates was observed. Mouse gastroc muscle expresses transferrin receptor and the conjugate have a mouse specific anti-transferrin antibody or Fab to target the payload, resulting in accumulation of the conjugates in gastroc muscle and loading into the RISC complex. Receptor mediate uptake resulted in siRNA mediated MSTN mRNA downregulation.

Example 10: 2017-PK-304-WT-PK with MSTN Phenotype mAb vs Chol siRNA Design and Synthesis MSTN: A 21mer duplex with 19 bases of complementarity and 3' dinucleotide overhangs was designed against mouse MSTN. The sequence (5' to 3') of the guide/antisense strand was UUAUUAUUUGUUCUUUGCCUU (SEQ ID NO: 14226). Base, sugar and phosphate modifications that are well described in the field of RNAi were used to optimize the potency of the duplex and reduce immunogenicity. All siRNA single strands were fully assembled on solid phase using standard phosphoramidite chemistry and purified over HPLC. Purified single strands were duplexed to get the double stranded siRNA. The passenger strand contained two conjugation handles, a C6-NH2 at the 5' end and a C6-SH at the 3' end. Both conjugation handles were connected to siRNA passenger strand via phosphorothioate-inverted abasic-phosphorothioate linker. Because the free thiol was not being used for conjugation, it was end capped with N-ethylmaleimide.

Negative control siRNA sequence (scramble): A published (Burke et al. (2014) Pharm. Res., 31(12):3445-60) 21mer duplex with 19 bases of complementarity and 3' dinucleotide overhangs was used. The sequence (5' to 3') of the guide/antisense strand was UAUCGACGUGUCCAGC-UAGUU (SEQ ID NO: 14228). The same base, sugar and phosphate modifications that were used for the active MSTN siRNA duplex were used in the negative control siRNA. All siRNA single strands were fully assembled on solid phase using standard phosphoramidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphorothioate-inverted abasic-phosphorothiate linker. Because the free thiol was not being used for conjugation, it was end capped with N-ethylmaleimide.

ASC synthesis and Characterization

The CD71 mAb-siRNA DAR1 and DAR2 conjugates were made and characterized as described in example 3. Groups 5-12 were made through cysteine conjugation, a SMCC linker, the free thiol was end capped with NEM using architecture 1. Groups 13-16 were made through cysteine conjugation, a BisMal linker, the free thiol was end capped with NEM using architecture 3. Conjugates were characterized chromatographically as described in Table 10.

TABLE 10

HPLC retention time (RT) in minutes

| Groups | Conjugate | RT, SAX Method-2 | RT, SEC Method-1 |
|---|---|---|---|
| 5-8 | TfR-mAb-MSTN; DAR1 | 9.5 | 7.9 |
| 9-12 | TfR-mAb-MSTN; DAR2 | 10.3 | 7.6 |
| 13-16 | TfR-mAb-scramble; DAR1 | 9.1 | 7.3 |

In Vivo Study Design

Figure 13B:
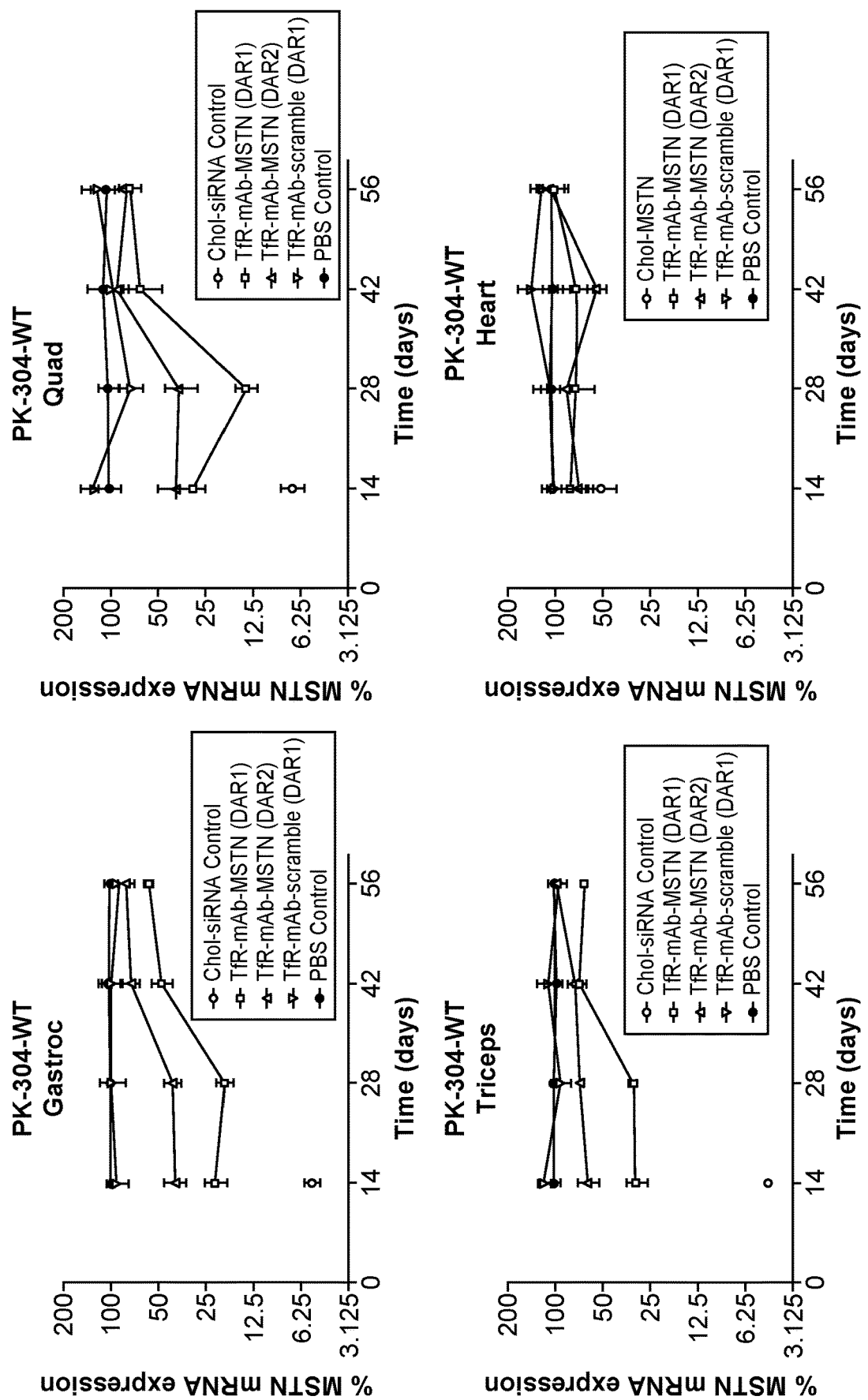
FIG. 13B shows siRNA-mediated mRNA knockdown of mouse MSTN in mouse gastrocnemius (gastroc), quadriceps, triceps, and heart.

The conjugates were assessed for their ability to mediate mRNA downregulation of myostatin (MSTN) in skeletal muscle in vivo in wild type CD-1 mice. Mice were dosed via intravenous (iv) injection with PBS vehicle control and the indicated ASCs at the doses indicated in FIG. 13A. Tissue samples were also taken as indicated in FIG. 13A. Gastrocnemius (gastroc) muscle tissues were harvested and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct). Quantitation of tissue siRNA concentrations was determined using a stem-loop qPCR assay as described in the methods section. The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

Intracellular RISC loading was determined as described in Example 2. Plasma MSTN protein levels were measured by ELISA as described in Example 2.

Changes in leg muscle area were determined: the leg-to-be measured were shaved and a line was drawn using indelible ink to mark region of measurement. Mice were restrained in a small decipinone beg. Digital calipers were used to take one measurement on the sagittal plane and another on the coronal plane. The procedure was repeated twice per week.

Results

Figure 13C:
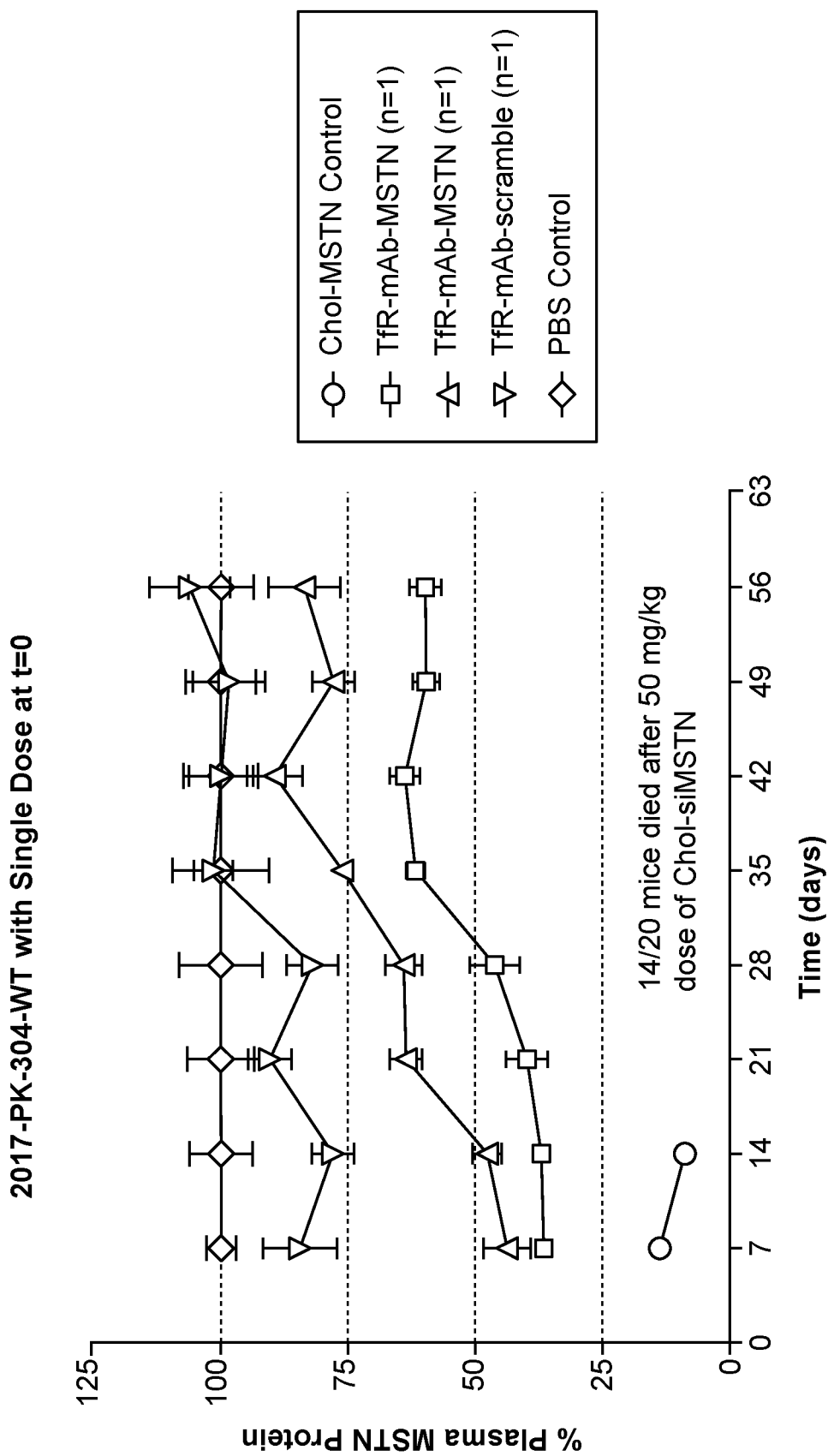
FIG. 13C illustrates plasma myostatin levels.
Figure 13D:
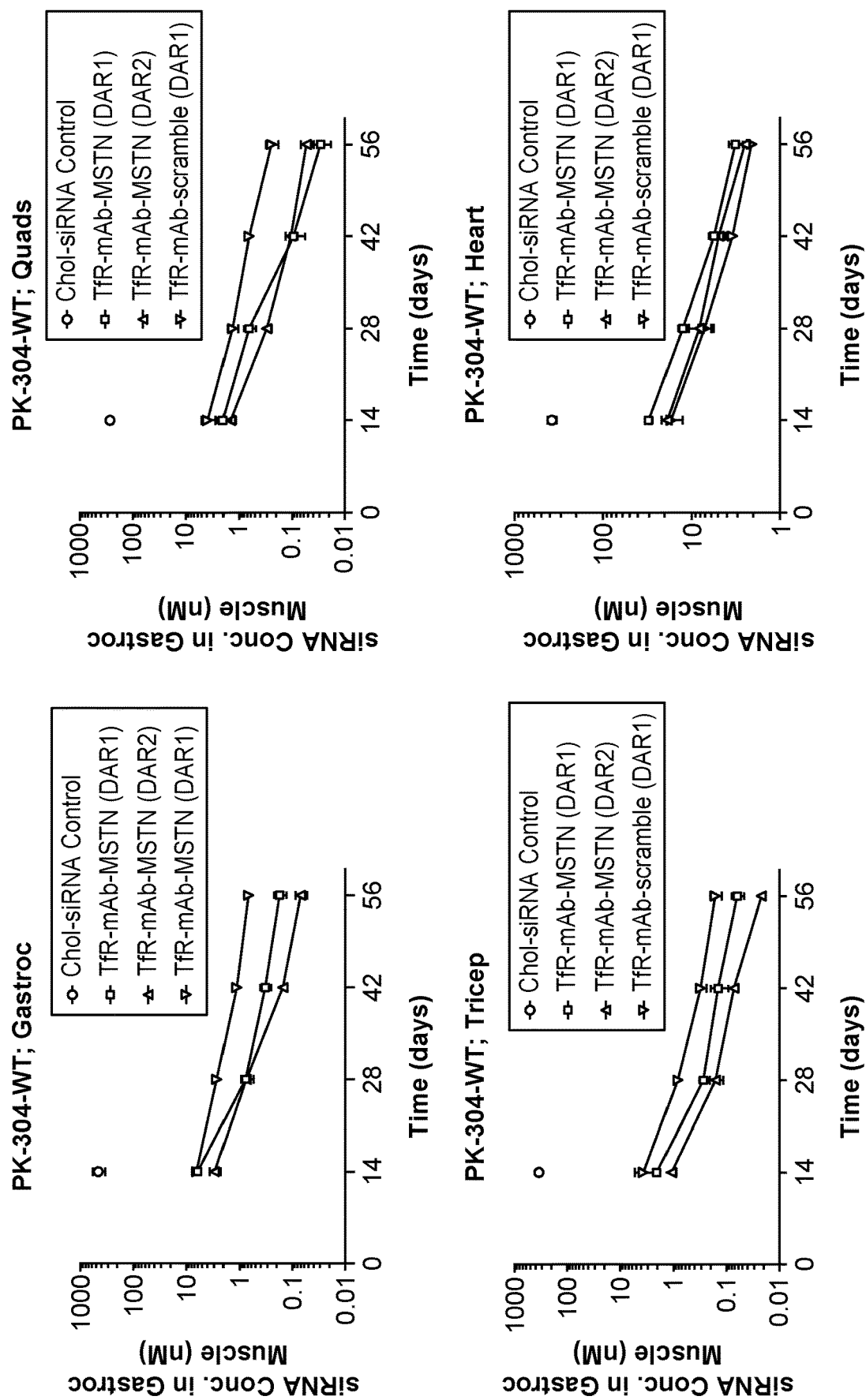
FIG. 13D illustrates siRNA accumulation in different tissue types: gastrocnemius, triceps, quadriceps, and heart tissues.
Figure 13E:
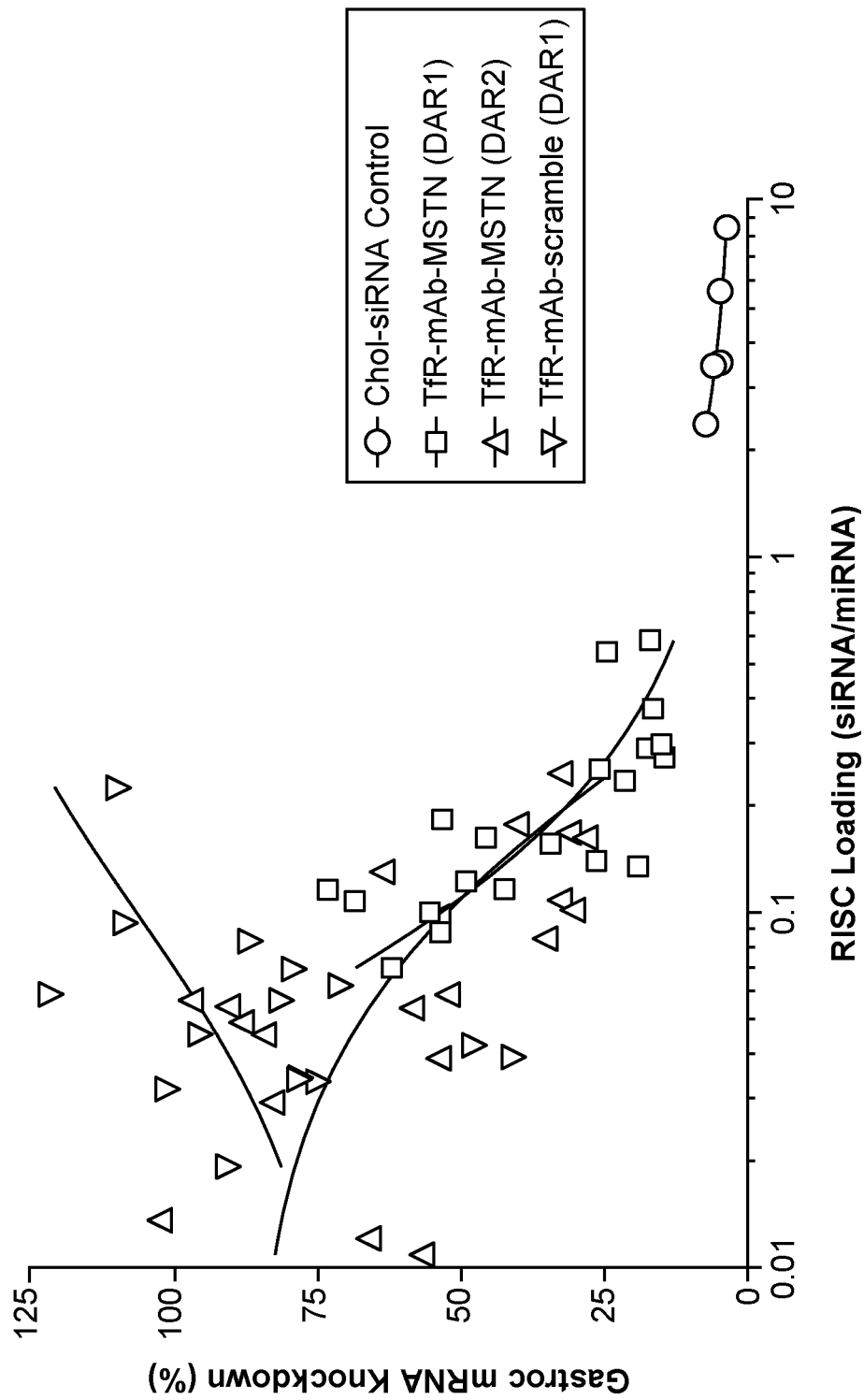
FIG. 13E shows RISC loading of the MSTN guide strand in mouse gastrocnemius (gastroc) muscle.
Figure 13F:
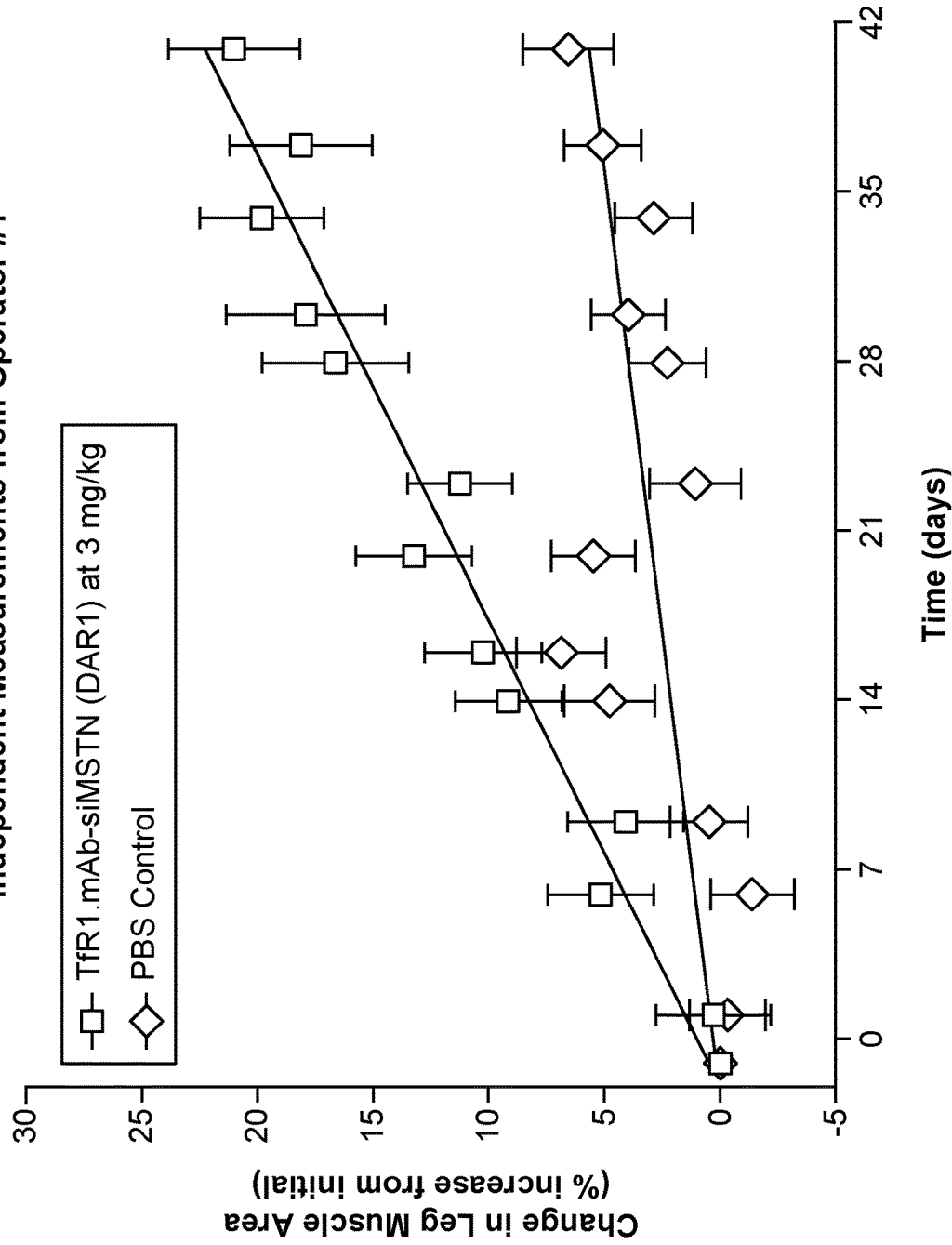
FIG. 13F shows change in muscle area.
Figure 13G:
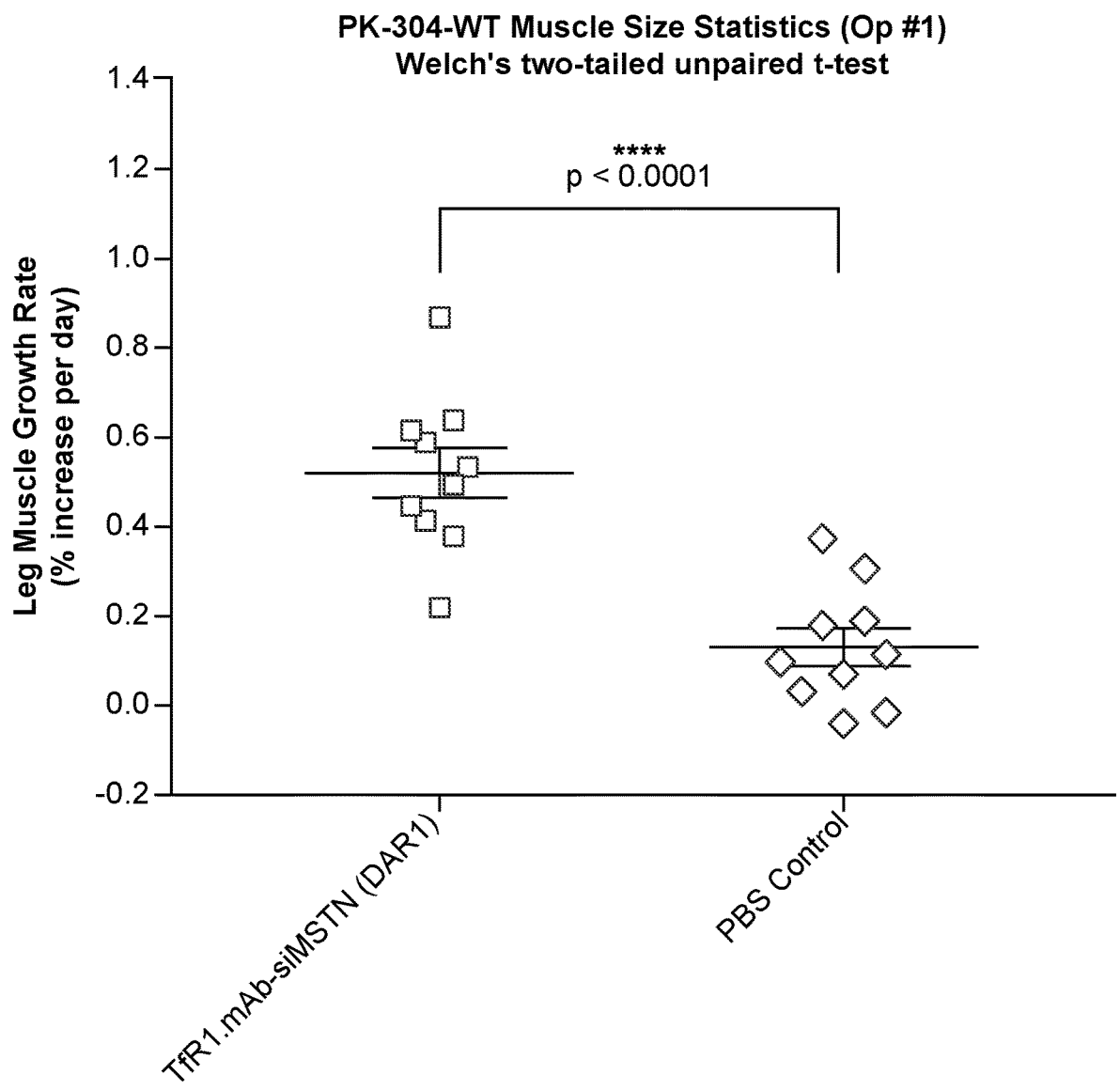
FIG. 13G shows Welch's two-tailed unpaired t-test of FIG. 13F.

Quantifiable levels of siRNA accumulated in gastrocnemius, triceps, quadriceps (Quad), and heart tissues, see FIG. 13D, after a single intravenous dose of the antibody siRNA conjugates at 3 mg/kg. MSTN mRNA downregulation was observed in gastrocnemius, quadriceps, and triceps with the DAR1 and DAR2 conjugates but not in heart tissue, see FIG. 13B. MSTN mRNA downregulation resulted in a reduction in the plasma concentration of MSTN protein, as measured by ELISA, see FIG. 13C. The amount of RISC loading of the MSTN siRNA guide strand correlated with downregulation of the mRNA, see FIG. 13E. Downregulation of MSTN resulted in statistically significant increases in muscle size, see FIG. 13F and FIG. 13G.

Conclusions

In this example it was demonstrated that accumulation of siRNA in gastrocnemius, quadriceps, and triceps muscle tissues after a single dose of anti-transferrin antibody siRNA conjugates, DAR1 and DAR2. In all three tissues, measurable siRNA mediated MSTN mRNA downregulation with the DAR1 and DAR2 anti-transferrin antibody conjugates was observed, mRNA downregulation correlated with a reduced level of plasma MSTN protein and RISC loading of the siRNA guide strand. All three muscle tissues expressed transferrin receptor and the conjugate has a mouse specific anti-transferrin antibody to target the siRNA, resulting in accumulation of the conjugates in muscle. Receptor mediate uptake resulted in siRNA mediated knockdown of the MSTN gene.

Example 11: 2017-PK-355-WT Multiple siRNA Dosing siRNA Design and Synthesis

HPRT: A 21mer duplex with 19 bases of complementarity and 3' dinucleotide overhangs was designed against mouse MSTN. The sequence (5' to 3') of the guide/antisense strand was UUAAAAUCUACAGUCAUAGUU (SEQ ID NO: 14227). Base, sugar and phosphate modifications that are well described in the field of RNAi were used to optimize the potency of the duplex and reduce immunogenicity. All siRNA single strands were fully assembled on solid phase using standard phospharamidite chemistry and purified over HPLC. Purified single strands were duplexed to get the double stranded siRNA. The passenger strand contained a single conjugation handles, a $C6-NH_2$ at the 5', which was connected to siRNA passenger strand via phosphorothioate-inverted abasic-phosphorothioate linker.

SSB: A 21mer duplex with 19 bases of complementarity and 3' dinucleotide overhangs was designed against mouse MSTN. The sequence (5' to 3') of the guide/antisense strand was UUACAUUAAAGUCUGUUGUUU (SEQ ID NO: 14229). Base, sugar and phosphate modifications that are well described in the field of RNAi were used to optimize the potency of the duplex and reduce immunogenicity. All siRNA single strands were fully assembled on solid phase using standard phospharamidite chemistry and purified over HPLC. Purified single strands were duplexed to get the double stranded siRNA. The passenger strand contained a single conjugation handles, a $C6-NH_2$ at the 5', which was connected to siRNA passenger strand via phosphorothioate-inverted abasic-phosphorothioate linker.

ASC Synthesis and Characterization

The CD71 mAb-siRNA conjugates were made and characterized as described in Example 3.

Groups 14 and 5-8 were made through cysteine conjugation, a BisMal linker, no 3' conjugation handle on the passenger strand using architecture 3. Groups 13-16 were made through cysteine conjugation, a BisMal linker, no 3' conjugation handle on the passenger strand, but were DAR2 conjugates made with a mixture of HPRT and SSB siRNAs using architecture 4. Conjugates were characterized chromatographically as described in Table 11.

TABLE 11

HPLC retention time (RT) in minutes

| Conjugate | RT, SAX Method-2 | RT, SEC Method-1 |
|---|---|---|
| TfR-mAb-HPRT; DAR1 | 9.0 | 12.5 (0.5 ml flow rate, 25 min run) |
| TfR-mAb-SSB; DAR1 | 9.4 | No Data |
| TfR-mAb-HPRT/SSB (1:1) DAR2 | 10.09 | No Data |

In Vivo Study Design

The conjugates were assessed for their ability to mediate mRNA downregulation of two house keeper genes (HPRT and SSB) in skeletal muscle in vivo in wild type CD-1 mice. Mice were dosed via intravenous (iv) injection with PBS vehicle control and the indicated ASCs at the doses indicated in FIG. 14A. Tissue samples were also taken as indicated in FIG. 14A. Gastrocnemius (gastroc) muscle tissues were harvested and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value (ΔCt) is calculated and then further normalized relative to the PBS control group by taking a second difference (ΔΔCt). Quantitation of tissue siRNA concentrations was determined using a stem-loop qPCR assay as described in the methods section. The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

The RISC loading assay was conducted as described in Example 2.

Results

Figure 14B:
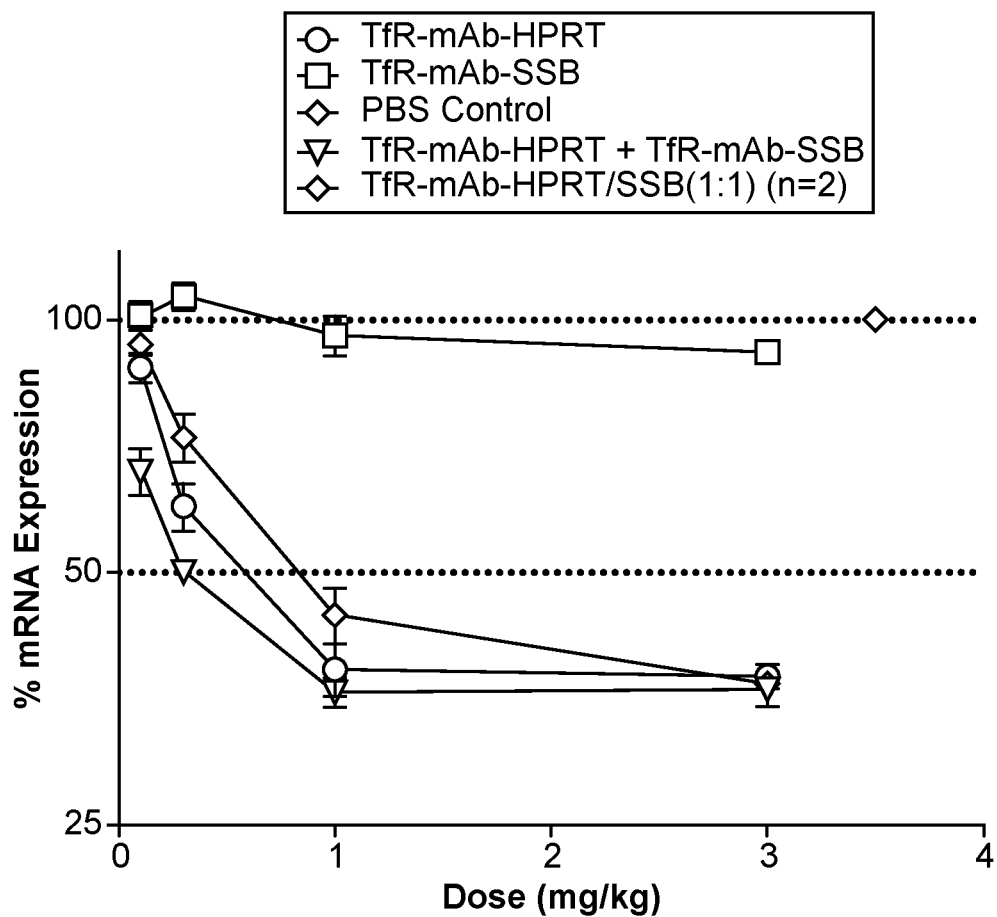
FIG. 14B shows HPRT mRNA expression of gastrocnemius muscle by exemplary conjugates described herein.
Figure 14C:
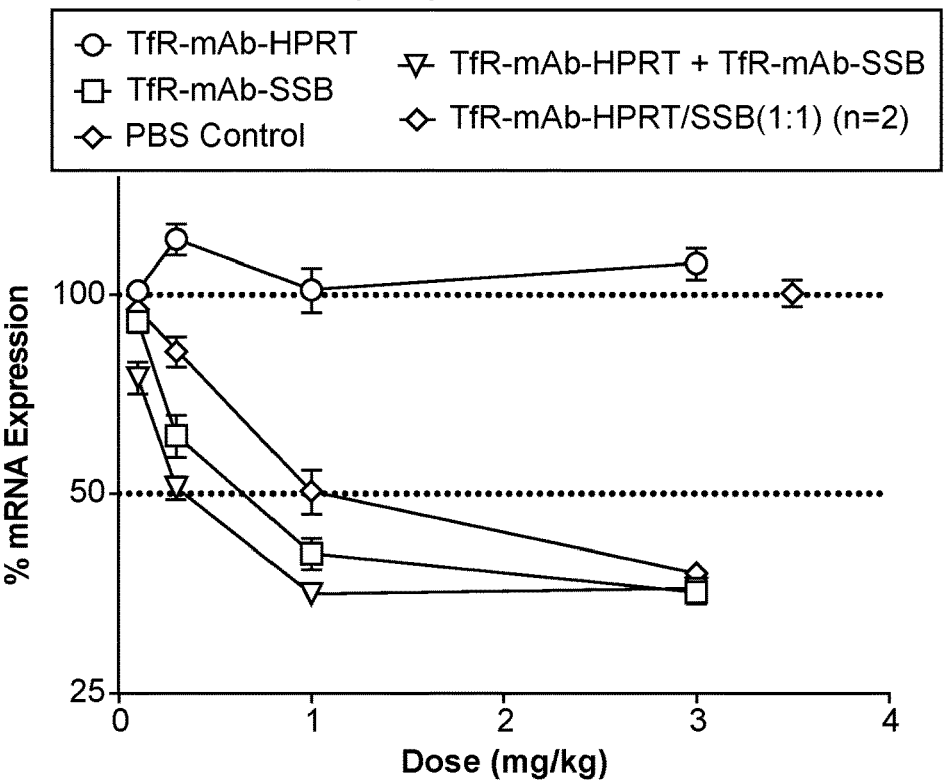
FIG. 14C shows SSB mRNA expression of gastrocnemius muscle by exemplary conjugates described herein.
Figure 14D:
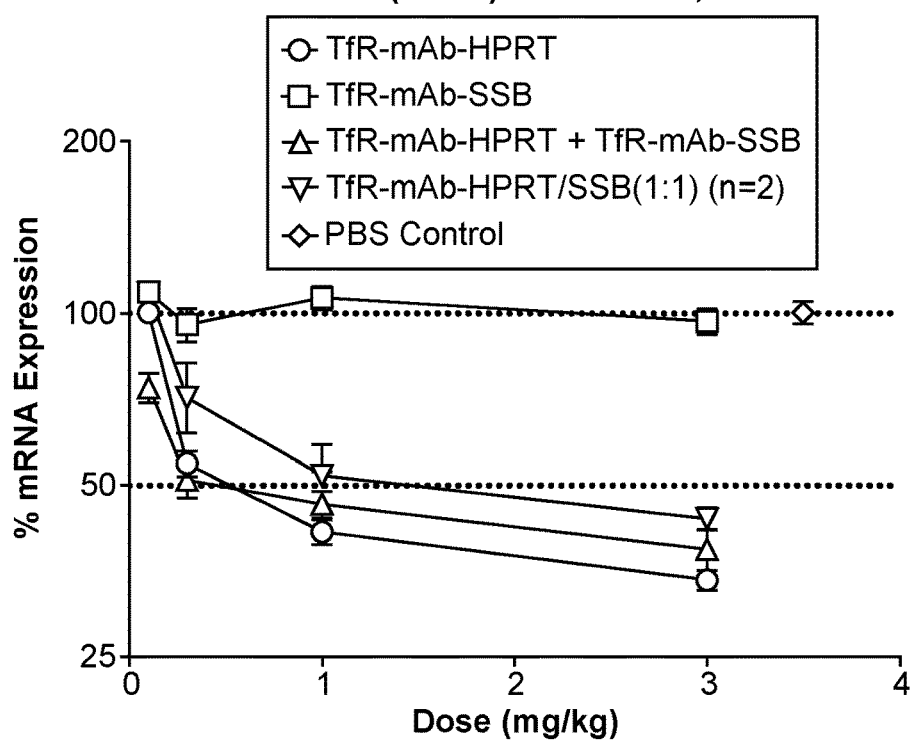
FIG. 14D shows HPRT mRNA expression of heart tissue by exemplary conjugates described herein.
Figure 14E:
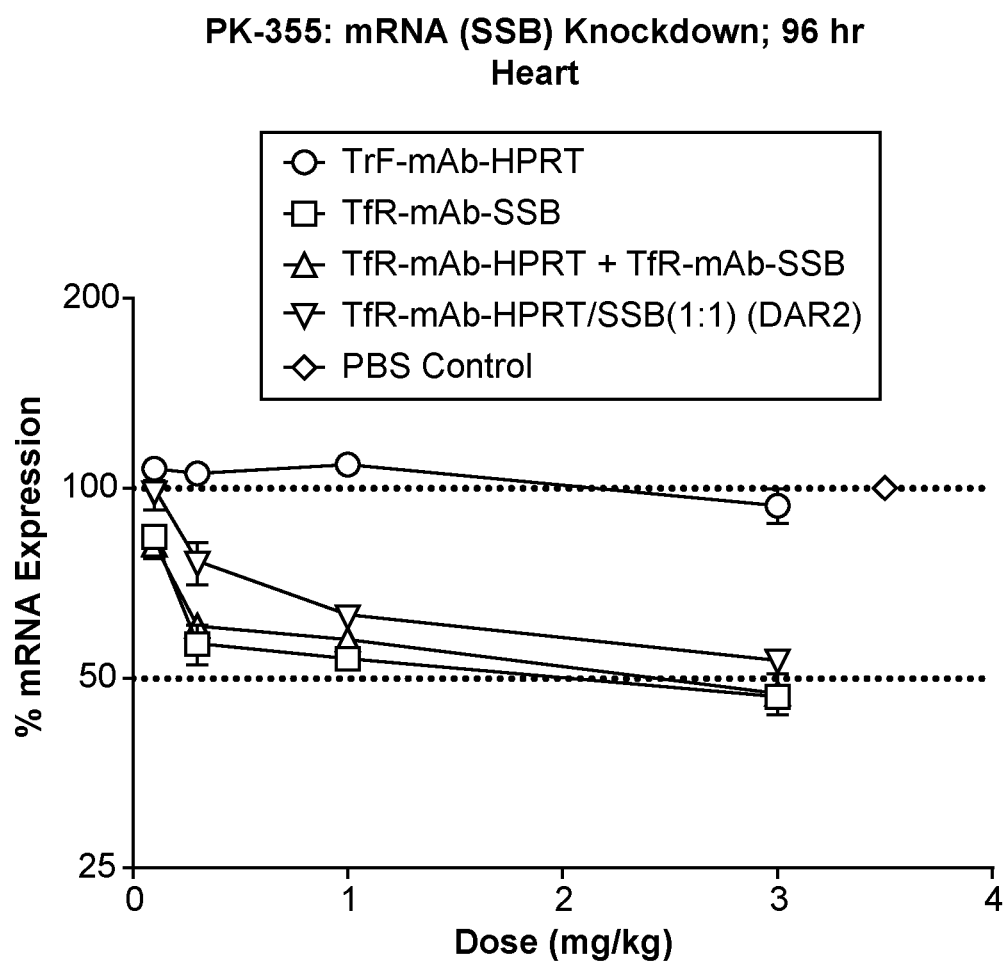
FIG. 14E shows SSB mRNA expression of heart tissue by exemplary conjugates described herein.
Figure 14F:
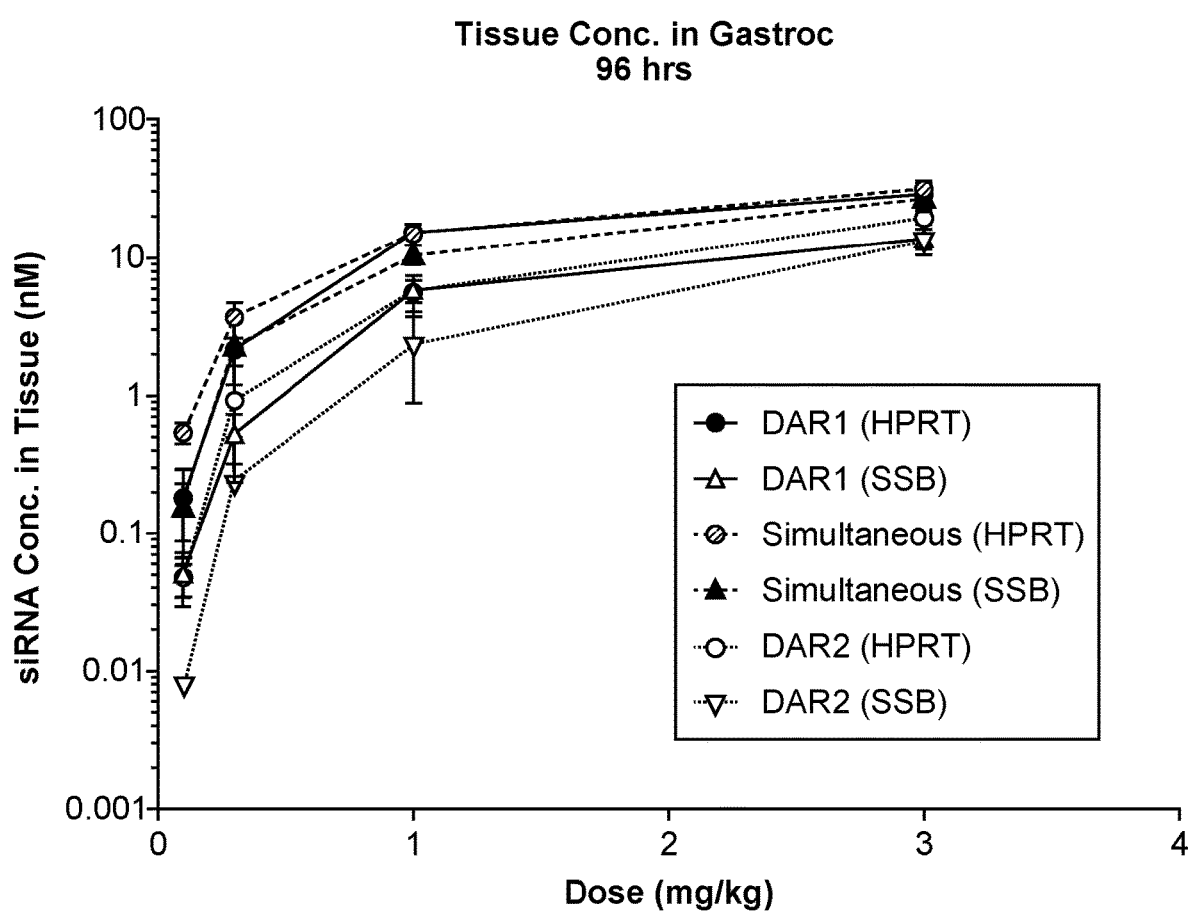
FIG. 14F shows accumulation of siRNA in gastrocnemius muscle.

After a single intravenous dose of the antibody siRNA conjugates at the indicated doses, mRNA downregulation was observed in gastroc and heart tissue, see FIG. 14B-FIG. 14D. Co-administration of a mixture of two ASC's, targeting two different genes (HPRT and SSB) resulted in efficient mRNA downregulation of both targets in gastroc and heart tissue. In addition, administration of a DAR2 conjugate synthesized using a 1:1 mixture of the two different siRNAs (HPRT and SSB) also resulted in efficient mRNA down regulation of both targets in gastroc and heart tissue. All approaches to delivery resulted in measurable amounts of siRNA accumulating in gatroc tissue, see FIG. 14F.

Conclusions

In this example, it was demonstrated that accumulation of siRNA in gastroc and heart tissue after a single dose of anti-transferrin antibody siRNA conjugates. Two genes were downregulated by co-administration of two ASC produced with the same anti-transferrin antibody but conjugated to two different siRNAs (HPRT and SSB). In addition, two genes were downregulated by an anti-transferrin mAb DAR2 conjugate synthesized using a 1:1 mixture of two different siRNAs (HPRT and SSB). In some instances, simultaneous downregulation of more than one gene is useful in muscle atrophy.

Example 12: 2017-PK-380-WT Activity of Atrogin-1 siRNAs In Vivo (Dose Response) siRNA Design and Synthesis Atrogin-1 siRNAs: 4 different 21mer duplexes with 19 bases of complementarity and 3' dinucleotide overhangs were designed against Atrogin-1, see Example 4 for details of the sequence. Base, sugar and phosphate modifications that are well described in the field of RNAi were used to optimize the potency of the duplex and reduce immunogenicity. The same design was used for all four siRNAs. All siRNA single strands were fully assembled on solid phase using standard phosphoramidite chemistry and purified over HPLC. Purified single strands were duplexed to get the double stranded siRNA. The passenger strand contained two conjugation handles, a C6-NH, at the 5' end and a C6-SH at the 3' end. Both conjugation handles were connected to siRNA passenger strand via phosphothioate-inverted abasic-phosphorothioate linker. Because the free thiol was not being used for conjugation, it was end capped with N-ethylmaleimide.

ASC Synthesis and Characterization

The CD71 mAb-siRNA conjugates were made and characterized as described in Example 3.

Groups 1-16 were made through cysteine conjugation, a BisMal linker, the free thiol was end capped with NEM using architecture 3. Conjugates were characterized chromatographically as described Table 12.

TABLE 12

| | | HPLC retention time (RT) in minutes | |
|---|---|---|---|
| Groups | Conjugate | RT, SAX Method-2 | RT, SEC Method-1 |
| 1-4 | mTfR1(Cys)-BisMal-N-mAtrogin#1179; DAR1 | 9.2 | 7.7 |
| 5-8 | mTfR1(Cys)-BisMal-N-mAtrogin#1504; DAR1 | 9.3 | 7.8 |
| 9-12 | mTfR1(Cys)-BisMal-N-mAtrogin#631; DAR1 | 9.3 | 7.8 |
| 13-16 | mTfR1(Cys)-BisMal-N-mAtrogin#586; DAR1 | 9.2 | 7.8 |

In Vivo Study Design

The conjugates were assessed for their ability to mediate mRNA downregulation of Atrogin-1 in skeletal muscle in vivo in wild type CD-1 mice. Mice were dosed via intravenous (iv) injection with PBS vehicle control and the indicated ASCs at the doses indicated in FIG. 15A. Tissue samples were taken as indicated in FIG. 15A. Gastrocnemius (gastroc) muscle tissues were harvested and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value (ΔCt) is calculated and then further normalized relative to the PBS control group by taking a second difference (ΔΔCt).

Results

Figure 15B:
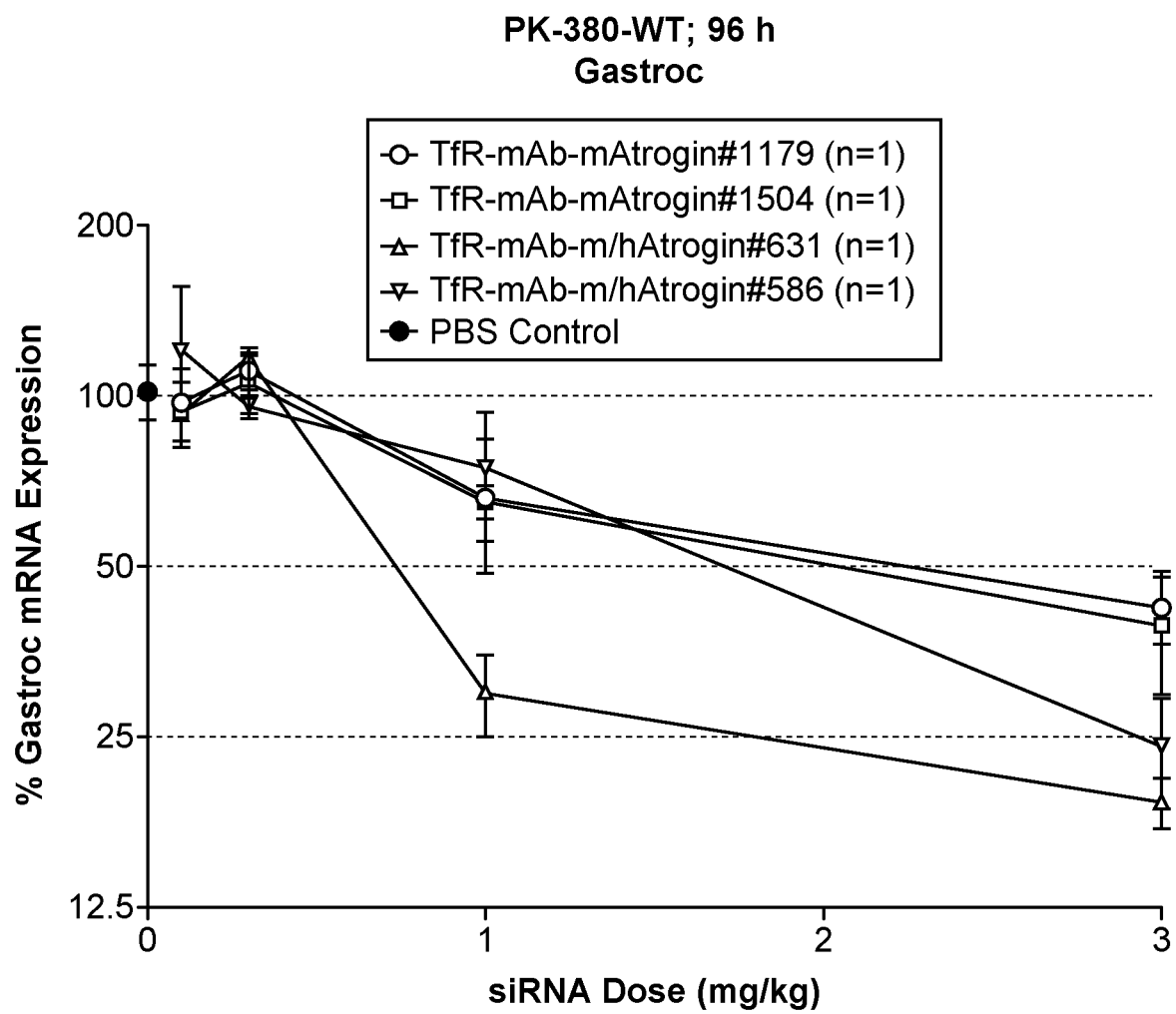
FIG. 15B shows Atrogin-1 downregulation in gastrocnemius (gastroc) muscle.
Figure 15C:
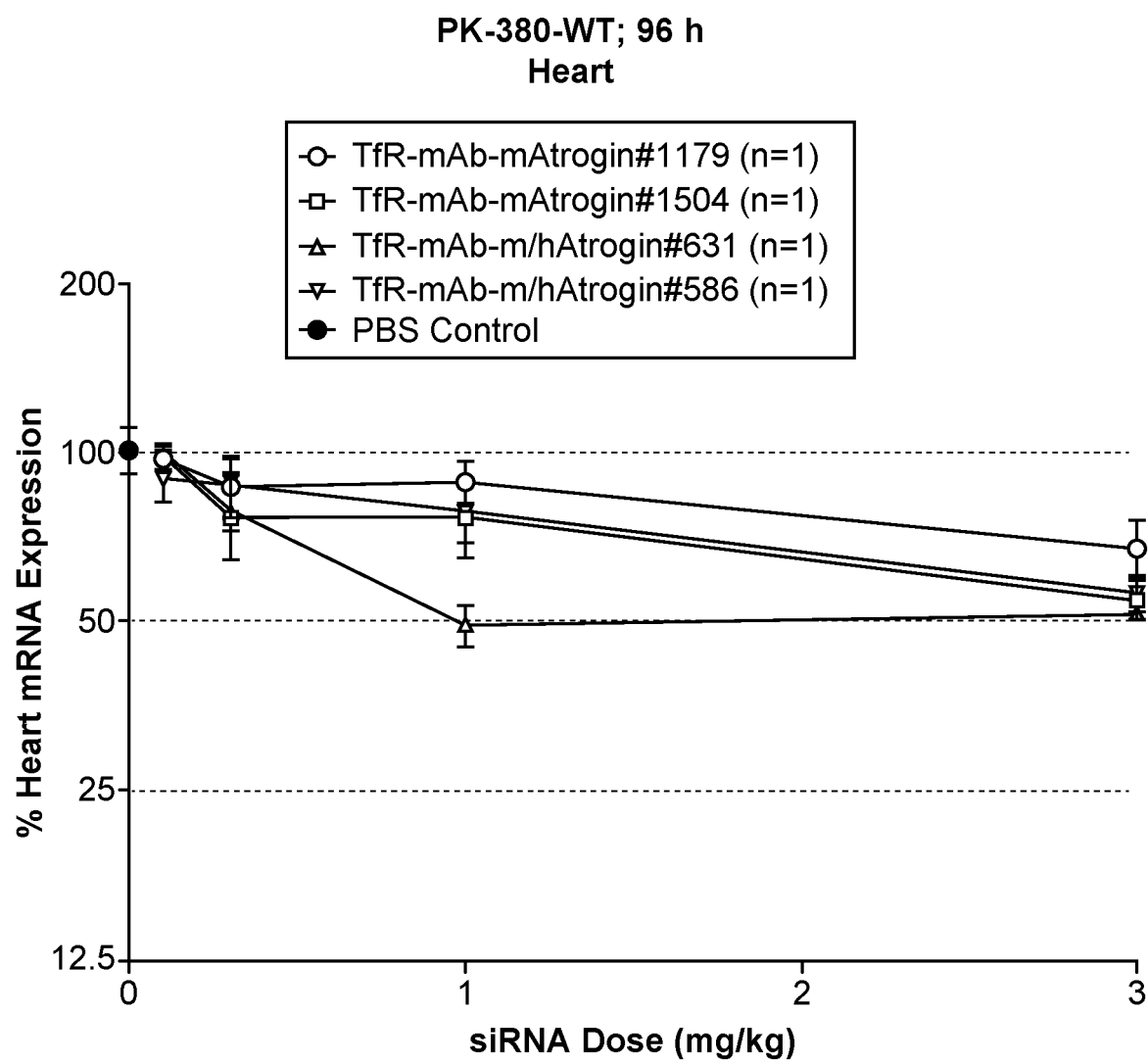
FIG. 15C shows Atrogin-1 downregulation in heart tissue.

After a single intravenous dose of the antibody siRNA conjugates at the indicated doses, up to 80% atrogin-1 mRNA downregulation was observed in gastroc muscle and up to 50% in heart tissue, see FIG. 15B and FIG. 15C.

Conclusions

As illustrated in this example, antibody siRNA conjugates differentially downregulate Atrogin-1 in muscle and heart.

Example 13: 2017-PK-383-WT Activity of MuRF1 siRNA In Vivo (Dose Response) siRNA Design and Synthesis MuRF1 siRNAs: 4 different 21mer duplexes with 19 bases of complementarity and 3' dinucleotide overhangs were designed against Atrogin-1, see Example 5 for details of the sequence. Base, sugar and phosphate modifications that are well described in the field of RNAi were used to optimize the potency of the duplex and reduce immunogenicity. The same design was used for all four siRNAs. All siRNA single strands were fully assembled on solid phase using standard phosphoramidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphorothioate-inverted abasic-phosphorothioate linker. Because the free thiol was not being used for conjugation, it was end capped with N-ethylmaleimide.

ASC Synthesis and Characterization

The CD71 mAb-siRNA conjugates were made and characterized as described in Example 3.

Groups 1-16 were made through cysteine conjugation, a BisMal linker, the free thiol was end capped with NEM using architecture 3. Conjugates were characterized chromatographically as described Table 13.

TABLE 13

HPLC retention time (RT) in minutes

| Groups | Conjugate | RT, SAX Method-2 | RT, SEC Method-1 |
|---|---|---|---|
| 1-4 | mTfR1(Cys)-BisMal-N-MuRF#651-S-NEM; DAR1 | 9.2 | 7.8 |
| 5-8 | mTfR1(Cys)-BisMal-N-MuRF#1387-S-NEM; DAR1 | 9.3 | 7.8 |
| 9-13 | mTfR1(Cys)-BisMal-N-MuRF#1454-S-NEM; DAR1 | 9.1 | 7.8 |
| 14-18 | mTfR1(Cys)-BisMal-N-MuRF#1660-S-NEM; DAR1 | 9.1 | 7.8 |

In Vivo Study Design

The conjugates were assessed for their ability to mediate mRNA downregulation of MuRF-1 in skeletal and heart muscle in vivo in wild type CD-1 mice. Mice were dosed via intravenous (iv) injection with PBS vehicle control and the indicated ASCs at the doses indicated in FIG. 16A. Tissue samples were taken as indicated in FIG. 16A. Gastrocnemius (gastroc) muscle tissues were harvested and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value (ΔCt) is calculated and then further normalized relative to the PBS control group by taking a second difference (ΔCt).

Results

Figure 16B:
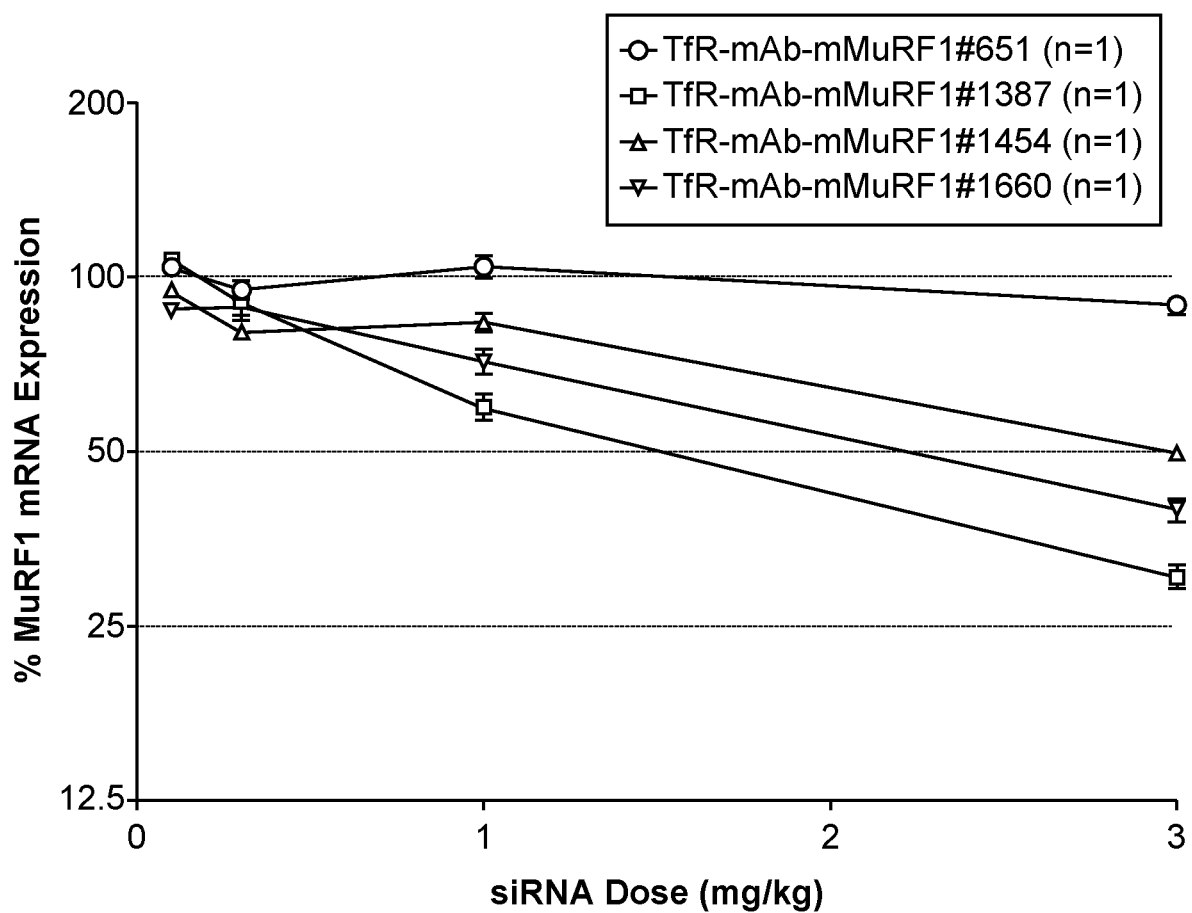
FIG. 16B shows MuRF-1 downregulation in gastrocnemius muscle.
Figure 16C:
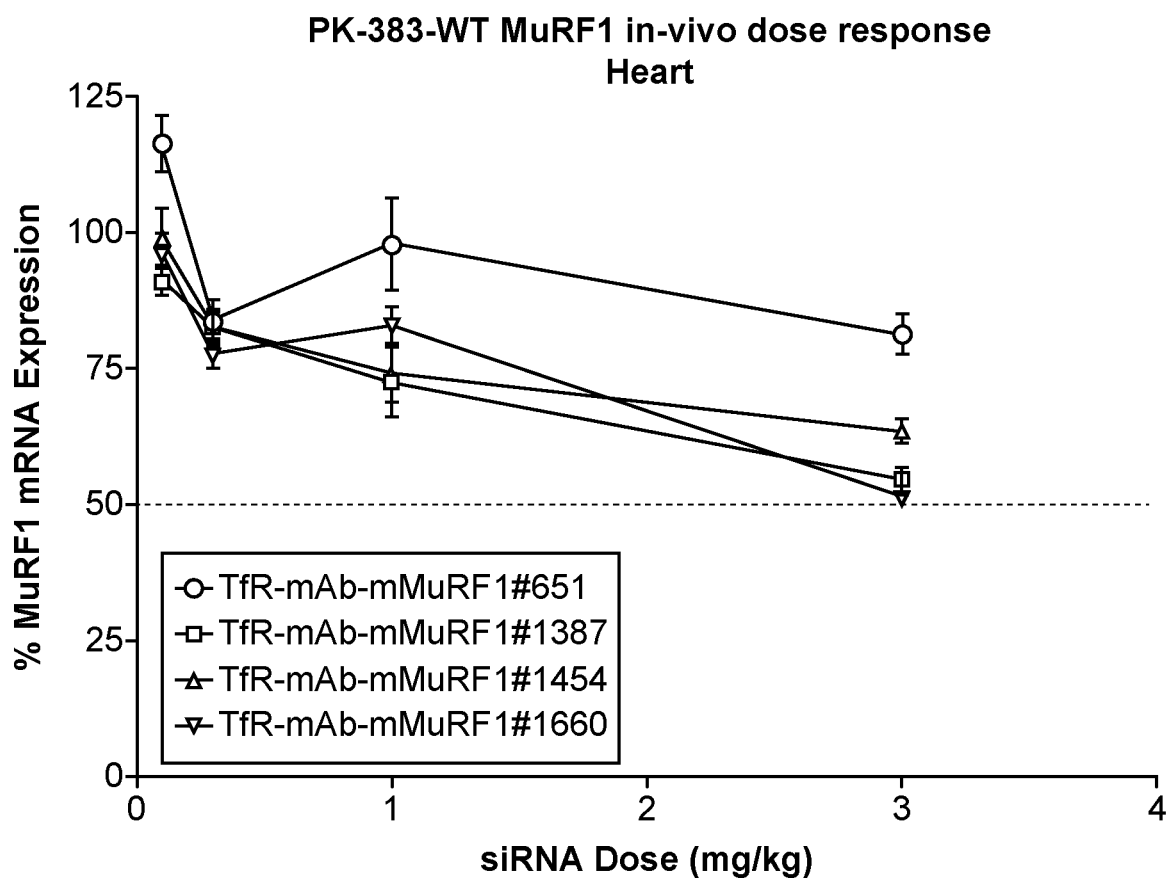
FIG. 16C shows MuRF-1 downregulation in heart tissue.

After a single intravenous dose of the antibody siRNA conjugates at the indicated doses, MuRF1 mRNA in gastroc muscle was downregulated to up to 70% and up to 50% in heart tissue, see FIG. 16B and FIG. 16C.

Conclusions

As illustrated in this example, antibody siRNA conjugates differentially downregulate MuRF1 in muscle and heart.

Example 14

Table 14 illustrates exemplary siRNA (or atrogene) targets to regulate muscle atrophy. In some instances, a polynucleic acid molecule hybridizes to a target region of an atrogene described in

TABLE 14

| Function | Gene | Name |
|---|---|---|
| Protein Degradation | FBXO32 | Atrogin-1 |
| | Trim63 | MuRF1 |
| | TRAF6 | TNF receptor-associated factor 6 |
| | USP14 | Ubiquitin specific protease 14 |
| | CTSL2 | Cathepsin L2 |
| Transcription | Foxo1 | Forkhead box O1 |
| | Foxo3 | Forkhead box O3 |
| | TGIF | TG interacting factor |
| | MYOG | myogenin |
| | HDAC2 | Histone deacetylase 2 |
| | HDAC3 | Histone deacetylase 3 |
| Stress Response | MT1L | Metallothionein 1L |
| | MT1B | Metallothionein 1B |

Example 15: Sequences 23-mer target sequences within one DMPK transcript variant (NM 001288766) are assigned with SEQ ID NOs: 703-3406. The set of 23-mer target sequences for this transcript variant was generated by walking down the length of the transcript one base at a time, and a similar set of target sequences could be generated for the other DMPK transcript variants using the same procedure. One common siRNA structure that can be used to target these sites in the DMPK transcript is a 19-mer fully complimentary duplex with 2 overhanging (not base-paired) nucleotides on the 3' end of each strand. Thus, adding the 19-mer with both of the 2 nucleotide overhangs results in a total of 23 bases for the target site. Since the overhangs can be comprised of a sequence reflecting that of the target transcript or other nucleotides (for example a non-related dinucleotide sequence such as "UU", the 19-mer fully complimentary sequence can be used to describe the siRNA for each 23-mer target site.

19-mer sense and antisense sequences for siRNA duplexes targeting each site within the DMPK transcript are assigned with SEQ ID NOs: 3407-8814 (with the first sense and antisense pairing as SEQ ID NO: 3407 and SEQ ID NO: 6111). SEQ ID NOs: 3407-6110 illustrate the sense strand. SEQ ID NOs: 6111-8814 illustrate the antisense strand. The DMPK transcript variant NM_001288766 has been used for illustration but a similar set of siRNA duplexes can be generated by walking through the other DMPK transcript variants. When the antisense strand of the siRNA loads into Ago2, the first base associates within the Ago2 binding pocket while the other bases (starting at position 2 of the antisense strand) are displayed for complimentary mRNA binding. Since "U" is the thermodynamically preferred first base for binding to Ago2 and does not bind the target mRNA, all of the antisense sequences can have "U" substituted into the first base without affecting the target complementarity and specificity. Correspondingly, the last base of the sense strand 19-mer (position 19) is switched to "A" to ensure base pairing with the "U" at the first position of the antisense strand.

SEQ ID NOs: 8815-11518 are similar to SEQ ID NOs: 3407-6110 except the last position of the 19-mer sense strand substituted with base "A".

SEQ ID NOs: 11519-14222 are similar to SEQ ID NOs: 6111-8814 except the first position of the 19-mer antisense strand substituted with base "U".

SEQ ID NO: 8815 and SEQ ID NO: 11519 for the first respective sense and antisense pairing.

Example 16: Initial Screening of a Selected Set of DMPK siRNAs for In Vitro Activity The initial set of DMPK siRNAs from SEQ ID NOs: 8815-14222 was narrowed down to a list of 81 siRNA sequences using a bioinformatic analysis aimed at selecting the sequences with the highest probability of on-target activity and the lowest probability of off-target activity. The bioinformatic methods for selecting active and specific siRNAs are well described in the field of RNAi and a person skilled in the arts would be able to generate a similar list of DMPK siRNA sequences against any of the other DMPK transcript variants. The DMPK siRNAs in the set of 81 sequences were synthesized on small scale using standard solid phase synthesis methods that are described in the oligonucleotide synthesis literature. Both unmodified and chemically modified siRNAs are known to produce effective knockdown following in vitro transfection. The DMPK siRNA sequences were synthesized using base, sugar and phosphate modifications that are described in the field of RNAi to optimize the potency of the duplex and reduce immunogenicity. Two human cell lines were used to assess the in vitro activity of the DMPK siRNAs: first. SJCRH30 human rhabdomyosarcoma cell line (ATCC® CRL-2061™); and second, Myotonic Dystrophy Type 1 (DM1) patient-derived immortalized human skeletal myoblasts. For the initial screening of the DMPK siRNA library, each DMPK siRNA was transfected into SJCRH30 cells at 1 nM and 0.01 nM final concentration, as well as into DM1 myoblasts at 10 nM and 1 nM final concentration. The siRNAs were formulated with transfection reagent Lipofectamine RNAiMAX (Life Technologies) according to the manufacturer's "forward transfection" instructions. Cells were plated 24 h prior to transfection in triplicate on 96-well tissue culture plates, with 8500 cells per well for SJCRH30 and 4000 cells per well for DM1 myoblasts. At 48 h (SJCRH30) or 72 h (DM1 myoblasts) post-transfection cells were washed with PBS and harvested with TRizol® reagent (Life Technologies). RNA was isolated using the Direct-zol-96 RNA Kit (Zymo Research) according to the manufacturer's instructions, 10 µl of RNA was reverse transcribed to cDNA using the High Capacity cDNA Reverse Transcription Kit (Applied Biosystems) according to the manufacturer's instructions. cDNA samples were evaluated by qPCR with DMPK-specific and PPIB-specific TaqMan human gene expression probes (Thermo Fisher) using TaqMan® Fast Advanced Master Mix (Applied Biosystems). DMPK values were normalized within each sample to PPTB gene expression. The quantification of DMPK downregulation was performed using the standard $2^{-\Delta\Delta Ct}$ method. All experiments were performed in triplicate, with Table 15A and Table 15B) presenting the mean values of the triplicates.

TABLE 15A

| ID #[1] | sense strand sequence (5'-3') Passenger Strand (PS) | SEQ ID NO: | antisense strand sequence (5'-3') Guide Strand (GS) | SEQ ID NO: |
|---|---|---|---|---|
| 385 | GCUUAAGGAGGUCCGACUA | 9199 | UAGUCGGACCUCCUUAAGC | 11903 |
| 443 | GGGGCGUUCAGCGAGGUAA | 9257 | UUACCUCGCUGAACGCCCC | 11961 |
| 444 | GGGCGUUCAGCGAGGUAGA | 9258 | UCUACCUCGCUGAACGCCC | 11962 |
| 445 | GGCGUUCAGCGAGGUAGCA | 9259 | UGCUACCUCGCUGAACGCC | 11963 |
| 533 | AGGGGCGAGGUGUCGUGCA | 9347 | UGCACGACACCUCGCCCCU | 12051 |
| 534 | GGGGCGAGGUGUCGUGCUA | 9348 | UAGCACGACACCUCGCCCC | 12052 |
| 535 | GGGCGAGGUGUCGUGCUUA | 9349 | UAAGCACGACACCUCGCCC | 12053 |
| 539 | GAGGUGUCGUGCUUCCGUA | 9353 | UACGGAAGCACGACACCUC | 12057 |
| 540 | AGGUGUCGUGCUUCCGUGA | 9354 | UCACGGAAGCACGACACCU | 12058 |
| 541 | GGUGUCGUGCUUCCGUGAA | 9355 | UUCACGGAAGCACGACACC | 12059 |
| 543 | UGUCGUGCUUCCGUGAGGA | 9357 | UCCUCACGGAAGCACGACA | 12061 |
| 544 | GUCGUGCUUCCGUGAGGAA | 9358 | UUCCUCACGGAAGCACGAC | 12062 |
| 576 | UGAAUGGGGACCGGCGGUA | 9390 | UACCGCCGGUCCCCAUUCA | 12094 |
| 577 | GAAUGGGGACCGGCGGUGA | 9391 | UCACCGCCGGUCCCCAUUC | 12095 |
| 581 | GGGGACCGGCGGUGGAUCA | 9395 | UGAUCCACCGCCGGUCCCC | 12099 |
| 583 | GGACCGGCGGUGGAUCACA | 9397 | UGUGAUCCACCGCCGGUCC | 12101 |
| 584 | GACCGGCGGUGGAUCACGA | 9398 | UCGUGAUCCACCGCCGGUC | 12102 |
| 690 | AGUUUGGGGAGCGGAUUCA | 9504 | UGAAUCCGCUCCCCAAACU | 12208 |
| 716 | AUGGCGCGCUUCUACCUGA | 9530 | UCAGGUAGAAGCGCGCCAU | 12234 |
| 717 | UGGCGCGCUUCUACCUGGA | 9531 | UCCAGGUAGAAGCGCGCCA | 12235 |
| 785 | AGGGACAUCAAACCCGACA | 9599 | UGUCGGGUUUGAUGUCCCU | 12303 |
| 786 | GGGACAUCAAACCCGACAA | 9600 | UUGUCGGGUUUGAUGUCCC | 12304 |
| 789 | ACAUCAAACCCGACAACAA | 9603 | UUGUUGUCGGGUUUGAUGU | 12307 |
| 1026 | GGCAGACGCCCUUCUACGA | 9840 | UCGUAGAAGGGCGUCUGCC | 12544 |
| 1027 | GCAGACGCCCUUCUACGCA | 9841 | UGCGUAGAAGGGCGUCUGC | 12545 |
| 1028 | CAGACGCCCUUCUACGCGA | 9842 | UCGCGUAGAAGGGCGUCUG | 12546 |

TABLE 15A-continued

| ID #[1] | sense strand sequence (5'-3') Passenger Strand (PS) | SEQ ID NO: | antisense strand sequence (5'-3') Guide Strand (GS) | SEQ ID NO: |
|---|---|---|---|---|
| 1029 | AGACGCCCUUCUACGCGGA | 9843 | UCCGCGUAGAAGGGCGUCU | 12547 |
| 1037 | UUCUACGCGGAUUCCACGA | 9851 | UCGUGGAAUCCGCGUAGAA | 12555 |
| 1039 | CUACGCGGAUUCCACGGCA | 9853 | UGCCGUGGAAUCCGCGUAG | 12557 |
| 1041 | ACGCGGAUUCCACGGCGGA | 9855 | UCCGCCGUGGAAUCCGCGU | 12559 |
| 1043 | GCGGAUUCCACGGCGGAGA | 9857 | UCUCCGCCGUGGAAUCCGC | 12561 |
| 1044 | CGGAUUCCACGGCGGAGAA | 9858 | UUCUCCGCCGUGGAAUCCG | 12562 |
| 1047 | AUUCCACGGCGGAGACCUA | 9861 | UAGGUCUCCGCCGUGGAAU | 12565 |
| 1071 | AGAUCGUCCACUACAAGGA | 9885 | UCCUUGUAGUGGACGAUCU | 12589 |
| 1073 | AUCGUCCACUACAAGGAGA | 9887 | UCUCCUUGUAGUGGACGAU | 12591 |
| 1262 | CCCUUUACACCGGAUUUCA | 10076 | UGAAAUCCGGUGUAAAGGG | 12780 |
| 1263 | CCUUUACACCGGAUUUCGA | 10077 | UCGAAAUCCGGUGUAAAGG | 12781 |
| 1264 | CUUUACACCGGAUUUCGAA | 10078 | UUCGAAAUCCGGUGUAAAG | 12782 |
| 1265 | UUUACACCGGAUUUCGAAA | 10079 | UUUCGAAAUCCGGUGUAAA | 12783 |
| 1267 | UACACCGGAUUUCGAAGGA | 10081 | UCCUUCGAAAUCCGGUGUA | 12785 |
| 1268 | ACACCGGAUUUCGAAGGUA | 10082 | UACCUUCGAAAUCCGGUGU | 12786 |
| 1269 | CACCGGAUUUCGAAGGUGA | 10083 | UCACCUUCGAAAUCCGGUG | 12787 |
| 1274 | GAUUUCGAAGGUGCCACCA | 10088 | UGGUGGCACCUUCGAAAUC | 12792 |
| 1276 | UUUCGAAGGUGCCACCGAA | 10090 | UUCGGUGGCACCUUCGAAA | 12794 |
| 1283 | GGUGCCACCGACACAUGCA | 10097 | UGCAUGUGUCGGUGGCACC | 12801 |
| 1297 | AUGCAACUUCGACUUGGUA | 10111 | UACCAAGUCGAAGUUGCAU | 12815 |
| 1342 | ACUGUCGGACAUUCGGGAA | 10156 | UUCCCGAAUGUCCGACAGU | 12860 |
| 1343 | CUGUCGGACAUUCGGGAAA | 10157 | UUUCCCGAAUGUCCGACAG | 12861 |
| 1344 | UGUCGGACAUUCGGGAAGA | 10158 | UCUUCCCGAAUGUCCGACA | 12862 |
| 1346 | UCGGACAUUCGGGAAGGUA | 10160 | UACCUUCCCGAAUGUCCGA | 12864 |
| 1825 | UGCUCCUGUUCGCCGUUGA | 10639 | UCAACGGCGAACAGGAGCA | 13343 |
| 1886 | CCACGCCGGCCAACUCACA | 10700 | UGUGAGUUGGCCGGCGUGG | 13404 |
| 1890 | GCCGGCCAACUCACCGCAA | 10704 | UUGCGGUGAGUUGGCCGGC | 13408 |
| 1898 | ACUCACCGCAGUCUGGCGA | 10712 | UCGCCAGACUGCGGUGAGU | 13416 |
| 1945 | CCCUAGAACUGUCUUCAA | 10759 | UUCGAAGACAGUUCUAGGG | 13463 |
| 1960 | CGACUCCGGGGCCCCGUUA | 10774 | UAACGGGGCCCCGGAGUCG | 13478 |
| 2126 | GCCGGCGAACGGGGCUCGA | 10940 | UCGAGCCCCGUUCGCCGGC | 13644 |
| 2127 | CCGGCGAACGGGGCUCGAA | 10941 | UUCGAGCCCCGUUCGCCGG | 13645 |
| 2149 | UCCUUGUAGCCGGGAAUGA | 10963 | UCAUUCCCGGCUACAAGGA | 13667 |
| 2150 | CCUUGUAGCCGGGAAUGCA | 10964 | UGCAUUCCCGGCUACAAGG | 13668 |
| 2268 | CCCUGACGUGGAUGGGCAA | 11082 | UUGCCCAUCCACGUCAGGG | 13786 |
| 2272 | GACGUGGAUGGGCAAACUA | 11086 | UAGUUUGCCCAUCCACGUC | 13790 |
| 2528 | GCUUCGGCGGUUUGGAUAA | 11342 | UUAUCCAAACCGCCGAAGC | 14046 |
| 2529 | CUUCGGCGGUUUGGAUAUA | 11343 | UAUAUCCAAACCGCCGAAG | 14047 |

TABLE 15A-continued

| ID #[1] | sense strand sequence (5'-3') Passenger Strand (PS) | SEQ ID NO: | antisense strand sequence (5'-3') Guide Strand (GS) | SEQ ID NO: |
|---|---|---|---|---|
| 2530 | UUCGGCGGUUUGGAUAUUA | 11344 | UAAUAUCCAAACCGCCGAA | 14048 |
| 2531 | UCGGCGGUUUGGAUAUUUA | 11345 | UAAAUAUCCAAACCGCCGA | 14049 |
| 2532 | CGGCGGUUUGGAUAUUUAA | 11346 | UUAAAUAUCCAAACCGCCG | 14050 |
| 2554 | CCUCGUCCUCCGACUCGCA | 11368 | UGCGAGUCGGAGGACGAGG | 14072 |
| 2558 | GUCCUCCGACUCGCUGACA | 11372 | UGUCAGCGAGUCGGAGGAC | 14076 |
| 2600 | CAAUCCACGUUUUGGAUGA | 11414 | UCAUCCAAAACGUGGAUUG | 14118 |
| 2628 | CCGACAUUCCUCGGUAUUA | 11442 | UAAUACCGAGGAAUGUCGG | 14146 |
| 2629 | CGACAUUCCUCGGUAUUUA | 11443 | UAAAUACCGAGGAAUGUCG | 14147 |
| 2631 | ACAUUCCUCGGUAUUUAUA | 11445 | UAUAAAUACCGAGGAAUGU | 14149 |
| 2636 | CCUCGGUAUUUAUUGUCUA | 11450 | UAGACAAUAAAUACCGAGG | 14154 |
| 2639 | CGGUAUUUAUUGUCUGUCA | 11453 | UGACAGACAAUAAAUACCG | 14157 |
| 2675 | CCCCGACCCUCGCGAAUAA | 11489 | UUAUUCGCGAGGGUCGGGG | 14193 |
| 2676 | CCCGACCCUCGCGAAUAAA | 11490 | UUUAUUCGCGAGGGUCGGG | 14194 |
| 2679 | GACCCUCGCGAAUAAAAGA | 11493 | UCUUUUAUUCGCGAGGGUC | 14197 |
| 2680 | ACCCUCGCGAAUAAAAGGA | 11494 | UCCUUUUAUUCGCGAGGGU | 14198 |
| 2681 | CCCUCGCGAAUAAAAGGCA | 11495 | UGCCUUUUAUUCGCGAGGG | 14199 |
| 2682 | CCUCGCGAAUAAAAGGCCA | 11496 | UGGCCUUUUAUUCGCGAGG | 14200 |
| Neg. Control | n/a | n/a | n/a | n/a |

[1] 19mer position in NM_001288766.1

TABLE 15B

| ID #[1] | qPCR[2] | qPCR[3] | qPCR[4] | qPCR[5] | ID #[1] | qPCR[22] | qPCR[3] | qPCR[4] | qPCR[5] |
|---|---|---|---|---|---|---|---|---|---|
| 385 | 150.8 | 153.8 | 64.1 | 142.5 | 1269 | 42.6 | 49.1 | 42.4 | 96.7 |
| 443 | 112.7 | 95.8 | 56.7 | 127.8 | 1274 | 63.6 | 55.4 | 78.0 | 98.5 |
| 444 | 76.5 | 66.2 | 36.7 | 113.6 | 1276 | 52.2 | 36.9 | 35.2 | 82.5 |
| 445 | 61.4 | 107.7 | 29.4 | 110.8 | 1283 | 35.2 | 62.8 | 56.6 | 95.9 |
| 533 | 168.8 | 119.8 | 85.7 | 118.1 | 1297 | 20.3 | 55.7 | 32.2 | 91.0 |
| 534 | 91.4 | 44.8 | 26.7 | 94.2 | 1342 | 44.6 | 46.7 | 41.5 | 94.5 |
| 535 | 101.0 | 65.9 | 33.1 | 109.9 | 1343 | 65.8 | 80.0 | 56.1 | 119.2 |
| 539 | 81.7 | 70.2 | 34.1 | 102.4 | 1344 | 30.9 | 63.7 | 51.7 | 116.7 |
| 540 | 68.3 | 56.8 | 40.0 | 114.6 | 1346 | 133.8 | 102.9 | 98.0 | 104.0 |
| 541 | 112.1 | 107.3 | 73.8 | 120.6 | 1825 | 54.1 | 69.2 | 28.6 | 86.7 |
| 543 | 42.6 | 59.9 | 41.9 | 117.8 | 1886 | 786.9 | 282.0 | 130.5 | 98.4 |
| 544 | 42.4 | 107.5 | 66.9 | 154.7 | 1890 | 28.8 | 30.3 | 51.5 | 94.4 |
| 576 | 107.4 | 119.0 | 85.0 | 127.5 | 1898 | 125.5 | 57.5 | 67.7 | 97.6 |
| 577 | 101.6 | 90.1 | 72.1 | 106.6 | 1945 | 23.5 | 22.6 | 21.8 | 57.6 |
| 581 | 199.3 | 97.7 | 69.9 | 103.5 | 1960 | 28.4 | 33.7 | 35.7 | 87.9 |
| 583 | 66.6 | 77.5 | 66.4 | 100.3 | 2126 | 147.9 | 87.2 | 86.8 | 98.1 |
| 584 | 26.3 | 37.3 | 31.0 | 88.3 | 2127 | 46.5 | 51.9 | 52.7 | 96.2 |
| 690 | 163.6 | 84.1 | 58.0 | 92.7 | 2149 | 44.7 | 41.5 | 62.0 | 99.6 |
| 716 | 29.0 | 39.6 | 29.4 | 86.0 | 2150 | 110.4 | 89.1 | 63.4 | 114.1 |
| 717 | 44.4 | 45.7 | 52.8 | 102.5 | 2268 | 53.5 | 48.6 | 60.8 | 113.1 |
| 785 | 79.9 | 93.2 | 71.3 | 101.0 | 2272 | 56.5 | 54.7 | 46.9 | 92.5 |
| 786 | 85.5 | 63.8 | 54.3 | 92.2 | 2528 | 32.5 | 32.8 | 32.7 | 76.9 |
| 789 | 45.4 | 51.3 | 43.8 | 96.9 | 2529 | 19.6 | 25.8 | 21.4 | 59.5 |
| 1026 | 55.6 | 77.3 | 32.0 | 110.4 | 2530 | 29.5 | 25.9 | 32.8 | 68.1 |
| 1027 | 98.9 | 94.7 | 35.2 | 108.3 | 2531 | 22.2 | 31.6 | 25.4 | 64.3 |
| 1028 | 132.1 | 104.9 | 27.3 | 87.3 | 2532 | 44.4 | 35.6 | 29.2 | 74.0 |
| 1029 | 62.2 | 95.5 | 45.9 | 94.2 | 2554 | 13.7 | 22.6 | 26.8 | 60.9 |
| 1037 | 68.2 | 80.2 | 65.3 | 97.0 | 2558 | 54.6 | 47.4 | 28.0 | 72.0 |
| 1039 | 42.3 | 79.3 | 53.6 | 97.0 | 2600 | 205.4 | 209.6 | n.d. | n.d. |
| 1041 | 67.2 | 64.4 | 73.2 | 98.6 | 2628 | 12.6 | 28.5 | 20.1 | 56.2 |
| 1043 | 342.8 | 86.6 | 61.5 | 96.5 | 2629 | 12.8 | 39.5 | 20.6 | 63.8 |

TABLE 15B-continued

| ID #[1] | qPCR[2] | qPCR[3] | qPCR[4] | qPCR[5] | ID #[1] | qPCR[22] | qPCR[3] | qPCR[4] | qPCR[5] |
|---|---|---|---|---|---|---|---|---|---|
| 1044 | 109.5 | 84.8 | 42.7 | 94.0 | 2631 | 97.4 | 68.6 | 39.7 | 104.4 |
| 1047 | 101.3 | 72.1 | 35.2 | 90.7 | 2636 | 62.0 | 68.6 | 16.8 | 58.7 |
| 1071 | 88.5 | 99.6 | 91.6 | 101.3 | 2639 | 33.2 | 46.1 | 22.2 | 81.0 |
| 1073 | 134.3 | 63.0 | 36.3 | 93.6 | 2675 | 57.7 | 82.5 | n.d. | n.d. |
| 1262 | 36.5 | 59.6 | 27.3 | 117.5 | 2676 | 31.1 | 53.0 | n.d. | n.d. |
| 1263 | 47.6 | 79.7 | 33.9 | 104.3 | 2679 | 44.7 | 75.7 | n.d. | n.d. |
| 1264 | 64.2 | 54.5 | 43.7 | 95.4 | 2680 | 89.2 | 61.5 | n.d. | n.d. |
| 1265 | 19.8 | 57.6 | 30.9 | 91.6 | 2681 | 19.0 | 28.6 | n.d. | n.d. |
| 1267 | 61.3 | 85.9 | 73.4 | 97.1 | 2682 | 98.2 | 61.8 | n.d. | n.d. |
| 1268 | 32.0 | 28.3 | 38.0 | 92.3 | Neg. Control | 101.2 | 100.6 | 101.1 | 106.4 |

[2]DM1 myoblasts; 10 nM; % DMPK mRNA
[3]DM1 myoblasts; 1 nM; % DMPK mRNA
[4]SJCRH30; 1 nM; % DMPK mRNA
[5]SJCRH30; 0.01 nM; % DMPK mRNA

Example 17: In Vitro Dose Response Curves for a Selected Set of DMPK siRNAs

To further validate the activity of the DMPK siRNAs, many of the sequences that showed the best activity in the initial screen were selected for a follow-up evaluation in dose response format. Once again, two human cell lines were used to assess the in vitro activity of the DMPK siRNAs: first, SJCRH30 human rhabdomyosarcoma cell line; and second, Myotonic Dystrophy Type 1 (DM1) patient-derived immortalized human skeletal myoblasts. The selected siRNAs were transfected in a 10-fold dose response at 100, 10, 1, 0.1, 0.01, 0.001, and 0,0001 nM final concentrations or in a 9-fold dose response at 50, 5.55556, 0.617284, 0.068587, 0.007621, 0,000847, and 0,000094 nM final concentrations. The siRNAs were formulated with transfection reagent Lipofectamine RNAiMAX (Life Technologies) according to the manufacturer's "forward transfection" instructions. Cells were plated 24 h prior to transfection in triplicate on 96-well tissue culture plates, with 8500 cells per well for SJCRH30 and 4000 cells per well for DM1 myoblasts. At 48 h (SJCRH30) or 72 h (DM1 myoblasts) post-transfection cells were washed with PBS and harvested with TRIzol® reagent (Life Technologies). RNA was isolated using the Direct-zol-96 RNA Kit (Zymo Research) according to the manufacturer's instructions. 10 µl of RNA was reverse transcribed to cDNA using the High Capacity cDNA Reverse Transcription Kit (Applied Biosystems) according to the manufacturer's instructions. cDNA samples were evaluated by qPCR with DMPK-specific and PPIB-specific TaqMan human gene expression probes (Thermo Fisher) using TaqMan® Fast Advanced Master Mix (Applied Biosystems). DMPK values were normalized within each sample to PPIB gene expression. The quantification of DMPK downregulation was performed using the standard $2^{-\Delta\Delta Ct}$ method. All experiments were performed in triplicate, with Tables 16A-B, 17A-B, and 18A-B presenting the mean values of the triplicates as well as the calculated $IC_{50}$ values determined from fitting curves to the dose-response data by non-linear regression.

TABLE 16A

| ID #[1] | sense strand sequence (5'-3') Passenger Strand (PS) | SEQ ID NO: | antisense strand sequence (5'-3') Guide Strand (GS) | SEQ ID NO: |
|---|---|---|---|---|
| 535 | GGGCGAGGUGUCGUGCUUA | 9349 | UAAGCACGACACCUCGCCC | 12053 |
| 584 | GACCGGCGGUGGAUCACGA | 9398 | UCGUGAUCCACCGCCGGUC | 12102 |
| 716 | AUGGCGCGCUUCUACCUGA | 9530 | UCAGGUAGAAGCGCGCCAU | 12234 |
| 1028 | CAGACGCCCUUCUACGCGA | 9842 | UCGCGUAGAAGGGCGUCUG | 12546 |
| 1276 | UUUCGAAGGUGCCACCGAA | 10090 | UUCGGUGGCACCUUCGAAA | 12794 |
| 1825 | UGCUCCUGUUCGCCGUUGA | 10639 | UCAACGGCGAACAGGAGCA | 13343 |
| 1945 | CCCUAGAACUGUCUUCGAA | 10759 | UUCGAAGACAGUUCUAGGG | 13463 |
| 2529 | CUUCGGCGGUUUGGAUAUA | 11343 | UAUAUCCAAACCGCCGAAG | 14047 |
| 2558 | GUCCUCCGACUCGCUGACA | 11372 | UGUCAGCGAGUCGGAGGAC | 14076 |
| 2628 | CCGACAUUCCUCGGUAUUA | 11442 | UAAUACCGAGGAAUGUCGG | 14146 |
| 2636 | CCUCGGUAUUUAUUGUCUA | 11450 | UAGACAAUAAAUACCGAGG | 14154 |

[1]19mer position in NM_001288766.1

TABLE 16B

| ID #[1] | qPCR[2] | qPCR[3] | qPCR[4] | qPCR[5] | qPCR[6] | qPCR[7] | qPCR[8] | IC50 (nM) |
|---|---|---|---|---|---|---|---|---|
| 535 | 111.9 | 105.4 | 106.3 | 82.4 | 36.7 | 29.5 | 35.7 | 0.165 |
| 584 | 90.5 | 90.2 | 84.7 | 67.8 | 38.0 | 25.8 | 28.3 | 0.190 |
| 716 | 88.9 | 85.2 | 81.9 | 62.0 | 32.6 | 19.3 | 20.3 | 0.181 |
| 1028 | 88.5 | 81.8 | 83.0 | 61.3 | 32.7 | 27.3 | 31.5 | 0.127 |
| 1276 | 87.0 | 85.0 | 84.0 | 66.1 | 40.5 | 34.0 | 36.4 | 0.150 |
| 1825 | 85.1 | 85.9 | 83.7 | 69.1 | 36.2 | 25.2 | 25.0 | 0.259 |
| 1945 | 85.0 | 81.7 | 74.4 | 44.9 | 22.9 | 17.7 | 17.2 | 0.070 |
| 2529 | 83.3 | 81.8 | 75.3 | 50.6 | 24.6 | 17.5 | 17.7 | 0.103 |
| 2558 | 84.3 | 81.1 | 74.3 | 45.4 | 23.4 | 13.3 | 11.8 | 0.088 |
| 2628 | 85.3 | 84.0 | 79.5 | 59.8 | 30.3 | 23.5 | 25.1 | 0.140 |
| 2636 | 86.3 | 86.9 | 74.3 | 44.0 | 19.8 | 12.4 | 13.0 | 0.070 |

[2]SJCRH30; 0.0001 nM; % DMPK mRNA
[3]SJCRH30; 0.001 nM; % DMPK mRNA
[4]SJCRH30; 0.01 nM; % DMPK mRNA
[5]SJCRH30; 0.1 nM; % DMPK mRNA
[6]SJCRH30; 1 nM; % DMPK mRNA
[7]SJCRH30; 10 nM; % DMPK mRNA
[8]SJCRH30; 100 nM; % DMPK mRNA

TABLE 17A

| ID #[1] | sense strand sequence (5'-3') Passenger Strand (PS) | SEQ ID NO: | antisense strand sequence (5'-3') Guide Strand (GS) | SEQ ID NO: |
|---|---|---|---|---|
| 2600 | CAAUCCACGUUUUGGAUGA | 11414 | UCAUCCAAAACGUGGAUUG | 14118 |
| 2636 | CCUCGGUAUUUAUUGUCUA | 11450 | UAGACAAUAAAUACCGAGG | 14154 |
| 2675 | CCCCGACCCUCGCGAAUAA | 11489 | UUAUUCGCGAGGGUCGGGG | 14193 |
| 2676 | CCCGACCCUCGCGAAUAAA | 11490 | UUUAUUCGCGAGGGUCGGG | 14194 |
| 2679 | GACCCUCGCGAAUAAAAGA | 11493 | UCUUUUAUUCGCGAGGGUC | 14197 |
| 2680 | ACCCUCGCGAAUAAAAGGA | 11494 | UCCUUUUAUUCGCGAGGGU | 14198 |
| 2681 | CCCUCGCGAAUAAAAGGCA | 11495 | UGCCUUUUAUUCGCGAGGG | 14199 |
| 2682 | CCUCGCGAAUAAAAGGCCA | 11496 | UGGCCUUUUAUUCGCGAGG | 14200 |

[1]19mer position in NM_001288766.1

TABLE 17B

| ID #[1] | qPCR[2] | qPCR[3] | qPCR[4] | qPCR[5] | qPCR[6] | qPCR[7] | IC50 (nM) |
|---|---|---|---|---|---|---|---|
| 2600 | 107.5 | 107.6 | 108.1 | 106.3 | 103.1 | 72.7 | 31.31 |
| 2636 | 81.1 | 81.1 | 74.0 | 47.2 | 25.7 | 11.5 | 0.073 |
| 2675 | 88.1 | 88.3 | 84.3 | 64.6 | 38.1 | 20.7 | 0.151 |
| 2676 | 88.9 | 78.9 | 84.4 | 72.7 | 44.9 | 35.6 | 0.204 |
| 2679 | 84.0 | 87.3 | 82.7 | 53.3 | 31.4 | 13.5 | 0.091 |
| 2680 | 87.4 | 85.3 | 85.1 | 68.5 | 44.5 | 39.6 | 0.110 |
| 2681 | 87.0 | 85.4 | 77.6 | 49.6 | 26.5 | 16.0 | 0.061 |
| 2682 | 82.4 | 83.9 | 77.1 | 50.8 | 27.3 | 31.1 | 0.047 |

[2]SJCRH30. 0.000094 nM; % DMPK mRNA
[3]SJCRH30. 0.000847 nM; % DMPK mRNA
[4]SJCRH30. 0.007621 nM; % DMPK mRNA
[5]SJCRH30. 0.068587 nM; % DMPK mRNA
[6]SJCRH30. 0.617284 nM; % DMPK mRNA
[7]SJCRH30. 5.55556 nM; % DMPK mRNA

TABLE 18A

| ID #[1] | sense strand sequence (5'-3') Passenger Strand (PS) | SEQ ID NO: | antisense strand sequence (5'-3') Guide Strand (GS) | SEQ ID NO: |
|---|---|---|---|---|
| 584 | GACCGGCGGUGGAUCACGA | 9398 | UCGUGAUCCACCGCCGGUC | 12102 |
| 716 | AUGGCGCGCUUCUACCUGA | 9530 | UCAGGUAGAAGCGCGCCAU | 12234 |
| 1265 | UUUACACCGGAUUUCGAAA | 10079 | UUUCGAAAUCCGGUGUAAA | 12783 |
| 1297 | AUGCAACUUCGACUUGGUA | 10111 | UACCAAGUCGAAGUUGCAU | 12815 |
| 1945 | CCCUAGAACUGUCUUCGAA | 10759 | UUCGAAGACAGUUCUAGGG | 13463 |
| 1960 | CGACUCCGGGGCCCCGUUA | 10774 | UAACGGGGCCCCGGAGUCG | 13478 |
| 2529 | CUUCGGCGGUUUGGAUAUA | 11343 | UAUAUCCAAACCGCCGAAG | 14047 |
| 2530 | UUCGGCGGUUUGGAUAUUA | 11344 | UAAUAUCCAAACCGCCGAA | 14048 |
| 2531 | UCGGCGGUUUGGAUAUUUA | 11345 | UAAAUAUCCAAACCGCCGA | 14049 |
| 2554 | CCUCGUCCUCCGACUCGCA | 11368 | UGCGAGUCGGAGGACGAGG | 14072 |
| 2628 | CCGACAUUCCUCGGUAUUA | 11442 | UAAUACCGAGGAAUGUCGG | 14146 |
| 2629 | CGACAUUCCUCGGUAUUUA | 11443 | UAAAUACCGAGGAAUGUCG | 14147 |
| 2681 | CCCUCGCGAAUAAAAGGCA | 11495 | UGCCUUUUAUUCGCGAGGG | 14199 |

[1] 19mer position in NM_001288766.1

TABLE 18B

| ID #[1] | qPCR[2] | qPCR[3] | qPCR[4] | qPCR[5] | qPCR[6] | qPCR[7] | IC50 (nM) |
|---|---|---|---|---|---|---|---|
| 584 | 90.8 | 77.0 | 97.7 | 71.9 | 45.0 | 29.7 | 0.228 |
| 716 | 96.5 | 82.5 | 77.0 | 64.6 | 43.3 | 33.9 | 0.080 |
| 1265 | 68.5 | 80.9 | 68.0 | 57.1 | 37.5 | 25.7 | 0.146 |
| 1297 | 71.4 | 67.2 | 69.4 | 53.5 | 40.5 | 25.4 | 0.171 |
| 1945 | 71.8 | 62.3 | 41.7 | 29.8 | 22.4 | 15.3 | 0.006 |
| 1960 | 63.0 | 65.4 | 62.1 | 45.8 | 31.1 | 28.3 | 0.068 |
| 2529 | 63.5 | 58.7 | 49.2 | 31.1 | 22.9 | 21.9 | 0.017 |
| 2530 | 69.3 | 66.7 | 53.1 | 43.2 | 38.8 | 24.5 | 0.016 |
| 2531 | 69.9 | 72.4 | 57.3 | 40.2 | 35.4 | 25.6 | 0.018 |
| 2554 | 68.2 | 70.1 | 51.2 | 43.0 | 32.1 | 17.3 | 0.043 |
| 2628 | 69.7 | 67.9 | 62.5 | 38.4 | 31.6 | 17.1 | 0.042 |
| 2629 | 72.1 | 65.6 | 69.0 | 42.1 | 34.4 | 13.7 | 0.078 |
| 2681 | 82.4 | 91.5 | 87.6 | 55.5 | 29.3 | 19.6 | 0.084 |

Figure 17:
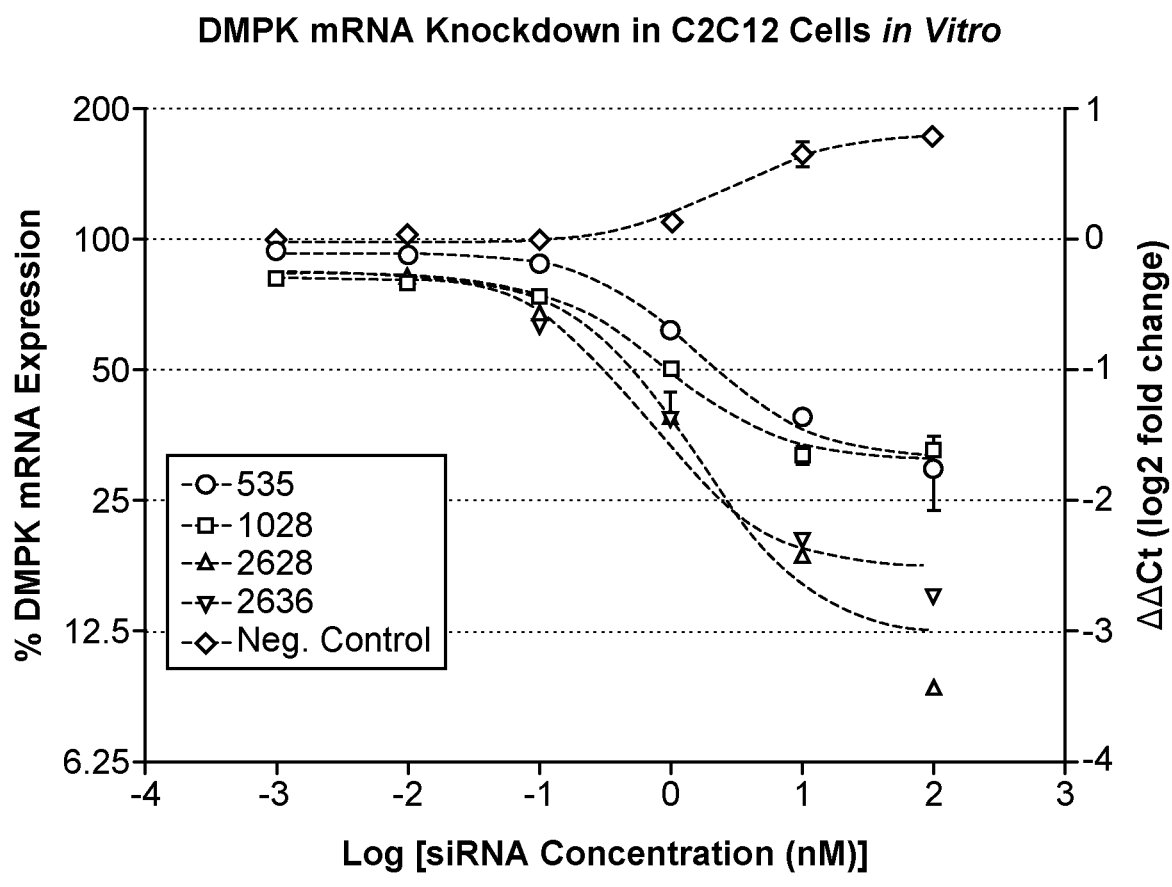
FIG. 17 illustrates siRNAs that were transfected into mouse C2C12 myoblasts in vitro. The four DMPK siRNAs assessed all showed DMPK mRNA knockdown, while the negative control siRNA did not. The dotted lines are three-parameter curves fit by non-linear regression.
Figure 18A:
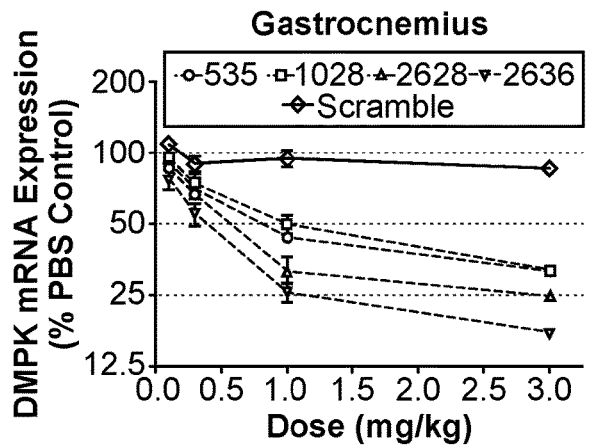
FIG. 18A-FIG. 18F show in vivo results demonstrating robust dose-responses for DMPK mRNA knockdown 7 days after a single i.v. administration of DMPK siRNA-antibody conjugates.
Figure 18B:
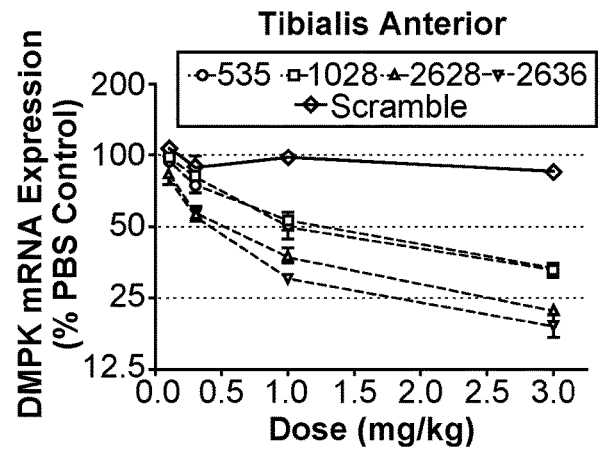
Figure 18C:
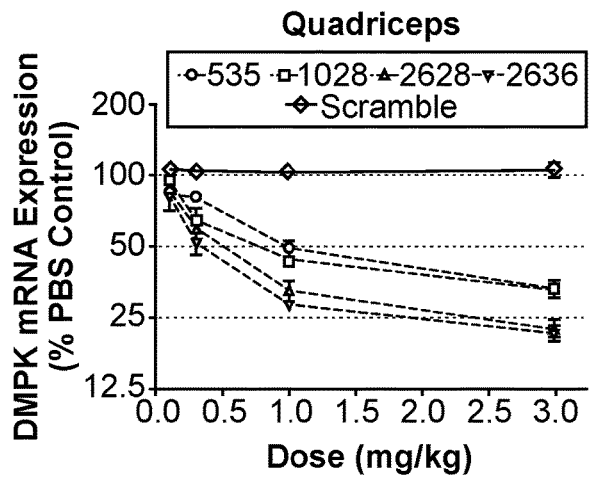
Figure 18D:
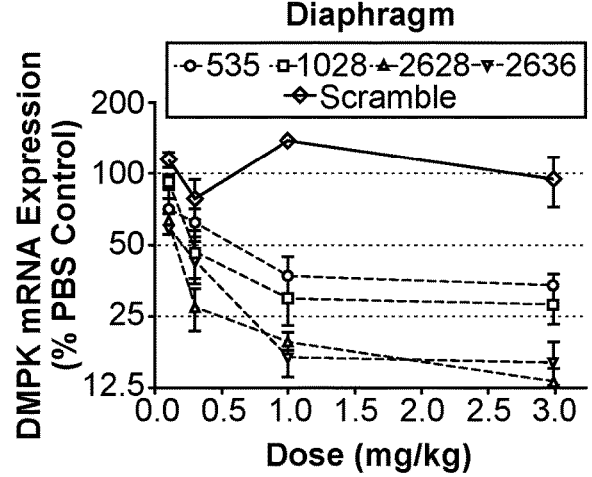
Figure 18E:
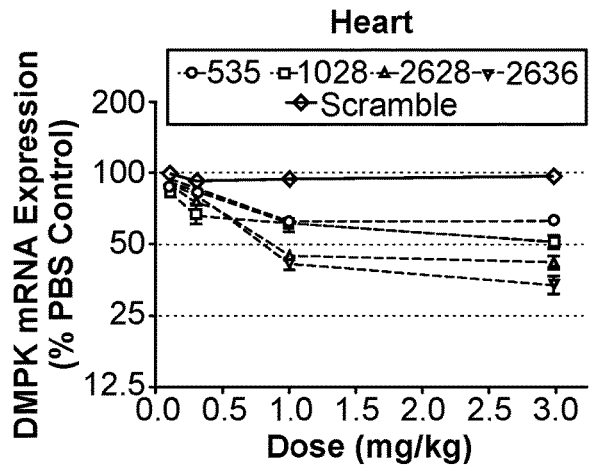
Figure 18F:
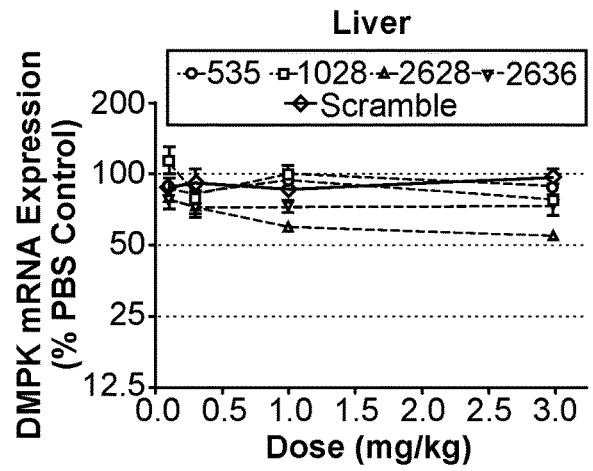

[2] DM1 myoblasts; 0.000094 nM; % DMPK mRNA
[3] DM1 myoblasts; 0.000847 nM; % DMPK mRNA
[4] DM1 myoblasts; 0.007621 nM; % DMPK mRNA
[5] DM1 myoblasts; 0.068587 nM; % DMPK mRNA
[6] DM1 myoblasts; 0.617284 nM; % DMPK mRNA
[7] DM1 myoblasts; 5.55556 nM; % DMPK mRNA Example 18: In Vitro Experiments to Determine Species Cross-Reactivity in Mouse The selected siRNAs were transfected at 100, 10, 1, 0.1, 0.01, 0.001, and 0,000 nM final concentrations into C2C12 mouse muscle myoblasts (ATCC® CRL-1772™). The siRNAs were formulated with transfection reagent Lipofectamine RNAiMAX (Life Technologies) according to the manufacturer's "forward transfection" instructions. Cells were plated 24 h prior to transfection in triplicate on 96-well tissue culture plates, with 4000 cells per well for C2C12 seeding. At 48 h post-transfection cells were washed with PBS and harvested with TRIzol® reagent (Life Technologies). RNA was isolated using the Direct-zol-96 RNA Kit (Zymo Research) according to the manufacturer's instructions. 10 μl of RNA was reverse transcribed to cDNA using the High Capacity cDNA Reverse Transcription Kit (Applied Biosystems) according to the manufacturer's instructions. cDNA samples were evaluated by qPCR with DMPK-specific and PPIB-specific TaqMan mouse gene expression probes (Thermo Fisher) using TaqMan® Fast Advanced Master Mix (Applied Biosystems). DMPK values were normalized within each sample to PPIB gene expression. The quantification of DMPK downregulation was performed using the standard $2^{-\Delta\Delta Ct}$ method. All experiments were performed in triplicate, with the results shown in FIG. 17. Four DMPK siRNAs (the numbers indicated in the FIG. 17 legend correspond to the ID # that is listed in Table 19 (Tables 19A-19B)) were shown to effectively cross-react with mouse DMPK mRNA, producing robust mRNA knockdown in the mouse C2C12 myoblast cell line. Two of the siRNAs (ID #s 535 and 1028) were slightly less effective and only produced approximately 70% maximum mRNA knockdown. Two of the siRNAs (ID #s 2628 and 2636) were more effective and produced approximately 90% maximum mRNA knockdown.

Example 19: In Vivo Experiments to Determine Species Cross-Reactivity in Mouse

Animals

All animal studies were conducted following protocols in accordance with the Institutional Animal Care and Use Committee (IACUC) at Explore BioLabs, which adhere to the regulations outlined in the USDA Animal Welfare Act as well as the "Guide for the Care and Use of Laboratory Animals" (National Research Council publication, 8° Ed., revised in 2011). All mice were obtained from either Charles River Laboratories or Harlan Laboratories.

Conjugate Preparation

The in vivo studies used a total of five siRNAs: four DMPK siRNAs that were shown to be cross-reactive with mouse in vitro (FIG. 17) and one siRNA with a scrambled sequence that does not produce DMPK knockdown and can be used as a negative control. All siRNAs were synthesized using standard solid phase synthesis methods that are described in the oligonucleotide synthesis literature. The single strands were purified by HPLC using standard methods and then pure single strands were mixed at equimolar ratios to generate pure duplexes. All siRNAs were synthesized with a hexylamine linker on the 5' end of the passenger (sense) strand that can act as a conjugation handle for linkage to the antibody. The siRNAs were synthesized using optimal base, sugar, and phosphate modifications that are well described in the field of RNAi to maximize the potency, maximize the metabolic stability, and minimize the immunogenicity of the duplex.

The anti-mouse transferrin receptor (TfR1, also known as CD71) monoclonal antibody (mAb) is a rat IgG2a subclass monoclonal antibody that binds mouse CD71 protein with high affinity. This CD71 antibody was produced by BioXcell and it is commercially available (Catalog #BE0175). The antibody-siRNA conjugates were synthesized using the CD71 mAb from BioXcell and the respective DMPK or scramble siRNAs. All conjugates were synthesized through cysteine conjugation to the antibody and amine conjugation to the siRNA (through the hexylamine) utilizing a bismaleimide-TFP ester linker as previously described. All conjugates were purified by strong cation exchange (SAX) to isolate only the conjugate with a drug-antibody ratio (DAR) equal to 1 (i.e. a molar ratio of 1 siRNA per mAb), as previously described. All antibody-siRNA conjugates were formulated by dilution in PBS for in vivo dosing.

In Vivo Dosing and Analysis

Purified DAR1 antibody-siRNA conjugates were dosed into groups (n=4) of female wild-type CD-1 mice (446 weeks old) at 0.1, 0.3, 1, and 3 mg/kg (based on the weight of siRNA) by a single i.v. bolus injection into the tail vein at a dosing volume of 5 mL/kg. A single sham dose of PBS vehicle was injected at matched dose volumes into a control group (n=5) of female wild-type CD-1 mice (also 4-6 weeks old). The mice were sacrificed by $CO_2$ asphyxiation 7 days post-dose and 20-30 mg pieces of multiple tissues (gastrocnemius, tibialis anterior, quadriceps, diaphragm, heart, and liver) were harvested from each mouse and snap-frozen in liquid nitrogen. TRIzol® reagent (Life Technologies) was added and then each tissue piece was homogenized using a TissueLyser II (Qiagen). RNA was isolated using the Directzol-96 RNA Kit (Zymo Research) according to the manufacturer's instructions. 10 µl of RNA was reverse transcribed to cDNA using the High Capacity cDNA Reverse Transcription Kit (Applied Biosystems) according to the manufacturer's instructions. cDNA samples were evaluated by qPCR with DMPK-specific and PPIB-specific TaqMan mouse gene expression probes (Thermo Fisher) using TaqMan® Fast Advanced Master Mix (Applied Biosystems). DMPK values were normalized within each sample to PPIB gene expression. The quantification of DMPK downregulation was performed using the standard $2^{-\Delta\Delta Ct}$ method by comparing the treated animals to the PBS control group. The in vivo DMPK mRNA knockdown results are presented in FIG. 18A-FIG. 18F. All four DMPK siRNAs (the numbers indicated in the FIG. 18A-FIG. 18F legends correspond to the ID # that is listed in Table 19 (Tables 19A-19B)) were shown to effectively reduce levels of DMPK mRNA in all skeletal muscles that were analyzed (gastrocnemius, tibialis anterior, quadriceps, and diaphragm) in a dose-dependent manner. The most active siRNA achieved greater than 75% DMPK mRNA knockdown in all skeletal muscles at the highest dose (3 mg/kg). The in vivo DMPK knockdown observed in skeletal muscles of mice (FIG. 18A-FIG. 18F) correlated well with the in vivo DMPK knockdown observed in the mouse C2C12 myoblast cell line (FIG. 17), with siRNA ID #s 2628 and 2636 demonstrating higher mRNA knockdown than siRNA ID #s 535 and 1028. In addition to DMPK mRNA knockdown in skeletal muscle, strong activity (greater than 50% mRNA knockdown) was observed in mouse cardiac muscle (heart) as well. Finally, poor activity (less than 50% mRNA knockdown) was observed in mouse liver. These results demonstrate that it is possible to achieve robust DMPK mRNA knockdown in multiple mouse muscle groups (including both skeletal and cardiac), while minimizing the knockdown in off-target tissues such as the liver.

Example 20: siRNA Synthesis

All siRNA single strands were fully assembled on solid phase using standard phospharamidite chemistry and purified using HPLC. Base, sugar and phosphate modifications that are well described in the field of RNAi were used to optimize the potency of the duplex and reduce immunogenicity. All the siRNA passenger strands contained a C6-NH$_2$ conjugation handle on the 5' end, sec FIG. 20A-FIG. 21B. For the 21mer duplex with 19 bases of complementarity and 3' dinucleotide overhangs, the conjugation handle was connected to siRNA passenger strand via an inverted abasic phosphodiester, see FIG. 20A-FIG. 20B for the structures. For the blunt ended duplex with 19 bases of complementarity and one 3' dinucleotide overhang the conjugation handle was connected to siRNA passenger strand via a phosphodiester on the terminal base, see FIG. 21A-FIG. 21B for the structures.

Purified single strands were duplexed to get the double stranded siRNA.

Example 21: 2017-PK-401-C57BL6: In Vivo Transferrin mAb Conjugate Delivery of Various Atrogin-1 siRNAs For groups 1-4, see study design in FIG. 22, the 21mer Atrogin-1 guide strand was designed. The sequence (5' to 3') of the guide/antisense strand was UCUACGUAGUUGAAUCUUCUU (SEQ ID NO: 14230). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linker. Because the free thiol was not being used for conjugation, it was end capped with N-ethylmaleimide.

Antibody siRNA Conjugate Synthesis using bis-maleimide (BisMal) linker

Step 1: Antibody Reduction with TCEP

Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated, and buffer exchanged with pH 7.4 PBS.

Anion Exchange Chromatography Method (SAX)-1.

Column: Tosoh Bioscience, TSKGel SuperQ-5PW, 21.5 mm ID×15 cm, 13 um

Solvent A: 20 mM TRIS buffer, pH 8.0; Solvent B: 20 mM TRIS, 1.5 M NaCl, pH 8.0; Flow Rate: 6.0 ml/min Gradient:

|    | % A | % B | Column Volume |
|----|-----|-----|---------------|
| a. |     |     |               |
| b. | 100 | 0   | 1             |
| c. | 81  | 19  | 0.5           |
| d. | 50  | 50  | 13            |
| e. | 40  | 60  | 0.5           |
| f. | 0   | 100 | 0.5           |
| g. | 1000|     | 2             |

Anion Exchange Chromatography (SAX) Method-2

Column: Thermo Scientific. ProPac™ SAX-10, Bio LC™, 4×250 mm

Solvent A: 80%, 10 mM TRIS pH 8, 20% ethanol; Solvent B: 80% 10 mM TRIS pH 8, 20% ethanol, 1.5 M NaCl; Flow Rate: 0.75 ml/min Gradient:

|    | Time  | % A | % B |
|----|-------|-----|-----|
| a. |       |     |     |
| b. | 0.0   | 90  | 10  |
| c. | 3.00  | 90  | 10  |
| d. | 11.00 | 40  | 60  |
| e. | 14.00 | 40  | 60  |
| f. | 15.00 | 20  | 80  |
| g. | 16.00 | 90  | 10  |
| h. | 20.00 | 90  | 10  |

Step-3: Analysis of the Purified Conjugate

The purity of the conjugate was assessed by analytical HPLC using anion exchange chromatography method-2. For conjugate mTfR1-mAb-Atrogin-1 (DAR1), the SAX retention time was 9.1 min and % purity (by chromatographic peak area) was 99.

In Vivo Study Design

The conjugates were assessed for their ability to mediate mRNA downregulation of Atrogin-1 in skeletal muscle, in an in vivo experiment (C57BL6 mice). Mice were dosed via intravenous (iv) injection with PBS vehicle control and the indicated ASCs and doses, see FIG. 22. After the indicated time points, gastrocnemius (gastroc) and heart muscle tissues were harvested and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct).

Results

Figure 23:
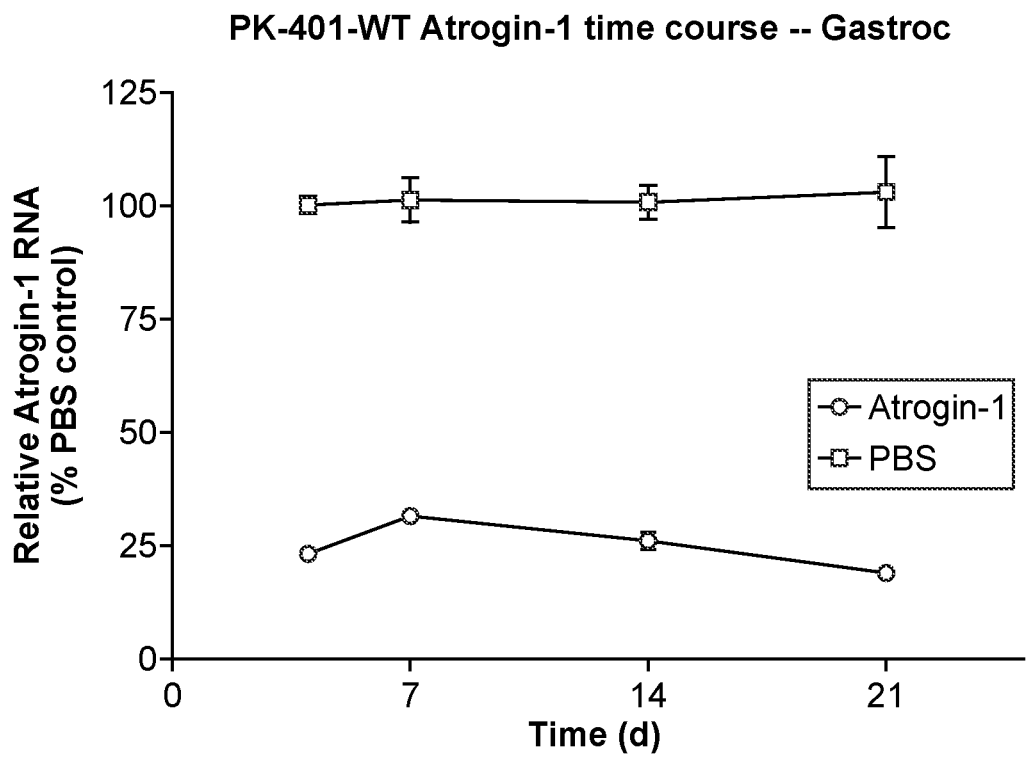
FIG. 23 illustrates a time course of Atrogin-1 mRNA downregulation in gastroc muscle mediated by a TfR1 antibody siRNA conjugate after IV delivery at a dose of a single dose of 3 mg/kg.
Figure 24:
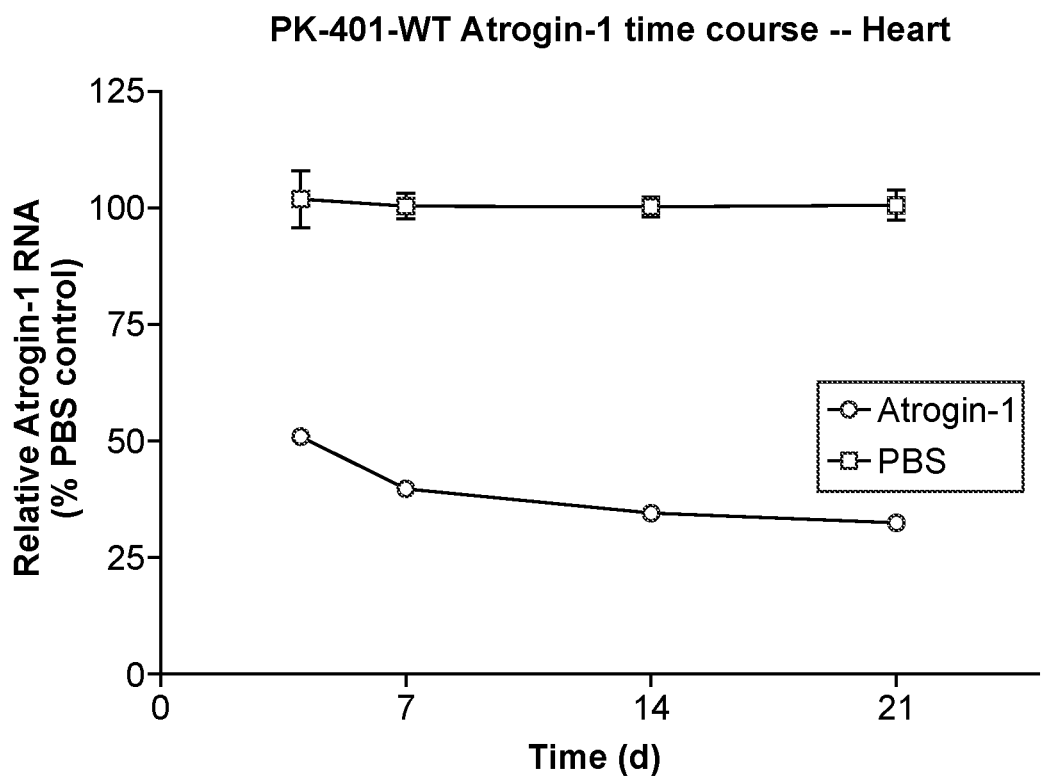
FIG. 24 illustrates a time course of Atrogin-1 mRNA downregulation in heart muscle mediate by a TfR1 antibody siRNA conjugate after IV delivery at a dose of a single dose of 3 mg/kg.

The Atrogin-1 siRNA guide strands was able to mediate downregulation of the target gene in gastroc and heart muscle when conjugated to an anti-TfR mAb targeting the transferrin receptor, see FIG. 23 and FIG. 24.

Conclusions

In this example, it was demonstrated that a TfR1-siAtrogin-1 conjugate, after in vivo delivery, mediated specific down regulation of the target gene in gastroc and heart muscle. The ASC was made with an anti-transferrin antibody, mouse gastroc and heart muscle expresses the transferrin receptor and the conjugate has a mouse specific anti-transferrin antibody to target the siRNA, resulting in accumulation of the conjugates in gastroc and heart muscle. Receptor mediate uptake resulted in siRNA mediated knockdown of the target mRNA.

Example 22: 2017-PK-413-C57BL6: In Vivo Transferrin mAb Conjugate Delivery of Various MuRF1 Sequence For groups 1-2, see study design in FIG. 25, the 21mer MuRF1 (2089) guide strand was designed. The sequence (5' to 3') of the guide/antisense strand was UUUCGCAC-CAACGUAGAAAUU (SEQ ID NO: 14231). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linkers. Because the free thiol was not being used for conjugation, it was end capped with N-ethylmaleimide.

For groups 3-6, see study design in figure G, the 21mer MuRF1 (2265) guide strand was designed. The sequence (5' to 3') of the guide/antisense strand was UCGUGAGAC-AGUAGAUGUUUU (SEQ ID NO: 14232). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained a single conjugation handle, a C6-NH$_2$ at the 5' end connected to siRNA passenger strand via phosphodiester-inverted abasic-phosphodiester linker.

For groups 7-10, see study design in figure G, the 21mer MuRF1 (2266) guide strand was designed. The sequence (5' to 3') of the guide/antisense strand was UCACACGUGA-GACAGUAGAUU (SEQ ID NO: 14233). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained a single conjugation handle, a C6-NH$_2$ at the 5' end connected to siRNA passenger strand via phosphodiester-inverted abasic-phosphodiester linker.

For groups 11-14, see study design in figure G, the 21mer MuRF1 (2267) guide strand was designed. The sequence (5' to 3') of the guide/antisense strand was UUCACACGUGA-GACAGUAGUU (SEQ ID NO: 14234). The guide and fully complementary RNA passenger strands were assembled on solid phase using standard phosphoramidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained a single conjugation handle, a C6-NH$_2$ at the 5' end connected to siRNA passenger strand via phosphodiester-inverted abasic-phosphodiester linker.

For groups 15-18, see study design in figure G, the 21mer MuRF1 (2268) guide strand was designed. The sequence (5' to 3') of the guide/antisense strand was UAAUAUUU-CAUUUCGCACCUU (SEQ ID NO: 14235). The guide and fully complementary RNA passenger strands were assembled on solid phase using standard phosphoramidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained a single conjugation handle, a C6-NH2 at the 5' end connected to siRNA passenger strand via phosphodiester-inverted abasic-phosphodiester linker.

For groups 19-22, see study design in figure G, the 21mer MuRF1 (2269) guide strand was designed. The sequence (5' to 3') of the guide/antisense strand was UAAGCAC-CAAAUUGGCAUAUU (SEQ ID NO: 14236). The guide and fully complementary RNA passenger strands were assembled on solid phase using standard phosphoramidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained a single conjugation handle, a C6-NH$_2$ at the 5' end connected to siRNA passenger strand via phosphodiester-inverted abasic-phosphodiester linker.

Antibody siRNA Conjugate Synthesis Using Bis-Maleimide (BisMal) Linker

Step 1: Antibody Reduction with TCEP

Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography Method (SAX)-1.

Column: Tosoh Bioscience, TSKGel SuperQ-5PW, 21.5 mm ID×15 cm, 13 um

Solvent A: 20 mM TRIS buffer, pH 8.0; Solvent B: 20 mM TRIS, 1.5 M NaCl, pH 8.0; Flow Rate: 6.0 ml/min Gradient:

| | % A | % B | Column Volume |
|---|---|---|---|
| b. | 100 | 0 | 1 |
| c. | 81 | 19 | 0.5 |
| d. | 50 | 50 | 13 |
| e. | 40 | 60 | 0.5 |
| f | 0 | 100 | 0.5 |
| g. | 100 | 0 | 2 |

Anion Exchange Chromatography (SAX) Method-2

Column: Thermo Scientific. ProPac™ SAX-10, Bio LC™, 4×250 mm

Solvent A: 80% 10 mM TRIS pH 8, 20% ethanol; Solvent B: 80% 10 mM TRIS pH 8, 20% ethanol, 1.5 M NaCl; Flow Rate: 0.75 ml/min Gradient:

| a. | Time | % A | % B |
|---|---|---|---|
| b. | 0.0 | 90 | 10 |
| c. | 3.00 | 90 | 10 |
| d. | 11.00 | 40 | 60 |
| e. | 14.00 | 40 | 60 |
| f. | 15.00 | 20 | 80 |
| g. | 16.00 | 90 | 10 |
| h. | 20.00 | 90 | 10 |

Step-3: Analysis of the Purified Conjugate

The purity of the conjugate was assessed by analytical HPLC using anion exchange chromatography method-2 (Table 19).

TABLE 19

| Conjugate | SAX retention time (mm) | % purity (by peak area) |
|---|---|---|
| mTfR1-mAb-MuRF1(R2089) (DAR1) | 9.3 | 99 |
| mTfR1-mAb-MuRF1(R2265) (DAR1) | 9.1 | 95 |
| mTfR1-mAb-MuRF1(R2266) (DAR1) | 9.1 | 98 |
| mTfR1-mAb-MuRF1(R2267) (DAR1) | 9.1 | 98 |
| mTfR1-mAb-MuRF1(R2268) (DAR1) | 9.1 | 97 |
| mTfR1-mAb-MuRF1(R2269) (DAR1) | 9.2 | 97 |

In Vivo Study Design

The conjugates were assessed for their ability to mediate mRNA downregulation of MuRF1 in muscle (gastroc and heart), in an in vivo experiment (C57BL6 mice). Mice were dosed via intravenous (iv) injection with PBS vehicle control and the indicated ASCs and doses, see FIG. 25. After % hours, gastrocnemius (gastroc) and heart muscle tissues were harvested and snap-frozen in liquid nitrogen. mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value (ΔCt) is calculated and then further normalized relative to the PBS control group by taking a second difference (ΔΔCt).

Results

Figure 26:
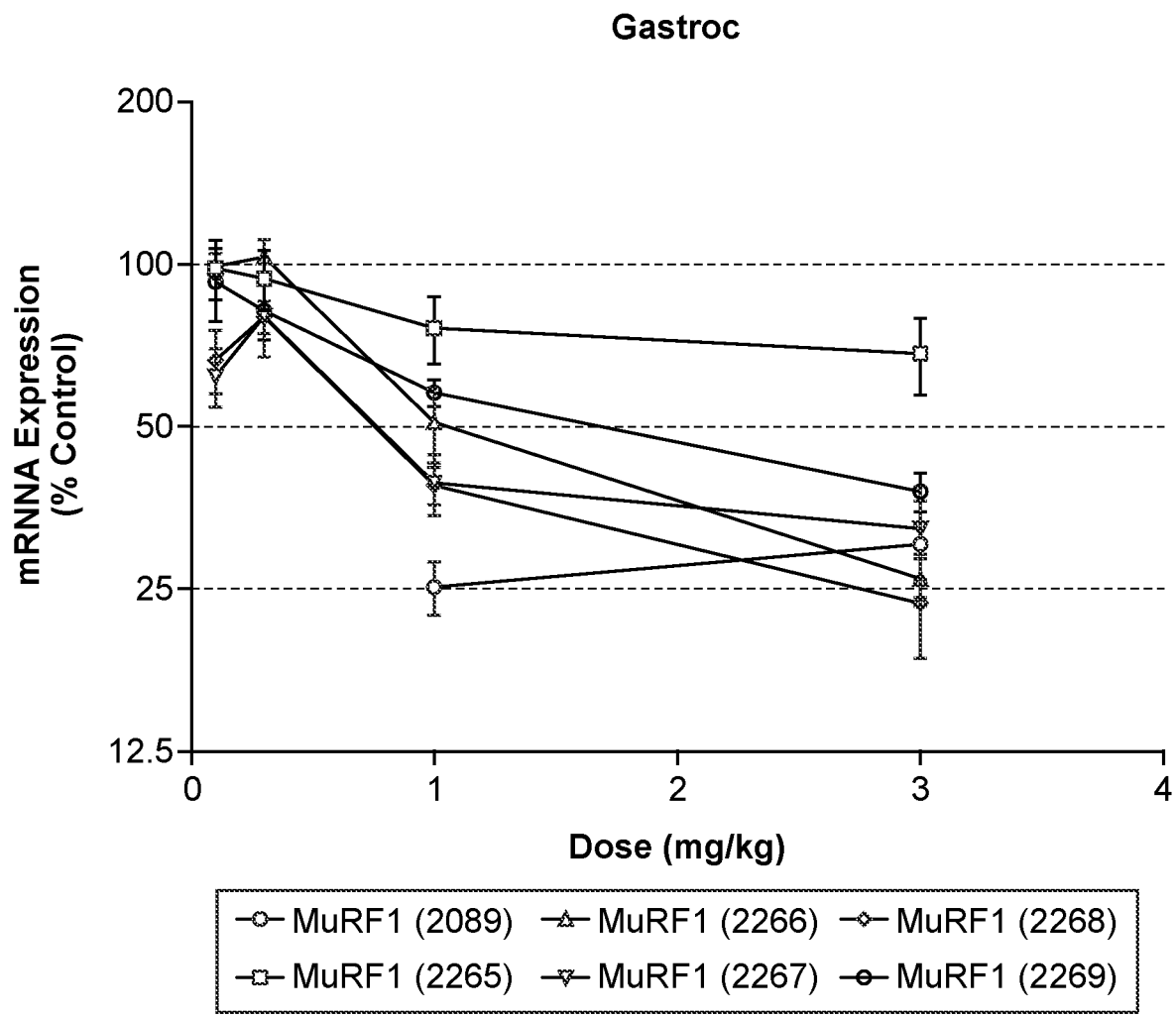
FIG. 26 shows MuRF1 mRNA downregulation at 96 hours in gastroc muscle mediated by a TfR1 antibody siRNA conjugate after IV delivery at the doses indicated.
Figure 27:
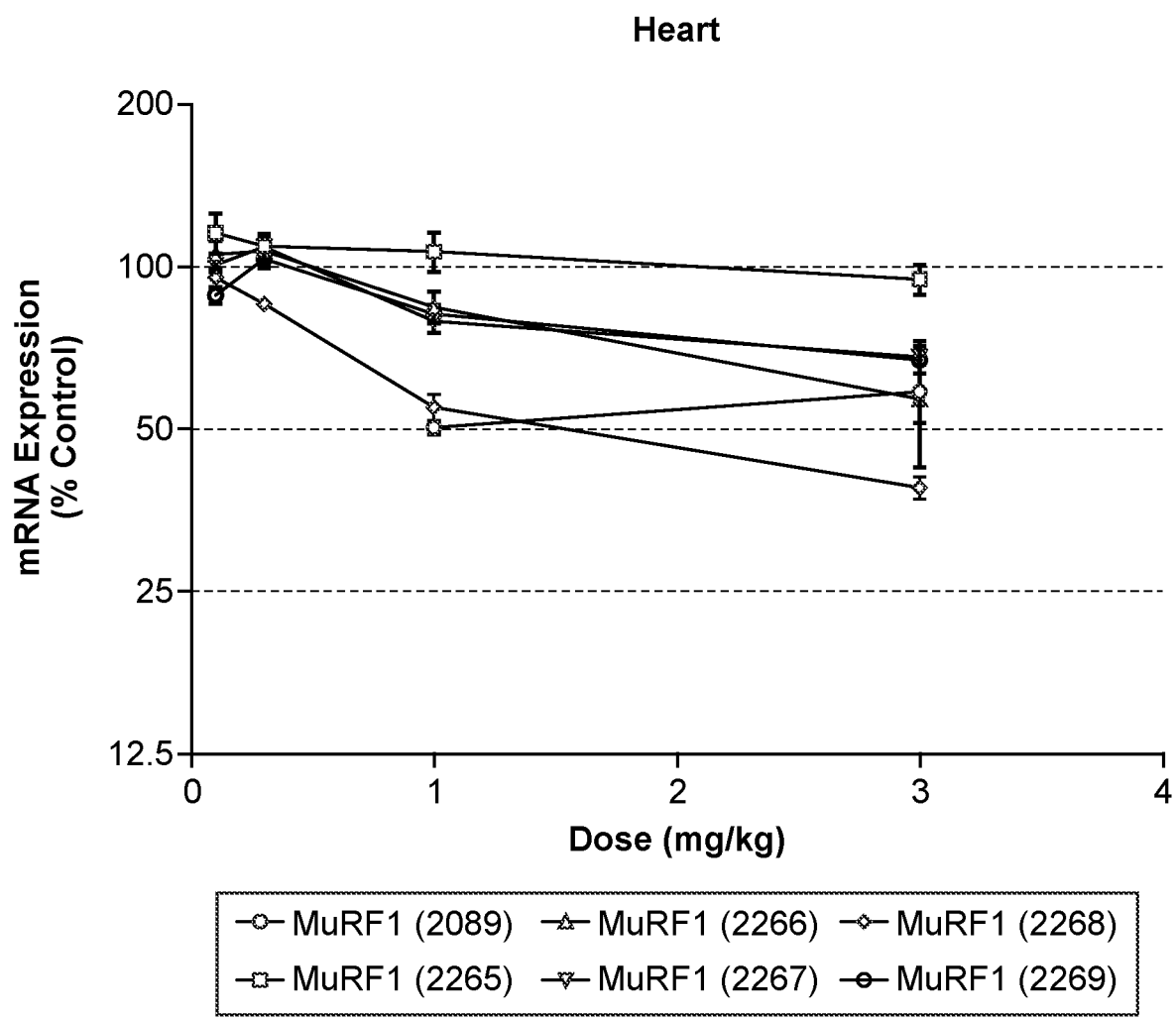
FIG. 27 shows MuRF1 mRNA downregulation at 96 hours in heart muscle mediated by a TfR1 antibody siRNA conjugate after IV delivery at the doses indicated.
Figure 28:
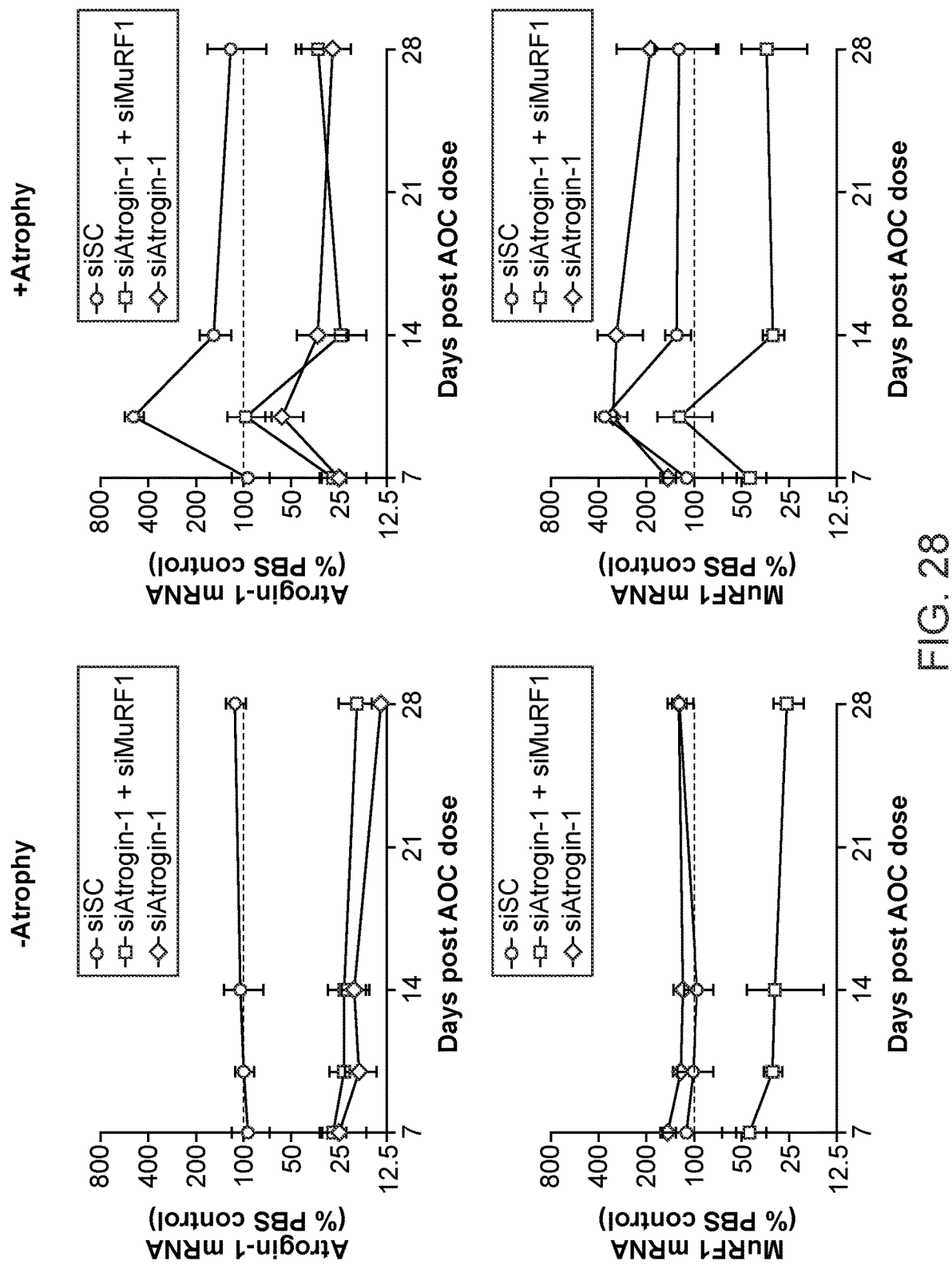
FIG. 28 shows a time course of MuRF1 and Atrogin-1 mRNA downregulation in gastroc muscle mediated by a TfR1 antibody siRNA conjugate (IV delivery at 3 mg/kg siRNA), in the absence and presence of dexamethasone induce muscle atrophy.
Figure 29:
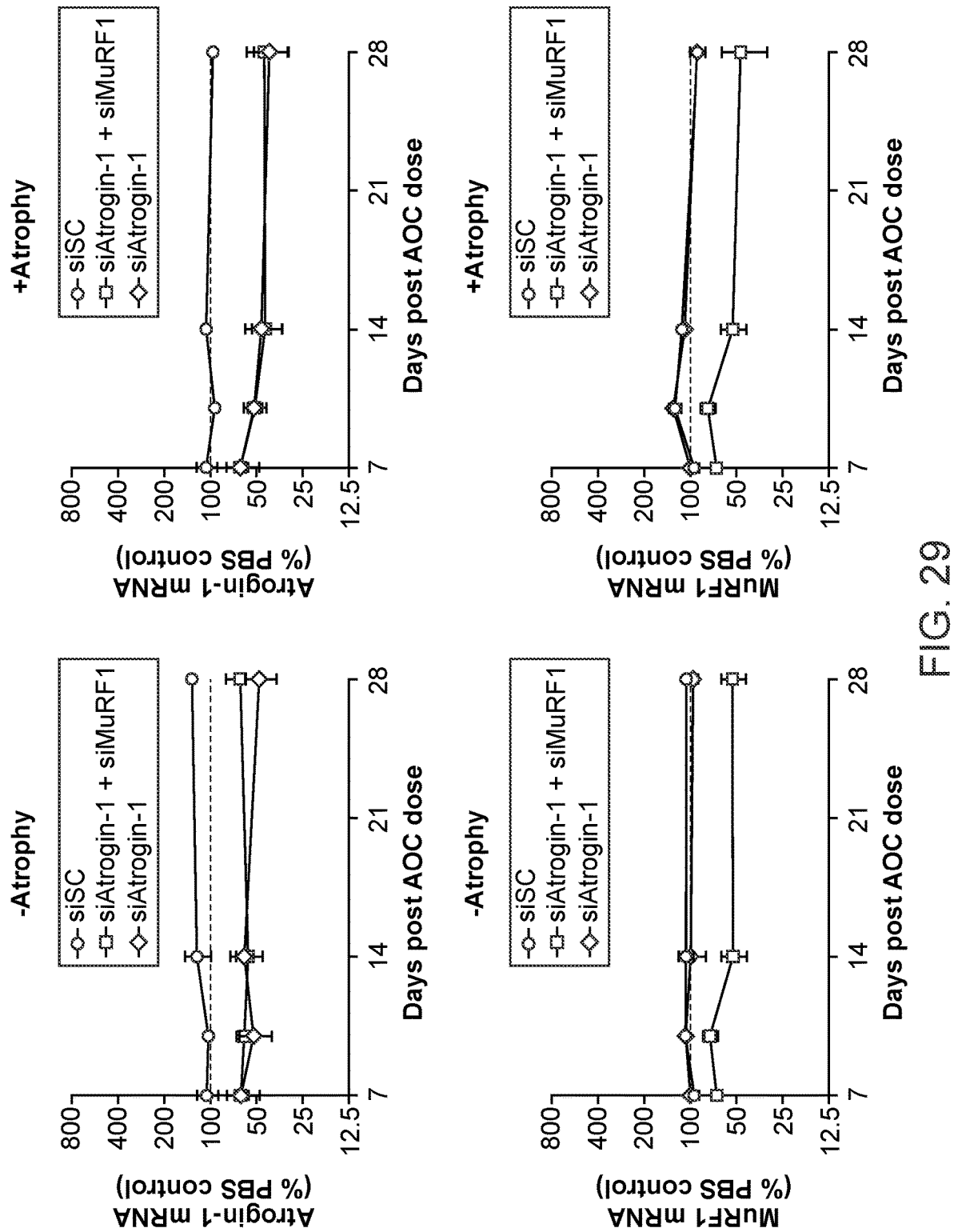
FIG. 29 shows a time course of MuRF1 and Agtrogin1 mRNA downregulation in heart muscle mediated by a TfR1 antibody siRNA conjugate (IV delivery at 3 mg/kg siRNA), in the absence and presence of dexamethasone induce muscle atrophy.
Figure 30:
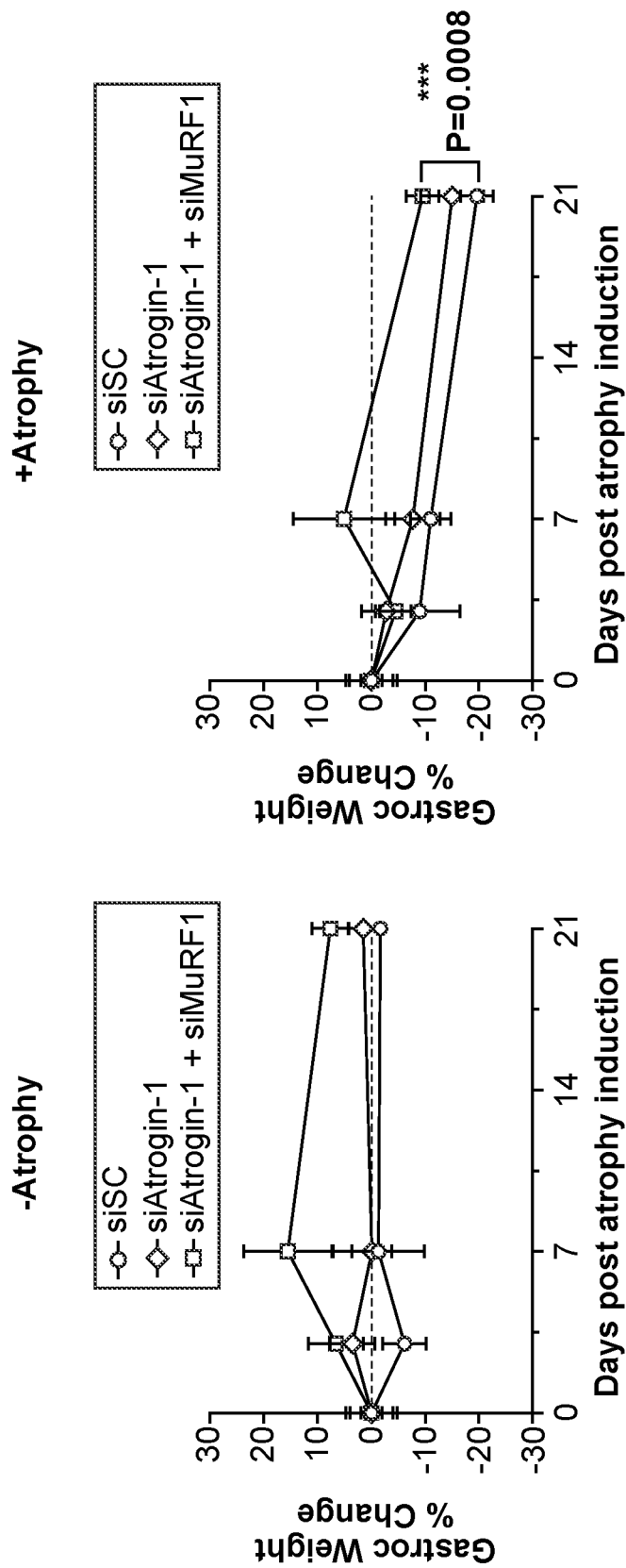
FIG. 30 shows a time course of gastroc weight changes mediated by a TfR1 antibody siRNA conjugate (IV delivery at 3 mg/kg siRNA), in the absence and presence of muscle atrophy.
Figure 31:
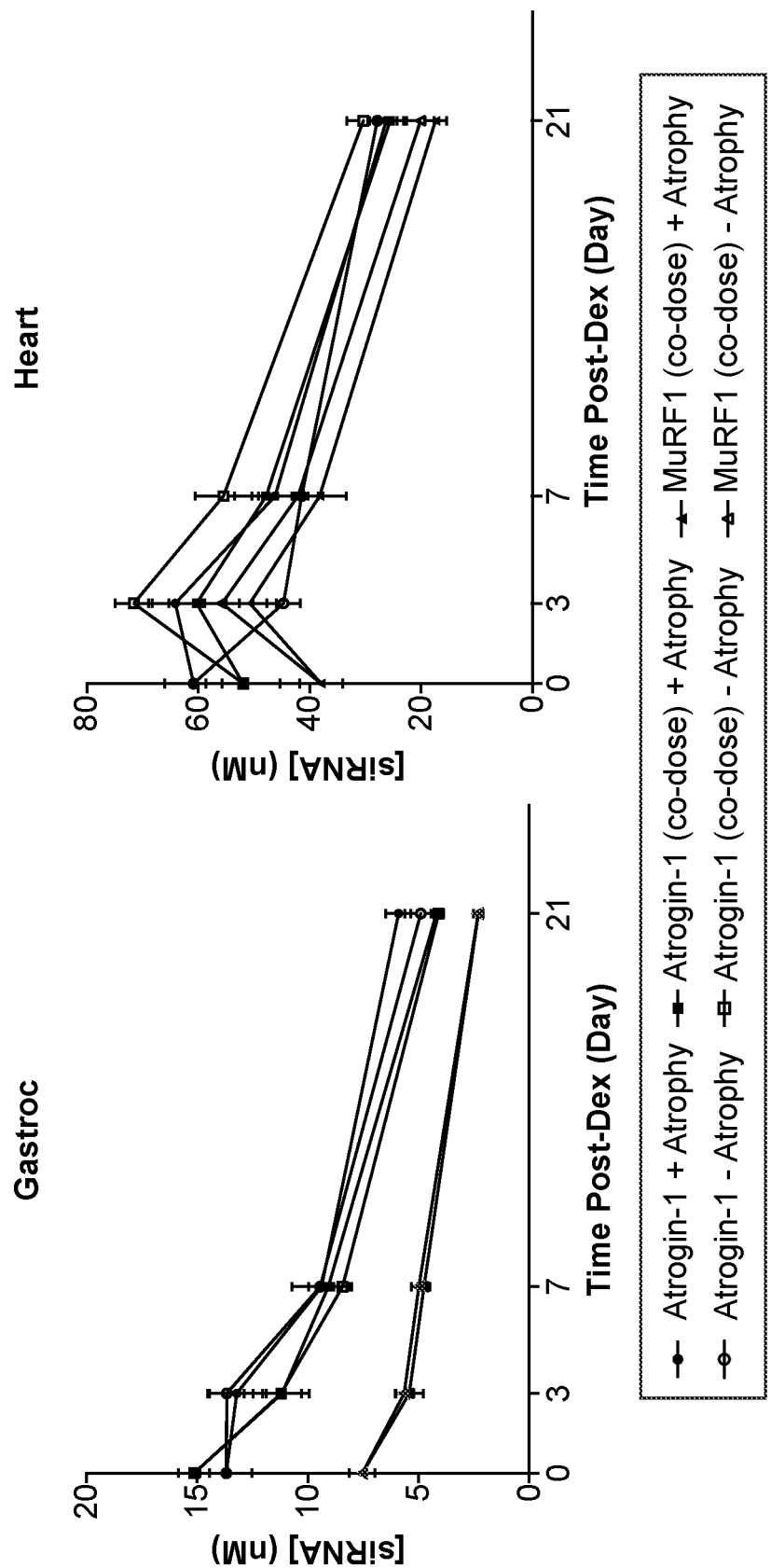
FIG. 31 shows a time course of siRNA tissue concentrations in gastroc and heart muscle mediated by a TfR1 antibody siRNA conjugate (IV delivery at 3 mg/kg siRNA), in the absence and presence of muscle atrophy.

The MuRF1 siRNA guide strands was able to mediate downregulation of the target gene in gastroc and heart muscle when conjugated to an anti-TfR1 mAb targeting the transferrin receptor 1, see FIG. 26 and FIG. 27.

Conclusions

In this example, it was demonstrated that TfR1-MuRF1 conjugates, after in vivo delivery, mediated specific down regulation of the target gene in gastroc and heart muscle. The ASC was made with an anti-transferring antibody, mouse gastroc and heart muscle expresses the transferrin receptor 1 and the conjugate has a mouse specific anti-transferrin antibody to target the siRNA, resulting in accumulation of the conjugates in gastroc muscle. Receptor mediate uptake resulted in siRNA mediated knockdown of the target mRNA.

Example 23: 2017-PK-412-C57BL6: Prevention of Dexamethasone Induce Muscle Atrophy with Atrogin-1 and MuRF1 TfR1-mAb Conjugates For this experiment three different siRNAs were used:

(1): A 21mer Atrogin-1 guide strand was designed. The sequence (5' to 3') of the guide/antisense strand was UCUACGUAGUUGAAUCUUCUU (SEQ ID NO: 14230). The guide and fully complementary RNA passenger strands were assembled on solid phase using standard phosphoramidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained two conjugation handles, a C6-N1H$_2$ at the 5' end and a C6-SH at the 3' end. Both conjugation handles were connected to siRNA passenger strand via phosphodiester-inverted abasic-phosphodiester linkers. Because the free thiol was not being used for conjugation, it was end capped with N-ethylmaleimide.

(2): A 21mer MuRF1 guide strand was designed. The sequence (5' to 3') of the guide/antisense strand was UUUCGCACCAACGUAGAAAUU (SEQ ID NO: 14231). The guide and fully complementary RNA passenger strands were assembled on solid phase using standard phosphoramidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linkers. Because the free thiol was not being used for conjugation, it was end capped with N-ethylmaleimide.

(3): Negative control siRNA sequence (scramble): A published (Burke et al. (2014) Pharm. Res., 31(12):3445-60) 21mer duplex with 19 bases of complementarity and 3' dinucleotide overhangs was used. The sequence (5' to 3') of the guide/antisense strand was UAUCGACGUGUCCAGC-UAGUU (SEQ ID NO: 14228). The same base, sugar and phosphate modifications that were used for the active MSTN siRNA duplex were used in the negative control siRNA. All siRNA single strands were fully assembled on solid phase using standard phospharamidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linker. Because the free thiol was not being used for conjugation, it was end capped with N-ethylmaleimide.

Antibody siRNA Conjugate Synthesis Using Bis-Maleimide (BisMal) Linker

Step 1: Antibody Reduction with TCEP

Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography Method (SAX)-1.

Column: Tosob Bioscience, TSKGel SuperQ-5PW, 21.5 mm ID×15 cm, 13 um

Solvent A: 20 mM TRIS buffer, pH 8.0; Solvent B: 20 mM TRIS, 1.5 M NaCl, pH 8.0; Flow Rate: 6.0 ml/min Gradient:

| a. | % A | % B | Column Volume |
|---|---|---|---|
| b. | 100 | 0 | 1 |
| c. | 81 | 19 | 0.5 |
| d. | 50 | 50 | 13 |
| e. | 40 | 60 | 0.5 |
| f. | 0 | 100 | 0.5 |
| g. | 100 | 0 | 2 |

Anion Exchange Chromatography (SAX) Method-2

Column: Thermo Scientific. ProPac™ SAX-10, Bio LC™, 4×250 mm

Solvent A: 80% 10 mM TRIS pH 8, 20% ethanol: Solvent B: 80% 10 mM TRIS pH 8, 20% ethanol, 1.5 M NaCl; Flow Rate: 0.75 ml/min Gradient:

| a. | Time  | % A | % B |
|----|-------|-----|-----|
| b. | 0.0   | 90  | 10  |
| c. | 3.00  | 90  | 10  |
| d. | 11.00 | 40  | 60  |
| e. | 14.00 | 40  | 60  |
| f. | 15.00 | 20  | 80  |
| g. | 16.00 | 90  | 10  |
| h. | 20.00 | 90  | 10  |

Step-3: Analysis of the Purified Conjugate

The purity of the conjugate was assessed by analytical HPLC using anion exchange chromatography method-2 (Table 20).

TABLE 20

| Conjugate | SAX retention time (min) | % purity (by peak area) |
|---|---|---|
| mTfR1-Atrogin-1 (DAR1) | 9.3 | 97 |
| mTfR1-MuRF1 (DAR1) | 9.5 | 98 |
| mTfR1-SC (DAR1) | 9.0 | 99 |

In Vivo Study Design

The conjugates were assessed for their ability to mediate mRNA downregulation of MuRF1 and Atrogin-1 in muscle (gastroc) in the presence and absence of muscle atrophy, in an in vivo experiment (C57BL6 mice). Mice were dosed via intravenous (iv) injection with PBS vehicle control and the indicated ASCs and doses, see Table 21. Seven days post conjugate delivery, for groups 2-4, 9-11, and 16-18, muscle atrophy was induced by the daily administration, via intraperitoneal injection (10 mg/kg) of dexamethasone for 21 days. For the control groups 5-7, 12-14 and 19-21 (no induction of muscle atrophy) PBS was administered by the daily intraperitoneal injection. Groups 1, 8, 15 and 22 were harvested at day 7 to establish the baseline measurements of mRNA expression and muscle weighted, prior to induction of muscle atrophy. At the time points indicated, gastrocnemius (gastroc) and heart muscle tissues were harvested, weighed and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct).

Quantitation of tissue siRNA concentrations was determined using a stem-loop qPCR assay as described in the methods section. The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

TABLE 21

| | Animal and Group Info | | | Dex/PBS Dosing | | | | Compound Info | | |
| | | | | Dose Volume | # of | Dose | | siRNA Dose | | Harvest Time |
| Group | Test Article | N | ROA | (mL/kg) | Doses | Schedule | | (mg/kg) | #of Doses | (d) |
|---|---|---|---|---|---|---|---|---|---|---|
| 1 | mTfR1-Atrogin-1 (DAR1) | 5 | — | — | — | — | | 3 | 1 | 7 |
| 2 | mTfR1-Atrogin-1 (DAR1), +DEX (10 mg/kg) | 5 | IP | 6.25 | Daily; 21 Days | 192 h Post ASC | | 3 | 1 | 10 |
| 3 | mTfR1-Atrogin-1 (DAR1), +DEX (10 mg/kg) | 5 | IP | 6.25 | Daily; 21 Days | 192 h Post ASC | | 3 | 1 | 17 |
| 4 | mTfR1-Atrogin-1 (DAR1), +DEX (10 mg/kg) | 5 | IP | 6.25 | Daily; 21 Days | 192 h Post ASC | | 3 | 1 | 28 |
| 5 | mTfR1-Atrogin-1 (DAR1), PBS | 5 | IP | 6.25 | Daily; 21 Days | 192 h Post ASC | | 3 | 1 | 10 |
| 6 | mTfR1-Atrogin-1 (DAR1), PBS | 5 | IP | 6.25 | Daily; 21 Days | 192 h Post ASC | | 3 | 1 | 17 |
| 7 | mTfR1-Atrogin-1 (DAR1), PBS | 5 | IP | 6.25 | Daily; 21 Days | 19 2h Post ASC | | 3 | 1 | 28 |
| 8 | mTfR1-Atrogin-1 (DAR1) + mTfR1-MuRF1 (DAR1) | 5 | — | — | — | — | | 3 + 3 | 1 | 7 |
| 9 | mTfR1-Atrogin-1 (DAR1) + mTfR1-MuRF1 (DAR1), +DEX (10 mg/kg) | 5 | IP | 6.25 | Daily; 21 Days | 192 h Post ASC | | 3 + 3 | 1 | 10 |
| 10 | mTfR1-Atrogin-1 (DAR1) + mTfR1-MuRF1 (DAR1), +DEX (10 mg/kg) | 5 | IP | 6.25 | Daily; 21 Days | 192 h Post ASC | | 3 + 3 | 1 | 17 |

TABLE 21-continued

| | | | | Dex/PBS Dosing | | | Compound Info | | |
|---|---|---|---|---|---|---|---|---|---|
| Group | Test Article | N | ROA | Dose Volume (mL/kg) | # of Doses | Dose Schedule | siRNA Dose (mg/kg) | #of Doses | Harvest Time (d) |
| 11 | mTfR1-Atrogin-1 (DAR1), + mTfR1-MuRF1 (DAR1), +DEX (10 mg/kg) | 5 | IP | 6.25 | Daily; 21 Days | 192 h Post ASC | 3 + 3 | 1 | 28 |
| 12 | mTfR1-Atrogin-1 (DAR1) + mTfR1-MuRF1 (DAR1), +PBS | 5 | IP | 6.25 | Daily; 21 Days | 192 h Post ASC | 3 + 3 | 1 | 10 |
| 13 | mTfR1-Atrogin-1 (DAR1) + mTfR1-MuRF1 (DAR1), +PBS | 5 | IP | 6.25 | Daily; 21 Days | 192 h Post ASC | 3 + 3 | 1 | 17 |
| 14 | mTfR1-Atrogin-1 (DAR1) + mTfR1-MuRF1 (DAR1), +PBS | 5 | IP | 6.25 | Daily; 21 Days | 192 h Post ASC | 3 + 3 | 1 | 28 |
| 15 | mTfR1-SC (DAR1) | 5 | — | — | — | — | 3 | 1 | 7 |
| 16 | mTfR1-SC DAR1), +DEX (10 mg/kg) | 5 | IP | 6.25 | Daily; 21 Days | 192 h Post ASC | 3 | 1 | 10 |
| 17 | mTfR1-SC (DAR1), +DEX (10 mg/kg) | 5 | IP | 6.25 | Daily; 21 Days | 192 h Post ASC | 3 | 1 | 17 |
| 18 | mTfR1-SC (DAR1), +DEX (10 mg/kg) | 5 | IP | 6.25 | Daily; 21 Days | 192 h Post ASC | 3 | 1 | 28 |
| 19 | mTfR1-SC (DAR1), PBS | 5 | IP | 6.25 | Daily; 21 Days | 192 h Post ASC | 3 | 1 | 10 |
| 20 | mTfR1-SC (DAR1), PBS | 5 | IP | 6.25 | Daily; 21 Days | 192 h Post ASC | 3 | 1 | 17 |
| 21 | mTfR1-SC (DAR1), PBS | 5 | IP | 6.25 | Daily; 21 Days | 192 h Post ASC | 3 | 1 | 28 |
| 22 | PBS Control | 5 | — | — | — | — | — | 1 | 7 |

Results

The data are summarized in FIG. 28-FIG. 31. Co-delivery of Atrogin-1 and MuRF1 siRNAs efficiently downregulated Atrogin-1 and MuRF1 mRNA expression in normal and atrophic muscles, when delivered using a TfR1 mAb conjugate. Induction of atrophy transiently induces Atrogin-1 and MuRF1 expression about 4-fold. A single dose of mTfR1-Atrogin-1+TfR1.mAb-siMuRF1 (3 mg/kg, each and dose as a mixture) reduced Atrogin-1 and MuRF1 mRNA levels by >70% in normal and atrophic gastrocnemius muscle. Downregulation of MuRF1 and Atrogin-1 mRNA increases gastrocnemius weight by 5-10% and reduces DEX-induced gastrocnemius weight loss by 50%. Downregulation of Atrogin-1 alone has no significant effect on gastrocnemius weight changes. In the absence of muscle atrophy treatment with Atrogin-1/MuRF1 siRNAs induces muscle hypertrophy.

Conclusions

In this example, it was demonstrated that co-delivery of Atrogin-1 and MuRF1 siRNAs efficiently downregulated Atrogin-1 and MuRF1 mRNA expression in normal and atrophic gastroc muscles, when delivered using a TfR1 mAb conjugate. The conjugates had little effect on heart muscle, where downregulation of Atrogin-1 could be detrimental. Downregulation of MuRF1 and Atrogin-1 mRNA increased gastroc muscle weight by 5-10% and reduced DEX-induced gastroc muscle weight loss by 50%. Downregulation of Atrogin-1 alone has no significant effect on gastrocnemius weight changes. The ASC were made with an anti-transferrin antibody, mouse gastroc muscle expresses the transferrin receptor and the conjugate has a mouse specific anti-transferrin antibody to target the siRNA, resulting in accumulation of the conjugates in gastroc muscle. Receptor mediate uptake resulted in siRNA mediated knockdown of the target mRNA.

Example 24: 2017-PK-435-C57BL6: In Vivo Dose Response Experiment for Transferrin mAb Conjugate Delivery of Atrogin-1

For groups 1-12, see study design in FIG. 32, the 21mer Atrogin-1 guide strand was designed. The sequence (5' to 3') of the guide/antisense strand was UCGUAGUUAAAUC-UUCUGGUU (SEQ ID NO: 14237). The guide and fully complementary RNA passenger strands were assembled on solid phase using standard phosphoramidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in figure A. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linkers. Because the free thiol was not being used for conjugation, it was end capped with N-ethylmaleimide.

For groups 13-18 see study design in FIG. 32, a 21mer negative control siRNA sequence (scramble) (published by Burke et al. (2014) Pharm. Res., 31(12):3445-60) with 19 bases of complementarity and 3' dinucleotide overhangs was used. The sequence (5' to 3') of the guide/antisense strand was UAUCGACGUGUCCAGCUAGUU (SEQ ID NO: 14228). The same base, sugar and phosphate modifications that were used for the active MSTN siRNA duplex were used in the negative control siRNA. All siRNA single strands were fully assembled on solid phase using standard phosphoramidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linker. Because the free thiol was not being used for conjugation, it was end capped with N-ethylmaleimide.

Antibody siRNA Conjugate Synthesis Using Bis-Maleimide (BisMal) Linker

Step 1: Antibody Reduction with TCEP

Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography Method (SAX)-1.

Column: Tosoh Bioscience, TSKGel SuperQ-5PW, 21.5 mm ID×15 cm, 13 um

Solvent A: 20 mM TRIS buffer, pH 8.0; Solvent B: 20 mM TRIS, 1.5 M NaCl, pH 8.0; Flow Rate: 6.0 ml/min Gradient:

| a. | % A | % B | Column Volume |
|---|---|---|---|
| b. | 100 | 0 | 1 |
| c. | 81 | 19 | 0.5 |
| d. | 50 | 50 | 13 |
| e. | 40 | 60 | 0.5 |
| f | 0 | 100 | 0.5 |
| g. | 100 | 0 | 2 |

Anion Exchange Chromatography (SAX) method-2

Column: Thermo Scientific, ProPac™ SAX-10, Bio LC™, 4×250 mm

Solvent A: 80% 10 mM TRIS pH 8, 20% ethanol; Solvent B: 80% 10 mM TRIS pH 8.20% ethanol, 1.5 M NaCl; Flow Rate: 0.75 ml/min Gradient:

| a. | Time | % A | % B | |
|---|---|---|---|---|
| b. | 0.0 | | 90 | 10 |
| c. | 3.00 | 90 | 10 | |
| d. | 11.00 | 40 | 60 | |
| e. | 14.00 | 40 | 60 | |
| f. | 15.00 | 20 | 80 | |
| g. | 16.00 | 90 | 10 | |
| h. | 20.00 | 90 | 10 | |

Step-3: Analysis of the Purified Conjugate

The purity of the conjugate was assessed by analytical HPLC using anion exchange chromatography method-2 (Table 22).

TABLE 22

| Conjugate | SAX retention time (min) | % purity (by peak area) |
|---|---|---|
| TfR1-Atrogin-1 DAR1 | 9.2 | 99 |
| TfR1-Scramble DAR1 | 8.9 | 93 |

In Vivo Study Design

The conjugates were assessed for their ability to mediate mRNA downregulation of Atrogin-1 in muscle (gastroc) in the presence and absence of muscle atrophy, in an in vivo experiment (C57BL6 mice). Mice were dosed via intravenous (iv) injection with PBS vehicle control and the indicated ASCs and doses, see FIG. 32. Seven days post conjugate delivery, for groups 3, 6, 9, 12, and 15, muscle atrophy was induced by the daily administration via intraperitoneal injection (10 mg/kg) of dexamethasone for 3 days. For the control groups 2, 5, 8, 11, and 14 (no induction of muscle atrophy) PBS was administered by the daily intraperitoneal injection. Groups 1, 4, 7, 10, and 13 were harvested at day 7 to establish the baseline measurements of mRNA expression and muscle weighted, prior to induction of muscle atrophy. At three days post-atrophy induction (or 10 days post conjugate delivery), gastrocnemius (gastroc) muscle tissues were harvested, weighed and snap-frozen in liquid nitrogen. mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct).

Quantitation of tissue siRNA concentrations was determined using a stem-loop qPCR assay as described in the methods section. The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

Results

The data are summarized in FIG. 33-FIG. 35. The Atrogin-1 siRNA guide strands were able to mediate downregulation of the target gene in gastroc muscle when conjugated to an anti-TfR mAb targeting the transferrin receptor, see FIG. 33. Increasing the dose from 3 to 9 mg/kg reduced atrophy-induced Atrogin-1 mRNA levels 2-3 fold.

The maximal KD achievable with this siRNA was 80% and a tissue concentration of 40 nM was needed to achieve maximal KD in atrophic muscles. This highlights the conjugate delivery approach is able to change disease induce mRNA expression levels of Atrogin-1 (see FIG. 34), by increasing the increasing the dose. FIG. 35 highlights that mRNA down regulation is mediated by RISC loading of the Atrogin-1 guide strands and is concentration dependent.

Conclusions

In this example, it was demonstrated that a TfR1-Atrogin-1 conjugates, after in vivo delivery, mediated specific down regulation of the target gene in gastroc muscle in a dose dependent manner. After induction of atrophy the conjugate was able to mediate disease induce mRNA expression levels of Atrogin-1 at the higher doses. Higher RISC loading of the Atrogin-1 guide strand correlated with increased mRNA downregulation.

Example 25: 2017-PK-381-C57BL6: Myostatin (MSTN) Downregulation Reduces Muscle Loss in Dexamethasone-Treated Mice For groups 1-12, see study design in Table 24, the 21mer Atrogin-1 guide strand was designed. The sequence (5' to 3') of the guide/antisense stand was UCGUAGUUAAAUC-UUCUGGUU (SEQ ID NO: 14237). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained two conjugation handles, a C6-NH2 at the 5' end and a C6-SH at the 3' end. Both conjugation handles were connected to siRNA passenger strand via phosphodiester-inverted abasic-phosphodiester linkers. Because the free thiol was not being used for conjugation, it was end capped with N-ethylmaleimide.

For groups 13-18 see study design in Table 24, a 21mer negative control siRNA sequence (scramble) (published by Burke et al. (2014) Pharm. Res., 31(12):3445-60) with 19 bases of complementarity and 3' dinucleotide overhangs were used. The sequence (5' to 3') of the guide/antisense strand was UAUCGACGUGUCCAGCUAGUU (SEQ ID NO: 14228). The same base, sugar and phosphate modifications that were used for the active MSTN siRNA duplex were used in the negative control siRNA. All siRNA single strands were fully assembled on solid phase using standard phospharamidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linker. Because the free thiol was not being used for conjugation, it was end capped with N-ethylmaleimide.

Antibody siRNA Conjugate Synthesis Using Bis-Maleimide (BisMal) Linker

Step 1: Antibody Reduction with TCEP

Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography Method (SAX)-1.

Column: Tosoh Bioscience. TSKGel SuperQ-5PW, 21.5 mm ID×15 cm, 13 um

Solvent A: 20 mM TRIS buffer, pH 8.0; Solvent B: 20 mM TRIS, 1.5 M NaCl, pH 8.0; Flow Rate: 6.0 ml/min Gradient:

| | % A | % B | Column Volume |
|---|---|---|---|
| a. | | | |
| b. | 100 | 0 | 1 |
| c. | 81 | 19 | 0.5 |
| d. | 50 | 50 | 13 |
| e. | 40 | 60 | 0.5 |
| f. | 0 | 100 | 0.5 |
| g. | 100 | 0 | 2 |

Anion Exchange Chromatography (SAX) Method-2

Column: Thermo Scientific, ProPac™ SAX-10, Bio LC™, 4×250 mm

Solvent A: 80% 10 mM TRIS pH 8, 20% ethanol; Solvent B: 80% 10 mM TRIS pH 8, 20% ethanol, 1.5 M NaCl; Flow Rate: 0.75 ml/min Gradient:

| | Time | % A | % B |
|---|---|---|---|
| a. | | | |
| b. | 0.0 | 90 | 10 |
| c. | 3.00 | 90 | 10 |
| d. | 11.00 | 40 | 60 |
| e. | 14.00 | 40 | 60 |
| f. | 15.00 | 20 | 80 |
| g. | 16.00 | 90 | 10 |
| h. | 20.00 | 90 | 10 |

Step-3: Analysis of the Purified Conjugate

The purity of the conjugate was assessed by analytical HPLC using anion exchange chromatography method-2 (Table 23).

TABLE 23

| Conjugate | SAX retention time (min) | % purity (by peak area) |
|---|---|---|
| mTfR1-MSTN (DAR1) | 9.2 | 98 |
| mTfR1-SC (DAR1) | 8.9 | 98 |

In Vivo Study Design

The conjugates were assessed for their ability to mediate mRNA downregulation of MSTN in muscle (gastroc) in the presence and absence of muscle atrophy, in an in vivo experiment (C57BL6 mice). Mice were dosed via intravenous (iv) injection with PBS vehicle control and the indicated ASCs and doses, see Table 24. Seven days post conjugate delivery, for groups 2, 3, 4, 9, 10 and 11, muscle atrophy was induced by the daily administration via intraperitoneal injection (10 mg/kg) of dexamethasone for 13 days. For the control groups 5, 6, 7, 12, 13 and 14 (no induction of muscle atrophy), PBS was administered by the daily intraperitoneal injection. Groups 1 and 8 were harvested at day 7 to establish the baseline measurements of mRNA expression and muscle weighted, prior to induction of muscle atrophy. At 3, 7, and 14 days post-atrophy induction (or 10, 14, and 21 days post conjugate delivery), gastrocnemius (gastroc) muscle tissues were harvested, weighed and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct).

Quantitation of tissue siRNA concentrations was determined using a stem-loop qPCR assay as described in the methods section. The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

TABLE 24

| Animal and Group Info | | | Dex/PBS Dosing | | | | Compound Info | | Harvest |
|---|---|---|---|---|---|---|---|---|---|
| | | | | Dose | | | siRNA | | |
| Group | Test Article | N | ROA | Volume (mL/kg) | # of Doses | Dose Schedule | Dose (mg/kg) | ROA | Time (d) |
| 1 | mTfR1-MSTN (DAR1) | 5 | — | — | — | — | 3 | IV | 7 |
| 2 | mTfR1-MSTN (DAR1), +DEX (10 mg/kg) | 5 | IP | 6.25 | Daily; 13 Days | 192 h Post ASC | 3 | IV | 10 |
| 3 | mTfR1-MSTN (DAR = 1), +DEX (10 mg/kg) | 5 | IP | 6.25 | Daily; 13 Days | 192 h Post ASC | 3 | IV | 14 |
| 4 | mTfR1-MSTN (DAR = 1), +DEX (10 mg/kg) | 5 | IP | 6.25 | Daily; 13 Days | 192 h Post ASC | 3 | IV | 21 |
| 5 | mTfR1-MSTN (DAR1), PBS | 5 | IP | 6.25 | Daily; 13 Days | 192 h Post ASC | 3 | IV | 10 |
| 6 | mTfR1-MSTN (DAR1), PBS | 5 | IP | 6.25 | Daily; 13 Days | 192 h Post ASC | 3 | IV | 14 |
| 7 | mTfR1-MSTN (DAR1), PBS | 5 | IP | 6.25 | Daily. 13 Days | 192 h Post ASC | 3 | IV | 21 |
| 8 | mTfR1-SC (DAR1) | 5 | — | — | — | — | 3 | IV | 7 |
| 9 | mTfR1-SC (DAR1), +DEX (10 mg/kg) | 5 | IP | 6.25 | Daily; 13 Days | 192 h Post ASC | 3 | IV | 10 |
| 10 | mTfR1-SC (DAR1), +DEX (10 mg/kg) | 5 | IP | 6.25 | Daily; 13 Days | 192 h Post ASC | 3 | IV | 14 |
| 11 | mTfR1-SC (DAR1), +DEX (10 mg/kg) | 5 | IP | 6.25 | Daily; 13 Days | 192 h Post ASC | 3 | IV | 21 |
| 12 | mTfR1-SC (DAR1), PBS | 5 | IP | 6.25 | Daily; 13 Days | 192 h Post ASC | 3 | IV | 10 |
| 13 | mTfR1-SC (DAR1), PBS | 5 | IP | 6.25 | Daily; 13 Days | 192 h Post ASC | 3 | IV | 14 |
| 14 | mTfR1-SC (DAR1), PBS | 5 | IP | 6.25 | Daily; 13 Days | 192 h Post ASC | 3 | IV | 21 |
| 15 | PBS Control | 5 | — | — | — | — | — | IV | 7 |

Results

The data are summarized in FIG. 36 and FIG. 37. The MSTN siRNA guide strands were able to mediate downregulation of the target gene in gastroc muscle when conjugated to an anti-TfR mAb targeting the transferrin receptor, see FIG. 36, in the presence and absence of dexamethasone induced atrophy. A single of 3 mg/kg siRNA downregulated MSTN mRNA levels by >75%. In the presence of dexamethasone induced atrophy, MSTN downregulation increased muscle mass and attenuates Dex-induced muscle loss, see FIG. 37.

Conclusions

In this example, it was demonstrated that a TfR1-MSTN conjugate, after in vivo delivery, mediated specific down regulation of the target gene in gastroc muscle. After induction of atrophy the conjugate was able to increase muscle mass and attenuate Dex-induced muscle loss.

Example 26: 2017-PK-496-C57BL6: Atrogin-1 and MuRF1 Downregulation Reduces Leg Muscle Loss Upon Sciatic Nerve Denervation in Mice For groups 14, see study design in FIG. 38, the 21mer Atrogin-1 guide strand was designed. The sequence (5' to 3') of the guide/antisense strand was UUGGGUAA-CAUCGUACAAGUU (SEQ ID NO: 14238). The guide and fully complementary RNA passenger strands were assembled on solid phase using standard phosharamidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linkers. Because the free thiol was not being used for conjugation, it was end capped with N-ethylmaleimide.

For groups 5-6, see study design in figure V, the 21mer MuRF1 guide strand was designed. The sequence (5' to 3') of the guide/antisense strand was UUUCGCAC-CAACGUAGAAAUU (SEQ ID NO: 14231). The guide and fully complementary RNA passenger strands were assembled on solid phase using standard phosharamidite chemistry and purified over HPLC. Base, sugar and phosphate modifications that are well described in the field of RNAi were used to optimize the potency of the duplex and reduce immunogenicity. Purified single strands were duplexed to get the double stranded siRNA described in FIG. 20B. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linkers. Because the free thiol was not being used for conjugation, it was end capped with N-ethylmaleimide.

For groups 7-12, the Atrogin-1 and MuRF1 were design as above. After conjugation to the TfR1 mAb and after purification and isolation of the individual DAR1 species, were mixed and co-administered.

For group 13, see study design in FIG. 38, a 21mer negative control siRNA sequence (scramble) (published by Burke et a. (2014) Pharm. Res., 31(12):3445-60) with 19 bases of complementarity and 3' dinucleotide overhangs was used. The sequence (5' to 3') of the guide/antisense strand was UAUCGACGUGUCCAGCUAGUU (SEQ ID NO: 14228). The same base, sugar and phosphate modifications that were used for the active MSTN siRNA duplex were used in the negative control siRNA. All siRNA single strands were fully assembled on solid phase using standard phosharamidite chemistry and purified over HPLC. Purified single strands were duplexed to get the double stranded siRNA. The passenger strand contained two conjugation handles, a C6-NH$_2$ at the 5' end and a C6-SH at the 3' end. Both conjugation handles were connected to siRNA passenger strand via phosphodiester-inverted abasic-phosphodiester linker. Because the free thiol was not being used for conjugation, it was end capped with N-ethylmaleimide.

Antibody siRNA Conjugate Synthesis Using Bis-Maleimide (BisMal) Linker

Step 1: Antibody Reduction with TCEP

Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography Method (SAX)-1.

Column: Tosoh Bioscience, TSKGel SuperQ-5PW, 21.5 mm ID×15 cm, 13 um

Solvent A: 20 mM TRIS buffer, pH 8.0; Solvent B: 20 mM TRIS, 1.5 M NaCl, pH 8.0: Flow Rate: 6.0 ml/min Gradient:

| a. | % A | % B | Column Volume |
|---|---|---|---|
| b. | 100 | 0 | 1 |
| c. | 81 | 19 | 0.5 |
| d. | 50 | 50 | 13 |
| e. | 40 | 60 | 0.5 |
| f. | 0 | 100 | 0.5 |
| g. | 100 | 0 | 2 |

Anion Exchange Chromatography (SAX) Method-2

Column: Thermo Scientific, ProPac™ SAX-10. Bio LC™, 4×250 mm

Solvent A: 80% 10 mM TRIS pH 8, 20% ethanol; Solvent B: 80% 10 mM TRIS pH 8.20% ethanol, 1.5 M NaCl; Flow Rate: 0.75 ml/min Gradient:

| a. | Time | % A | % B |
|---|---|---|---|
| b. | 0.0 | 90 | 10 |
| c. | 3.00 | 90 | 10 |
| d. | 11.00 | 40 | 60 |
| e. | 14.00 | 40 | 60 |
| f. | 15.00 | 20 | 80 |
| g. | 16.00 | 90 | 10 |
| h. | 20.00 | 90 | 10 |

Step-3: Analysis of the Purified Conjugate

The purity of the conjugate was assessed by analytical HPLC using anion exchange chromatography method-2 (Table 25).

TABLE 25

| Conjugate | SAX retention time (min) | % purity (by peak area) |
|---|---|---|
| TfR1-Atrogin-1 DAR1 | 9.2 | 95 |
| TfR1-MuRF1 DAR1 | 9.3 | 92 |
| mTfR1-SC (DAR1) | 8.9 | 76 |

In Vivo Study Design

The conjugates were assessed for their ability to mediate mRNA downregulation of MuRF1 and Atrogin-1 in muscle (gastroc) in the presence and absence of sciatic nerve denervation, in an in vivo experiment (C57BL6 mice). Mice were dosed via intravenous (iv) injection with PBS vehicle control and the indicated ASCs and doses, see FIG. 38. Seven days post conjugate delivery, for groups 24, 6-8, 10-12 and 14-16, leg muscle atrophy was induced by sciatic nerve denervation. Denervation was not induced for the control groups 1, 5, 9, 13, and 17.

For the Denervation procedure at day 7, mice were anesthesed (5% isoflurane) and administer a subcutaneous dose of 0.1 mg/kg Buprenorphine. The right dorsal pelvic region was shaved from the sciatic notch to the knee. The area was disinfected with alternating alcohol and povidone-iodine. The sciatic notch was identified by palpation and an incision made from the sciatic notch towards the knee, approximately 1 cm. The bicep femoris muscle was split to expose the sciatic nerve and about a 1cm fragment was removed by cauterizing both ends. The muscle and skin were then sutured to close the incision. The operative limb was then inspected daily to observe the condition of the surgical wound and observe the animal for overall health.

For groups 4, 8, 12, and 16 changes in leg muscle area were determined: The leg-to-be-measured were shaved and a line was drawn using indelible ink to mark region of measurement. Mice were restrained in a cone restraint and the right leg was held by hand. Digital calipers were used to take one measurement on the sagittal plane and another on the coronal plane. The procedure was repeated twice per week. For all groups at the time points indicated, gastrocnemius (gastroc) and heart muscle tissues were harvested, weighed and snap-frozen in liquid nitrogen, mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct).

Quantitation of tissue siRNA concentrations was determined using a stem-loop qPCR assay as described in the methods section. The antisense strand of the siRNA was reverse transcribed using a TaqMan MicroRNA reverse transcription kit using a sequence-specific stem-loop RT primer. The cDNA from the RT step was then utilized for real-time PCR and Ct values were transformed into plasma or tissue concentrations using the linear equations derived from the standard curves.

FIG. 39A shows a single treatment of 4.5 mg/kg (siRNA) of either Atrogin-1 siRNA or MuRF1 siRNA or a single dose of both siRNAs combined resulted in up to 75% downregulation of each target in the gastrocnemius.

FIG. 39B shows mRNA knockdown of both targets in gastrocnemius is maintained at 75% in the intact leg out to 37 days post ASC dose.

In the denerved leg, Atrogin1 mRNA knockdown is maintained 3 days post denervation, but is reduced to 20% by 10 days post denervation and to 0% by 30 days post denervation. MuRF1 mRNA knockdown in the denerved leg is enhanced to 80-85% 3 days post denervation, but is reduced to 50% by 10 days post denervation and to 40% by 30 days post denervation (FIG. 39C).

The mRNA knockdown of each target was not impacted by the knockdown of the other target when treated with the combination of both siRNAs (FIG. 39D).

Based on leg muscle area measurements, siRNA-mediated downregulation of MuRF1 and the combination of MuRF1 and Atrogin-1 reduced denervation-induced muscle wasting by up to 30%. Treatment with MuRF1 siRNA alone showed similar responses than treatment with the combination of MuRF1 and Atrogin-1. Downregulation of Atrogin-1 alone had no significant effect on leg muscle area. The statistical analysis compared the treatment groups to the scramble siRNA control group using a Welch's TTest. See FIG. 39E.

Based on the Gastrocnemius weight only MuRF1 showed statistically significant differences from the scramble siRNA control group. Similar to the results obtained by measuring leg muscle area, downregulation of MuRF1 showed an up to 35% reduction in denervation-induced muscle wasting. These results agree with effects of MuRF1 knock out in mice (Bodine et al., Science 291, 2001). See FIG. 39F.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11554176B2). An electronic copy of the "Sequence Listing" will also be available from the USPTO upon request and payment of the fee set forth in 37 CFR 1.19(b)(3).

What is claimed is:

1. A small interfering RNA (siRNA)-antibody conjugate comprising an anti-transferrin receptor antibody or antigen-binding fragment thereof conjugated to an siRNA that hybridizes to a target sequence of human Murf1 mRNA and mediates RNA interference against the human Murf1 mRNA preferentially in a muscle cell, wherein the siRNA is a double stranded RNA comprising a guide strand and a passenger strand, and wherein the guide strand is a sequence selected from SEQ ID NOs: 651-702.

2. The siRNA-antibody conjugate of claim 1, wherein the siRNA comprises at least one 2' modified nucleotide, at least one modified internucleotide linkage, or at least one inverted abasic moiety.

3. The siRNA-antibody conjugate of claim 1, wherein mediation of RNA interference against the human Murf1 mRNA in the muscle cell modulates muscle atrophy or myotonic dystrophy in a subject.

4. The siRNA-antibody conjugate of claim 1, wherein the anti-transferrin receptor antibody or antigen-binding fragment thereof binds to a transferrin receptor on cell surface of the muscle cell.

5. The siRNA-antibody conjugate of claim 1, wherein the muscle cell is a skeletal muscle cell or a cardiac muscle cell.

6. The siRNA-antibody conjugate of claim 1, wherein the guide strand hybridizes to at least 8 contiguous bases of the target sequence of the human Murf1 mRNA.

7. The siRNA-antibody conjugate of claim 1, wherein the siRNA is from about 19 to about 30 nucleotides in length.

8. The siRNA-antibody conjugate of claim 1, wherein the siRNA antibody conjugate comprises a linker connecting the anti-transferrin receptor antibody or antigen-binding fragment thereof to the siRNA.

9. The siRNA-antibody conjugate of claim 3, wherein the at least one 2' modified nucleotide:
- comprises 2'-O-methyl, 2'-O-methoxyethyl (2'-O-MOE), 2'-O-aminopropyl, 2'-deoxy, 2'-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) modified nucleotide;
- comprises locked nucleic acid (LNA) or ethylene nucleic acid (ENA); or
- comprises a combination thereof.

10. The siRNA-antibody conjugate of claim 2, wherein the at least one modified internucleotide linkage comprises a phosphorothioate linkage or a phosphorodithioate linkage.

11. The siRNA-antibody conjugate of claim 2, wherein the siRNA comprises 3 or more 2' modified nucleotides selected from 2'-O-methyl and 2'-deoxy-2'-fluoro.

12. The siRNA-antibody conjugate of claim 1, wherein the siRNA-antibody conjugate has an siRNA to antibody ratio of from about 1 to about 4.

13. The siRNA-antibody conjugate of claim 1, wherein the siRNA comprises a 5'-terminal vinylphosphonate modified nucleotide.

14. The siRNA-antibody conjugate of claim 4, wherein the muscle atrophy is associated with myotonic dystrophy.

15. The siRNA-antibody conjugate of claim 1, wherein the siRNA-antibody conjugate is formulated for parenteral administration.

16. The siRNA antibody conjugate of claim 1, wherein the passenger strand is a sequence selected from SEQ ID NOs: 540-591.

* * * * *